US012617782B2

(12) United States Patent
Perl et al.

(10) Patent No.: US 12,617,782 B2
(45) Date of Patent: May 5, 2026

(54) PYRIDAZINONES AS PARP7 INHIBITORS

(71) Applicant: Ribon Therapeutics, Inc., Cambridge, MA (US)

(72) Inventors: Nicholas Robert Perl, Somerville, MA (US); Melissa Marie Vasbinder, Newton, MA (US); Kevin Wayne Kuntz, Woburn, MA (US)

(73) Assignee: Ribon Therapeutics, Inc., Cambridge, MA (US)

( * ) Notice: Subject to any disclaimer, the term of this patent is extended or adjusted under 35 U.S.C. 154(b) by 17 days.

(21) Appl. No.: 18/196,601

(22) Filed: May 12, 2023

(65) Prior Publication Data

US 2024/0034728 A1 Feb. 1, 2024

Related U.S. Application Data

(62) Division of application No. 17/083,442, filed on Oct. 29, 2020, now Pat. No. 11,691,969.

(60) Provisional application No. 62/927,934, filed on Oct. 30, 2019.

(51) Int. Cl.

| | |
|---|---|
| ***A61K 31/501*** | (2006.01) |
| ***A61P 35/00*** | (2006.01) |
| ***C07D 401/14*** | (2006.01) |
| ***C07D 403/14*** | (2006.01) |
| ***C07D 417/14*** | (2006.01) |

(52) U.S. Cl.

CPC .......... *C07D 417/14* (2013.01); *A61K 31/501* (2013.01); *A61P 35/00* (2018.01); *C07D 401/14* (2013.01); *C07D 403/14* (2013.01)

(58) Field of Classification Search

CPC .................................................... A61K 31/501

See application file for complete search history.

(56) References Cited

U.S. PATENT DOCUMENTS

| | | | |
|---|---|---|---|
| 6,432,632 | B2 | 8/2002 | Nakayama et al. |
| 7,875,621 | B2 | 1/2011 | Van Der Aa et al. |
| 10,189,831 | B2 | 1/2019 | Arrington et al. |
| 10,550,105 | B2 | 2/2020 | Vasbinder et al. |
| 10,870,641 | B2 | 12/2020 | Vasbinder et al. |
| 11,014,913 | B2 | 5/2021 | Vasbinder et al. |
| 11,293,927 | B2 | 4/2022 | Wigle et al. |
| 11,566,020 | B1 | 1/2023 | Vasbinder et al. |
| 11,691,969 | B2 | 7/2023 | Perl et al. |
| 12,371,421 | B2 | 7/2025 | Vasbinder et al. |
| 2003/0082665 | A1 | 5/2003 | Ingraham et al. |
| 2004/0115710 | A1 | 6/2004 | Li et al. |
| 2008/0161280 | A1 | 7/2008 | Gandhi et al. |
| 2009/0176765 | A1 | 7/2009 | Jones et al. |
| 2012/0258180 | A1 | 10/2012 | Giranda et al. |
| 2015/0166544 | A1 | 6/2015 | Zhang et al. |
| 2015/0182490 | A1 | 7/2015 | Brown et al. |
| 2019/0330194 | A1 | 10/2019 | Vasbinder et al. |
| 2019/0331688 | A1 | 10/2019 | Wigle et al. |
| 2020/0109123 | A1 | 4/2020 | McCann |
| 2020/0123134 | A1 | 4/2020 | Vasbinder et al. |
| 2021/0024470 | A1 | 1/2021 | Smits et al. |
| 2021/0024502 | A1 | 1/2021 | Vasbinder et al. |
| 2021/0130342 | A1 | 5/2021 | Perl et al. |
| 2022/0162196 | A1 | 5/2022 | Vasbinder et al. |
| 2022/0206008 | A1 | 6/2022 | Wigle et al. |
| 2023/0192664 | A1 | 6/2023 | Vasbinder et al. |
| 2024/0190844 | A1 | 6/2024 | Perl et al. |
| 2025/0020654 | A1 | 1/2025 | Wigle et al. |
| 2025/0034120 | A1 | 1/2025 | Vasbinder et al. |
| 2025/0074897 | A1 | 3/2025 | Perl et al. |

FOREIGN PATENT DOCUMENTS

| | | | |
|---|---|---|---|
| CA | 2653529 | A1 | 12/2007 |
| CA | 2653529 | C | 2/2016 |
| CN | 101501006 | A | 8/2009 |
| CN | 101855221 | A | 10/2010 |
| CN | 112424188 | | 2/2021 |
| CN | 112424188 | A | 2/2021 |
| ES | 2524787 | T3 | 12/2014 |
| ES | 2548353 | | 10/2015 |
| ES | 2548353 | T3 | 10/2015 |
| JP | 2009-538896 | A | 11/2009 |
| JP | 2011-503166 | A | 1/2011 |
| JP | 2011-515450 | A | 5/2011 |
| JP | 2013-502424 | A | 1/2013 |
| JP | 2015-527336 | A | 9/2015 |
| JP | 2016-512239 | A | 4/2016 |
| JP | 2018-535229 | A | 11/2018 |

(Continued)

OTHER PUBLICATIONS

Office Action in Chinese Appln. No. 202080083214.3, dated on Jul. 17, 2023, 14 pages (With English translation).

Office Action in Japanese Appln. No. 2020-145986, Mailed on May 16, 2023, 18 pages (with English translation).

Schwartz et al., "Applications of tert-amino effect and a nitrone-olefin 1,3-dipolar cycloaddition reaction: synthesis of novel angularly annelated diazino heterocycles," Journal of Molecular Structure: THEOCHEM, Aug. 2000, 528(1-3):49-57.

STN Registry No. 1375963-69-1, "CN 4-Chloro-5-[[3-[4-(3-methylpheny1)-1-piperaziny1]propyl]amino]-3(2H)-pyridazinone," Jun. 7, 2012, 1 page.

(Continued)

*Primary Examiner* — Brian E Mcdowell

(74) *Attorney, Agent, or Firm* — Fish & Richardson P.C.

(57) ABSTRACT

The present invention relates to pyridazinones and related compounds which are inhibitors of PARP7 and are useful in the treatment of cancer, wherein the compounds have the formula:

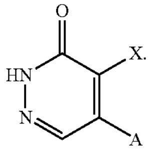

40 Claims, 1 Drawing Sheet

(56) References Cited

FOREIGN PATENT DOCUMENTS

| | | | |
|---|---|---|---|
| JP | 2020/560916 | | 4/2019 |
| JP | 2020-560916 | A | 4/2019 |
| JP | 2021-145986 | A | 9/2021 |
| JP | 6942896 | B2 | 9/2021 |
| JP | 7518049 | B2 | 7/2024 |
| TW | I361188 | | 4/2012 |
| TW | I361188 | B | 4/2012 |
| WO | WO 2003/027078 | | 4/2003 |
| WO | WO 2003/027078 | A1 | 4/2003 |
| WO | WO 2003/027097 | | 4/2003 |
| WO | WO 2003/027097 | A1 | 4/2003 |
| WO | WO 2008/013838 | A2 | 1/2008 |
| WO | WO 2009/063244 | A1 | 5/2009 |
| WO | WO 2016/116602 | A1 | 7/2016 |
| WO | WO 2019/055966 | A2 | 3/2019 |
| WO | WO 2019/212937 | A1 | 11/2019 |
| WO | WO 2019/212946 | A1 | 11/2019 |
| WO | WO 2020/223229 | A1 | 11/2020 |
| WO | WO 2021/087018 | A1 | 5/2021 |
| WO | WO 2021/087025 | A1 | 5/2021 |

OTHER PUBLICATIONS

STN Registry No. 1707598-02-4, "CN 4-Chloro-5-[3-(1H-pyrazol-1-yl)propyllamino]-3(2H)-pyridazinone," May 19, 2015, 1 page.
STN Registry No. 1710349-07-7, "CN 4-Bromo-5-[[3-(4-morpholinyl)-3-oxopropyl]amino]-3(2H)-pyridazinone," May 22, 2015, 1 page.
STN Registry No. 1713221-50-1, "CN 4-Chloro-5-[[3-(4-morpholinyl)-3-oxopropyl]amino]-3(2H)-pyridazinone," 26 May , 2015, 1 page.
Office Action in Indian Appln. No. 202217029911, mailed on Sep. 25, 2024, 6 pages (with English translation).
Office Action in Japanese Appln. No. 2022-525496, mailed on Sep. 17, 2024, 7 pages (with English translation).
Promega Technical Buletin, "NanoBRET™ Target Engagement Intracellular HDAC Assay," Promega Corporation, 2800 Woods Hollow Road, Madison, WI, 2016, pp. 1-24.
Vasta et al., "Quantitative, wide-spectrum kinase profiling in live cells for assessing the effect of cellular ATP on target engagement," Cell chemical biology, Feb. 15, 2018, 25(2):206-14.
Written Opinion in Singaporean Appln. No. 11202204293P, mailed on Nov. 20, 2024, 5 pages.
ClinicalTrials.gov [online], "Phase 1 Study of RBN-2397, an Oral PARP7 Inhibitor, in Patients With Solid Tumors," NCT04053673, last updated Mar. 28, 2023, retrieved on Jul. 2, 2025, retrieved from URL <https://clinicaltrials.gov/study/NCT04053673?term=NCT04053673&rank=1>, 15 pages.
Extended European Search Report in European Appln No. 23161423.1, mailed on Sep. 11, 2023, 5 pages.
Office Action in Australian Appln. No. 2019262927, mailed on Oct. 27, 2022, 2 pages.
Office Action in Brazilian Appln. No. 112020022006-0, mailed on Apr. 4, 2023, 5 pages (with English translation).
Office Action in Canadian Appln. No. 3098585, mailed on May 16, 2025, 5 pages.
Office Action in Chilean Appln. No. 2020-002821, mailed on Dec. 20, 2021, 22 pages (with English translation).
Office Action in Chilean Appln. No. 2020-002821, mailed on Sep. 13, 2022, 22 pages (with English translation).
Office Action in Chinese Appln. No. 201980044076.5, mailed on Jan. 22, 2025, 8 pages (with English translation).
Office Action in Chinese Appln. No. 201980044076.5, mailed on Mar. 18, 2023, 15 pages (with English translation).
Office Action in Chinese Appln. No. 202080083214.3, mailed on Jan. 21, 2025, 14 pages (with English translation).
Office Action in Colombian Appln. No. NC 2020/0013599, mailed on Nov. 25, 2022, 11 pages (with English translation).
Office Action in Colombian Appln. No. NC 2020/0013599, mailed on Nov. 7, 2020, 2 pages (with English translation).
Office Action in Costa Rican Appln. No. 2020-000518, mailed on Mar. 4, 2024, 18 pages (with English translation).
Office Action in Costa Rican Appln. No. 2020-000518, mailed on Nov. 20, 2024, 18 pages (with English translation).
Office Action in Ecuadorian Appln. No. SENADI-2020-69404, mailed on Nov. 25, 2020, 2 pages (with English translation).
Office Action in Eurasian Appln. No. 202092590, mailed on Jan. 20, 2022, 6 pages (with English translation).
Office Action in Eurasian Appln. No. 202092590, mailed on Jan. 22, 2024, 8 pages (with English translation).
Office Action in Eurasian Appln. No. 202092590, mailed on May 21, 2025, 4 pages (with English translation).
Office Action in Eurasian Appln. No. 202291315, mailed on Jun. 15, 2023, 6 pages (with English translation).
Office Action in Eurasian Appln. No. 202291315, mailed on May 5, 2025, 4 pages (with English translation).
Office Action in Eurasian Appln. No. 202291315, mailed on Nov. 20, 2024, 2 pages (with English translation).
Office Action in European Appln. No. 19723272.1, mailed on Dec. 9, 2020, 3 pages.
Office Action in European Appln. No. 19723272.1, mailed on Sep. 20, 2021, 4 pages.
Office Action in European Appln. No. 23161423.1, mailed on Jan. 13, 2025, 4 pages.
Office Action in Indian Appln. No. 202017046239, mailed on Jul. 20, 2022, 6 pages (with English translation).
Office Action in Indian Appln. No. 202017046239, mailed on Oct. 16, 2023, 2 pages (with English translation).
Office Action in Indonesian Appln. No. P00202205488, mailed on May 2, 2024, 5 pages (with English translation).
Office Action in Israeli Appln. No. 278,116, mailed on Jun. 6, 2021, 6 pages (with English translation).
Office Action in Israeli Appln. No. 278,116, mailed on Nov. 14, 2022, 3 pages (English translation only).
Office Action in Israeli Appln. No. 292,432, mailed on Dec. 26, 2024, 4 pages (with English translation).
Office Action in Israeli Appln. No. 292,432, mailed on Nov. 17, 2022, 5 pages (with English translation).
Office Action in Israeli Appln. No. 308,983, mailed on Dec. 18, 2023, 6 pages (with English translation).
Office Action in Israeli Appln. No. 308,983, mailed on Nov. 13, 2024, 3 pages (English translation only).
Office Action in Japanese Appln. No. 2021-145986, mailed on Feb. 13, 2024, 4 pages (with English translation).
Office Action in Japanese Appln. No. 2021-145986, mailed on Jan. 16, 2024, 5 pages (with English translation).
Office Action in Korean Appln. No. 10-2020-7034323, mailed on Jul. 18, 2024, 9 pages (with English translation).
Office Action in Mexican Appln. No. MX/A/2020/011465, mailed on Oct. 18, 2022, 8 pages (with English translation).
Office Action in Mexican Appln. No. MX/A/2022/005216, mailed on Apr. 25, 2025, 13 pages (with English translation).
Office Action in Peru Appln. No. 0001749-2020/DIN, mailed on Mar. 10, 2025, 9 pages.
Office Action in Peru Appln. No. 0001749-2020/DIN, mailed on Sep. 20, 2024, 14 pages (with English translation).
Office Action in Philippine Appln. No. 1-2020-551760, mailed on Apr. 14, 2025, 3 pages.
Office Action in Philippine Appln. No. 1-2020-551760, mailed on Dec. 2, 2024, 5 pages.
Office Action in Taiwanese Appln. No. 108114978, mailed on Jan. 13, 2023, 25 pages (with English translation).
Office Action in Taiwanese Appln. No. 109137556, mailed on Jan. 9, 2025, 8 pages (with English translation).
Office Action in Taiwanese Appln. No. 112127538, mailed on Sep. 5, 2023, 8 pages (with English translation).
Office Action in Taiwanese Appln. No. 109137556, mailed on Jul. 9, 2024, 20 pages (with English translation).
Office Action in Thai Appln. No. 2001006218, mailed on Dec. 25, 2023, 9 pages (with English translation).
Office Action in Ukrainian Appln. No. a202007549, mailed on Feb. 7, 2024, 4 pages (with English translation).

(56) References Cited

OTHER PUBLICATIONS

Office Action in Vietnamese Appln. No. 1-2022-03297, mailed on Jun. 25, 2024, 3 pages (with English translation).
STN Registry No. 2123847-27-6, "3(2H)-Pyridazinone, 4-chloro-5-[(3aR,7aS)-octahydro-2H-isoindol-2-yl]-,rel-", Sep. 1, 2017, 8 pages.
Gamba et al., "Identification of novel 2-benzoxazolinone derivatives with specific inhibitory activity against the HIV-1 nucleocapsid protein," European Journal of Medicinal Chemistry, Feb. 2018, 145:154-164.
Office Action in Chinese Appln. No. 202080083214.3, mailed on Jul. 15, 2023, 12 pages (with English translation).
Office Action in Japanese Appln. No. 2021-145986, mailed on May 7, 2024, 14 pages (with English translation).
Schwartz et al., "Applications of tert-amino effect and a nitrone-olefin 1,3-dipolar cycloaddition reaction: synthesis of novel angularly annelated diazino heterocycles," Journal of Molecular Struture: THEOCHEM, Aug. 2000, 528(1-3):49-57.
STN Registry No. 1252156-61-8, "CN 4-Chloro-5-[[3-(3,4-dihydro-1(2H)- quinoliny1)-3-oxopropyl]amino]-3(2H)-pyridazinone," Nov. 9, 2010, 1 page.
STN Registry No. 1375963-69-1, "CN 4-Chloro-5-[[3-[4-(3-methylphenyl)-1-piperazinyl]propyl]amino]-3(2H)-pyridazinone," Jun. 7, 2012, 1 page.
STN Registry No. 1484783-67-6, "CN 4-chloro-5-[[2-methyl-3-(1-piperidinyl)propyl]amino]-3(2H)-pyridazinone," Dec. 1, 2013, 1 page.
STN Registry No. 1485466-57-6, "CN 4-Chloro-5-[[3-(2-methyl-1-piperidinyl)propyl]amino]-3(2H)-pyridazinone," Dec. 2, 2013, 1 page.
STN Registry No. 1490079-97-4, "CN 4-Chloro-5-[[3-(1H-imidazol-1-yl)propyl]amino]-3(2H)-pyridazinone," Dec. 8, 2013, 1 page.
STN Registry No. 1495798-46-3, "CN 4-Chloro-5-[[3-(1-pyrrolidinyl)propyl]amino]-3(2H)-pyridazinone," Dec. 16, 2013, 1 page.
STN Registry No. 1510953-57-7, "CN 4-Chloro-5-[[2-methyl-3-(1-pyrrolidinyl)propyl]amino]-3(2H)-pyridazinone," Jan. 5, 2014, 1 page.
STN Registry No. 1521001-17-1, "CN 4-Chloro-5-[[4-(1H-imidazol-1-yl)butyl]amino]-3(2H)-pyridazinone," Jan. 15, 2014, 1 page.
STN Registry No. 1542530-79-9, "CN 4-Chloro-5-[[3-(1-piperazinyl)propyl]amino]-3(2H)-pyridazinone," Feb. 13, 2014, 1 page.
STN Registry No. 1707598-02-4, "CN 4-Chloro-5-[[3-(1H-pyrazol-1-yl)propyl]amino]-3(2H)-pyridazinone," May 19, 2015, 1 page.
STN Registry No. 1707983-59-2, "CN 4-Bromo-5-[[3-(4-morpholinyl)propyl]amino]-3(2H)-pyridazinone," May 19, 2015, 1 page.
STN Registry No. 1710191-97-1, "CN 4-Bromo-5-[[3-(2-methyl-1-piperidinyl)propyl]amino]-3(2H)-pyridazinone," May 22, 2015, 1 page.
STN Registry No. 1710334-93-2, "CN 4-Bromo-5-[[3-(1H-pyrazol-1-yl)propyl]amino]-3(2H)-pyridazinone," May 22, 2015, 1 page.
STN Registry No. 1710343-80-8, "CN 4-Bromo-5-[[3-oxo-3-(1-pyrrolidinyl)propyl]amino]-3(2H)-pyridazinone," May 22, 2015, 1 page.
STN Registry No. 1710349-07-7, "CN 4-Bromo-5-[[3-(4-morpholiny1)-3- oxopropyl]amino]-3(2H)-pyridazinone," May 22, 2015, 1 page.
STN Registry No. 1710531-07-9, "CN 4-Chloro-5-[[3-oxo-3-(1-pyrrolidinyl)propyl]amino]-3(2H)-pyridazinone," May 22, 2015, 1 page.
STN Registry No. 1710945-38-2, "CN 4-Bromo-5-[[3-(3,5-dimethyl-1H-pyrazol-1-yl)propyl]amino]-3(2H)-pyridazinone," May 24, 2015, 1 page.
STN Registry No. 1711796-42-7, "CN 4-Bromo-5-[[3-oxo-3-(1-piperidinyl)propyl]amino]-3(2H)-pyridazinone," May 25, 2015, 1 page.
STN Registry No. 1713221-50-1, "CN 4-Chloro-5-[[3-(4-morpholiny1)-3-oxopropyl]amino]-3(2H)-pyridazinone," May 26, 2015, 1 page.
STN Registry No. 1713222-21-9, "CN 4-Bromo-5-[[3-(1-pyrrolidinyl)propyl]amino]-3(2H)-pyridazinone," May 26, 2015, 1 page.
STN Registry No. 1770153-94-0, "CN 4-Bromo-5-[[2-methyl-3-(1-piperidinyl)propyl]amino]-3(2H)-pyridazinone," Jun. 1, 2015, 1 page.
STN Registry No. 1770154-16-9, "CN 4-Bromo-5-[[2-methyl-3-(1-pyrrolidinyl)propyl]amino]-3(2H)-pyridazinone," Jun. 1, 2015, 1 page.
STN Registry No. 1770154-34-1, "CN 4-Bromo-5-[[3-(1H-1,2,3-triazol-1-yl)propyl]amino]-3(2H)-pyridazinone," Jun. 1, 2015, 1 page.
STN Registry No. 1774932-00-1, "CN 4-Bromo-5-[[3-(1H-imidazol-1-yl)propyl]amino]-3(2H)-pyridazinone," Jun. 7, 2015, 1 page.
STN Registry No. 1774949-89-1, "CN 4-Chloro-5-[[3-(3,5-dimethyl-1H-pyrazol-1-yl)propyl]amino]-3(2H)-pyridazinone," Jun. 7, 2015, 1 page.
STN Registry No. 1775918-08-5, "CN 4-Chloro-5-[[3-oxo-3-(1-piperidinyl)propyl]amino]-3(2H)-pyridazinone," Jun. 8, 2015, 1 page.
STN Registry No. 1777885-96-7, "CN 4-Bromo-5-[[4-(1H-imidazol-1-yl)butyl]amino]-3(2H)-pyridazinone," Jun. 11, 2015, 1 page.
STN Registry No. 1797223-27-8, "CN 4-Chloro-5-[[4-(2,3-dihydro-1H-indol-1-y1)-4-oxobutyl] amino]-3(2H)-pyridazinone," Jul. 8, 2015, 1 page.
STN Registry No. 1797312-44-7, "CN 4-Chloro-5-[[4-(2,6-dimethyl-4-morpholinyl)butyl] amino]-3(2H)-pyridazinone," Jul. 8, 2015, 1 page.
STN Registry No. 1916850-83-3, "CN 4-Chloro-5-[[3-(1H-1,2,3-triazol-1-yl) propyl] amino]-3(2H)-pyridazinone, "Aug. 16, 2023, 1 page.
STN Registry No. 2001824-09-3, "CN 5-[[3-(1-azetidinyl) propyl] amino]-4-bromo- 3(2H)-pyridazinone," Sep. 29, 2016, 1 page.
STN Registry No. 2007011-73-4, "CN 5-[[3-(1-azetidinyl) propyl] amino]-4-chloro- 3(2H)-pyridazinone," Oct. 6, 2016, 1 page.
STN Registry No. 807665-16-3, "CN 4-Chloro-5-[[3-(4-morpholinyl)propyl]amino]- 3(2H)-pyridazinone," Jan. 4, 2005, 1 page.
STN Search, conducted Mar. 16, 2023, 8 pages.
Office Action in Korean Appln. No. 10-2022-7018075, mailed on Jan. 13, 2026, 13 pages (with English translation).

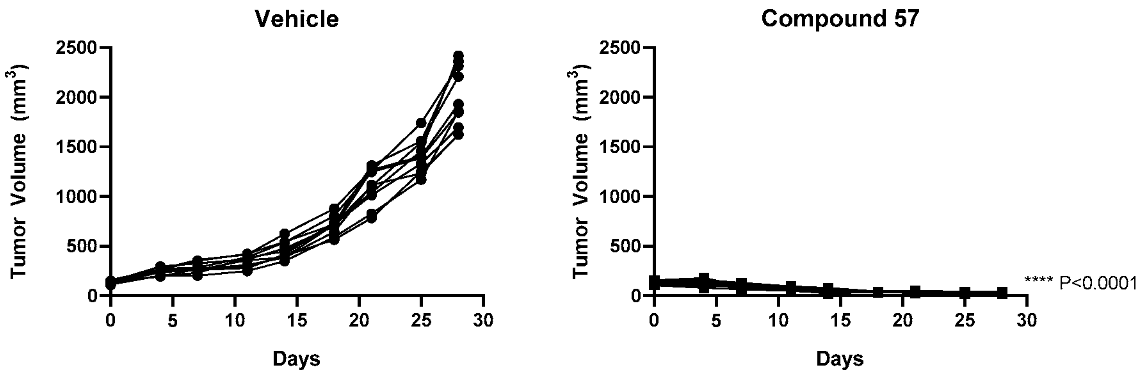
Vehicle
Tumor Volume (mm³)
2500
2000
1500
1000
500
0
0 5 10 15 20 25 30
Days
Compound 57
Tumor Volume (mm³)
2500
2000
1500
1000
500
0
0 5 10 15 20 25 30
Days
**** P<0.0001

PYRIDAZINONES AS PARP7 INHIBITORS

FIELD OF THE INVENTION

The present invention relates to pyridazinones and related compounds which are inhibitors of PARP7 and are useful in the treatment of cancer.

BACKGROUND OF THE INVENTION

Poly(ADP-ribose) polymerases (PARPs) are members of a family of seventeen enzymes that regulate fundamental cellular processes including gene expression, protein degradation, and multiple cellular stress responses (M. S. Cohen, P. Chang, Insights into the biogenesis, function, and regulation of ADP-ribosylation. *Nat Chem Biol* 14, 236-243 (2018)). The ability of cancer cells to survive under stress is a fundamental cancer mechanism and an emerging approach for novel therapeutics. One member of the PARP family, PARP1, has already been shown to be an effective cancer target in connection to cellular stress induced by DNA damage, either induced by genetic mutation or with cytotoxic chemotherapy, with four approved drugs in the clinic and several others in late stage development (A. Ohmoto, S. Yachida, Current status of poly(ADP-ribose) polymerase inhibitors and future directions. *Onco Targets Ther* 10, 5195-5208 (2017)).

The seventeen members of the PARP family were identified in the human genome based on the homology within their catalytic domains (S. Vyas, M. Chesarone-Cataldo, T. Todorova, Y. H. Huang, P. Chang, A systematic analysis of the PARP protein family identifies new functions critical for cell physiology. *Nat Commun* 4, 2240 (2013)). However, their catalytic activities fall into 3 different categories (S. Vyas et al., Family-wide analysis of poly(ADP-ribose) polymerase activity. *Nat Commun* 5, 4426 (2014)). The majority of PARP family members catalyze the transfer of mono-ADP-ribose units onto their substrates (monoPARPs), while others (PARP1, PARP2, TNKS, TNKS2) catalyze the transfer of poly-ADP-ribose units onto substrates (polyPARPs). Finally, PARP13 is thus far the only PARP for which catalytic activity could not be demonstrated either in vitro or in vivo.

The aryl hydrocarbon receptor (AHR) is a ligand-activated transcription factor involved in regulating multiple cellular functions including proinflammatory responses and xenobiotic metabolism (S. Feng, Z. Cao, X. Wang, Role of aryl hydrocarbon receptor in cancer. *Biochim Biophys Acta* 1836, 197-210 (2013); and B. Stockinger, P. Di Meglio, M. Gialitakis, J. H. Duarte, The aryl hydrocarbon receptor: multitasking in the immune system. *Annu Rev Immunol* 32, 403-432 (2014)). The AHR can be activated by a broad number of ligands including endogenous tryptophan metabolites such as kynurenine (C. A. Opitz et al., An endogenous tumour-promoting ligand of the human aryl hydrocarbon receptor. *Nature* 478, 197-203 (2011)) and certain polycyclic aromatic hydrocarbons such as 2,3,7,8-tetrachlorodibenzo-p-dioxin (TCDD) (K. W. Bock, Toward elucidation of dioxin-mediated chloracne and Ah receptor functions. *Biochem Pharmacol* 112, 1-5 (2016)). Activation of the AHR induces target gene expression including genes involved in metabolism such as cytochrome P4501A1 and P4501B1. Activation of AHR also leads to an increase in the AHR target gene, TCDD-inducible poly(ADP-ribose)polymerase (TIPARP, also referred to as PARP7), which functions as a negative regulator of certain AHR transcriptional targets (L. MacPherson et al., Aryl hydrocarbon receptor repressor and TIPARP (ARTD14) use similar, but also distinct mechanisms to repress aryl hydrocarbon receptor signaling. *Int J Mol Sci* 15, 7939-7957 (2014); and L. MacPherson et al., 2,3,7,8-Tetrachlorodibenzo-p-dioxin poly(ADP-ribose) polymerase (TIPARP, ARTD14) is a mono-ADP-ribosyltransferase and repressor of aryl hydrocarbon receptor transactivation. *Nucleic Acids Res* 41, 1604-1621 (2013)).

PARP7 can also be regulated by other transcription factors and signaling pathways including androgen receptor (E. C. Bolton et al., Cell- and gene-specific regulation of primary target genes by the androgen receptor. *Genes Dev* 21, 2005-2017 (2007)), platelet derived growth factor (J. Schmahl, C. S. Raymond, P. Soriano, PDGF signaling specificity is mediated through multiple immediate early genes. *Nat Genet* 39, 52-60 (2007)) and hypoxia inducible factor 1 (N. Hao et al., Xenobiotics and loss of cell adhesion drive distinct transcriptional outcomes by aryl hydrocarbon receptor signaling. *Mol Pharmacol* 82, 1082-1093 (2012)). The PARP7 gene is located on chromosome 3 (3q25) in a region that is frequently amplified in cancers of squamous histology (http://www.cbioportal.org/index.do?session_id=5ae1bcde498eb8b3d565d8b2). A genome-wide association study identified 3q25 as susceptibility loci for ovarian cancer suggesting a role for PARP7 in this cancer type (E. L. Goode et al., A genome-wide association study identifies susceptibility loci for ovarian cancer at 2q31 and 8q24. *Nat Genet* 42, 874-879 (2010)). PARP7 has multiple cellular functions. In the context of AHR signaling PARP7 acts as a negative feedback mechanism to regulate the expression of P4501A1 and P4501B1 (L. MacPherson et al., Aryl hydrocarbon receptor repressor and TIPARP (ARTD14) use similar, but also distinct mechanisms to repress aryl hydrocarbon receptor signaling. *Int J Mol Sci* 15, 7939-7957 (2014), and L. MacPherson et al., 2,3,7,8-Tetrachlorodibenzo-p-dioxin poly(ADP-ribose) polymerase (TIPARP, ARTD14) is a mono-ADP-ribosyltransferase and repressor of aryl hydrocarbon receptor transactivation. *Nucleic Acids Res* 41, 1604-1621 (2013)). PARP7 has also been described to ADP-ribosylate liver X receptors which leads to the modulation of their transcriptional activity (C. Bindesboll et al., TCDD-inducible poly-ADP-ribose polymerase (TIPARP/PARP7) mono-ADP-ribosylates and co-activates liver X receptors. *Biochem J* 473, 899-910 (2016). During viral infection PARP7 can bind to Sindbis virus (SINV) to promote viral RNA degradation (T. Kozaki et al., Mitochondrial damage elicits a TCDD-inducible poly(ADP-ribose) polymerase-mediated antiviral response. *Proc Natl Acad Sci USA* 114, 2681-2686 (2017)). Also in the context of viral infection, AHR-induced PARP7 can interact with TBK1, a major kinase that is activated during the onset of pathogen-associated molecular pattern pathways leading to an activation of the Type I interferon response and antiviral immunity (T. Yamada et al., Constitutive aryl hydrocarbon receptor signaling constrains Type I interferon-mediated antiviral innate defense. *Nat Immunol* 17, 687-694 (2016)). PARP7 was shown to ADP-ribosylate TBK1 which prevents its activation, thereby repressing the Type I interferon response.

Based on these results from viral infection one could hypothesize that cancer cells can use aberrantly expressed and/or activated PARP7 as a mechanism to evade the host immune system through suppression of the Type I interferons and thereby T cell mediated antitumor immunity. Indeed, in a recent genetic screen to identify tumor factors that suppress T cell activation PARP7 was identified as a hit (D. Pan et al., A major chromatin regulator determines resistance of tumor cells to T cell-mediated killing. *Science* 359, 770-775 (2018)). PARP7 knockout in a mouse melanoma cell line was shown to increase the proliferation and activation of co-cultured T cells suggesting that PARP7 inhibition may be a viable strategy to activate T cell mediated tumor killing. Thus, there is an ongoing need for the development of PARP7 inhibitors.

SUMMARY OF THE INVENTION

The present invention is directed to a compound of Formula I.

I

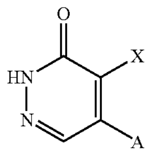

or a pharmaceutically acceptable salt thereof, wherein constituent members are defined below.

The present invention is further directed to a pharmaceutical composition comprising a compound of Formula I, or a pharmaceutically acceptable salt thereof, and at least one pharmaceutically acceptable carrier.

The present invention is further directed to a method of inhibiting the activity of PARP7 comprising contacting a compound of Formula I, or a pharmaceutically acceptable salt thereof, with PARP7.

The present invention is further directed to a method of treating a disease or disorder in a patient in need of treatment, where the disease or disorder is characterized by overexpression or increased activity of PARP7, comprising administering to the patient a therapeutically effective amount of a compound of Formula I, or a pharmaceutically acceptable salt thereof.

The present invention is further directed to a method of treating cancer in a subject in need thereof, the method comprising administering to the subject a therapeutically effective amount of an agent that inhibits PARP7 activity, such as a compound of Formula I, or a pharmaceutically acceptable salt thereof. The present disclosure also provides uses of the compounds described herein in the manufacture of a medicament for use in therapy. The present disclosure also provides the compounds described herein for use in therapy.

BRIEF DESCRIPTION OF THE DRAWINGS

FIG. 1 shows the effect of a compound of the invention on mean tumor volume in animal models as described in Example B.

DETAILED DESCRIPTION

The present invention is directed to a compound of Formula I:

I

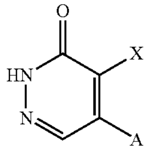

or a pharmaceutically acceptable salt thereof, wherein:

X is Cl, Br, F, $CH_3$, $CF_3$, $CF_2H$, CN, $OCH_3$, ethyl, cyclopropyl, $SCH_3$, or isopropyl;

A is a group having a formula that is (A-1):

(A-1)

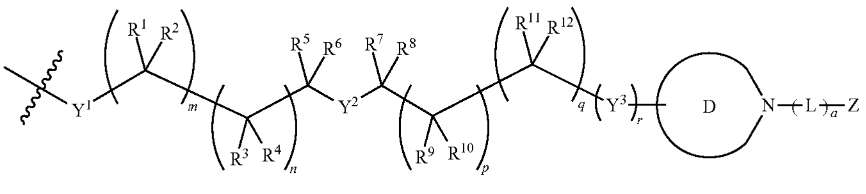

$Y^1$, $Y^2$, and $Y^3$ are each independently selected from O, S, NR, C(=O), C(=O)O, C(=O)$NR^Y$, S(=O), S(=O)$_2$, S(=O)$NR^Y$, S(=O)$_2NR^Y$ or $NR^Y$C(=O)$NR^Y$, wherein each $R^Y$ is independently H, $C_{1-4}$ alkyl, or $C_{1-4}$ haloalkyl;

L is $C_{1-3}$ alkylene, O, S, $NR^Y$, C(=O), C(=O)O, C(=O)$NR^Y$, S(=O), S(=O)NR, or $NR^Y$C(=O)$NR^Y$;

Z is H, $Cy^Z$, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, C(O)$R^b$, C(O)$NR^cR^d$, C(O)$OR^a$, OC(O)$R^b$, OC(O)$NR^cR^d$, $NR^cR^d$, $NR^c$C(O)$R^b$, $NR^c$C(O)$OR^a$, $NR^c$C(O)$NR^cR^d$, C(=$NR^e$)$R^b$, C(=$NR^e$)$NR^cR^d$, $NR^c$C(=$NR^e$)$NR^cR^d$, $NR^c$S(O)$R^b$, $NR^c$S(O)$_2R^b$, $NR^c$S(O)$_2NR^cR^d$, S(O)$R^b$, S(O)$NR^cR^d$, S(O)$_2R^b$, and S(O)$_2NR^cR^d$; wherein said $C_{1-6}$ alkyl, $C_{2-6}$ alkenyl, $C_{2-6}$ alkynyl, and $C_{1-6}$ haloalkyl of Z are each optionally substituted with 1, 2, 3, 4, or 5 substituents independently selected from $Cy^Z$, halo, CN, $NO_2$, $OR^a$, $SR^a$, C(O)$R^b$, C(O)$NR^cR^d$, C(O)$OR^a$, OC(O)$R^b$, OC(O)$NR^cR^d$, C(=$NR^e$)$NR^cR^d$, $NR^c$C(=$NR^e$)$NR^cR^d$, $NR^cR^d$, $NR^c$C(O)$R^b$, $NR^c$C(O)$OR^a$, $NR^c$C(O)$NR^cR^d$, $NR^c$S(O)$R^b$, $NR^c$S(O)$_2R^b$, $NR^c$S(O)$_2NR^cR^d$, S(O)$R^b$, S(O)$NR^cR^d$, S(O)$_2R^b$, and S(O)$_2NR^cR^d$; $Cy^Z$ is selected from $C_{6-10}$ aryl, $C_{3-7}$ cycloalkyl, 5-10 membered heteroaryl, and 4-10 membered heterocycloalkyl, each optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, C(O)$R^{b1}$, C(O)$NR^{c1}R^{d1}$, C(O)$OR^{a1}$, OC(O)$R^{b1}$, OC(O)$NR^{c1}R^{d1}$, C(=$NR^{e1}$)$NR^{c1}R^{d1}$, $NR^{c1}$C(=$NR^{e1}$)$NR^{c1}R^{d1}$, $NR^{c1}R^{d1}$, $NR^{c1}$C(O)$R^{b1}$, $NR^{c1}$C(O)$OR^{a1}$, $NR^{c1}$C(O)$NR^{c1}R^{d1}$, $NR^{c1}$S(O)$R^{b1}$, $NR^{c1}$S(O)$_2R^{b1}$, $NR^{c1}$S(O)$_2NR^{c1}R^{d1}$, S(O)$R^{b1}$, S(O)$NR^{c1}R^{d1}$, S(O)$_2R^{b1}$, and S(O)$_2NR^{c1}R^{d1}$, wherein the alkyl, $C_{2-6}$ alkenyl, and $C_{2-6}$ alkynyl are optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

Ring D is a monocyclic or polycyclic 4-10 membered heterocycloalkyl group optionally substituted with 1, 2, or 3 groups independently selected from halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$, wherein the $C_{1-6}$ alkyl, $C_{2-6}$ alkenyl, and $C_{2-6}$ alkynyl are each optionally substituted with 1, 2, or 3 groups independently selected from halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$.

$R^1$, $R^2$, $R^3$, $R^4$, $R^5$, $R^6$, $R^7$, $R^8$, $R^9$, $R^{10}$, $R^{11}$, and $R^{12}$ are each independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$ $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2$ $R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of said $R^1$, $R^2$, $R^3$, $R^4$, $R^5$, $R^6$, $R^7$, $R^8$, $R^9$, $R^{10}$, $R^{11}$, and $R^{12}$ are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$ $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$ $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

or $R^1$ and an $R^Y$ group of $Y^1$, together with the atoms to which they are attached and together with the atoms forming $Y^1$ form a 4-10 membered heterocycloalkyl ring, optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$ or $R^7$ and an $R^Y$ group of $Y^3$, together with the atoms to which they are attached and together with the atoms forming $Y^3$ and together with the carbon atoms substituted by $R^9$, $R^{10}$, $R^{11}$, and $R^{12}$, if present, form a 4-10 membered heterocycloalkyl ring, optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$ or $R^1$ and $R^3$ together with the carbon atoms to which they are attached form a $C_{5-10}$ cycloalkyl ring or a 5-10 membered heterocycloalkyl ring, each optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

or $R^3$ and $R^5$ together with the carbon atoms to which they are attached form a $C_{5-10}$ cycloalkyl ring or a 5-10 membered heterocycloalkyl ring, each optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

or $R^7$ and $R^9$ together with the carbon atoms to which they are attached form a $C_{5-10}$ cycloalkyl ring or a 5-10 membered heterocycloalkyl ring, each optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

or $R^9$ and $R^{11}$ together with the carbon atoms to which they are attached form a $C_{5-10}$ cycloalkyl ring or a 5-10 membered heterocycloalkyl ring, each optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

or $R^5$ and $R^7$ together with the carbon atoms to which they are attached and together with $Y^2$ form a 5-10 membered heterocycloalkyl ring optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

or $R^1$ and $R^3$ together form a double bond between the carbon atoms to which they are attached;

or $R^3$ and $R^5$ together form a double bond between the carbon atoms to which they are attached;

or $R^7$ and $R^9$ together form a double bond between the carbon atoms to which they are attached;

or $R^9$ and $R^{11}$ together form a double bond between the carbon atoms to which they are attached;

or $R^9$, $R^{10}$, $R^{11}$, and $R^{12}$ together form a triple bond between the carbon atoms to which they are attached;

each $R^a$, $R^b$, $R^c$, $R^d$, $R^{a1}$, $R^{b1}$, $R^{c1}$, $R^{a1}$, $R^{a2}$, $R^{b2}$, $R^{c2}$, $R^{d2}$, $R^{a3}$, $R^{b3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of said $R^a$, $R^b$, $R^c$, $R^d$, $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, and $R^{d3}$ is optionally substituted with 1, 2, or 3 substituents independently selected from halo, $C_{1-4}$ alkyl, $C_{1-4}$ haloalkyl, $C_{2-6}$ alkenyl, $C_{2-6}$ alkynyl, CN, $OR^{ay}$, $SR^{ay}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c3}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

or $R^c$ and $R^d$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^7)NR^{c7}R^{d7}$, $NR^{c7}C(=NR^{e7})NR^{c3}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

or $R^{c1}$ and $R^{d2}$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^7C(=NR^{e7})NR^{c3}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

or $R^{c2}$ and $R^{d2}$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}$, $R^{d7}$, $NR^{c7}C(O)OR^{a7}$, $C(=NR^{e7})NR^{c7}R^{d7}$, $NR^{c7}C(=NR^{e}7)NR^{c3}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

or $R^{c3}$ and $R^{d3}$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$ $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c3}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

$R^{a7}$, $R^{b7}$, $R^{c7}$, and $R^{d7}$ are independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl are each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

each $R^e$, $R^{e1}$, $R^{e2}$, $R^{e3}$, and $R^{c7}$ is independently selected from H, $C_{1-4}$ alkyl, and CN;

a is 0 or 1;

m is 0 or 1;

n is 0 or 1;

p is 0 or 1;

q is 0 or 1;

r is 0 or 1;

wherein any aforementioned heteroaryl or heterocycloalkyl group comprises 1, 2, 3, or 4 ring-forming heteroatoms independently selected from O, N, and S; and wherein one or more ring-forming C or N atoms of any aforementioned heterocycloalkyl group is optionally substituted by 1 or 2 oxo (=O) groups.

In some embodiments, X is $CF_3$, Br, or Cl. In some embodiments, X is $CF_3$. In some embodiments, X is Br or Cl. In some embodiments, X is Br. In some embodiments, X is Cl.

In some embodiments, $Y^1$ is NR or O. In some embodiments, $Y^1$ is $NR^Y$. In some embodiments, $Y^1$ is NH. In some embodiments, $Y^1$ is O. In some embodiments, $Y^1$ is NH or O.

In some embodiments, $Y^2$ is O, $NR^Y$, or C(=O)NR. In some embodiments, $Y^2$ is O, NH, $NCH_3$, or C(=O)NH. In some embodiments, $Y^2$ is O or $NR^Y$. In some embodiments, $Y^2$ is O. In some embodiments, $Y^2$ is $NR^Y$. In some embodiments, $Y^2$ is O, NH, or $NCH_3$. In some embodiments, $Y^2$ is NH or $NCH_3$. In some embodiments, $Y^2$ is NH. In some embodiments, $Y^2$ is $NCH_3$.

In some embodiments, $Y^3$ is C(=O)NR. In some embodiments, $Y^3$ is C(=O)NH. In some embodiments, $Y^3$ is C(=O)$NCH_3$. In some embodiments, $Y^3$ is C(=O)$NCH_2$. In some embodiments, $Y^3$ is C(=O)NH or C(=O)$NCH_3$.

In some embodiments, $R^Y$ of $Y^1$ is H.

In some embodiments, $R^Y$ of $Y^2$ is H or $C_{1-4}$ alkyl. In some embodiments, $R^Y$ of $Y^2$ is H or methyl. In some embodiments, $R^Y$ of $Y^2$ is H. In some embodiments, $R^Y$ of $Y^2$ is methyl.

In some embodiments, $R^Y$ of $Y^3$ is H or $C_{1-4}$ alkyl. In some embodiments, $R^Y$ of $Y^3$ is H, methyl, or ethyl. In some embodiments, $R^Y$ of $Y^3$ is H. In some embodiments, $R^Y$ of $Y^3$ is methyl. In some embodiments, $R^Y$ of $Y^3$ is ethyl. In some embodiments, $R^Y$ of $Y^3$ is $CH_2$.

In some embodiments, $R^1$, $R^2$, $R^3$, $R^4$, $R^5$, $R^6$, $R^7$, $R^8$, $R^9$, $R^{10}$, $R^{11}$, and $R^{12}$ are each independently selected from H, halo, $C_{1-6}$ alkyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)_2R^{b3}$, $NR^{c3}S(O)_2NR^{c3}R^{d3}$, $S(O)_2R^{b3}$, and $S(O)_2NR^{c3}R^{d3}$; wherein said $C_{1-6}$ alkyl is optionally substituted with 1, 2, 3, 4, or 5 substituents independently selected from halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)_2R^{b3}$, $NR^{c3}S(O)_2NR^{c3}R^{d3}$, $S(O)_2R^3$, and $S(O)_2NR^{c3}R^{d3}$.

In some embodiments, $R^1$, $R^2$, $R^3$, $R^4$, $R^5$, $R^6$, $R^7$, $R^8$, $R^9$, $R^{10}$, $R^{11}$, and $R^{12}$ are each independently selected from H, halo, $C_{1-6}$ alkyl, and $C_{1-6}$ haloalkyl, wherein said $C_{1-6}$ alkyl is optionally substituted with 1 or 2 substituents independently selected from halo, CN, $NO_2$, $OR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$ $S(O)_2R^{b3}$, and $S(O)_2NR^{c3}R^{d3}$.

In some embodiments, $R^1$, $R^2$, $R^3$, $R^4$, $R^6$, $R^7$, $R^8$, $R^9$, $R^{10}$, $R^{11}$, and $R^{12}$ are each independently selected from H, halo, $C_{1-6}$ alkyl, and $C_{1-6}$ haloalkyl, wherein said $C_{1-6}$ alkyl is optionally substituted with $OR^{a3}$.

In some embodiments, $R^1$, $R^2$, $R^5$, $R^6$, $R^7$, and $R^8$ are each independently selected from H, halo, $C_{1-6}$ alkyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)_2R^{b3}$, $NR^{c3}S(O)_2NR^{c3}R^{d3}$, $S(O)_2R^{b3}$, and $S(O)_2NR^{c3}R^{d3}$; wherein said $C_{1-6}$ alkyl is optionally substituted with 1, 2, 3, 4, or 5 substituents independently selected from halo, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$ $NR^{c3}C(O)R^{b3}$, $NR^{c3}C(O)OR^{a3}$, $NR^{c3}C(O)NR^{c3}R^{d3}$, $NR^{c3}S(O)_2R^{b3}$, $NR^{c3}S(O)_2NR^{c3}R^{d3}$, $S(O)_2R^{b3}$, and $S(O)_2NR^{c3}R^{d3}$.

In some embodiments, $R^1$, $R^2$, $R^5$, $R^6$, $R^7$, and $R^8$ are each independently selected from H, halo, $C_{1-6}$ alkyl, and $C_{1-6}$ haloalkyl, wherein said $C_{1-6}$ alkyl is optionally substituted with 1 or 2 substituents independently selected from halo, CN, $NO_2$, $OR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $S(O)_2R^{b3}$, and $S(O)_2NR^{c3}R^{d3}$.

In some embodiments, $R^1$, $R^2$, $R^5$, $R^6$, $R^7$, and $R^8$ are each independently selected from H, halo, $C_{1-6}$ alkyl, and $C_{1-6}$ haloalkyl, wherein said $C_{1-6}$ alkyl is optionally substituted with $OR^{a3}$.

In some embodiments, $R^1$ is H or $C_{1-6}$ alkyl; wherein said $C_{1-6}$ alkyl is optionally substituted with $OR^{a3}$, $NR^{c3}R^{d3}$ and $NR^{c3}C(O)R^{b3}$. In some embodiments, $R^1$ is H or $C_{1-6}$ alkyl; wherein said $C_{1-6}$ alkyl is optionally substituted with $OR^{a3}$. In some embodiments, $R^1$ is H or $C_{1-6}$ alkyl; wherein said $C_{1-6}$ alkyl is optionally substituted with methoxy. In some embodiments, $R^1$ is H or methyl; wherein said methyl is optionally substituted with methoxy. In some embodiments, $R^1$ is H, methyl, methoxymethyl, $CH_2OH$, $CH(OH)CH_3$, $CH_2NHCH_2CF_3$ or $CH_2NHC(O)CH_3$. In some embodiments, $R^1$ is H, methyl, or methoxymethyl.

In some embodiments, $R^1$ is $C_{1-6}$ alkyl optionally substituted with $OR^{a3}$. In some embodiments, $R^1$ is $C_{1-6}$ alkyl optionally substituted with methoxy. In some embodiments, $R^1$ is methyl optionally substituted with methoxy. In some embodiments, $R^1$ is methyl. In some embodiments, $R^1$ is methoxymethyl.

In some embodiments, $R^1$ is H.

In some embodiments, $R^2$ is H.

In some embodiments, $R^5$ is H or $C_{1-6}$ alkyl.

In some embodiments, $R^5$ is methyl.

In some embodiments, $R^5$ is H.

In some embodiments, $R^6$ is H.

In some embodiments, $R^7$ is H or $C_{1-6}$ alkyl.

In some embodiments, $R^7$ is $CH_2$.

In some embodiments, $R^7$ is H.

In some embodiments, $R^8$ is H.

In some embodiments, $R^1$ and an $R^Y$ group of $Y^1$, together with the atoms to which they are attached and together with the atoms forming $Y^1$ form a 4-10 membered heterocycloalkyl ring, optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$.

In some embodiments, $R^1$ and an $R^Y$ group of $Y^1$, together with the atoms to which they are attached and together with the atoms forming $Y^1$ form an azetidine ring, optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^3$, and $S(O)_2NR^{c3}R^{d3}$.

In some embodiments, $R^1$ and an $R^Y$ group of $Y^1$, together with the atoms to which they are attached and together with the atoms forming $Y^1$ form an azetidine ring.

In some embodiments, $R^7$ and an $R^Y$ group of $Y^3$, together with the atoms to which they are attached and together with the atoms forming $Y^3$ and together with the carbon atoms substituted by $R^9$, $R^{10}$, $R^{11}$, and $R^{12}$, if present, form a 4-10 membered heterocycloalkyl ring, optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2 R^{b3}$, and $S(O)_2NR^{c3}R^{d3}$.

In some embodiments, $R^7$ and an $R^Y$ group of $Y^3$, together with the atoms to which they are attached and together with the atoms forming $Y^3$ and together with the carbon atoms substituted by $R^9$, $R^{10}$, $R^{11}$, and $R^{12}$, if present, form an oxopyrrolidine ring or pyrrolidine ring, optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$.

In some embodiments, $R^7$ and an $R^Y$ group of $Y^3$, together with the atoms to which they are attached and together with the atoms forming $Y^3$ and together with the carbon atoms substituted by $R^9$, $R^{10}$, $R^{11}$, and $R^{12}$, if present, form an pyrrolidine ring or oxopyrrolidine ring.

In some embodiments, $R^7$ and an $R^Y$ group of $Y^3$, together with the atoms to which they are attached and together with the atoms forming $Y^3$ and together with the carbon atoms substituted by $R^9$, $R^{10}$, $R^{11}$, and $R^{12}$, if present, form an oxopyrrolidine ring.

In some embodiments, $R^7$ and an $R^Y$ group of $Y^3$, together with the atoms to which they are attached and together with the atoms forming $Y^3$ and together with the carbon atoms substituted by $R^9$, $R^{10}$, $R^{11}$, and $R^{12}$, if present, form an oxopiperidine ring.

In some embodiments, Ring D is a monocyclic or polycyclic 4-10 membered heterocycloalkyl group optionally substituted with 1, 2, or 3 groups independently selected from halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$ $NR^{c2}C(=NR^{e2})NR^{e2}R^{d2}$, $NR^{c2}R^{d2}$, $NR^{2}C(O)R^{b2}$, $NR^{c2}C(O)OR^{a2}$, $NR^{2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{e2}R^{d2}$, wherein the $C_{1-6}$ alkyl, $C_{2-6}$ alkenyl, and $C_{2-6}$ alkynyl are each optionally substituted with 1, 2, or 3 groups independently selected from halo, CN, $NO_2$, $OR^{a}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{e2}R^{d2}$, $NR^{c2}R^{d2}$, $NR^{2}C(O)R^{b2}$, $NR^{c2}C(O)OR^{a2}$, $NR^{2}C(O)NR^{e2}R^{d2}$ $NR^{2}S(O)R^{b2}$, $NR^{2}S(O)_2R^{b2}$, $NR^{e2}S(O)_2NR^{e2}R^{d2}$, $S(O)R^{b2}$, $S(O)NR^{c2}R^{d2}$, $S(O)_2R^{b2}$, and $S(O)_2NR^{c2}R^{d2}$.

In some embodiments, Ring D is a monocyclic or polycyclic 4-6 membered heterocycloalkyl group optionally substituted with 1, 2, 3, or 4 substituents independently selected from halo, CN, $OR^{a2}$, $C(O)NR^{e2}R^{d2}$, $C_{1-6}$ alkyl, and $C_{1-6}$ haloalkyl.

In some embodiments, Ring D is a monocyclic or polycyclic 4-6 membered heterocycloalkyl group optionally substituted with 1, 2, 3, or 4 substituents independently selected from halo, $OR^{a2}$, $C_{1-6}$ alkyl, and $C_{1-6}$ haloalkyl.

In some embodiments, Ring D is 3-azabicyclo[3.1.0]hexane.

In some embodiments, Ring D is a monocyclic 4-6 membered heterocycloalkyl group optionally substituted with 1, 2, 3, or 4 substituents independently selected from halo, $OR^{a2}$ $C_{1-6}$ alkyl, and $C_{1-6}$ haloalkyl. In some embodiments, Ring D is a polycyclic 10-membered heterocycloalkyl group optionally substituted with 1, 2, 3, or 4 substituents independently selected from halo, $OR^{a2}$, $C_{1-6}$ alkyl, and $C_{1-6}$ haloalkyl. In some embodiments, Ring D is an azetidine ring or piperidine ring; each of which is optionally substituted with 1, 2, 3, or 4 substituents independently selected from halo, $OR^{a2}$, $C_{1-6}$ alkyl, and $C_{1-6}$ haloalkyl. In some embodiments, Ring D is a piperidine ring optionally substituted with 1, 2, 3, or 4 substituents independently selected from halo, $OR^{a2}$, $C_{1-6}$ alkyl, and $C_{1-6}$ haloalkyl. In some embodiments, Ring D is a piperidine ring optionally substituted with 1 or 2 substitutents independently selected from OH, F, $C(O)NH_2$, or CN. In some embodiments, Ring D is an azetidine ring optionally substituted with 1, 2, 3, or 4 substituents independently selected from halo, $OR^{a2}$, $C_{1-6}$ alkyl, and $C_{1-6}$ haloalkyl.

In some embodiments, Ring D is a monocyclic 4-6 membered heterocycloalkyl group. In some embodiments, Ring D is a polycyclic 10-membered heterocycloalkyl group. In some embodiments, Ring D is an azetidine ring or piperidine ring. In some embodiments, Ring D is a piperidine ring. In some embodiments, Ring D is an azetidine ring.

In some embodiments, Ring D is a monocyclic 4-6 membered heterocycloalkyl group optionally substituted with 1, 2, 3, or 4 substituents independently selected from halo, $OR^{a2}$ $C_{1-6}$ alkyl, and $C_{1-6}$ haloalkyl.

In some embodiments, Ring D is an azetidine ring or piperidine ring optionally substituted with $OR^{a2}$.

In some embodiments, Ring D is a piperidine ring optionally substituted with OH.

In some embodiments, Ring D is a piperidine ring.

In some embodiments, Z is $Cy^Z$, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^dNR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-6}$ haloalkyl of Z are each optionally substituted with 1, 2, 3, 4, or 5 substituents independently selected from $Cy^Z$, halo, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$.

In some embodiments, Z is $Cy^Z$, halo, $C_{1-6}$ alkyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $NR^cS(O)_2R^b$, $NR^cS(O)_2NR^cR^d$, $S(O)_2R^b$, and $S(O)_2NR^cR^d$; wherein said $C_{1-6}$ alkyl of Z is optionally substituted with 1, 2, 3, 4, or 5 substituents independently selected from $Cy^Z$, halo, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^c(O)OR^a$, $NR^cC(O)NR^cR^d$, $NR^cS(O)_2R^b$, $NR^cS(O)_2NR^cR^d$, $S(O)_2R^b$, and $S(O)_2NR^cR^d$.

In some embodiments, Z is $Cy^Z$, halo, $C_{1-6}$ alkyl, $C_{1-6}$ haloalkyl, or CN.

In some embodiments, Z is $Cy^Z$.

In some embodiments, $Cy^Z$ is a 5-6 membered heteroaryl group optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{a}$, $NR^cC(O)R^{b1}$ $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the alkyl, $C_{2-6}$ alkenyl, and $C_{2-6}$ alkynyl are optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NRCS(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

In some embodiments, $Cy^Z$ is a 5 or 6-membered heteroaryl group substituted with halo, CN, methyl, or $C_{1-3}$ haloalkyl.

In some embodiments, $Cy^Z$ is a 5 membered heteroaryl group substituted with halo, CN or $C_{1-3}$ haloalkyl. In some embodiments, $Cy^Z$ is a a 6-membered heteroaryl group substituted with halo, CN, methyl, or $C_{1-3}$ haloalkyl. In some embodiments, $Cy^Z$ is a 6 membered heteroaryl group substituted with halo, CN or $C_{1-3}$ haloalkyl.

In some embodiments, $Cy^Z$ is a pyrimidinyl, pyrazinyl, pyridinyl, or thiazolyl group substituted with halo, CN or $C_{1-3}$ haloalkyl. In some embodiments, $Cy^Z$ is a pyrimidinyl, pyrazinyl, or pyridinyl group substituted with halo, CN or $C_{1-3}$ haloalkyl. In some embodiments, $Cy^Z$ is a pyrimidinyl or pyrazinyl group substituted with halo, CN or $C_{1-3}$ haloalkyl. In some embodiments, $Cy^Z$ is pyrimidinyl substituted with $CF_3$. In some embodiments, $Cy^Z$ is a thiazolyl group substituted with halo, CN or $C_{1-3}$ haloalkyl.

In some embodiments, $Cy^Z$ is selected from 5-(trifluoromethyl)pyrimidin-2-yl, 5-(trifluoromethyl)thiazol-2-yl, 5-(trifluoromethyl)pyrazin-2-yl, 5-(difluoromethyl)pyrimidin-2-yl, 5-(difluoromethyl)pyrazin-2-yl, 5-floropyrimidin-2-yl, 5-chloropyrimidin-2-yl, 5-chloropyrazin-2-yl, 5-bromopyrimidin-2-yl, 5-cyanopyridin-2-yl, 5-cyanothiazol-2-yl, 5-cyanopyrazin-2-yl, 5-methylpyrimidin-2-yl.

In some embodiments, $Cy^Z$ is selected from 5-(trifluoromethyl)pyrimidin-2-yl, 5-(trifluoromethyl)thiazol-2-yl, 5-(trifluoromethyl)pyrazin-2-yl, 5-cyanopyridin-2-yl, 5-(difluoromethyl)pyrimidin-2-yl, 5-chloropyrimidin-2-yl, 5-(difluoromethyl)pyrazin-2-yl, and 5-bromopyrimidin-2-yl.

In some embodiments, $Cy^Z$ is 5-(trifluoromethyl)pyrimidin-2-yl.

In some embodiments, m is 1.

In some embodiments, n is 0.

In some embodiments, p is 0.

In some embodiments, q is 0.

In some embodiments, r is 1. In some embodiments, r is 0.

In some embodiments, a is 0.

In some embodiments, X is $CF_3$, $Y^1$ is $NR^Y$, $Y^2$ is O, $Y^3$ is $C(=O)NR^Y$, $R^1$ is methyl, $R^2$ is H, $R^5$ is H, $R^6$ is H, $R^7$ is $CH_2$, $R^8$ is H, Ring D is piperidine substituted with OH, and Z is $Cy^Z$ wherein $Cy^Z$ is pyrimidinyl substituted with $CF_3$.

In some embodiments, provided herein is a compound having Formula IIa:

IIa

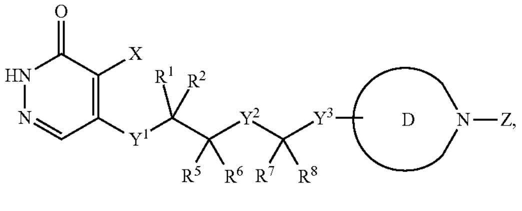

or a pharmaceutically acceptable salt thereof.

In some embodiments, provided herein is a compound having Formula IIb:

IIb

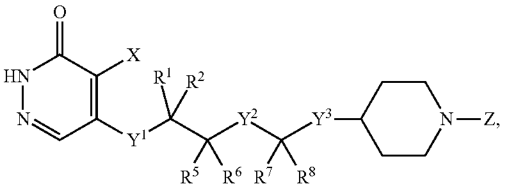

or a pharmaceutically acceptable salt thereof.

In some embodiments, provided herein is a compound having Formula IIc:

IIc

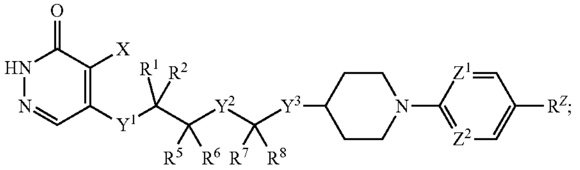

or a pharmaceutically acceptable salt thereof, wherein $Z^1$ and $Z^2$ are each independently selected from N and CH, and wherein $R^Z$ is halo, CN or $C_{1-3}$ haloalkyl. In some embodiments, $R^Z$ is selected from $CF_3$, CN, $CF_2H$, and Cl.

In some embodiments, the compound of the invention has Formula IId:

IId

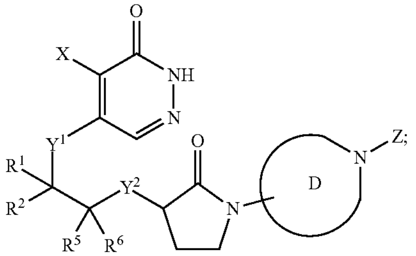

or a pharmaceutically acceptable salt thereof.

In some embodiments, the compound of the invention has Formula IIe:

IIe

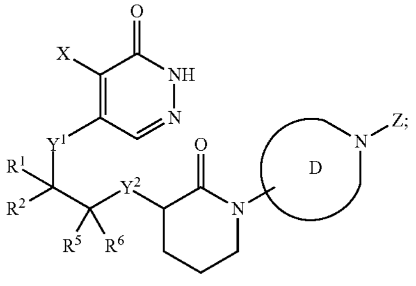

or a pharmaceutically acceptable salt thereof.

In some embodiments, provided herein is a compound of Formula I, or a pharmaceutically acceptable salt thereof, wherein:

X is Cl, Br, or $CF_3$;

A is a group having a formula that is (A-la):

(A-1a)

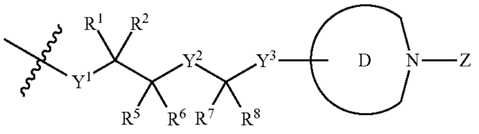

$Y^1$, $Y^2$, and $Y^3$ are each independently selected from O, $NR^Y$, C(=O), and C(=O)NR, wherein each $R^Y$ is independently H or $C_{1-4}$ alkyl;

Z is $Cy^Z$;

$Cy^Z$ is selected from 5-10 membered heteroaryl optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{a1}$, $OC(O)N^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}$ $S(O)_2NR^{c1}R^{d1}$, $S(O)R^{b1}$, $S(O)NR^{c1}R^{d1}$, $S(O)_2R^{b1}$, and $S(O)_2$ $NR^{c1}R^{d1}$, wherein the alkyl, $C_{2-6}$ alkenyl, and $C_{2-6}$ alkynyl are optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}(=NR^{e1})NR^{c1}R^{d1}$, $NR^{c1}R^{d1}$, $NR^{c1}C(O)R^{b1}$, $NR^{c}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

Ring D is a monocyclic or polycyclic 4-10 membered heterocycloalkyl group optionally substituted with 1, 2, or 3 groups independently selected from halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^2C(O)R^{b2}$ $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$, wherein the $C_{1-6}$ alkyl, $C_{2-6}$ alkenyl, and $C_{2-6}$ alkynyl are each optionally substituted with 1, 2, or 3 groups independently selected from halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^2C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

$R^1$, $R^2$, $R^5$, $R^6$, $R^7$, and $R^8$ are each independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$ $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of said $R^1$, $R^2$, $R^5$, $R^6$, $R^7$, and $R^8$ are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

or $R^1$ and an $R^Y$ group of $Y^1$, together with the atoms to which they are attached and together with the atoms forming $Y^1$ form a 4-10 membered heterocycloalkyl ring, optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$ or $R^7$ and an $R^Y$ group of $Y^3$, together with the atoms to which they are attached and together with the atoms forming $Y^3$ form a 4-10 membered heterocycloalkyl ring, optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

each $R^a$, $R^b$, $R^c$, $R^d$, $R^{a1}$, $R^{b1}$, $R^{d}$, $R^d$, $R^{a2}$, $R^{b2}$, $R^{c2}$, $R^{d2}$, $R^{a3}$, $R^{b3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of said $R^a$, $R^b$, $R^c$, $R^d$, $R^{a1}$, $R^{b1}$, $R^{d1}$, $R^{d1}$, $R^{a2}$, $R^{b2}$, $R^{c2}$, $R^{d2}$, $R^{a3}$, $R^{b3}$, $R^3$, and $R^{d3}$ is optionally substituted with 1, 2, or 3 substituents independently selected from halo, $C_{1-4}$ alkyl, $C_{1-4}$ haloalkyl, $C_{2-6}$ alkenyl, $C_{2-6}$ alkynyl, CN, $OR^{ay}$, $SR^{ay}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^3R^{d7}$, $S(O)R^{b7}$, $S(O)NR^{c7}R^{d7}$, $S(O)_2$ $R^{b7}$, $NR^{c7}S(O)_2R^{b7}$, $NR^{c7}S(O)_2NR^{c7}R^{d7}$, and $S(O)_2NR^{c7}R^{d7}$;

$R^{a7}$, $R^{b7}$, $R^{c7}$, and $R^{d7}$ are independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl are each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy; and each $R^e$, $R^{e1}$, $R^{e2}$, $R^{e3}$, and $R^7$ is independently selected from H, $C_{1-4}$ alkyl, and CN;

wherein any aforementioned heteroaryl or heterocycloalkyl group comprises 1, 2, 3, or 4 ring-forming heteroatoms independently selected from O, N, and S; and wherein one or more ring-forming C or N atoms of any aforementioned heterocycloalkyl group is optionally substituted by 1 or 2 oxo (=O) groups.

In some embodiments, provided herein is a compound selected from:

(S)-2-(2-(6-oxo-5-(trifluoromethyl)-1,6-dihydropyridazin-4-ylamino)propoxy)-N-(1-(5-(trifluoromethyl)pyrimidin-2-yl)piperidin-4-yl)acetamide;

(S)—N-methyl-2-(2-(6-oxo-5-(trifluoromethyl)-1,6-dihydropyridazin-4-ylamino)propoxy)-N-(1-(5-(trifluoromethyl)pyrimidin-2-yl)piperidin-4-yl)acetamide;

(S)—N-methyl-2-(2-((6-oxo-5-(trifluoromethyl)-1,6-dihydropyridazin-4-yl)amino)propoxy)-N-(1-(5-(trifluoromethyl)thiazol-2-yl)piperidin-4-yl)acetamide;

(S)—N-methyl-2-(2-(6-oxo-5-(trifluoromethyl)-1,6-dihydropyridazin-4-ylamino)propoxy)-N-(1-(5-(trifluoromethyl)pyrazin-2-yl)piperidin-4-yl)acetamide;

((S)—N-methyl-2-(2-(6-oxo-5-(trifluoromethyl)-1,6-dihydropyridazin-4-ylamino)propoxy)-N-(1-(5-(trifluoromethyl)pyrimidin-2-yl)azetidin-3-yl)acetamide;

(S)—N-(1-(5-cyanopyridin-2-yl)piperidin-4-yl)-N-methyl-2-(2-((6-oxo-5-(trifluoromethyl)-1,6-dihydropyridazin-4-yl)amino)propoxy)acetamide;

(S)—N-ethyl-2-(2-((6-oxo-5-(trifluoromethyl)-1,6-dihydropyridazin-4-yl)amino)propoxy)-N-(1-(5-(trifluoromethyl)pyrimidin-2-yl)piperidin-4-yl)acetamide;

(S)—N-methyl-2-((1-(6-oxo-5-(trifluoromethyl)-1,6-dihydropyridazin-4-yl)azetidin-2-yl)methoxy)-N-(1-(5-(trifluoromethyl)pyrimidin-2-yl)piperidin-4-yl)acetamide;

(S)-2-(3-methoxy-2-((6-oxo-5-(trifluoromethyl)-1,6-dihydropyridazin-4-yl)amino)propoxy)-N-methyl-N-(1-(5-(trifluoromethyl)pyrimidin-2-yl)piperidin-4-yl)acetamide;

5-((S)-1-((S)-1-(1-(5-(trifluoromethyl)pyrimidin-2-yl)piperidin-4-yl)-2-oxopyrrolidin-3-yloxy)propan-2-ylamino)-4-(trifluoromethyl)pyridazin-3(2H)-one;

5-((S)-1-((R)-1-(1-(5-(trifluoromethyl)pyrimidin-2-yl)piperidin-4-yl)-2-oxopyrrolidin-3-yloxy)propan-2-ylamino)-4-(trifluoromethyl)pyridazin-3(2H)-one;

4-chloro-5-((S)-1-(2-oxo-1-(1-(5-(trifluoromethyl)pyrimidin-2-yl)piperidin-4-yl)pyrrolidin-3-yloxy)propan-2-ylamino)pyridazin-3(2H)-one;

4-bromo-5-(((2S)-1-((2-oxo-1-(1-(5-(trifluoromethyl)pyrazin-2-yl)piperidin-4-yl)pyrrolidin-3-yl)oxy)propan-2-yl)amino)pyridazin-3(2H)-one;

5-(((S)-1-(((S)-2-oxo-1-(1-(5-(trifluoromethyl)pyrazin-2-yl)piperidin-4-yl)pyrrolidin-3-yl)oxy)propan-2-yl)amino)-4-(trifluoromethyl)pyridazin-3(2H)-one;

5-(((S)-1-(((R)-2-oxo-1-(1-(5-(trifluoromethyl)pyrazin-2-yl)piperidin-4-yl)pyrrolidin-3-yl)oxy)propan-2-yl)amino)-4-(trifluoromethyl)pyridazin-3(2H)-one;

6-(4-((R)-2-oxo-3-((S)-2-((6-oxo-5-(trifluoromethyl)-1,6-dihydropyridazin-4-yl)amino)propoxy)pyrrolidin-1-yl)piperidin-1-yl)nicotinonitrile;

6-(4-((S)-2-oxo-3-((S)-2-((6-oxo-5-(trifluoromethyl)-1,6-dihydropyridazin-4-yl)amino)propoxy)pyrrolidin-1-yl)piperidin-1-yl)nicotinonitrile;

5-(((S)-1-(((S)-1-(1-(5-(difluoromethyl)pyrimidin-2-yl)piperidin-4-yl)-2-oxopyrrolidin-3-yl)oxy)propan-2-yl)amino)-4-(trifluoromethyl)pyridazin-3(2H)-one;

5-(((S)-1-(((R)-1-(1-(5-(difluoromethyl)pyrimidin-2-yl)piperidin-4-yl)-2-oxopyrrolidin-3-yl)oxy)propan-2-yl)amino)-4-(trifluoromethyl)pyridazin-3(2H)-one;

5-(((S)-1-(((R)-1-(1-(5-chloropyrimidin-2-yl)piperidin-4-yl)-2-oxopyrrolidin-3-yl)oxy)propan-2-yl)amino)-4-(trifluoromethyl)pyridazin-3(2H)-one;

6-(4-((S)-3-((S)-3-methoxy-2-((6-oxo-5-(trifluoromethyl)-1,6-dihydropyridazin-4-yl)amino)propoxy)-2-oxopyrrolidin-1-yl)piperidin-1-yl)nicotinonitrile;

6-(4-((R)-3-((S)-3-methoxy-2-((6-oxo-5-(trifluoromethyl)-1,6-dihydropyridazin-4-yl)amino)propoxy)-2-oxopyrrolidin-1-yl)piperidin-1-yl)nicotinonitrile;

5-(((S)-1-methoxy-3-(((S)-2-oxo-1-(1-(5-(trifluoromethyl)pyrazin-2-yl)piperidin-4-yl)pyrrolidin-3-yl)oxy)propan-2-yl)amino)-4-(trifluoromethyl)pyridazin-3(2H)-one;

(S)—N-methyl-2-(2-(6-oxo-5-(trifluoromethyl)-1,6-dihydropyridazin-4-ylamino)propoxy)-N-(1-(5-(trifluoromethyl)pyrazin-2-yl)piperidin-4-yl)acetamide;

5-(((S)-1-methoxy-3-(((S)-2-oxo-1-(1-(5-(trifluoromethyl)pyrimidin-2-yl)piperidin-4-yl)pyrrolidin-3-yl)oxy)propan-2-yl)amino)-4-(trifluoromethyl)pyridazin-3(2H)-one;

5-(((S)-1-methoxy-3-(((R)-2-oxo-1-(1-(5-(trifluoromethyl)pyrimidin-2-yl)piperidin-4-yl)pyrrolidin-3-yl)oxy)propan-2-yl)amino)-4-(trifluoromethyl)pyridazin-3(2H)-one;

5-(((S)-1-(((S)-2-oxo-1-(1-(5-(trifluoromethyl)pyrimidin-2-yl)piperidin-4-yl)pyrrolidin-3-yl)oxy)propan-2-yl)oxy)-4-(trifluoromethyl)pyridazin-3(2H)-one;

5-(((S)-1-(((R)-2-oxo-1-(1-(5-(trifluoromethyl)pyrimidin-2-yl)piperidin-4-yl)pyrrolidin-3-yl)oxy)propan-2-yl)oxy)-4-(trifluoromethyl)pyridazin-3(2H)-one;

4-(trifluoromethyl)-5-(((2S)-1-((1-(1-(5-(trifluoromethyl)pyrimidin-2-yl)piperidin-4-yl)pyrrolidin-3-yl)oxy)propan-2-yl)amino)pyridazin-3(2H)-one;

5-(((S)-1-(((S)-1-(1-(5-(difluoromethyl)pyrazin-2-yl)piperidin-4-yl)-2-oxopyrrolidin-3-yl)oxy)propan-2-yl)amino)-4-(trifluoromethyl)pyridazin-3(2H)-one;

5-(((S)-1-(((R)-1-(1-(5-(difluoromethyl)pyrazin-2-yl)piperidin-4-yl)-2-oxopyrrolidin-3-yl)oxy)propan-2-yl)amino)-4-(trifluoromethyl)pyridazin-3(2H)-one;

4-bromo-5-(((S)-1-(((S)-2-oxo-1-(1-(5-(trifluoromethyl)pyrimidin-2-yl)piperidin-4-yl)pyrrolidin-3-yl)oxy)propan-2-yl)oxy)pyridazin-3(2H)-one;

5-(((S)-1-(((R)-1-(1-(5-bromopyrimidin-2-yl)piperidin-4-yl)-2-oxopyrrolidin-3-yl)oxy)propan-2-yl)amino)-4-(trifluoromethyl)pyridazin-3(2H)-one;

(S)—N-methyl-2-(2-((6-oxo-5-(trifluoromethyl)-1,6-dihydropyridazin-4-yl)oxy)propoxy)-N-(1-(5-(trifluoromethyl)pyrimidin-2-yl)piperidin-4-yl)acetamide;

5-(((S)-1-(((S)-2-oxo-1-(1-(5-(trifluoromethyl)pyrimidin-2-yl)piperidin-4-yl)pyrrolidin-3-yl)amino)propan-2-yl)amino)-4-(trifluoromethyl)pyridazin-3(2H)-one;

5-(((S)-1-(((R)-2-oxo-1-(1-(5-(trifluoromethyl)pyrimidin-2-yl)piperidin-4-yl)pyrrolidin-3-yl)amino)propan-2-yl)amino)-4-(trifluoromethyl)pyridazin-3(2H)-one;

5-(((R)-1-(((S)-2-oxo-1-(1-(5-(trifluoromethyl)pyrimidin-2-yl)piperidin-4-yl)pyrrolidin-3-yl)amino)propan-2-yl)amino)-4-(trifluoromethyl)pyridazin-3(2H)-one;
5-(((R)-1-(((R)-2-oxo-1-(1-(5-(trifluoromethyl)pyrimidin-2-yl)piperidin-4-yl)pyrrolidin-3-yl)amino)propan-2-yl)amino)-4-(trifluoromethyl)pyridazin-3(2H)-one;
5-(((2S)-1-((1-(1-(5-(difluoromethyl)pyrimidin-2-yl)piperidin-4-yl)-2-oxopyrrolidin-3-yl)oxy)propan-2-yl)oxy)-4-(trifluoromethyl)pyridazin-3(2H)-one;
(S)-2-(2-((5-bromo-6-oxo-1,6-dihydropyridazin-4-yl)oxy)propoxy)-N-methyl-N-(1-(5-(trifluoromethyl)pyrimidin-2-yl)piperidin-4-yl)acetamide;
5-(((2S)-1-(methyl(2-oxo-1-(1-(5-(trifluoromethyl)pyrimidin-2-yl)piperidin-4-yl)pyrrolidin-3-yl)amino)propan-2-yl)amino)-4-(trifluoromethyl)pyridazin-3(2H)-one;
6-(4-(2-oxo-3-((S)-2-((6-oxo-5-(trifluoromethyl)-1,6-dihydropyridazin-4-yl)oxy)propoxy)pyrrolidin-1-yl)piperidin-1-yl)nicotinonitrile;
5-(((S)-1-(((S)-2-oxo-1-(1-(5-(trifluoromethyl)pyrazin-2-yl)piperidin-4-yl)pyrrolidin-3-yl)oxy)propan-2-yl)oxy)-4-(trifluoromethyl)pyridazin-3(2H)-one;
5-(((S)-1-(((R)-2-oxo-1-(1-(5-(trifluoromethyl)pyrazin-2-yl)piperidin-4-yl)pyrrolidin-3-yl)oxy)propan-2-yl)oxy)-4-(trifluoromethyl)pyridazin-3(2H)-one;
4-bromo-5-(((S)-1-(((R)-2-oxo-1-(1-(5-(trifluoromethyl)pyrimidin-2-yl)piperidin-4-yl)pyrrolidin-3-yl)oxy)propan-2-yl)amino)pyridazin-3(2H)-one;
N-((3R,4R)-3-hydroxy-1-(5-(trifluoromethyl)pyrimidin-2-yl)piperidin-4-yl)-2-((S)-2-((6-oxo-5-(trifluoromethyl)-1,6-dihydropyridazin-4-yl)amino)propoxy)acetamide; and
N-((3S,4S)-3-hydroxy-1-(5-(trifluoromethyl)pyrimidin-2-yl)piperidin-4-yl)-2-((S)-2-((6-oxo-5-(trifluoromethyl)-1,6-dihydropyridazin-4-yl)amino)propoxy)acetamide;
or a pharmaceutically acceptable salt of any of the aforementioned.

In some embodiments, provided herein is a compound selected from:
(S)-3-((S)-2-((6-oxo-5-(trifluoromethyl)-1,6-dihydropyridazin-4-yl)amino)propoCyxy)-1'-(5-(trifluoromethyl)pyrimidin-2-yl)-[1,4'-bipiperidin]-2-one;
(R)-3-((S)-2-((6-oxo-5-(trifluoromethyl)-1,6-dihydropyridazin-4-yl)amino)propoxy)-1'-(5-(trifluoromethyl)pyrimidin-2-yl)-[1,4'-bipiperidin]-2-one;
5-(((S)-1-(((S)-4,4-dimethyl-2-oxo-1-(1-(5-(trifluoromethyl)pyrimidin-2-yl)piperidin-4-yl)pyrrolidin-3-yl)oxy)propan-2-yl)amino)-4-(trifluoromethyl)pyridazin-3(2H)-one;
5-(((S)-1-(((R)-4,4-dimethyl-2-oxo-1-(1-(5-(trifluoromethyl)pyrimidin-2-yl)piperidin-4-yl)pyrrolidin-3-yl)oxy)propan-2-yl)amino)-4-(trifluoromethyl)pyridazin-3(2H)-one;
(R)-6-(4-(2-oxo-3-(2-((6-oxo-5-(trifluoromethyl)-1,6-dihydropyridazin-4-yl)amino)ethoxy)pyrrolidin-1-yl)piperidin-1-yl)nicotinonitrile;
(S)-6-(4-(2-oxo-3-(2-((6-oxo-5-(trifluoromethyl)-1,6-dihydropyridazin-4-yl)amino)ethoxy)pyrrolidin-1-yl)piperidin-1-yl)nicotinonitrile;
5-(((S)-1-(((3S,4R)-4-methyl-2-oxo-1-(1-(5-(trifluoromethyl)pyrimidin-2-yl)piperidin-4-yl)pyrrolidin-3-yl)oxy)propan-2-yl)amino)-4-(trifluoromethyl)pyridazin-3(2H)-one;
5-(((S)-1-(((3R,4S)-4-methyl-2-oxo-1-(1-(5-(trifluoromethyl)pyrimidin-2-yl)piperidin-4-yl)pyrrolidin-3-yl)oxy)propan-2-yl)amino)-4-(trifluoromethyl)pyridazin-3(2H)-one;
5-(((S)-1-(((R)-1-((3R,4R)-3-fluoro-1-(5-(trifluoromethyl)pyrimidin-2-yl)piperidin-4-yl)-2-oxopyrrolidin-3-yl)oxy)propan-2-yl)amino)-4-(trifluoromethyl)pyridazin-3(2H)-one;
5-(((S)-1-(((R)-1-((3S,4S)-3-fluoro-1-(5-(trifluoromethyl)pyrimidin-2-yl)piperidin-4-yl)-2-oxopyrrolidin-3-yl)oxy)propan-2-yl)amino)-4-(trifluoromethyl)pyridazin-3(2H)-one;
5-(((S)-1-(((R)-1-((3S,4R)-3-fluoro-1-(5-(trifluoromethyl)pyrimidin-2-yl)piperidin-4-yl)-2-oxopyrrolidin-3-yl)oxy)propan-2-yl)amino)-4-(trifluoromethyl)pyridazin-3(2H)-one;
5-(((S)-1-(((R)-1-((3R,4S)-3-fluoro-1-(5-(trifluoromethyl)pyrimidin-2-yl)piperidin-4-yl)-2-oxopyrrolidin-3-yl)oxy)propan-2-yl)amino)-4-(trifluoromethyl)pyridazin-3(2H)-one;
6-((R)-3,3-difluoro-4-((R)-2-oxo-3-((S)-2-((6-oxo-5-(trifluoromethyl)-1,6-dihydropyridazin-4-yl)amino)propoxy)pyrrolidin-1-yl)piperidin-1-yl)nicotinonitrile;
6-((S)-3,3-difluoro-4-((R)-2-oxo-3-((S)-2-((6-oxo-5-(trifluoromethyl)-1,6-dihydropyridazin-4-yl)amino)propoxy)pyrrolidin-1-yl)piperidin-1-yl)nicotinonitrile;
5-(((S)-1-(((R)-1-(1-(5-chloropyrazin-2-yl)piperidin-4-yl)-2-oxopyrrolidin-3-yl)oxy)propan-2-yl)amino)-4-(trifluoromethyl)pyridazin-3(2H)-one;
5-(((S)-1-(((R)-1-(1-(5-fluoropyrimidin-2-yl)piperidin-4-yl)-2-oxopyrrolidin-3-yl)oxy)propan-2-yl)amino)-4-(trifluoromethyl)pyridazin-3(2H)-one;
5-(((S)-1-(((R)-2-oxo-1-((1R,5S,6s)-3-(5-(trifluoromethyl)pyrimidin-2-yl)-3-azabicyclo[3.1.0]hexan-6-yl)pyrrolidin-3-yl)oxy)propan-2-yl)amino)-4-(trifluoromethyl)pyridazin-3(2H)-one;
5-(((S)-1-(((R)-1-(1-(5-methylpyrimidin-2-yl)piperidin-4-yl)-2-oxopyrrolidin-3-yl)oxy)propan-2-yl)amino)-4-(trifluoromethyl)pyridazin-3(2H)-one;
5-(4-((R)-2-oxo-3-((S)-2-((6-oxo-5-(trifluoromethyl)-1,6-dihydropyridazin-4-yl)amino)propoxy)pyrrolidin-1-yl)piperidin-1-yl)pyrazine-2-carbonitrile;
4-bromo-5-(((S)-1-(((S)-2-oxo-1-(1-(5-(trifluoromethyl)pyrazin-2-yl)piperidin-4-yl)pyrrolidin-3-yl)oxy)propan-2-yl)oxy)pyridazin-3(2H)-one;
4-bromo-5-(((S)-1-(((R)-2-oxo-1-(1-(5-(trifluoromethyl)pyrazin-2-yl)piperidin-4-yl)pyrrolidin-3-yl)oxy)propan-2-yl)oxy)pyridazin-3(2H)-one;
4-chloro-5-(((S)-1-(((S)-2-oxo-1-(1-(5-(trifluoromethyl)pyrimidin-2-yl)piperidin-4-yl)pyrrolidin-3-yl)oxy)propan-2-yl)oxy)pyridazin-3(2H)-one;
4-chloro-5-(((S)-1-(((R)-2-oxo-1-(1-(5-(trifluoromethyl)pyrimidin-2-yl)piperidin-4-yl)pyrrolidin-3-yl)oxy)propan-2-yl)oxy)pyridazin-3(2H)-one;
6-(4-((R)-3-((S)-2-((5-bromo-6-oxo-1,6-dihydropyridazin-4-yl)oxy)propoxy)-2-oxopyrrolidin-1-yl)piperidin-1-yl)nicotinonitrile;
6-(4-((S)-3-((S)-2-((5-bromo-6-oxo-1,6-dihydropyridazin-4-yl)oxy)propoxy)-2-oxopyrrolidin-1-yl)piperidin-1-yl)nicotinonitrile;
5-(((S)-1-(((S)-1-(1-(5-methylpyrimidin-2-yl)piperidin-4-yl)-2-oxopyrrolidin-3-yl)oxy)propan-2-yl)oxy)-4-(trifluoromethyl)pyridazin-3(2H)-one;
5-(((S)-1-(((R)-1-(1-(5-methylpyrimidin-2-yl)piperidin-4-yl)-2-oxopyrrolidin-3-yl)oxy)propan-2-yl)oxy)-4-(trifluoromethyl)pyridazin-3(2H)-one;
6-(4-((S)-3-((S)-3-methoxy-2-((6-oxo-5-(trifluoromethyl)-1,6-dihydropyridazin-4-yl)oxy)propoxy)-2-oxopyrrolidin-1-yl)piperidin-1-yl)nicotinonitrile;

6-(4-((R)-3-((S)-3-methoxy-2-((6-oxo-5-(trifluoromethyl)-1,6-dihydropyridazin-4-yl)oxy)propoxy)-2-oxopyrrolidin-1-yl)piperidin-1-yl)nicotinonitrile;

5-(((S)-1-methoxy-3-(((S)-2-oxo-1-(1-(5-(trifluoromethyl)pyrimidin-2-yl)piperidin-4-yl)pyrrolidin-3-yl)oxy)propan-2-yl)oxy)-4-(trifluoromethyl)pyridazin-3(2H)-one;

5-(((S)-1-methoxy-3-(((R)-2-oxo-1-(1-(5-(trifluoromethyl)pyrimidin-2-yl)piperidin-4-yl)pyrrolidin-3-yl)oxy)propan-2-yl)oxy)-4-(trifluoromethyl)pyridazin-3(2H)-one;

5-(((S)-1-methoxy-3-(((S)-1-(1-(5-methylpyrimidin-2-yl)piperidin-4-yl)-2-oxopyrrolidin-3-yl)oxy)propan-2-yl)oxy)-4-(trifluoromethyl)pyridazin-3(2H)-one;

5-(((S)-1-methoxy-3-(((R)-1-(1-(5-methylpyrimidin-2-yl)piperidin-4-yl)-2-oxopyrrolidin-3-yl)oxy)propan-2-yl)oxy)-4-(trifluoromethyl)pyridazin-3(2H)-one;

5-(((S)-1-methoxy-3-(((R)-1-(1-(5-methylpyrimidin-2-yl)piperidin-4-yl)-2-oxopyrrolidin-3-yl)oxy)propan-2-yl)amino)-4-(trifluoromethyl)pyridazin-3(2H)-one;

2-(4-((R)-3-((S)-3-methoxy-2-((6-oxo-5-(trifluoromethyl)-1,6-dihydropyridazin-4-yl)amino)propoxy)-2-oxopyrrolidin-1-yl)piperidin-1-yl)thiazole-5-carbonitrile;

6-(4-((S)-3-((S)-2-((5-bromo-6-oxo-1,6-dihydropyridazin-4-yl)oxy)-3-methoxypropoxy)-2-oxopyrrolidin-1-yl)piperidin-1-yl)nicotinonitrile;

6-(4-((R)-3-((S)-2-((5-bromo-6-oxo-1,6-dihydropyridazin-4-yl)oxy)-3-methoxypropoxy)-2-oxopyrrolidin-1-yl)piperidin-1-yl)nicotinonitrile;

4-Bromo-5-(((S)-1-methoxy-3-(((S)-2-oxo-1-(1-(5-(trifluoromethyl)pyrimidin-2-yl)piperidin-4-yl)pyrrolidin-3-yl)oxy)propan-2-yl)oxy)pyridazin-3(2H)-one;

4-Bromo-5-(((S)-1-methoxy-3-(((R)-2-oxo-1-(1-(5-(trifluoromethyl)pyrimidin-2-yl)piperidin-4-yl)pyrrolidin-3-yl)oxy)propan-2-yl)oxy)pyridazin-3(2H)-one;

5-(((S)-1-(((R)-1-((3R,4R)-3-hydroxy-1-(5-(trifluoromethyl)pyrimidin-2-yl)piperidin-4-yl)-2-oxopyrrolidin-3-yl)oxy)propan-2-yl)amino)-4-(trifluoromethyl)pyridazin-3(2H)-one;

5-(((S)-1-(((R)-1-((3S,4S)-3-hydroxy-1-(5-(trifluoromethyl)pyrimidin-2-yl)piperidin-4-yl)-2-oxopyrrolidin-3-yl)oxy)propan-2-yl)amino)-4-(trifluoromethyl)pyridazin-3(2H)-one;

5-(((S)-1-(((R)-1-((3S,4R)-3-hydroxy-1-(5-(trifluoromethyl)pyrimidin-2-yl)piperidin-4-yl)-2-oxopyrrolidin-3-yl)oxy)propan-2-yl)amino)-4-(trifluoromethyl)pyridazin-3(2H)-one;

5-(((S)-1-(((R)-1-((3R,4S)-3-hydroxy-1-(5-(trifluoromethyl)pyrimidin-2-yl)piperidin-4-yl)-2-oxopyrrolidin-3-yl)oxy)propan-2-yl)amino)-4-(trifluoromethyl)pyridazin-3(2H)-one;

(S)—N—((R)-2-oxo-1-(1-(5-(trifluoromethyl)pyrimidin-2-yl)piperidin-4-yl)pyrrolidin-3-yl)-2-((6-oxo-5-(trifluoromethyl)-1,6-dihydropyridazin-4-yl)amino)propanamide;

5-(((S)-1-(((R)-2-oxo-1-(1-(5-(trifluoromethyl)pyrimidin-2-yl)piperidin-4-yl)pyrrolidin-3-yl)oxy)-3-((2,2,2-trifluoroethyl)amino)propan-2-yl)amino)-4-(trifluoromethyl)pyridazin-3(2H)-one;

5-(((S)-1-hydroxy-3-(((R)-2-oxo-1-(1-(5-(trifluoromethyl)pyrimidin-2-yl)piperidin-4-yl)pyrrolidin-3-yl)oxy)propan-2-yl)amino)-4-(trifluoromethyl)pyridazin-3(2H)-one;

5-(((S)-1-(((S)-1-((3R,4S)-3-hydroxy-1-(5-(trifluoromethyl)pyrimidin-2-yl)piperidin-4-yl)-2-oxopyrrolidin-3-yl)oxy)propan-2-yl)oxy)-4-(trifluoromethyl)pyridazin-3(2H)-one;

5-(((S)-1-(((R)-1-((3S,4R)-3-hydroxy-1-(5-(trifluoromethyl)pyrimidin-2-yl)piperidin-4-yl)-2-oxopyrrolidin-3-yl)oxy)propan-2-yl)oxy)-4-(trifluoromethyl)pyridazin-3(2H)-one;

5-(((2S)-1-((1-((3R,4R)-3-hydroxy-1-(5-(trifluoromethyl)pyrimidin-2-yl)piperidin-4-yl)-2-oxopyrrolidin-3-yl)oxy)propan-2-yl)oxy)-4-(trifluoromethyl)pyridazin-3(2H)-one;

N—((S)-3-(((R)-2-oxo-1-(1-(5-(trifluoromethyl)pyrimidin-2-yl)piperidin-4-yl)pyrrolidin-3-yl)oxy)-2-((6-oxo-5-(trifluoromethyl)-1,6-dihydropyridazin-4-yl)amino)propyl)acetamide;

5-(((2R,3R)-3-hydroxy-1-(((R)-2-oxo-1-(1-(5-(trifluoromethyl)pyrimidin-2-yl)piperidin-4-yl)pyrrolidin-3-yl)oxy)butan-2-yl)amino)-4-(trifluoromethyl)pyridazin-3(2H)-one;

4-((R)-2-oxo-3-((S)-2-((6-oxo-5-(trifluoromethyl)-1,6-dihydropyridazin-4-yl)amino)propoxy)pyrrolidin-1-yl)-1-(5-(trifluoromethyl)pyrimidin-2-yl)piperidine-3-carboxamide; and 4-((R)-2-oxo-3-((S)-2-((6-oxo-5-(trifluoromethyl)-1,6-dihydropyridazin-4-yl)amino)propoxy)pyrrolidin-1-yl)-1-(5-(trifluoromethyl)pyrimidin-2-yl)piperidine-3-carbonitrile;

or a pharmaceutically acceptable salt of any of the aforementioned.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification various aryl, heteroaryl, cycloalkyl, and heterocycloalkyl rings are described. Unless otherwise specified, these rings can be attached to the rest of the molecule at any ring member as permitted by valency. For example, the term "pyridinyl," "pyridyl," or "a pyridine ring" may refer to a pyridin-2-yl, pyridin-3-yl, or pyridin-4-yl ring.

The term "n-membered," where "n" is an integer, typically describes the number of ring-forming atoms in a moiety where the number of ring-forming atoms is "n". For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R.

As used herein, the phrase "optionally substituted" means unsubstituted or substituted.

As used herein, the term "substituted" means that a hydrogen atom is replaced by a non-hydrogen group. It is to be understood that substitution at a given atom is limited by valency.

As used herein, the term "Ci-j," where i and j are integers, employed in combination with a chemical group, designates a range of the number of carbon atoms in the chemical group with i-j defining the range. For example, $C_{1-6}$ alkyl refers to an alkyl group having 1, 2, 3, 4, 5, or 6 carbon atoms.

As used herein, the term "alkyl," employed alone or in combination with other terms, refers to a saturated hydrocarbon group that may be straight-chain or branched. In some embodiments, the alkyl group contains 1 to 7, 1 to 6, 1 to 4, or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, n-heptyl, and the like. In some embodiments, the alkyl group is methyl, ethyl, or propyl.

As used herein, "halo" or "halogen", employed alone or in combination with other terms, includes fluoro, chloro, bromo, and iodo. In some embodiments, halo is F or $C_1$.

As used herein, the term "haloalkyl," employed alone or in combination with other terms, refers to an alkyl group having up to the full valency of halogen atom substituents, which may either be the same or different. In some embodiments, the halogen atoms are fluoro atoms. In some embodiments, the alkyl group has 1 to 6 or 1 to 4 carbon atoms. Example haloalkyl groups include $CF_3$, $C_2F_5$, $CHF_2$, $CCl_3$, $CHCl_2$, $C_2Cl_5$, and the like.

As used herein, the term "alkoxy," employed alone or in combination with other terms, refers to a group of formula —O-alkyl. Example alkoxy groups include methoxy, ethoxy, propoxy (e.g., n-propoxy and isopropoxy), t-butoxy, and the like. In some embodiments, the alkyl group has 1 to 6 or 1 to 4 carbon atoms.

As used herein, "haloalkoxy," employed alone or in combination with other terms, refers to a group of formula —O-(haloalkyl). In some embodiments, the alkyl group has 1 to 6 or 1 to 4 carbon atoms. An example haloalkoxy group is $—OCF_3$.

As used herein, "amino," employed alone or in combination with other terms, refers to $NH_2$.

As used herein, the term "alkylamino," employed alone or in combination with other terms, refers to a group of formula —NH(alkyl). In some embodiments, the alkylamino group has 1 to 6 or 1 to 4 carbon atoms. Example alkylamino groups include methylamino, ethylamino, propylamino (e.g., n-propylamino and isopropylamino), and the like.

As used herein, the term "dialkylamino," employed alone or in combination with other terms, refers to a group of formula $—N(alkyl)_2$. Example dialkylamino groups include dimethylamino, diethylamino, dipropylamino (e.g., di(n-propyl)amino and di(isopropyl)amino), and the like. In some embodiments, each alkyl group independently has 1 to 6 or 1 to 4 carbon atoms.

As used herein, the term "heterocycloalkyl," employed alone or in combination with other terms, refers to a non-aromatic ring or ring system, which may optionally contain one or more alkenylene or alkynylene groups as part of the ring structure, which has at least one heteroatom ring member independently selected from nitrogen, sulfur, oxygen, and phosphorus. Heterocycloalkyl groups can include mono- or polycyclic (e.g., having 2, 3 or 4 fused, bridged, or spiro rings) ring systems. In some embodiments, the heterocycloalkyl group is a monocyclic or bicyclic group having 1, 2, 3, or 4 heteroatoms independently selected from nitrogen, sulfur and oxygen. Also included in the definition of heterocycloalkyl are moieties that have one or more aromatic rings (e.g., aryl or heteroaryl rings) fused (i.e., having a bond in common with) to the non-aromatic heterocycloalkyl ring, for example, 1,2,3,4-tetrahydro-quinoline and the like. Heterocycloalkyl groups can also include bridgehead heterocycloalkyl groups (e.g., a heterocycloalkyl moiety containing at least one bridgehead atom, such as azaadmantan-1-yl and the like) and spiroheterocycloalkyl groups (e.g., a heterocycloalkyl moiety containing at least two rings fused at a single atom, such as [1,4-dioxa-8-aza-spiro[4.5]decan-N-yl] and the like). In some embodiments, the heterocycloalkyl group has 3 to 10 ring-forming atoms, 4 to 10 ring-forming atoms, or about 3 to 8 ring forming atoms. In some embodiments, the heterocycloalkyl group has 2 to 20 carbon atoms, 2 to 15 carbon atoms, 2 to 10 carbon atoms, or about 2 to 8 carbon atoms. In some embodiments, the heterocycloalkyl group has 1 to 5 heteroatoms, 1 to 4 heteroatoms, 1 to 3 heteroatoms, or 1 to 2 heteroatoms. The carbon atoms or heteroatoms in the ring(s) of the heterocycloalkyl group can be oxidized to form a carbonyl, an N-oxide, or a sulfonyl group (or other oxidized linkage) or a nitrogen atom can be quaternized. In some embodiments, the heterocycloalkyl portion is a $C_{2-7}$ monocyclic heterocycloalkyl group. In some embodiments, the heterocycloalkyl group is a morpholine ring, pyrrolidine ring, piperazine ring, piperidine ring, tetrahydropyran ring, tetrahyropyridine, azetidine ring, or tetrahydrofuran ring.

As used herein, the term "heterocycloalkylalkyl," employed alone or in combination with other terms, refers to a group of formula heterocycloalkyl-alkyl-. In some embodiments, the alkyl portion has 1 to 4, 1 to 3, 1 to 2, or 1 carbon atom(s). In some embodiments, the alkyl portion is methylene. In some embodiments, the heterocycloalkyl portion has 3 to 10 ring members, 4 to 10 ring members, or 3 to 7 ring members. In some embodiments, the heterocycloalkyl group is monocyclic or bicyclic. In some embodiments, the heterocycloalkyl portion is monocyclic. In some embodiments, the heterocycloalkyl portion is a $C_{2-7}$ monocyclic heterocycloalkyl group.

As used herein, the term "aryl," employed alone or in combination with other terms, refers to a monocyclic or polycyclic (e.g., a fused ring system) aromatic hydrocarbon moiety, such as, but not limited to, phenyl, 1-naphthyl, 2-naphthyl, and the like. In some embodiments, aryl groups have from 6 to 10 carbon atoms or 6 carbon atoms. In some embodiments, the aryl group is a monocyclic or bicyclic group. In some embodiments, the aryl group is phenyl or naphthyl.

As used herein, the term "arylalkyl," employed alone or in combination with other terms, refers to a group of formula aryl-alkyl-. In some embodiments, the alkyl portion has 1 to 4, 1 to 3, 1 to 2, or 1 carbon atom(s). In some embodiments, the alkyl portion is methylene. In some embodiments, the aryl portion is phenyl. In some embodiments, the aryl group is a monocyclic or bicyclic group. In some embodiments, the arylalkyl group is benzyl.

As used herein, the term "heteroaryl," employed alone or in combination with other terms, refers to a monocyclic or polycyclic (e.g., a fused ring system) aromatic hydrocarbon moiety, having one or more heteroatom ring members independently selected from nitrogen, sulfur and oxygen. In some embodiments, the heteroaryl group is a monocyclic or a bicyclic group having 1, 2, 3, or 4 heteroatoms independently selected from nitrogen, sulfur and oxygen. Example heteroaryl groups include, but are not limited to, pyridyl, pyrimidinyl, pyrazinyl, pyridazinyl, triazinyl, furyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, pyrrolyl, azolyl, quinolinyl, isoquinolinyl, benzisoxazolyl, imidazo[1,2-b] thiazolyl or the like. The carbon atoms or heteroatoms in the ring(s) of the heteroaryl group can be oxidized to form a carbonyl, an N-oxide, or a sulfonyl group (or other oxidized linkage) or a nitrogen atom can be quaternized, provided the aromatic nature of the ring is preserved. In some embodiments, the heteroaryl group has from 3 to 10 carbon atoms, from 3 to 8 carbon atoms, from 3 to 5 carbon atoms, from 1 to 5 carbon atoms, or from 5 to 10 carbon atoms. In some embodiments, the heteroaryl group contains 3 to 14, 4 to 12, 4 to 8, 9 to 10, or 5 to 6 ring-forming atoms. In some embodiments, the heteroaryl group has 1 to 4, 1 to 3, or 1 to 2 heteroatoms.

As used herein, the term "heteroarylalkyl," employed alone or in combination with other terms, refers to a group of formula heteroaryl-alkyl-. In some embodiments, the alkyl portion has 1 to 4, 1 to 3, 1 to 2, or 1 carbon atom(s). In some embodiments, the alkyl portion is methylene. In some embodiments, the heteroaryl portion is a monocyclic or bicyclic group having 1, 2, 3, or 4 heteroatoms independently selected from nitrogen, sulfur and oxygen. In some embodiments, the heteroaryl portion has 5 to 10 carbon atoms.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Geometric isomers of olefins, C═N double bonds, and the like can also be present in the compounds described herein, and all such stable isomers are contemplated in the present invention. Cis and trans geometric isomers of the compounds of the present invention may be isolated as a mixture of isomers or as separated isomeric forms.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution. An example of tautomeric forms, pyridazin-3(2H)-one and pyridazin-3-ol, is depicted below:

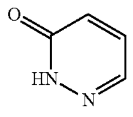

pyridazin-3(2H)-one

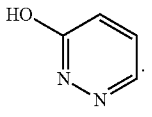

pyridazin-3-ol

Compounds of the invention also include all isotopes of atoms occurring in the intermediates or final compounds. Isotopes include those atoms having the same atomic number but different mass numbers. For example, isotopes of hydrogen include tritium and deuterium. In some embodiments, the compounds of the invention include at least one deuterium atom.

The term, "compound," as used herein is meant to include all stereoisomers, geometric iosomers, tautomers, and isotopes of the structures depicted, unless otherwise specified.

All compounds, and pharmaceutically acceptable salts thereof, can be found together with other substances such as water and solvents (e.g., in the form of hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P.G.M. Wuts, *Protective Groups in Organic Synthesis,* 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), or mass spectrometry, or by chromatography such as high performance liquid chromatography (HPLC) or thin layer chromatography.

The expressions, "ambient temperature," "room temperature," and "RT", as used herein, are understood in the art, and refer generally to a temperature, e.g. a reaction temperature, that is about the temperature of the room in which the reaction is carried out, for example, a temperature from about 20° C. to about 30° C.

Compounds of Formula I can be prepared according to numerous preparatory routes known in the literature. Example synthetic methods for preparing compounds of the invention are provided in the Schemes below. Unless noted otherwise, all substituents are as defined herein.

In the process depicted in Scheme 1, an appropriately substituted, halogen containing compound (i.e., $X_a$=Cl or Br) of Formula (1-1) is protected as the p-methoxybenzyl ether ("PMB") compound of Formula (1-2) by treatment with p-methoxybenzyl chloride ("PMB-Cl") in the presence of sodium hydride (NaH).

Scheme 1

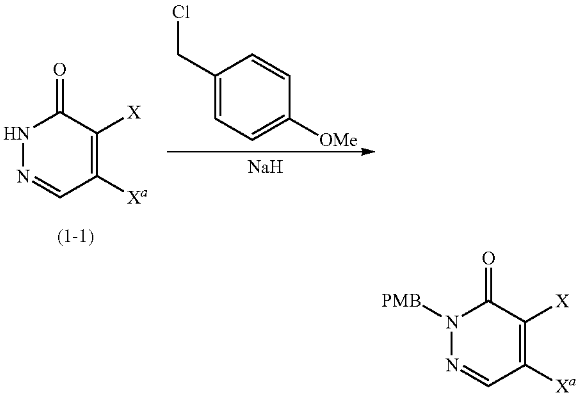

(1-1)

(1-2)

Compound of Formula (1-2) can be reacted with a variety of nucleophiles to provide compounds of Formula (I) following deprotection of the PMB protecting group, as shown in Schemes 2-4.

In the process depicted in Scheme 2, the compound of Formula (1-3) (wherein $Y^a$ is O, $NR^Y$, or S) is reacted with a compound having Formula (1-2) in the presence of a base (e.g., triethylamine, $Cs_2CO_3$, or potassium tert-butoxide) to provide a compound of formula (1-4). Deprotection with an acid (e.g., trifluoromethane sulfonic acid in trifluoroacetic acid or hydrochloric acid) provides a compound of Formula (IA).

Scheme 2

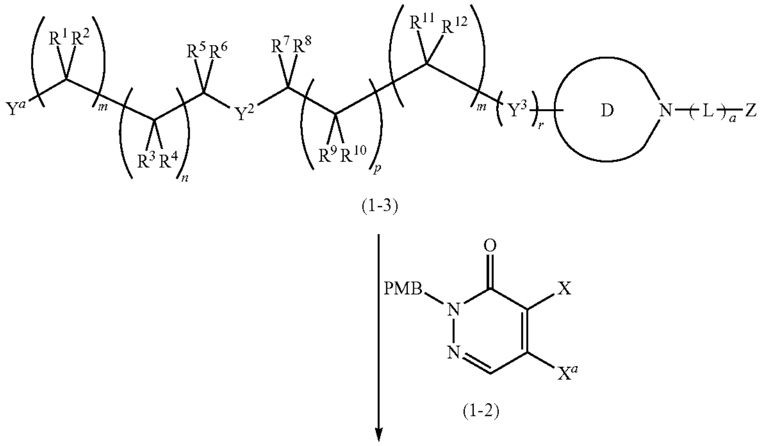

(1-3)

(1-2)

-continued

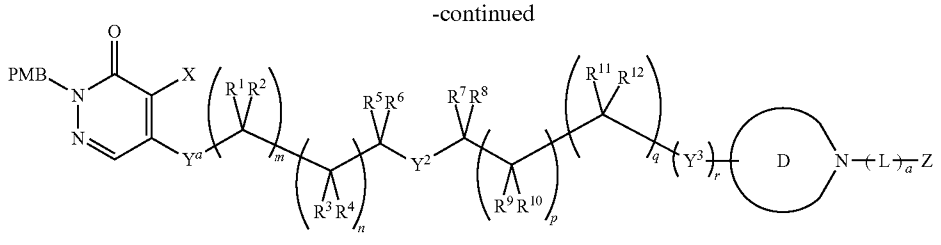

(1-4)

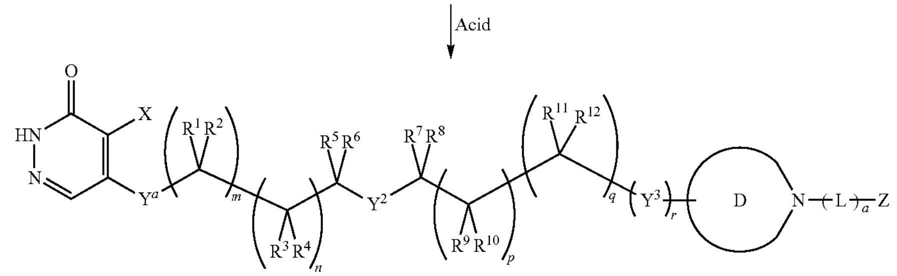

(IA)

Methods of Use

Compounds of the invention can inhibit the activity of PARP7. For example, the compounds of the invention can be used to inhibit activity of PARP7 in a cell or in an individual or patient in need of inhibition of the enzyme by administering an inhibiting amount of a compound of the invention to the cell, individual, or patient.

As PARP7 inhibitors, the compounds of the invention are useful in the treatment of various diseases associated with abnormal expression or activity of PARP7. For example, the compounds of the invention are useful in the treatment of cancer. In some embodiments, the cancers treatable according to the present invention include breast, central nervous system, endometrium, kidney, large intestine, lung, oesophagus, ovary, pancreas, prostate, stomach, head and neck (upper aerodigestive), urinary tract, colon, and others.

In some embodiments, the cancers treatable according to the present invention include hematopoietic malignancies such as leukemia and lymphoma. Example lymphomas include Hodgkin's or non-Hodgkin's lymphoma, multiple myeloma, B-cell lymphoma (e.g., diffuse large B-cell lymphoma (DLBCL)), chronic lymphocytic lymphoma (CLL), T-cell lymphoma, hairy cell lymphoma, and Burkett's lymphoma. Example leukemias include acute lymphocytic leukemia (ALL), acute myelogenous leukemia (AML), chronic lymphocytic leukemia (CLL), and chronic myelogenous leukemia (CML).

Other cancers treatable by the administration of the compounds of the invention include liver cancer (e.g., hepatocellular carcinoma), bladder cancer, bone cancer, glioma, breast cancer, cervical cancer, colon cancer, endometrial cancer, epithelial cancer, esophageal cancer, Ewing's sarcoma, pancreatic cancer, gallbladder cancer, gastric cancer, gastrointestinal tumors, head and neck cancer (upper aerodigestive cancer), intestinal cancers, Kaposi's sarcoma, kidney cancer, laryngeal cancer, liver cancer (e.g., hepatocellular carcinoma), lung cancer, prostate cancer, rectal cancer, skin cancer, stomach cancer, testicular cancer, thyroid cancer, and uterine cancer.

In some embodiments, the cancer treatable by administration of the compounds of the invention is multiple myeloma, DLBCL, hepatocellular carcinoma, bladder cancer, esophageal cancer, head and neck cancer (upper aerodigestive cancer), kidney cancer, prostate cancer, rectal cancer, stomach cancer, thyroid cancer, uterine cancer, and breast cancer.

The PARP7 inhibitors of the invention may also have therapeutic utility in PARP7-related disorders in disease areas such as cardiology, virology, neurodegeneration, inflammation, and pain, particularly where the diseases are characterized by overexpression or increased activity of PARP7.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" PARP7 or "contacting" a cell with a compound of the invention includes the administration of a compound of the present invention to an individual or patient, such as a human, having PARP7, as well as, for example, introducing a compound of the invention into a sample containing a cellular or purified preparation containing PARP7.

As used herein, the term "individual" or "patient," used interchangeably, refers to mammals, and particularly humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) inhibiting the disease in an individual who is experiencing or displaying the pathology or symptomatology of the disease (i.e., arresting further development of the pathology and/or symptomatology), or 2) ameliorating the disease in an individual who is experiencing or displaying the pathology or symptomatology of the disease (i.e., reversing the pathology and/or symptomatology).

As used herein the term "preventing" or "prevention" refers to preventing the disease in an individual who may be predisposed to the disease but does not yet experience or display the pathology or symptomatology of the disease.

Combination Therapy

One or more additional pharmaceutical agents or treatment methods such as, for example, chemotherapeutics or other anti-cancer agents, immune enhancers, immunosuppressants, immunotherapies, radiation, anti-tumor and antiviral vaccines, cytokine therapy (e.g., IL2, GM-CSF, etc.), and/or kinase (tyrosine or serine/threonine), epigenetic or signal transduction inhibitors can be used in combination with the compounds of the present invention. The agents can be combined with the present compounds in a single dosage form, or the agents can be administered simultaneously or sequentially as separate dosage forms.

Suitable agents for use in combination with the compounds of the present invention for the treatment of cancer include chemotherapeutic agents, targeted cancer therapies, immunotherapies or radiation therapy. Compounds of this invention may be effective in combination with anti-hormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with compounds of the present invention. These include anti-androgens including but not limited to flutamide, bicalutamide, and nilutamide, luteinizing hormone-releasing hormone (LHRH) analogs including leuprolide, goserelin, triptorelin, and histrelin, LHRH antagonists (e.g. degarelix), androgen receptor blockers (e.g. enzalutamide) and agents that inhibit androgen production (e.g. abiraterone).

Angiogenesis inhibitors may be efficacious in some tumors in combination with FGFR inhibitors. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Other anti-cancer agent(s) include antibody therapeutics to checkpoint or costimulatory molecules such as CTLA-4, PD-1, PD-L1 or 4-1BB, respectively, or antibodies to cytokines (IL-10, TGF-β, etc.). Exemplary cancer immunotherapy antibodies include pembrolizumab, ipilimumab, nivolumab, atezolizumab and durvalumab. Additional anti-cancer agent(s) include antibody therapeutics directed to surface molecules of hematological cancers such as ofatumumab, rituximab and alemtuzumab.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, NJ), the disclosure of which is incorporated herein by reference as if set forth in its entirety.

Pharmaceutical Formulations and Dosage Forms

When employed as pharmaceuticals, the compounds of the invention can be administered in the form of pharmaceutical compositions. A pharmaceutical composition refers to a combination of a compound of the invention, or its pharmaceutically acceptable salt, and at least one pharmaceutically acceptable carrier. These compositions can be prepared in a manner well known in the pharmaceutical art, and can be administered by a variety of routes, depending upon whether local or systemic treatment is desired and upon the area to be treated. Administration may be oral, topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, or parenteral.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

The compositions can be formulated in a unit dosage form. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration.

Effective doses can be extrapolated from dose-response curves derived from in vitro or animal model test systems.

The compounds of the invention can also be formulated in combination with one or more additional active ingredients which can include any pharmaceutical agent such as antiviral agents, anti-cancer agents, vaccines, antibodies, immune enhancers, immune suppressants, anti-inflammatory agents and the like.

EXAMPLES

Equipment: $^{1}H$ NMR Spectra were recorded at 300 or 400 MHz using a Bruker AVANCE 300 MHz/400 MHz spectrometer. NMR interpretation was performed using Bruker Topspin software to assign chemical shift and multiplicity. In cases where two adjacent peaks of equal or unequal height were observed, these two peaks may be labeled as either a multiplet or as a doublet. In the case of a doublet, a coupling constant using this software may be assigned. In any given example, one or more protons may not be observed due to obscurity by water and/or solvent peaks. LCMS equipment and conditions are as follows:

1. LC (basic condition): Shimadzu LC-20AD, Binary Pump, Diode Array Detector. Column: Kinetex 2.6 μm EVO C18 100A, 50*3.0 mm, 2.6 μm. Mobile phase: A: Water/5 mM $NH_4HCO_3$, B: Acetonitrile. Flow Rate: 1.2 mL/min at 40° C. Detector: 254 nm, 220 nm. Gradient stop time, 2.9 min. Timetable:

| T (min) | A(%) | B(%) |
|---|---|---|
| 0.01 | 90 | 10 |
| 2.10 | 5 | 95 |
| 2.70 | 5 | 95 |
| 2.90 | 90 | 10 |

2. LC (basic condition): Shimadzu LC-20ADXR, Binary Pump, Diode Array Detector, Column: Poroshell HPH-C18 50*3.0 mm, 2.7 μm. Mobile Phase A: 0.04% Ammonium hydroxide, Mobile Phase B: Acetonitrile. Flow Rate: 1.2 ml/min at 40° C. Detector: 254 nm, 220 nm. Gradient stop time 3.0 min Timetable:

| T (min) | A(%) | B(%) |
|---|---|---|
| 0.01 | 90 | 10 |
| 2.0 | 5 | 95 |
| 2.7 | 5 | 95 |
| 2.8 | 90 | 10 |

3. LC (acidic condition): Shimadzu LC-20AD, Binary Pump, Diode Array Detector. Column: Ascentis Express C18, 50*3.0 mm, 2.7 μm. Mobile phase: A: Water/0.05% TFA, B: Acetonitrile/0.05% TFA. Flow Rate: 1.5 mL/min at 40° C. Detector: 254 nm, 220 nm. Gradient stop time, 2.9 min. Timetable:

| T (min) | A(%) | B(%) |
|---|---|---|
| 0.01 | 90 | 5 |
| 2.10 | 5 | 95 |
| 2.70 | 5 | 95 |
| 2.90 | 90 | 5 |

4. LC (acidic condition): Shimadzu LC-30AD, Binary Pump, Diode Array Detector. Column: Accucore C18 50*2.1 mm, 2.6 μm. Mobile Phase A: Water/0.1% FA, Mobile Phase B: Acetonitrile/0.1% FA. Flow Rate: 1.0 ml/min at 40° C. Detector: 254 nm, 220 nm. Gradient stop time 3.0 min. Timetable:

| T (min) | A(%) | B(%) |
|---|---|---|
| 0.01 | 95 | 5 |
| 2.0 | 5 | 95 |
| 2.7 | 5 | 95 |
| 2.8 | 95 | 5 |

1. S:LCMS-2020, Quadrupole LC/MS, Ion Source: ES-API, TIC: 90~900 m/z, Fragmentor: 60, Drying gas flow: 15 L/min, Nebulizing Gas Flow: 1.5 L/min, Drying gas temperature: 250° C., Vcap: 1100V.
2. Sample preparation: samples were dissolved in ACN or methanol at 1-10 mg/mL, then filtered through a 0.22 m filter membrane. Injection volume: 1~10 μL.

Definitions: ACN (acetonitrile); $CH_3CN$ (acetonitrile); $CDCl_3$ (deuterated chloroform); $CD_3OD$ (deuterated methanol); DCM (dichloromethane); DEA (diethylamine); DIEA (diisopropylethylamine); DMF (N,N-dimethylformamide); DMAP (4-dimethyl aminopyridine); DMSO (dimethylsulfoxide); DMSO-$d_6$ (deuterated dimethylsulfoxide); equiv (equivalent); ESI (electrospray ionization); EtOAc (ethyl acetate); EtOH (ethanol); g (gram); h (hour); HATU (1-[bis (dimethylamino)methylene]-1H-1,2,3-triazolo[4,5-b]pyridinium 3-oxide hexafluorophosphate); $^1$H NMR (proton nuclear magnetic resonance); HCl (hydrochloric acid); Hz (hertz); $H_2O$ (water); Hex (hexanes); i-prOH (isopropyl alcohol); $K_2CO_3$ (potassium carbonate); L (litre); LCMS (liquid chromatography-mass spectrometry); M (molar); MeCN (acetonitrile); MeOH (methanol); mg (milligrams); MHz (megahertz); min (minutes); MtBE (methyl tert-butyl ether); mL (millilitres), mmol (millimoles); N (normal); $NaBH(AcO)_3$ (sodium triacetoxyborohydride); NaCl (sodium chloride); NaH (sodium hydride); $NaHCO_3$ (sodium bicarbonate); n-BuOH (n-butyl alcohol); $NH_4Cl$ (ammonium chloride); NMP (N-methyl-2-pyrrolidone); PE (petroleum ether); PMB (paramethoxy benzyl); prep-HPLC (preparative high-performance liquid chromatography); RT (room temperature); TEA (triethylamine); TFA (trifluoroacetic acid); tR (retention time); triflic (trifluoromethane sulfonic); AcOH (acetic acid); HATU (1-[Bis(dimethylamino)methylene]-1H-1,2,3-triazolo[4,5-b]pyridinium 3-oxide hexafluorophosphate); $Na_2CO_3$ (sodium carbonate); $NaBH_3CN$ (sodium cyanoborohydride); NaOH (sodium hydroxide); $NH_3$ (ammonia); Pd/C (palladium on carbon); PMB (p-methoxybenzyl); STAB (sodium triacetoxyborohydride); t-BuOK (potassium tert-butoxide); TEMPO ((2,2,6,6-Tetramethylpiperidin-1-yl)oxyl); $Tf_2O$ (trifluoromethanesulfonic anhydride); TfOH (triflic acid); THE (tetrahydrofuran); $Ti(Oi\text{-}Pr)_4$ (titanium isopropoxide).

Intermediate I-1: Synthesis of 5-Chloro-2-(4-methoxybenzyl)-4-(trifluoromethyl)pyridazin-3(2H)-one

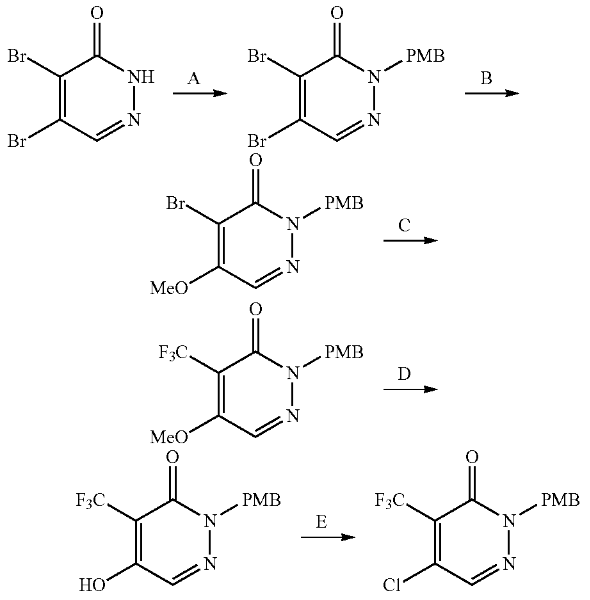

Step A

To a solution of 4,5-dibromo-2,3-dihydropyridazin-3-one (250 g, 984.71 mmol, 1 equiv) in DMF (2.5 L) was added NaH (59.1 g, 1477.07 mmol, 1.50 equiv, 60%) in several batches at 0-10° C. followed by the addition of 1-(chloromethyl)-4-methoxybenzene (230.3 g, 1470.53 mmol, 1.49 equiv) at 0° C. The resulting solution was stirred for 3 h at RT. The reaction was then quenched by the addition of 5 L of water/ice and extracted with 2×2.5 L of DCM. The organic layers were combined and concentrated. The solids were washed by MeOH (500 mL×2) to afford 290 g (79% yield) of 4,5-dibromo-2-[(4-methoxyphenyl)methyl]-2,3-dihydropyridazin-3-one as a solid. LCMS $[M+H]^+$ 378.00.

Step B

A solution of 4,5-dibromo-2-[(4-methoxyphenyl)methyl]-2,3-dihydropyridazin-3-one (290 g, 775.33 mmol, 1 equiv) and potassium hydroxide (130.5 g, 2326.00 mmol, 3.00 equiv) in MeOH (2.5 L) was stirred for 2 h at RT. The resulting mixture was concentrated to 500 mL and the solids were collected by filtration. The resulting cake was slurried for 1 h in water (1 L) to afford 232 g (92% yield) of 4-bromo-5-methoxy-2-[(4-methoxyphenyl)methyl]-2,3-dihydropyridazin-3-one as a solid. LCMS $[M+H]^+$ 326.90.

Step C

A solution of 4-bromo-5-methoxy-2-[(4-methoxyphenyl)methyl]-2,3-dihydropyridazin-3-one (232 g, 713.49 mmol, 1 equiv), methyl 2,2-difluoro-2-sulfoacetate (411.2 g, 2140.44 mmol, 3.00 equiv), and CuI (67.9 g, 356.52 mmol, 0.50 equiv) in NMP (1.2 L) was stirred for 3 h at 100° C. The reaction was then quenched by the addition of 1.5 L of water. The resulting solution was extracted with 3×1 L of DCM. The organic layers were combined and concentrated. The residue was applied onto a silica gel column with EtOAc/petroleum ether (1/1). The collected fractions were combined and concentrated to afford the crude oil to which was added 1 L of water. The solids were collected by filtration and washed with 100 mL of MeOH to afford 170 g (76% yield) of 5-methoxy-2-[(4-methoxyphenyl)methyl]-4-(trifluoromethyl)-2,3-dihydropyridazin-3-one as a solid. LCMS $[M+H]^+$ 315.10.

Step D

To a solution of 5-methoxy-2-[(4-methoxyphenyl) methyl]-4-(trifluoromethyl)-2,3-dihydropyridazin-3-one (170 g, 540.95 mmol, 1 equiv) in DMF (850 mL) was added TMSI (140 g, 699.67 mmol, 1.29 equiv) dropwise at 20° C. The resulting solution was stirred for 20 h at 85° C. The reaction mixture was then quenched by the addition of 850 mL of water and the resulting solution was extracted with 3×850 mL of DCM and the organic layers combined and dried over anhydrous sodium sulfate. The organic layers were concentrated under vacuum and the crude product was purified by silica gel column chromatography and then recrystallized with MtBE to afford 120 g (74% yield) of 5-hydroxy-2-[(4-methoxyphenyl)methyl]-4-(trifluoromethyl)-2,3-dihydropyridazin-3-one as a white solid. LCMS $[M+H]^+$ 301.07.

Step E

To a solution of 5-hydroxy-2-[(4-methoxyphenyl) methyl]-4-(trifluoromethyl)-2,3-dihydropyridazin-3-one (110 g, 366.38 mmol, 1 equiv) in DMF (550 mL) was added oxalic dichloride (93 g, 732.75 mmol, 2.00 equiv) dropwise at 0-5° C. The resulting solution was stirred for 8 h at RT. The reaction was then quenched by the addition of 550 mL of water. The solids were collected by filtration to afford 108 g (93%) of 5-chloro-2-[(4-methoxyphenyl)methyl]-4-(trifluoromethyl)-2,3-dihydropyridazin-3-one as a white solid. LCMS $[M+H]^+$ 319.04 $[M+H]^+$, $^1H$ NMR (30 MHz, DMSO-$d_6$) δ 8.22 (d, J=0.8 Hz, 1H), 7.33-7.22 (m, 2H), 6.94-6.84 (m, 2H), 5.18 (s, 2H), 3.71 (s, 3H).

Intermediate I-2: Synthesis of (S)-2-(2-((1-(4-methoxybenzyl)-6-oxo-5-(trifluoromethyl)-1,6-dihydropyridazin-4-yl)amino)propoxy)acetic acid

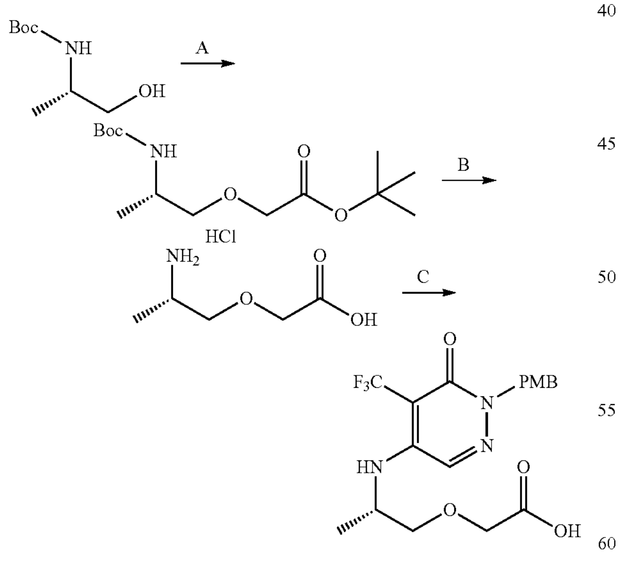

Step A

To a solution of tert-butyl (S)-(1-hydroxypropan-2-yl) carbamate (5.00 g, 28.5 mmol, 1.0 equiv) in DMF at 0° C. (80 mL) was added NaH (60% dispersion in oil, 3.4 g, 85.6 mmol, 3.0 equiv) batchwise. The mixture was stirred for 20 min at that temperature and to this suspension was added tert-butyl 2-bromoacetate (7.30 g, 57 mmol, 2.00 equiv). The resulting solution was stirred for 30 min at 0° C. and then water (60 mL) was added. The solution was extracted with 3×100 mL of ethyl acetate. The organic layers were combined and washed with 3×50 mL of brine. The organic layers were dried over magnesium sulfate, filtered, and concentrated in vacuo. The crude product was applied onto a silica gel column eluting with ethyl acetate/petroleum ether (3:7) to afford 2.8 g (34% yield) of tert-butyl (S)-2-(2-((tert-butoxycarbonyl)amino)propoxy)acetate as a colorless oil. LCMS (ESI, m/z): 290.20 $[M+H]^+$.

Step B

A solution of tert-butyl 2-[(2S)-2-[(tert-butoxycarbonyl) amino]propoxy]acetate (2.80 g, 9.7 mmol, 1.0 equiv) in 4N HCl in dioxane (30 mL) was stirred for 14 hours at room temperature. The mixture was concentrated to afford 2.5 g of crude (S)-2-(2-aminopropoxy)acetic acid hydrochloride as a red oil. LCMS (ESI, m/z): 133.15 $[M+H]^+$.

Step C

A solution of 5-chloro-2-(4-methoxybenzyl)-4-(trifluoromethyl)pyridazin-3(2H)-one (3.00 g, 9.4 mmol, 1.00 equiv; Intermediate I-1), TEA (2.86 g, 28.2 mmol, 3.0 equiv), and (S)-2-(2-aminopropoxy)acetic acid hydrochloride (2.50 g, 14.7 mmol, 1.6 equiv) in i-PrOH (100 mL) was stirred for 2 hours at 60° C. The mixture was concentrated and the crude product was applied onto a silica gel column eluting with dichloromethane/methanol (10:1) to afford 1.9 g (49% yield) of (S)-2-(2-((1-(4-methoxybenzyl)-6-oxo-5-(trifluoromethyl)-1,6-dihydropyridazin-4-yl)amino) propoxy)acetic acid as a yellow oil. LCMS (ESI, m/z): 415.2 $[M+H]^+$.

Intermediate I-3: Synthesis of 3-hydroxy-1-(piperidin-4-yl)pyrrolidin-2-one hydrochloride

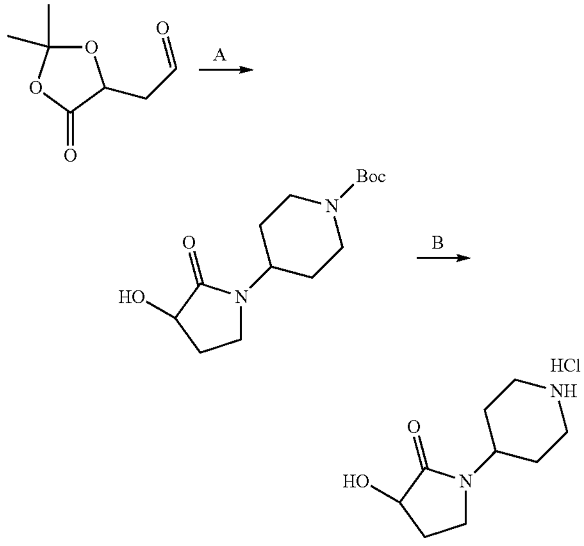

Step A

A solution of 2-(2,2-dimethyl-5-oxo-1,3-dioxolan-4-yl) acetaldehyde (6.00 g, 37.9 mmol, 1.0 equiv), acetic acid (2.73 g, 45.5 mmol, 1.2 equiv), and tert-butyl 4-aminopiperidine-1-carboxylate (15.2 g, 75.9 mmol, 2.0 equiv) in DCE (100 mL) was stirred for 1 hour and then STAB (24.0 grams, 114 mmol, 3.0 equiv) was added. The resulting solution was stirred for 14 hours at room temperature. The pH value of the solution was adjusted to pH 8 with saturated aqueous sodium bicarbonate solution. The resulting solution was extracted with 3×100 mL of dichloromethane. The organic layers were combined and washed with 50 mL of 10% aqueous citric acid and 50 mL of brine. The organic layers were dried over anhydrous sodium sulfate, filtered, and concentrated. The residue was applied onto a silica gel column eluting with ethyl acetate/petroleum ether (8:2) to give 5.1 g (47% yield) of tert-butyl 4-(3-hydroxy-2-oxopyrrolidin-1-yl)piperidine-1-carboxylate as a yellow solid. LCMS (ESI, m/z): 285.2 $[M+H]^+$.

Step B

A solution of tert-butyl 4-(3-hydroxy-2-oxopyrrolidin-1-yl)piperidine-1-carboxylate (2.0 g, 1.0 equiv) in 4N HCl in dioxane (30 mL) was stirred for 1 hour at room temperature. The resulting mixture was concentrated to afford 1.8 g of crude 3-hydroxy-1-(piperidin-4-yl)pyrrolidin-2-one hydrochloride as a white solid that was carried forward without further purification. LCMS (ESI, m/z): 185.1 $[M+H]^+$.

Intermediate I-4: Synthesis of N-methyl-1-(5-(trifluoromethyl)thiazol-2-yl)piperidin-4-amine

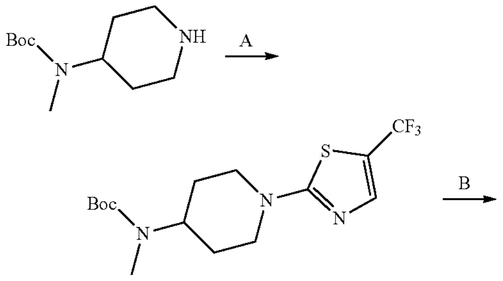

-continued

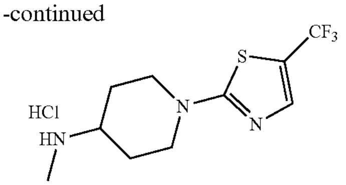

Step A

A solution of tert-butyl methyl(piperidin-4-yl)carbamate (214 mg, 0.99 mmol, 1.0 equiv), 2-bromo-5-(trifluoromethyl)thiazole (232 mg, 0.99 mmol, 1.0 equiv) and $K_2CO_3$ (207 mg, 1.49 mmol, 1.5 equiv) in NMP (5 mL) was stirred for 2 hours at 80° C. Water (20 mL) was added and the resulting solution was extracted with 3×15 mL of ethyl acetate. The organic layers were combined, dried over magnesium sulfate, filtered, and concentrated. The crude product was applied onto a silica gel column eluting with ethyl acetate/petroleum ether (2/3) to afford 343 mg (94% yield) of tert-butyl methyl(1-(5-(trifluoromethyl)thiazol-2-yl)piperidin-4-yl)carbamate as a white solid. LCMS (ESI, m/z): 366.1 $[M+H]^+$.

Step B

A solution of tert-butyl methyl(1-(5-(trifluoromethyl)thiazol-2-yl)piperidin-4-yl)carbamate (343 mg, 0.94 mmol, 1.00 equiv) in 4N HCl in dioxane (5 mL) was stirred for 1 hour and then the mixture was concentrated to afford 275 mg (97% yield) of N-methyl-1-(5-(trifluoromethyl)thiazol-2-yl)piperidin-4-amine hydrochloride as a white solid. LCMS (ESI, m/z): 266.00 $[M+H]^+$.

Intermediates I-5-I-6 were synthesized according to the procedures described for the synthesis of N-methyl-1-(5-(trifluoromethyl)thiazol-2-yl)piperidin-4-amine (Intermediate I-4) using appropriate building blocks and modified reaction conditions (such as reagent ratio, temperature, coupling conditions, and reaction time) as needed.

| Intermediate No. | Structure | Analytical Data |
|---|---|---|
| I-5 | 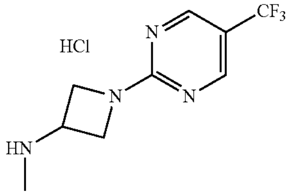 (N-methyl-1-(5-(trifluoromethyl)pyrimidin-2-yl)azetidin-3-amine hydrochloride | LCMS (ESI, m/z): 233.25 $[M + H]^+$ |
| I-6 | 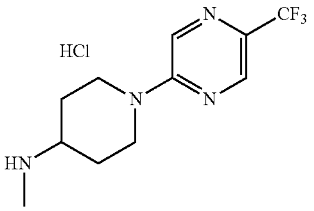 N-methyl-1-(5-(trifluoromethyl)pyrazin-2-yl)piperidin-4-amine hydrochloride | LCMS (ESI, m/z): 261.1 $[M + H]^+$ |

Example 1: Synthesis of (S)-2-(2-(6-oxo-5-(trifluoromethyl)-1,6-dihydropyridazin-4-ylamino)propoxy)-N-(1-(5-(trifluoromethyl)pyrimidin-2-yl)piperidin-4-yl)acetamide

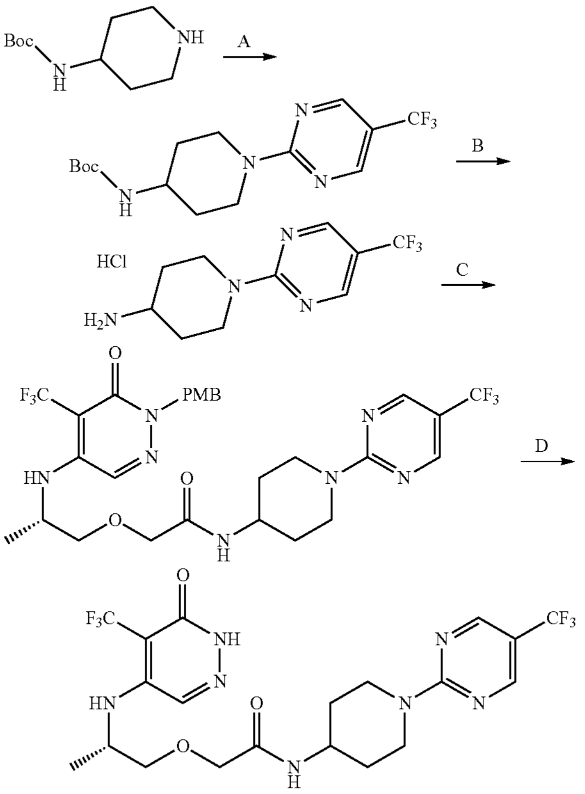

Step A

A solution of tert-butyl piperidin-4-ylcarbamate (2.00 g, 9.98 mmol, 1.0 equiv), 2-chloro-5-(trifluoromethyl)pyrimidine (1.82 g, 9.99 mmol, 1.0 equiv), and $K_2CO_3$ (1.38 g, 9.99 mmol, 1.0 equiv) in NMP (50 mL) was stirred for 2 hours at 80° C. Water (200 mL) was added and the solids were collected by filtration to afford tert-butyl 1-(5-(trifluoromethyl)pyrimidin-2-yl)piperidin-4-ylcarbamate (3.7 g, 96% yield, 90% purity) as a white solid. LCMS (ESI, m/z): 347.15 $[M+H]^+$.

Step B

A solution of tert-butyl 1-(5-(trifluoromethyl)pyrimidin-2-yl)piperidin-4-ylcarbamate (2.31 g, 6.0 mmol, 1.0 equiv, 90% purity) in 4N HCl in 1,4-dioxane (20 mL) was stirred for 1 hour at room temperature. The solids were collected by filtration to afford 1-(5-(trifluoromethyl)pyrimidin-2-yl)piperidin-4-amine hydrochloride (1.27 g, 82% yield) as a white solid. LCMS (ESI, m/z): 247.20 $[M+H]^+$.

Step C

A solution of (S)-2-(2-((1-(4-methoxybenzyl)-6-oxo-5-(trifluoromethyl)-1,6-dihydropyridazin-4-yl)amino)propoxy)acetic acid (200 mg, 0.48 mmol, 1.0 equiv, 50% purity; Intermediate I-2), DIEA (187 mg, 1.44 mmol, 3.0 equiv), HATU (183 mg, 0.48 mmol, 1.0 equiv), and 1-(5-(trifluoromethyl)pyrimidin-2-yl)piperidin-4-amine hydrochloride (119 mg, 0.48 mmol, 1.0 equiv) in DMF (2.0 mL) was stirred for 1 hour at room temperature. After concentration, the residue was applied onto a reverse phase column eluting with $H_2O/CH_3CN$ (31/69) to afford (S)-2-(2-(1-(4-methoxybenzyl)-6-oxo-5-(trifluoromethyl)-1,6-dihydropyridazin-4-ylamino)propoxy)-N-(1-(5-(trifluoromethyl)pyrimidin-2-yl)piperidin-4-yl)acetamide (51 mg, 15% yield) as a yellow oil. LCMS (ESI, m/z): 644.20 $[M+H]^+$.

Step D

To a solution of (S)-2-(2-(1-(4-methoxybenzyl)-6-oxo-5-(trifluoromethyl)-1,6-dihydropyridazin-4-ylamino)propoxy)-N-(1-(5-(trifluoromethyl)pyrimidin-2-yl)piperidin-4-yl)acetamide (49 mg, 0.076 mmol, 1.0 equiv) in TFA (1.00 mL) at 0° C. was added triflic acid (0.10 mL) and the solution was maintained at that temperature for 1 hour. Ice water (30 mL) was added and the pH value of the solution was adjusted to pH 7 with saturated aqueous $NaHCO_3$. The resulting solution was extracted with 3×60 mL of ethyl acetate. The organic layers were combined, dried over anhydrous sodium sulfate and concentrated under vacuum. The residue was applied onto a reverse phase column eluting with $H_2O/CH_3CN$ (50/50) to afford (S)-2-(2-(6-oxo-5-(trifluoromethyl)-1,6-dihydropyridazin-4-ylamino)propoxy)-N-(1-(5-(trifluoromethyl)pyrimidin-2-yl)piperidin-4-yl)acetamide (14 mg, 35% yield) as a white solid. LCMS (ESI, m/z): 524.2 $[M+H]^+$; $^1H$ NMR (300 MHz, DMSO-$d_6$) δ 12.48 (s, 1H), 8.74 (s, 2H), 7.97 (s, 1H), 7.58 (d, J=8.1 Hz, 1H), 6.46-6.39 (m, 1H), 4.62 (d, J=13.5 Hz, 2H), 4.22-4.15 (m, 1H), 4.01-3.90 (m, 2H), 3.89 (s, 2H), 3.52 (d, J=5.4 Hz, 2H), 3.16 (t, J=12.2 Hz, 2H), 1.80 (d, J=9.3 Hz, 2H), 1.42-1.30 (m, 2H), 1.18 (d, J=6.6 Hz, 3H).

Example 2: Synthesis of (S)—N-methyl-2-(2-(6-oxo-5-(trifluoromethyl)-1,6-dihydropyridazin-4-ylamino)propoxy)-N-(1-(5-(trifluoromethyl)pyrimidin-2-yl)piperidin-4-yl)acetamide

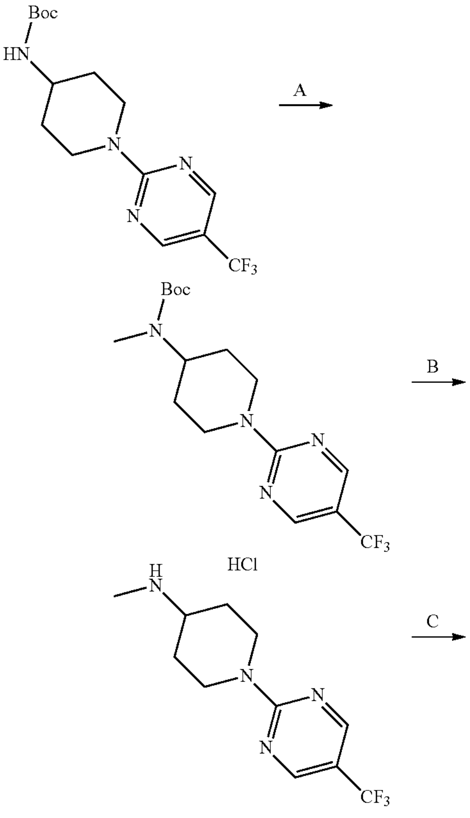

-continued

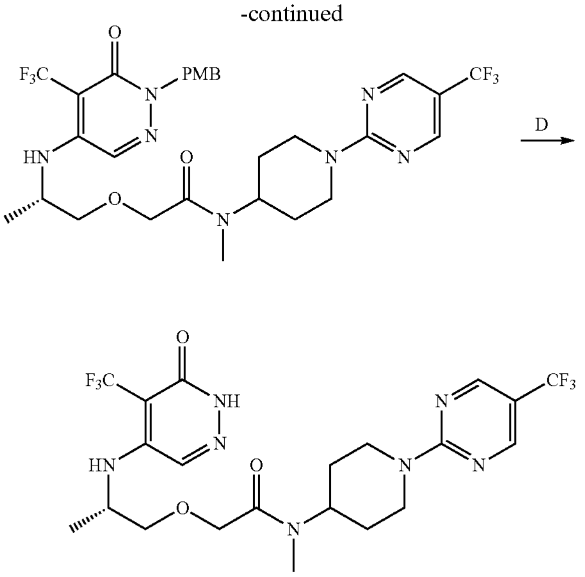

Step A

A solution of tert-butyl 1-(5-(trifluoromethyl)pyrimidin-2-yl)piperidin-4-ylcarbamate (2.31 g, 6.67 mmol, 1.00 equiv; Example 1, Step A) at 0° C. in DMF was treated with NaH (800 mg, 20.0 mmol, 3.0 equiv, 60% dispersion in mineral oil). After 15 minutes iodomethane (0.95 g, 6.67 mmol, 1.0 equiv) was added and the solution was stirred for 1 hour at room temperature. 50 mL of water was added and the solids were collected by filtration to afford tert-butyl methyl(1-(5-(trifluoromethyl)pyrimidin-2-yl)piperidin-4-yl) carbamate (1.65 g, 63% yield) as a white solid. LCMS (ESI, m/z): 361.20 $[M+H]^+$.

Step B

A solution of tert-butyl methyl(1-(5-(trifluoromethyl)pyrimidin-2-yl)piperidin-4-yl)carbamate (1.65 g, 4.578 mmol, 1.00 equiv) in 4N HCl in 1,4-dioxane (16 mL) was stirred for 1 h at room temperature. The solids were collected by filtration to afford N-methyl-1-(5-(trifluoromethyl)pyrimidin-2-yl)piperidin-4-amine hydrochloride (1.21 g, 96% yield) as a white solid. LCMS (ESI, m/z): 261.20 $[M+H]^+$.

Step C

A solution of (S)-2-(2-((1-(4-methoxybenzyl)-6-oxo-5-(trifluoromethyl)-1,6-dihydropyridazin-4-yl)amino) propoxy)acetic acid (200 mg, 0.48 mmol, 1.0 equiv; Intermediate I-2), N-methyl-1-(5-(trifluoromethyl)pyrimidin-2-yl)piperidin-4-amine hydrochloride (125 mg, 0.48 mmol, 1.0 equiv), DIEA (187 mg, 1.44 mmol, 3.0 equiv) and HATU (183 mg, 0.48 mmol, 1.0 equiv) in DMF (2 mL) was stirred for 1 hour at room temperature. After concentration, the residue was applied onto a reverse phase column eluting with $H_2O/CH_3CN$ (26/74) to afford (S)-2-(2-(1-(4-methoxybenzyl)-6-oxo-5-(trifluoromethyl)-1,6-dihydropyridazin-4-ylamino)propoxy)-N-methyl-N-(1-(5-(trifluoromethyl)pyrimidin-2-yl)piperidin-4-yl)acetamide (117 mg, 29% yield) as a yellow oil. LCMS (ESI, m/z): 658.25$[M+H]^+$.

Step D

A solution of (S)-2-(2-(1-(4-methoxybenzyl)-6-oxo-5-(trifluoromethyl)-1,6-dihydropyridazin-4-ylamino) propoxy)-N-methyl-N-(1-(5-(trifluoromethyl)pyrimidin-2-yl)piperidin-4-yl)acetamide (115 mg, 0.18 mmol, 1.0 equiv) in TFA (2.00 mL) at 0° C. was treated with triflic acid (0.20 mL) and maintained at that temperature for 20 min. Ice water (30 mL) was added and the pH value of the solution was adjusted to pH 7 with saturated aqueous $NaHCO_3$. The resulting solution was extracted with 3×100 mL of ethyl acetate. The organic layers were combined, dried over anhydrous sodium sulfate and concentrated under vacuum. The residue was applied onto a reverse phase column eluting with $H_2O/CH_3CN$ (42/58) to afford (S)—N-methyl-2-(2-(6-oxo-5-(trifluoromethyl)-1,6-dihydropyridazin-4-ylamino) propoxy)-N-(1-(5-(trifluoromethyl)pyrimidin-2-yl)piperidin-4-yl)acetamide (18 mg, 19% yield) as a white solid. LCMS (ESI, m/z): 538.2 $[M+H]^+$; $^1H$ NMR (300 MHz, DMSO-$d_6$) δ 12.22 (s, 1H), 8.65 (s, 2H), 7.89 (s, 1H), 6.75-6.50 (br, 1H), 4.86 (d, J=12.6 Hz, 2H), 4.60-4.40 (rotamer A, m, 1H), 4.30 (s, 1H), 4.22-4.12 (m, 3H), 3.85-3.79 (rotamer, m, 1H). 3.52-3.48 (m, 2H), 3.10-2.89 (i, 2H), 2.65-2.72 (n, 3H), 1.80-1.50 (N, 4H), 1.23 (d, J=6.6 Hz, 3H).

Examples 3-5 were synthesized according to the procedures described for the synthesis of (S)—N-methyl-2-(2-(6-oxo-5-(trifluoromethyl)-1,6-dihydropyridazin-4-ylamino) propoxy)-N-(1-(5-(trifluoromethyl)pyrimidin-2-yl) piperidin-4-yl)acetamide (see Example 2) using appropriate building blocks and modified reaction conditions (such as reagent ratio, temperature, coupling conditions, and reaction time) as needed.

| Example No. | Structure | Analytical Data |
| --- | --- | --- |
| 3 | 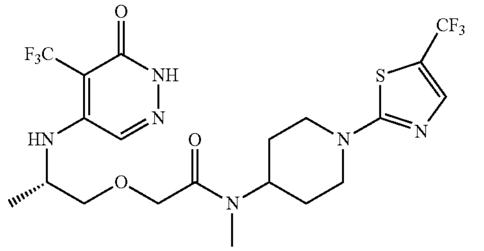 (S)-N-methyl-2-(2-((6-oxo-5-(trifluoromethyl)-1,6-dihydropyridazin-4-yl)amino)propoxy)-N-(1-(5-(trifluoromethyl)thiazol-2-yl)piperidin-4-yl)acetamide | LCMS (ESI, m/z): 543.20 $[M + H]^+$; $^1H$ NMR (300 MHz, DMSO-$d_6$) δ 12.46 (s, 1H), 7.92 (s, 1H), 7.70 (t, J = 1.5 Hz, 1H), 6.79-6.59 (m, 1H), 4.57-4.42 (m, 1H), 4.29 (s, 1H), 4.25-4.15 (m, 2H), 4.02-3.91 (m, 2H), 3.55-3.48 (m, 2H), 3.27-3.12 (m, 2H), 2.68 (d, J = 8.7 Hz, 3H), 1.91-1.62 (m, 3H), 1.61-1.55 (m, 1H), 1.16 (d, J = 6.4 Hz, 3H). |

-continued

| Example No. | Structure | Analytical Data |
|---|---|---|
| 4 | 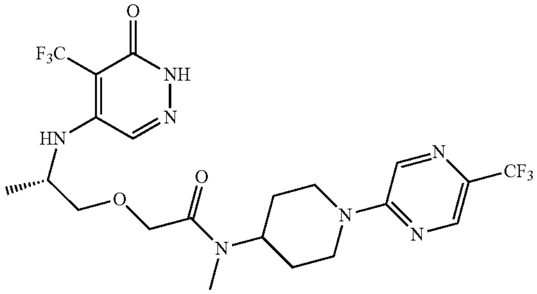 (S)-N-methyl-2-(2-(6-oxo-5-(trifluoromethyl)-1,6-dihydropyridazin-4-ylamino)propoxy)-N-(1-(5-(trifluoromethyl)pyrazin-2-yl)piperidin-4-yl)acetamide | LCMS (EIS, m/z): 538.20 $[M + H]^+$; $^1H$ NMR (300 MHz, DMSO-$d_6$) δ 12.47 (s, 1H), 8.47 (d, J = 1.8 Hz, 2H), 7.95 (s, 1H), 6.73-6.50 (m, 1 H), 4.62-4.58 (m, 3 H), 4.34-4.19 (m, 3 H), 3.61-3.54 (m, 2H), 3.10-2.91 m, 2 H), 2.68 (d, J = 9.3 Hz, 3H), 1.71-1.60 (m, 4H), 1.18 (d, J = 6.2 Hz, 3H). |
| 5 | 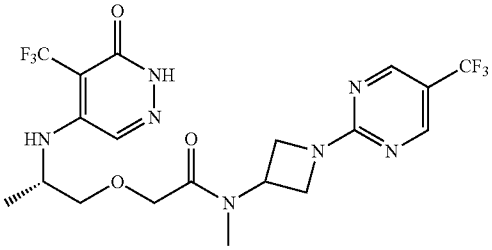 ((S)-N-methyl-2-(2-(6-oxo-5-(trifluoromethyl)-1,6-dihydropyridazin-4-ylamino)propoxy)-N-(1-(5-(trifluoromethyl)pyrimidin-2-yl)azetidin-3-yl)acetamide | LCMS (ESI, m/z): 510.20; $^1H$ NMR (400 MHz, DMSO-$d_6$) δ 12.48 (s, 1H), 8.71 (s, 2H), 7.95 (s, 1H), 6.80-6.71 (m, 1H), 5.34-5.24 (m, 1H), 4.45-4.15 (m, 7H), 3.54 (d, J = 5.9 Hz, 2H), 2.96 (s, 3H), 1.17 (d, J = 6.5 Hz, 3H). |

Example 6: Synthesis of (S)—N-(1-(5-cyanopyridin-2-yl)piperidin-4-yl)-N-methyl-2-(2-((6-oxo-5-(trifluoromethyl)-1,6-dihydropyridazin-4-yl)amino)propoxy)acetamide

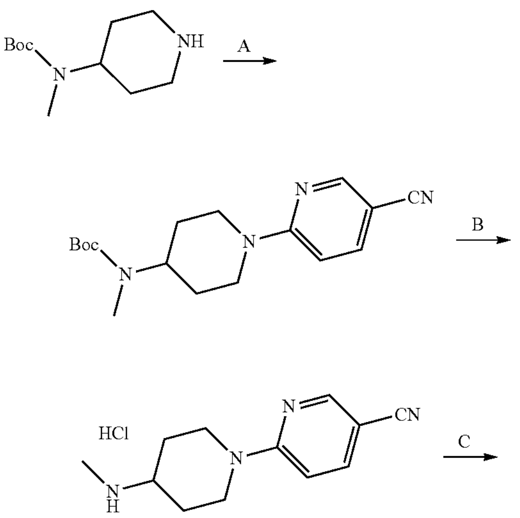

-continued

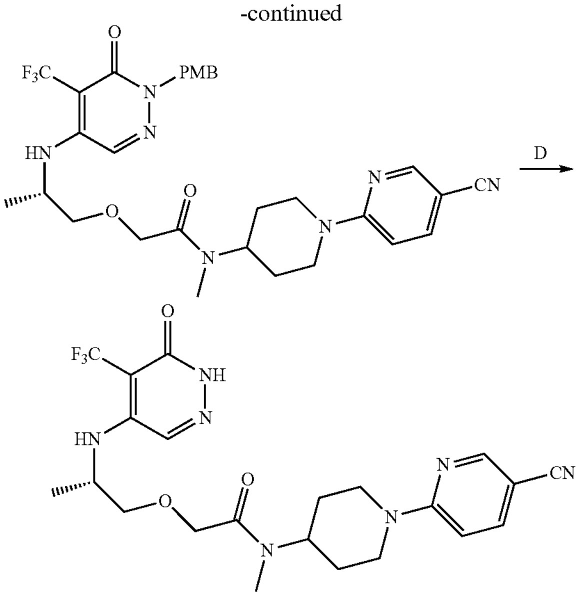

Step A

A solution of tert-butyl methyl(piperidin-4-yl)carbamate (1.00 g, 4.666 mmol, 1.00 equiv), 6-chloronicotinonitrile (0.52 g, 3.733 mmol, 0.80 equiv) and $K_2CO_3$ (0.64 g, 4.666 mmol, 1.0 equiv) in NMP (50 mL) was stirred for 2 hours at 80° C. 150 mL of water was added and the solids were collected by filtration to afford tert-butyl (1-(5-cyanopyridin-2-yl)piperidin-4-yl)(methyl)carbamate (970 mg, 59% yield) as a white solid. LCMS: $[M+H]^+$ 317.10.

Step B

A solution of tert-butyl (1-(5-cyanopyridin-2-yl)piperidin-4-yl)(methyl)carbamate (960 mg, 3.034 mmol, 1.00 equiv) in 4N HCl in 1,4-dioxane (20 mL) was stirred for 1 h at room temperature. The solution was concentrated to afford 6-(4-(methylamino)piperidin-1-yl)nicotinonitrile hydrochloride (810 mg, 99% yield) as a yellow oil. LCMS: $[M+H]^+$ 217.20.

Step C

A solution of (S)-2-(2-((1-(4-methoxybenzyl)-6-oxo-5-(trifluoromethyl)-1,6-dihydropyridazin-4-yl)amino)propoxy)acetic acid (77 mg, 0.185 mmol, 1.00 equiv; Intermediate I-2), 6-(4-(methylamino)piperidin-1-yl)nicotinonitrile hydrochloride (26 mg, 0.120 mmol, 0.65 equiv), DIEA (23 mg, 0.185 mmol, 1 equiv), and HATU (46 mg, 0.120 mmol, 0.65 equiv) in DMF (2 mL) was stirred for 1 hour. After concentration, the residue was applied onto a reverse phase column eluting with $H_2O/CH_3CN$ (37/63) to afford (S)—N-(1-(5-cyanopyridin-2-yl)piperidin-4-yl)-2-(2-((1-(4-methoxybenzyl)-6-oxo-5-(trifluoromethyl)-1,6-dihydropyridazin-4-yl)amino)propoxy)-N-methylacetamide (51 mg, 43% yield) as a yellow oil. LCMS: $[M+H]^+$ 614.25.

Step D

To a solution of (S)—N-(1-(5-cyanopyridin-2-yl)piperidin-4-yl)-2-(2-((1-(4-methoxybenzyl)-6-oxo-5-(trifluoromethyl)-1,6-dihydropyridazin-4-yl)amino)propoxy)-N-methylacetamide (50 mg, 0.081 mmol, 1.00 equiv) in TFA (1.00 mL) at 0° C. was added triflic acid (0.10 mL) and the mixture was stirred for 1 hour at that temperature. Ice water (30 mL) was added and the pH value of the solution was adjusted to 7 with saturated aqueous $NaHCO_3$. The resulting solution was extracted with 3×60 mL of ethyl acetate. The organic layers were combined, dried over anhydrous sodium sulfate and concentrated under vacuum. The residue was applied onto a reverse phase column eluting with $H_2O/CH_3CN$ (51/49) to afford (S)—N-(1-(5-cyanopyridin-2-yl)piperidin-4-yl)-N-methyl-2-(2-((6-oxo-5-(trifluoromethyl)-1,6-dihydropyridazin-4-yl)amino)propoxy)acetamide (15 mg, 36% yield) as a white solid. LCMS: $[M+H]^+$ 494.20. $^1H$ NMR (300 MHz, DMSO-$d_6$) δ 12.48 (s, 1H), 8.48 (d, J=3.0 Hz, 1H), 7.95 (s, 1H), 7.83 (dd, J=9.3, 2.4 Hz, 1H), 6.97 (d, J=9.1 Hz, 1H), 6.73-6.65 (m, 1H), 4.71-4.50 (m, 2H), 4.33 (s, 1H), 4.15 (s, 2H), 3.80-3.75 (m, 1H), 3.60-3.50 (m, 2H), 3.01-2.88 (m, 2H), 2.67 (d, J=9.6 Hz, 3H), 1.78-1.52 (m, 4H), 1.18 (d, J=6.4 Hz, 3H).

Example 7: Synthesis of (S)—N-ethyl-2-(2-((6-oxo-5-(trifluoromethyl)-1,6-dihydropyridazin-4-yl)amino)propoxy)-N-(1-(5-(trifluoromethyl)pyrimidin-2-yl)piperidin-4-yl)acetamide

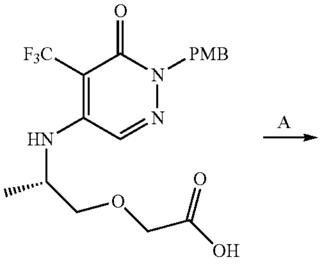

-continued

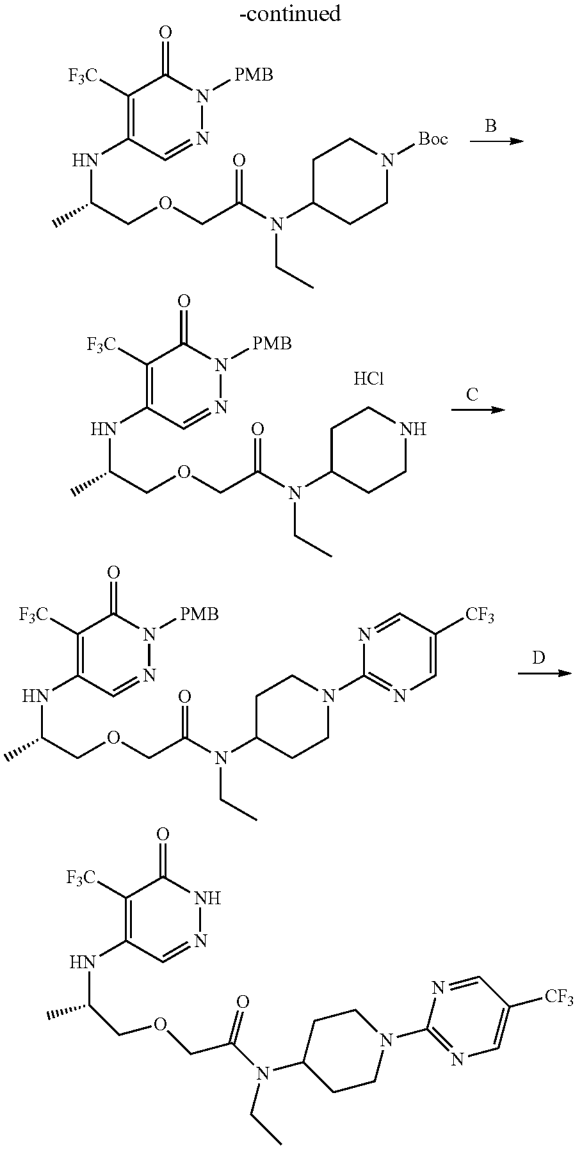

Step A

A solution of (S)-2-(2-((1-(4-methoxybenzyl)-6-oxo-5-(trifluoromethyl)-1,6-dihydropyridazin-4-yl)amino)propoxy)acetic acid (414 mg, 1.0 mmol, 1.0 equiv; Intermediate I-2), HATU (380 mg, 1.0 mmol, 1.0 equiv), DIEA (260 mg, 2 mmol, 2.00 equiv) and tert-butyl 4-(ethylamino)piperidine-1-carboxylate (230 mg, 1.0 mmol, 1.0 equiv) in DMF (4 mL) was stirred for 1 hour at room temperature. The residue was purified by reverse phase chromatography eluting with $H_2O/CH_3CN$ to afford 200 mg (32% yield) of tert-butyl (S)-4-(N-ethyl-2-(2-((1-(4-methoxybenzyl)-6-oxo-5-(trifluoromethyl)-1,6-dihydropyridazin-4-yl)amino)propoxy)acetamido)piperidine-1-carboxylate as a yellow oil. LCMS (ESI, m/z): 626.25 $[M+H]^+$.

Step B

A solution of tert-butyl (S)-4-(N-ethyl-2-(2-((1-(4-methoxybenzyl)-6-oxo-5-(trifluoromethyl)-1,6-dihydropyridazin-4-yl)amino)propoxy)acetamido)piperidine-1-carboxylate (200 mg, 0.32 mmol, 1.0 equiv) in 4N HCl in dioxane (5 mL) was stirred for 2 hours at room temperature. The solution was concentrated under vacuum to afford 130 mg (78% yield) of (S)—N-ethyl-2-(2-((1-(4-methoxybenzyl)-6-oxo-5-(trifluoromethyl)-1,6-dihydropyridazin-4-yl) amino)propoxy)-N-(piperidin-4-yl)acetamide hydrochloride as a yellow oil that was carried forward without further purification. LCMS (ESI, m/z): 526.25 $[M+H]^+$.

Step C

A solution of (S)—N-ethyl-2-(2-((1-(4-methoxybenzyl)-6-oxo-5-(trifluoromethyl)-1,6-dihydropyridazin-4-yl) amino)propoxy)-N-(piperidin-4-yl)acetamide (130 mg, 0.25 mmol, 1.0 equiv), $K_2CO_3$ (104 mg, 0.75 mmol, 3.0 equiv), and 2-chloro-5-(trifluoromethyl)pyrimidine hydrochloride (46 mg, 0.25 mmol, 1.0 equiv) in DMF (5 mL) was stirred for 2 hours at room temperature. Water was added and the resulting solution was extracted with dichloromethane. The organic layers were combined, dried over anhydrous sodium sulfate and concentrated under vacuum. The residue was purified by reverse phase chromatography eluting with $H_2O/CH_3CN$ to afford 140 mg (83% yield) of (S)—N-ethyl-2-(2-((1-(4-methoxybenzyl)-6-oxo-5-(trifluoromethyl)-1,6-dihydropyridazin-4-yl)amino)propoxy)-N-(1-(5-(trifluoromethyl)pyrimidin-2-yl)piperidin-4-yl)acetamide as a yellow solid. LCMS (ESI, m/z): 672.25 $[M+H]^+$.

Step D

A solution of (S)—N-ethyl-2-(2-((1-(4-methoxybenzyl)-6-oxo-5-(trifluoromethyl)-1,6-dihydropyridazin-4-yl) amino)propoxy)-N-(1-(5-(trifluoromethyl)pyrimidin-2-yl) piperidin-4-yl)acetamide (140 mg, 0.21 mmol, 1.00 equiv) in trifluoroacetic acid (3 mL) at 0° C. was treated with triflic acid (0.3 mL) and maintained at that temperature for 1 hour. Water was added and the pH value was adjusted to 6 with saturated aqueous $Na_2CO_3$ solution. The resulting solution was extracted with dichloromethane. The organic layers were dried over anhydrous sodium sulfate and concentrated under vacuum. The crude residue was purified by reverse phase chromatography eluting with $H_2O/CH_3CN$ to afford 80 mg (69% yield) of (S)—N-ethyl-2-(2-((6-oxo-5-(trifluoromethyl)-1,6-dihydropyridazin-4-yl)amino)propoxy)-N-(1-(5-(trifluoromethyl)pyrimidin-2-yl)piperidin-4-yl)acetamide as a white solid. LCMS (ESI, m/z): 552.20 $[M+H]^+$; $^1$HNMR (DMSO-$d_6$, 300 MHz) δ 12.47 (s, 1H), 8.69 (s, 2H), 7.93 (s, 1H), 6.75-6.68 (m, 1H), 4.82 (d, J=13.1 Hz, 2H), 4.27 (s, 1H), 4.18 (d, J=3.5 Hz, 2H), 3.80-3.71 (m, 1H), 3.56 (d, J=5.6 Hz, 2H), 3.15 (d, J=7.3 Hz, 2H), 3.01-2.89 (m, 2H), 1.78-1.62 (m, 4H), 1.18 (t, J=5.8 Hz, 3H), 1.12-0.93 (m, 3H).

Example 8: Synthesis of (S)—N-methyl-2-((1-(6-oxo-5-(trifluoromethyl)-1,6-dihydropyridazin-4-yl) azetidin-2-yl)methoxy)-N-(1-(5-(trifluoromethyl) pyrimidin-2-yl)piperidin-4-yl)acetamide

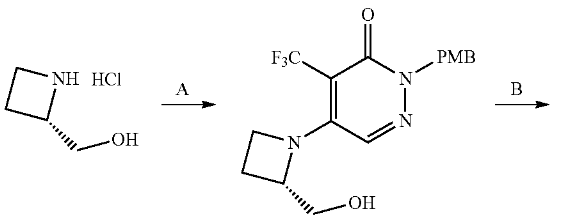

-continued

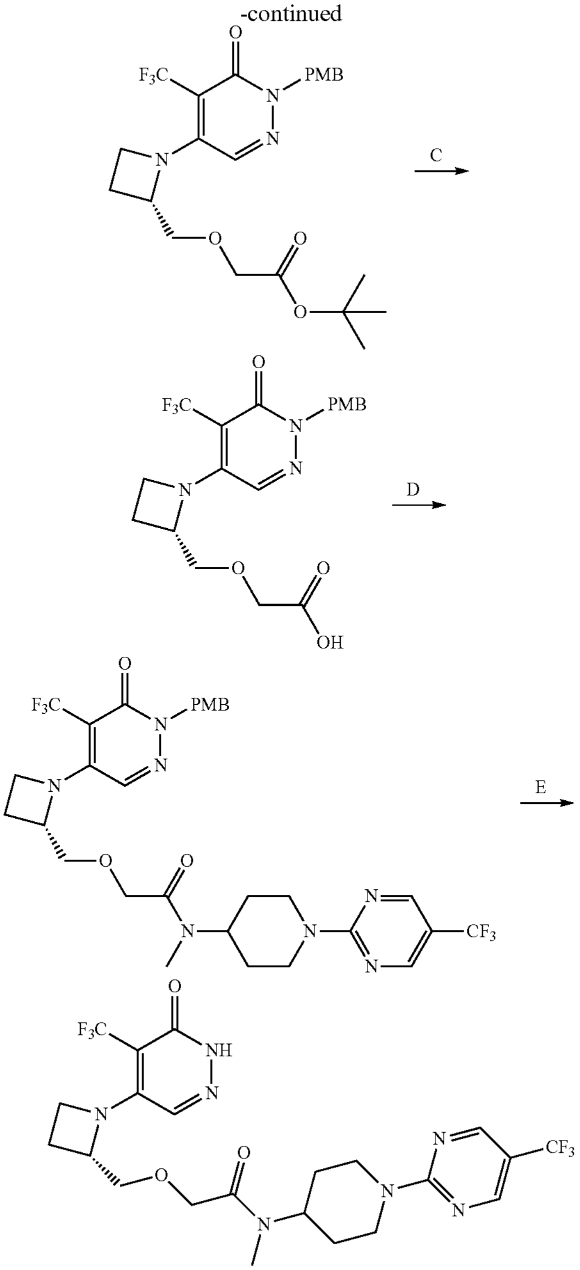

Step A

A solution of (S)-azetidin-2-ylmethanol hydrochloride (1.20 g, 9.71 mmol, 1.0 equiv), TEA (2.80 mL), and 5-chloro-2-(4-methoxybenzyl)-4-(trifluoromethyl) pyridazin-3(2H)-one (3.20 g, 10.0 mmol, 1.03 equiv; Intermediate I-1) in ethanol (20 mL) was stirred for 1 h at 60° C. After cooling to room temperature, the solution was concentrated under vacuum. The crude product was purified by reverse phase chromatography eluting with $H_2O/CH_3CN$ to afford 2.0 g (55% yield) of (S)-5-(2-(hydroxymethyl)azetidin-1-yl)-2-(4-methoxybenzyl)-4-(trifluoromethyl) pyridazin-3(2H)-one as a white solid. LCMS (ESI, m/z): 370.15 $[M+H]^+$.

Step B

A solution of (S)-5-(2-(hydroxymethyl)azetidin-1-yl)-2-(4-methoxybenzyl)-4-(trifluoromethyl)pyridazin-3(2H)-one (738 mg, 1.99 mmol, 1.0 equiv), tert-butyl 2-chloroacetate (604 mg, 4.01 mmol, 2.01 equiv), and NaH (60% dispersion in oil, 240 mg, 6.0 mmol, 3.0 equiv) in DMF (10 mL) was stirred for 2 hours at 0° C. After concentration, the residue was purified by C18 reverse phase chromatography eluting with $H_2O/CH_3CN$ to afford tert-butyl (S)-2-((1-(1-(4-methoxybenzyl)-6-oxo-5-(trifluoromethyl)-1,6-dihydropyridazin-4-yl)azetidin-2-yl)methoxy)acetate 430 mg (44% yield) as a yellow oil. LCMS (ESI, m/z): 483.15 $[M+H]^+$.

Step C

A solution of tert-butyl (S)-2-((1-(1-(4-methoxybenzyl)-6-oxo-5-(trifluoromethyl)-1,6-dihydropyridazin-4-yl)azetidin-2-yl)methoxy)acetate (420 mg, 0.87 mmol, 1.0 equiv) in TFA (5 mL) and DCM (5 mL) was stirred for 2 hours at room temperature and the solution was concentrated to afford 490 mg (92% yield) of (S)-2-((1-(1-(4-methoxybenzyl)-6-oxo-5-(trifluoromethyl)-1,6-dihydropyridazin-4-yl)azetidin-2-yl)methoxy)acetic acid as a brown oil. LCMS (ESI, m/z): 428.10 $[M+H]^+$.

Step D

A solution of (S)-2-((1-(1-(4-methoxybenzyl)-6-oxo-5-(trifluoromethyl)-1,6-dihydropyridazin-4-yl)azetidin-2-yl)methoxy)acetic acid (274 mg, 1.05 mmol, 1.0 equiv), DIEA (408 mg, 3.16 mmol, 3.0 equiv), and HATU (600 mg, 1.58 mmol, 1.5 equiv) in DMF (5 mL) was stirred for 1 hour at room temperature. The residue was purified directly by reverse phase chromatography eluting with $H_2O/CH_3CN$ to give 533 mg of (S)-2-((1-(1-(4-methoxybenzyl)-6-oxo-5-(trifluoromethyl)-1,6-dihydropyridazin-4-yl)azetidin-2-yl)methoxy)-N-methyl-N-(1-(5-(trifluoromethyl)pyrimidin-2-yl)piperidin-4-yl)acetamide (76% yield) as a colorless oil. LCMS (ESI, m/z): 670.20$[M+H]^+$.

Step E

A solution of (S)-2-((1-(1-(4-methoxybenzyl)-6-oxo-5-(trifluoromethyl)-1,6-dihydropyridazin-4-yl)azetidin-2-yl)methoxy)-N-methyl-N-(1-(5-(trifluoromethyl)pyrimidin-2-yl)piperidin-4-yl)acetamide (520 mg, 0.76 mmol, 1.0 equiv) and trifluoromethanesulfonic acid (0.33 mL) in trifluoroacetic acid (3.3 mL) was stirred for 1 hour at room temperature. 20 mL of water was added and the pH value of the solution was adjusted to 8 with saturated aqueous $Na_2CO_3$. The resulting solution was extracted with 3×15 mL of ethyl acetate. The organic layers were combined, dried over anhydrous sodium sulfate and concentrated under vacuum. The residue was purified by C18 reverse phase chromatography eluting with $H_2O/CH_3CN$ to afford 65 mg of (S)—N-methyl-2-((1-(6-oxo-5-(trifluoromethyl)-1,6-dihydropyridazin-4-yl)azetidin-2-yl)methoxy)-N-(1-(5-(trifluoromethyl)pyrimidin-2-yl)piperidin-4-yl)acetamide (15%) as a white solid. LCMS (ESI, m/z): 550.15 $[M+H]^+$; $^1$H NMR (400 MHz, DMSO-$d_6$) δ 12.36 (d, J=10.6 Hz, 1H), 8.69 (d, J=0.9 Hz, 2H), 7.75 (s, 1H), 4.89-4.78 (m, 3H), 4.57-4.52 (m, 1H), 4.42-4.27 (m, 2H), 4.24 (s, 1H), 3.88 (dr, 1H), 3.77 (dd, J=10.2, 4.5 Hz, 2H), 3.04-2.92 (m, 2H), 2.67 (d, J=16.7 Hz, 3H), 2.49-2.41 (m, 1H), 2.11-2.01 (m, 1H), 1.71-1.46 (m, 4H).

Example 9: Synthesis of (S)-2-(3-methoxy-2-((6-oxo-5-(trifluoromethyl)-1,6-dihydropyridazin-4-yl)amino)propoxy)-N-methyl-N-(1-(5-(trifluoromethyl)pyrimidin-2-yl)piperidin-4-yl)acetamide

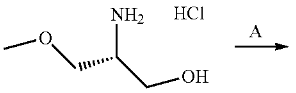

-continued

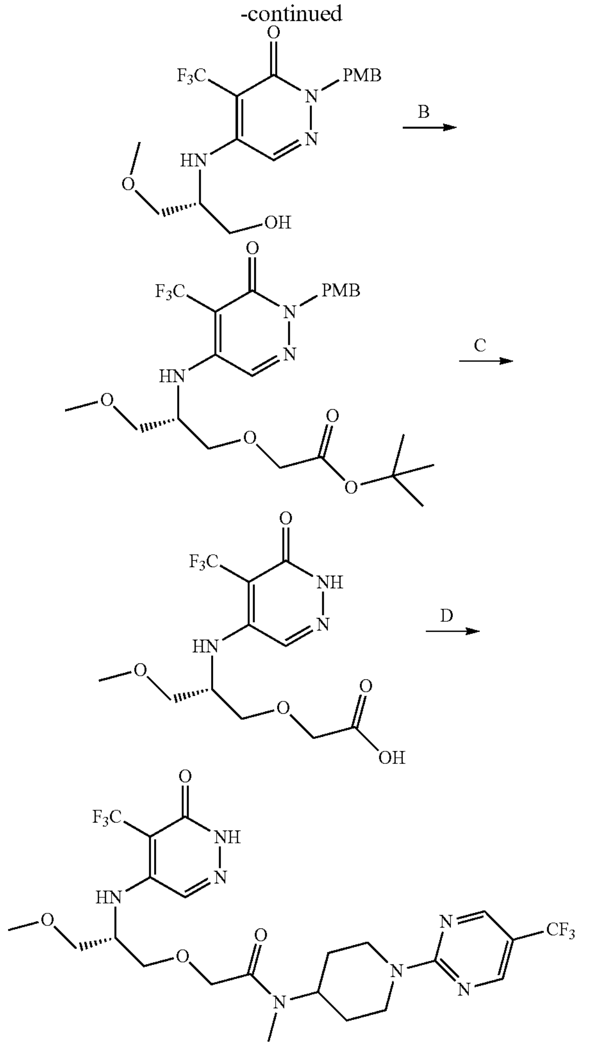

Step A

A solution of methyl (R)-2-amino-3-methoxypropan-1-ol hydrochloride (4.00 g, 28.3 mmol, 1.0 equiv), TEA (8.58 g, 84.8 mmol, 3.0 equiv), and 5-chloro-2-(4-methoxybenzyl)-4-(trifluoromethyl)pyridazin-3(2H)-one (9.00 g, 28.24 mmol, 1.0 equiv; Intermediate I-1) in i-PrOH (40 mL) was stirred for 2 hours at 60° C. The resulting mixture was concentrated under vacuum and the crude product was applied onto a silica gel column eluting with ethyl acetate/petroleum ether (7:3) to afford 10.5 g (96% yield) of (R)-5-((1-hydroxy-3-methoxypropan-2-yl)amino)-2-(4-methoxybenzyl)-4-(trifluoromethyl)pyridazin-3(2H)-one as a white solid. LCMS (ESI, m/z): 388.10$[M+H]^+$.

Step B

To a solution of (R)-5-((1-hydroxy-3-methoxypropan-2-yl)amino)-2-(4-methoxybenzyl)-4-(trifluoromethyl)pyridazin-3(2H)-one (2.0 g, 5.16 mmol, 1.0 equiv) in DMF (40 mL) at 0° C. was added NaH (60% dispersion in mineral oil, 207 mg, 5.16 mmol, 1.0 equiv) portionwise. The solution was stirred for 15 minutes and then tert-butyl 2-bromoacetate (2.01 g, 10.33 mmol, 2.0 equiv) was added to the resulting solution. The mixture was stirred for 1 hour at room temperature. 30 mL of water was added and the resulting solution was extracted with 3×50 mL of ethyl acetate. The organic layers were combined, dried over anhydrous sodium sulfate and concentrated under vacuum.

The crude product was applied onto a silica gel column eluting with ethyl acetate/petroleum ether (1:1) to afford 300 mg (12% yield) of tert-butyl (S)-2-(3-methoxy-2-((1-(4-methoxybenzyl)-6-oxo-5-(trifluoromethyl)-1,6-dihydropyridazin-4-yl)amino)propoxy)acetate as a yellow solid. LCMS (ESI, m/z): 502.20 $[M+H]^+$.

Step C

A solution of tert-butyl (S)-2-(3-methoxy-2-((1-(4-methoxybenzyl)-6-oxo-5-(trifluoromethyl)-1,6-dihydropyridazin-4-yl)amino)propoxy)acetate (240 mg, 0.48 mmol, 1.0 equiv) in trifluoroacetic acid/triflic acid (5:1, 2.4 mL) was stirred for 3 hours at room temperature. Water (20 mL) was added and the pH value of the solution was adjusted to 8 with saturated aqueous $NaHCO_3$. The resulting solution was extracted with 3×50 mL of dichloromethane. The organic layers were combined, dried over anhydrous sodium sulfate and concentrated. The crude product was applied onto a C18 reverse phase column eluting with $H_2O/CH_3CN$ (7:3) to afford 60 mg (39% yield) (S)-2-(3-methoxy-2-((6-oxo-5-(trifluoromethyl)-1,6-dihydropyridazin-4-yl)amino)propoxy)acetic acid as a yellow solid. LCMS (ESI, m/z): 326.10 $[M+H]^+$.

Step D

A solution of (S)-2-(3-methoxy-2-((6-oxo-5-(trifluoromethyl)-1,6-dihydropyridazin-4-yl)amino)propoxy)acetic acid (55 mg, 0.17 mmol, 1.0 equiv), N-methyl-1-(5-(trifluoromethyl)pyrimidin-2-yl)piperidin-4-amine (48 mg, 0.19 mmol, 1.10 equiv), HATU (71 mg, 0.19 mmol, 1.10 equiv), and DIEA (44 mg, 0.34 mmol, 2.0 equiv) in DMF (1 mL) was stirred for 2 hours at room temperature. 10 mL of water was added and the resulting solution was extracted with 2×50 mL of ethyl acetate. The organic layers were combined and dried over anhydrous sodium sulfate. After concentration, the crude product was purified by reverse phase chromatography eluting with $H_2O/CH_3CN$ (45:55) to afford 16 mg (17% yield) of (S)-2-(3-methoxy-2-((6-oxo-5-(trifluoromethyl)-1,6-dihydropyridazin-4-yl)amino)propoxy)-N-methyl-N-(1-(5-(trifluoromethyl)pyrimidin-2-yl)piperidin-4-yl)acetamide as a white solid. LCMS (ESI, m/z): 568.30 $[M+H]^+$; $^1H$ NMR (DMSO-$d_6$, 300 MHz) δ 12.48 (s, 1H), 8.68 (s, 2H), 7.94 (s, 1H), 6.70-6.55 (m, 1H), 4.82 (d, J=13.2 Hz, 2H), 4.53-4.41 (m, 1H), 4.48-4.29 (m, 2H), 4.18 (s, 1H), 3.58 (d, J=5.8 Hz, 2H), 3.47 (d, J=5.6 Hz, 2H), 3.27 (s, 3H), 3.10-2.90 (m, 2H), 2.65 (d, J=8.9 Hz, 3H), 1.80-1.61 (m, 4H).

Example 10: Synthesis of 5-((S)-1-((S)-1-(1-(5-(trifluoromethyl)pyrimidin-2-yl)piperidin-4-yl)-2-oxopyrrolidin-3-yloxy)propan-2-ylamino)-4-(trifluoromethyl)pyridazin-3(2H)-one (10A) and 5-((S)-1-((R)-1-(1-(5-(trifluoromethyl)pyrimidin-2-yl)piperidin-4-yl)-2-oxopyrrolidin-3-yloxy)propan-2-ylamino)-4-(trifluoromethyl)pyridazin-3(2H)-one (10B)

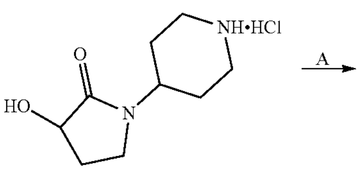

-continued

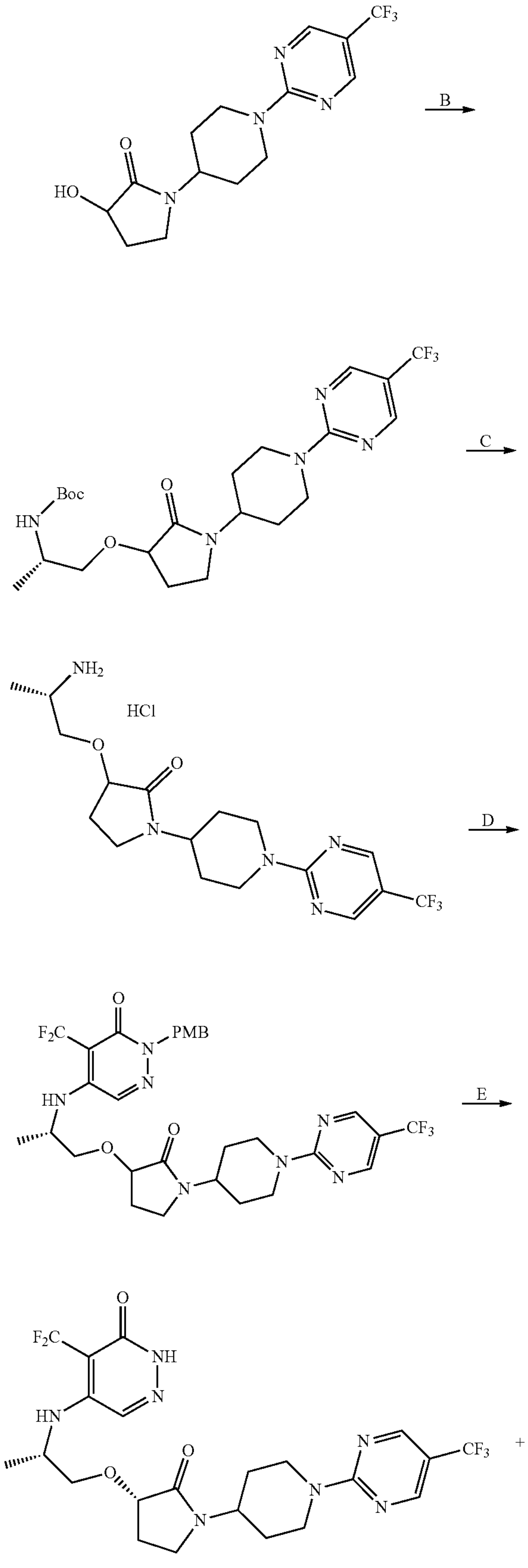

10A

-continued

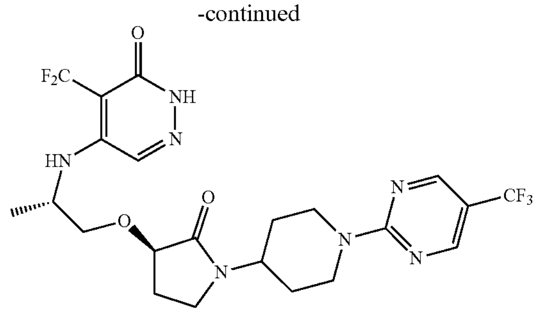

10B

Step A

A solution of 3-hydroxy-1-(piperidin-4-yl)pyrrolidin-2-one hydrochloride (600 mg, 2.72 mmol, 1.0 equiv; Intermediate I-3), 2-chloro-5-(trifluoromethyl)pyrimidine (496 mg, 2.72 mmol, 1.0 equiv), and $K_2CO_3$ (751 mg, 5.44 mmol, 2.0 equiv) in DMF (40 mL) was stirred for 2 hours at 60° C. Water (30 mL) was added and the solids were collected by filtration and dried in an oven under reduced pressure to give 550 mg (61% yield) of 1-(1-(5-(trifluoromethyl)pyrimidin-2-yl)piperidin-4-yl)-3-hydroxypyrrolidin-2-one as a white solid. LCMS (ESI, m/z): 331.1 $[M+H]^+$.

Step B

A solution of 1-(1-(5-(trifluoromethyl)pyrimidin-2-yl)piperidin-4-yl)-3-hydroxypyrrolidin-2-one (550 mg, 1.67 mmol, 1.00 equiv) in DMF (60 mL) at 0° C. was treated with NaH (60% dispersion in oil, 200 mg, 4.99 mmol, 3.0 equiv) portionwise. The mixture was stirred for 15 min at 0° C. tert-Butyl (S)-4-methyl-1,2,3-oxathiazolidine-3-carboxylate 2,2-dioxide (593 mg, 2.5 mmol, 1.5 equiv) was then added portionwise. After stirring for 1 hour at that temperature, 30 mL of water was added. The resulting solution was extracted with 3×50 mL of ethyl acetate. The organic layers were combined and washed with 3×30 ml of brine. The organics were dried over anhydrous sodium sulfate and concentrated. The crude product was applied onto a silica gel column eluting with ethyl acetate/hexane (9:1) to afford 480 mg (59% yield) of tert-butyl (S)-1-(1-(1-(5-(trifluoromethyl)pyrimidin-2-yl)piperidin-4-yl)-2-oxopyrrolidin-3-yloxy)propan-2-ylcarbamate as a yellow solid. LCMS (ESI, m/z): 488.2 $[M+H]^+$.

Step C

A solution of tert-butyl (S)-1-(1-(1-(5-(trifluoromethyl)pyrimidin-2-yl)piperidin-4-yl)-2-oxopyrrolidin-3-yloxy)propan-2-ylcarbamate (480 mg, 1.00 equiv) in 4N HCl in dioxane (30 mL) was stirred for 1 hour at room temperature. The mixture was concentrated to afford 420 mg of 3-((S)-2-aminopropoxy)-1-(1-(5-(trifluoromethyl)pyrimidin-2-yl)piperidin-4-yl)pyrrolidin-2-one hydrochloride as a yellow solid. LCMS (ESI, m/z): 388.2 $[M+H]^+$.

Step D

A solution of 3-((S)-2-aminopropoxy)-1-(1-(5-(trifluoromethyl)pyrimidin-2-yl)piperidin-4-yl)pyrrolidin-2-one hydrochloride (220 mg, 0.52 mmol, 1.0 equiv), triethylamine (157 mg, 1.56 mmol, 3.0 equiv), and 5-chloro-2-[(4-methoxyphenyl)methyl]-4-(trifluoromethyl)pyridazin-3-one (165 mg, 0.52 mmol, 1.00 equiv) in EtOH (40 mL) was stirred for 2 hours at 60° C. After concentration, the crude product was applied onto a silica gel column eluting with ethyl acetate/petroleum ether (9:1) to afford 280 mg (81% yield) of 5-((S)-1-(1-(1-(5-(trifluoromethyl)pyrimidin-2-yl)piperidin-4-yl)-2-oxopyrrolidin-3-yloxy)propan-2-ylamino)-2-(4-methoxybenzyl)-4-(trifluoromethyl)pyridazin-3(2H)-one as a yellow oil. LCMS (ESI, m/z): 670.2 $[M+H]^+$.

Step E

A solution of 5-((S)-1-(1-(1-(5-(trifluoromethyl)pyrimidin-2-yl)piperidin-4-yl)-2-oxopyrrolidin-3-yloxy)propan-2-ylamino)-2-(4-methoxybenzyl)-4-(trifluoromethyl)pyridazin-3(2H)-one (280 mg, 0.42 mmol, 1.0 equiv) in TFA (15 mL) at 0° C. was treated with triflic acid (1.50 mL). After stirring for 1 hour at 0° C., the pH value of the solution was adjusted to 8 with saturated aqueous sodium bicarbonate. The resulting solution was extracted with 3×70 mL of dichloromethane. The organic layers were combined, dried over anhydrous sodium sulfate, and concentrated. The crude product was purified by reverse phase chromatography and further purified by chiral prep-HPLC (Column: CHIRALPAK IA, 2*25 cm, Sum; Mobile Phase A: Hex:DCM=3:1 w/10 mM $NH_3$-MeOH, Mobile Phase B: EtOH; Flow rate: 20 mL/min; 10% B for 14 min; 220/254 nm) to afford the separated compounds. The stereochemistry was assigned based on an x-ray crystal structure of Example 10 Isomer B (10B).

Example 10 Isomer A (10A): 5-((S)-1-((S)-1-(1-(5-(trifluoromethyl)pyrimidin-2-yl)piperidin-4-yl)-2-oxopyrrolidin-3-yloxy)propan-2-ylamino)-4-(trifluoromethyl)pyridazin-3(2H)-one (59 mg, 35%, white solid). LC-MS: (ESI, m/z): 550.2 $[M+H]^+$; $^1H$ NMR (400 MHz, DMSO-$d_6$) δ 12.47 (s, 1H), 8.70 (s, 2H), 7.95 (s, 1H), 6.39-6.30 (m, 1H), 4.85-4.82 (m, 2H), 4.18-4.11 (m, 1H), 4.10-4.04 (dt, J=12.7, 6.8 Hz, 2H), 3.83 (dd, J=10.0, 6.5 Hz, 1H), 3.61 (dd, J=10.1, 4.7 Hz, 1H), 3.25-3.14 (m, 1H), 3.19-3.09 (m, 1H), 3.13-3.01 (m, 2H), 2.31-2.19 (m, 1H), 1.79-1.55 (m, 5H), 1.18 (d, J=6.5 Hz, 3H). Chiral HPLC: CHIRALPAK IA-3, 4.6*50 mm, 3 μm; detected at 254 nm; Mobile phase A: Hex:DCM=3:1 w/ 0.1% DEA, Mobile phase B: EtOH, 15% Mobile phase B; Flow rate: 1 mL/min; tR=1.472 min.

Example 10 Isomer B (10B): 5-((S)-1-((R)-1-(1-(5-(trifluoromethyl)pyrimidin-2-yl)piperidin-4-yl)-2-oxopyrrolidin-3-yloxy)propan-2-ylamino)-4-(trifluoromethyl)pyridazin-3(2H)-one (92 mg, 54%, white solid). LC-MS: (ESI, m/z): 550.2 $[M+H]^+$; $^1H$ NMR (400 MHz, DMSO-$d_6$) δ 12.47 (s, 1H), 8.70 (s, 2H), 7.95 (s, 1H), 6.39-6.30 (m, 1H), 4.84-4.81 (m, 2H), 4.18-4.08 (m, 3H), 3.83 (dd, J=10.0, 6.5 Hz, 1H), 3.61 (dd, J=10.1, 4.7 Hz, 1H), 3.25-3.24 (m, 1H), 3.18-3.11 (m, 1H), 3.10-2.98 (m, 2H), 2.31-2.19 (m, 1H), 1.79-1.45 (m, 5H), 1.18 (d, J=6.5 Hz, 3H). Chiral HPLC: CHIRALPAK IA-3, 4.6*50 mm, 3 μm; detected at 254 nm; Mobile phase A: Hex:DCM=3:1 w/ 0.1% DEA, Mobile phase B: EtOH, 15% Mobile phase B; Flow rate: 1 mL/min; tR=2.209 min.

Example 11: Synthesis of 4-chloro-5-((S)-1-(2-oxo-1-(1-(5-(trifluoromethyl)pyrimidin-2-yl)piperidin-4-yl)pyrrolidin-3-yloxy)propan-2-ylamino)pyridazin-3(2H)-one

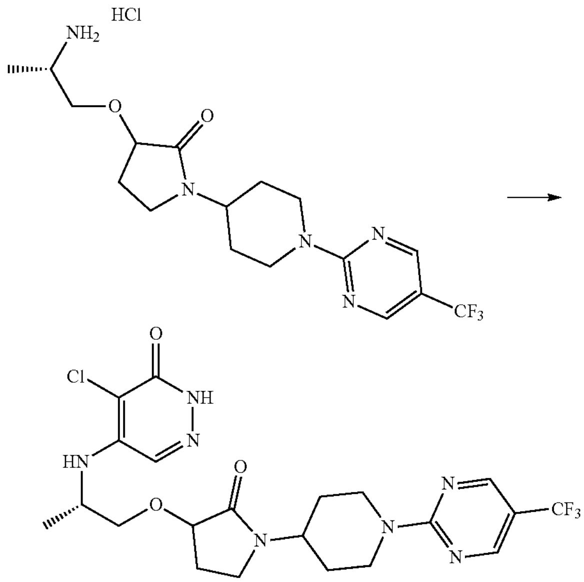

A solution of 3-((S)-2-aminopropoxy)-1-(1-(5-(trifluoromethyl)pyrimidin-2-yl)piperidin-4-yl)pyrrolidin-2-one (60 mg, 0.16 mmol, 1.0 equiv; see Example 10, step C), 4,5-dichloropyridazin-3(2H)-one (38 mg, 0.23 mmol, 1.5 equiv), and TEA (83 mg, 0.82 mmol, 5.3 equiv) in n-BuOH (3 mL) was stirred for 15 hours at 100° C. The residue was purified by reverse phase column eluting with $H_2O/CH_3CN$ (60/40). The product was further purified by prep-HPLC to afford 6 mg (8% yield) of 4-chloro-5-((S)-1-(2-oxo-1-(1-(5-(trifluoromethyl)pyrimidin-2-yl)piperidin-4-yl)pyrrolidin-3-yloxy)propan-2-ylamino)pyridazin-3(2H)-one as a white solid. LCMS (ESI, m/z): 516.20 $[M+H]^+$; $^1H$ NMR (400 MHz, Methanol-$d_4$) δ 8.55 (s, 2H), 7.96 (d, J=9.9 Hz, 1H), 5.01-4.91 (m, 2H), 4.24-4.06 (m, 3H), 4.00-3.86 (m, 1H), 3.72 (dd, J=9.7, 4.6 Hz, 1H), 3.41-3.33 (m, 1H), 3.31-3.23 (m, 1H), 3.10-2.97 (m, 2H), 2.42-2.27 (m, 1H), 1.89-1.87 (m, 1H), 1.85-1.63 (m, 4H), 1.31 (d, J=6.6 Hz, 3H).

Example 12: Synthesis of 4-bromo-5-(((2S)-1-((2-oxo-1-(1-(5-(trifluoromethyl)pyrazin-2-yl)piperidin-4-yl)pyrrolidin-3-yl)oxy)propan-2-yl)amino)pyridazin-3(2H)-one

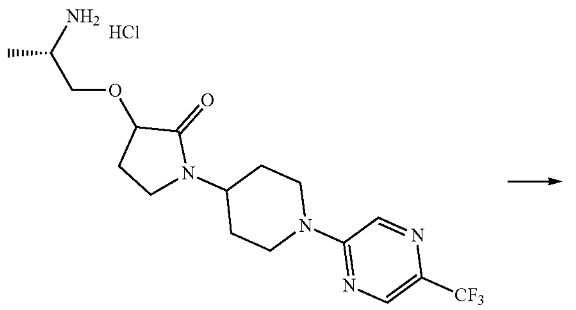

-continued

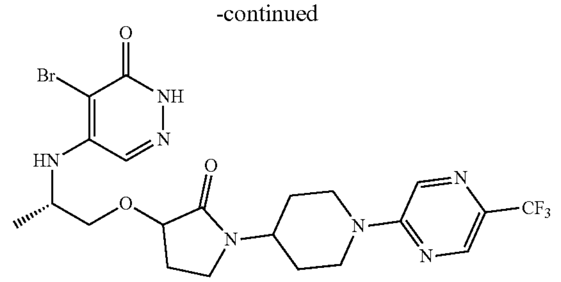

A solution of 3-((S)-2-aminopropoxy)-1-(1-(5-(trifluoromethyl)pyrazin-2-yl)piperidin-4-yl)pyrrolidin-2-one hydrochloride (90 mg, 0.212 mmol, 1.00 equiv; see Example 13, Step C), 4,5-dibromopyridazin-3(2H)-one (54 mg, 0.213 mmol, 1.00 equiv), and $Et_3N$ (65 mg, 0.637 mmol, 3.00 equiv) in n-butyl alcohol (2 mL) was stirred for 3 days at 100° C. The resulting solution was concentrated and purified by reverse phase chromatography eluting with $H_2O/CH_3CN$ (53/47) to afford impure desired product. The product was further purified by prep-HPLC to afford 11 mg (9% yield) of 4-bromo-5-(((2S)-1-((2-oxo-1-(1-(5-(trifluoromethyl)pyrazin-2-yl)piperidin-4-yl)pyrrolidin-3-yl)oxy)propan-2-yl)amino)pyridazin-3(2H)-one as a white solid. LCMS (ESI, m/z): 560.10 $[M+H]^+$; $^1H$ NMR (300 MHz, DMSO-$d_6$) δ 12.53 (s, 1H), 8.47 (s, 2H), 7.82 (s, 1H), 5.90-5.79 (m, 1H), 4.65-4.45 (m, 2H), 4.20-4.00 (m, 3H), 3.90-3.78 (m, 1H), 3.62-3.48 (m, 1H), 3.30-2.90 (m, 4H), 2.30-2.11 (m, 1H), 1.79-1.51 (m, 5H), 1.15 (d, J=6.5 Hz, 3H).

Example 13: 5-(((S)-1-(((S)-2-oxo-1-(1-(5-(trifluoromethyl)pyrazin-2-yl)piperidin-4-yl)pyrrolidin-3-yl)oxy)propan-2-yl)amino)-4-(trifluoromethyl)pyridazin-3(2H)-one (13A) and 5-(((S)-1-(((R)-2-oxo-1-(1-(5-(trifluoromethyl)pyrazin-2-yl)piperidin-4-yl)pyrrolidin-3-yl)oxy)propan-2-yl)amino)-4-(trifluoromethyl)pyridazin-3(2H)-one (13B)

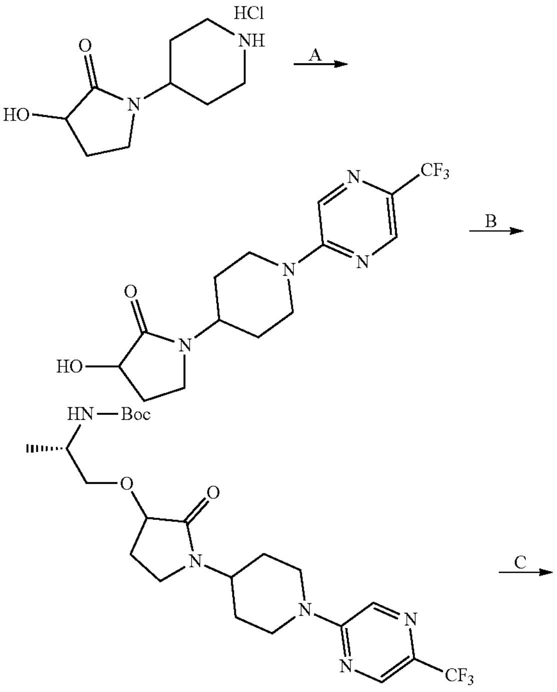

-continued

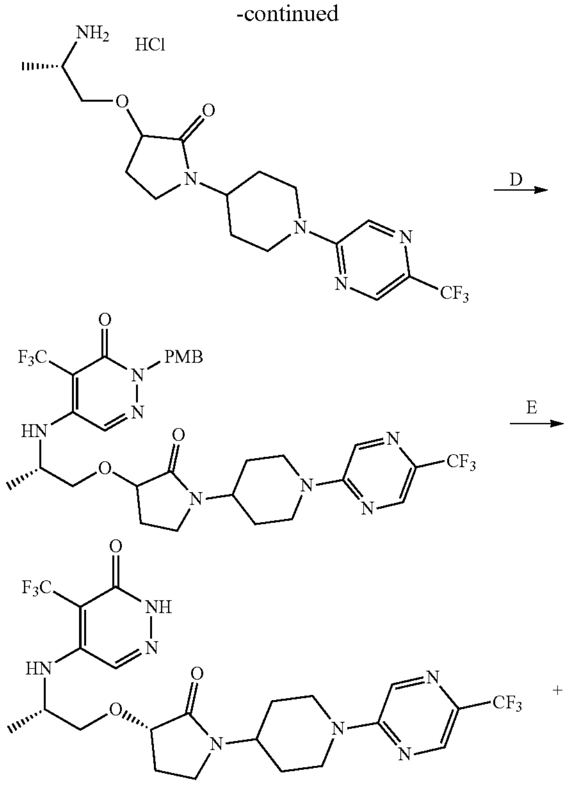

13A

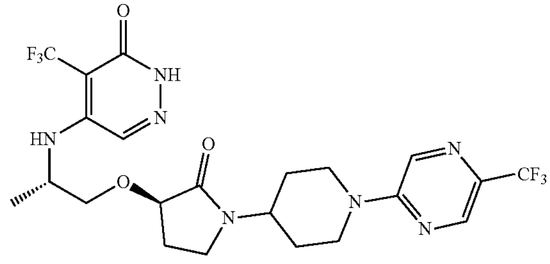

13B

Step A

A solution of 3-hydroxy-1-(piperidin-4-yl)pyrrolidin-2-one hydrochloride (717 mg, 3.26 mmol, 1.0 equiv; Intermediate I-3), 2-chloro-5-(trifluoromethyl)pyrazine (654 mg, 3.58 mmol, 1.1 equiv), and $K_2CO_3$ (900 mg, 6.51 mmol, 2.0 equiv) in DMF (8 mL) was stirred for 2 hours at 60° C. Water was added and the resulting solution was extracted with 3x10 mL of ethyl acetate. The organic layers were washed with 3x50 mL of brine, dried over anhydrous sodium sulfate and concentrated under vacuum. The crude product was applied onto a silica gel column and eluted with dichloromethane/methanol (97:3) to afford 702 mg (65% yield) of 3-hydroxy-1-(1-(5-(trifluoromethyl)pyrazin-2-yl)piperidin-4-yl)pyrrolidin-2-one as a yellow solid. LCMS (ES, m/z): 331.15 $[M+H]^+$.

Step B

To a solution of methyl 3-hydroxy-1-(1-(5-(trifluoromethyl)pyrazin-2-yl)piperidin-4-yl)pyrrolidin-2-one (680 mg, 2.06 mmol, 1.0 equiv) in DMF (6 mL) at 0° C. was added NaH (60% dispersion in oil, 82 mg, 2.06 mmol, 1.0 equiv) portionwise. The resulting solution was stirred for 15 minutes at that temperature and then tert-butyl (S)-4-methyl-1,2,3-oxathiazolidine-3-carboxylate 2,2-dioxide (537 mg, 2.27 mmol, 1.1 equiv) was added to the resulting solution. After stirring for 2 hours at 0° C., 5 mL of water was added and the mixture was concentrated under vacuum. The residue was applied onto a silica gel column eluting with ethyl acetate/petroleum ether (39:61) to afford 500 mg (50% yield) of tert-butyl ((2S)-1-((2-oxo-1-(1-(5-(trifluoromethyl)pyrazin-2-yl)piperidin-4-yl)pyrrolidin-3-yl)oxy)propan-2-yl)carbamate as a yellow oil. LCMS (ES, m/z): 488.25$[M+H]^+$.

Step C

A solution of tert-butyl ((2S)-1-((2-oxo-1-(1-(5-(trifluoromethyl)pyrazin-2-yl)piperidin-4-yl)pyrrolidin-3-yl)oxy)propan-2-yl)carbamate (300 mg, 0.62 mmol, 1.0 equiv) in 4N HCl in dioxane (5 mL) was stirred for 1 hour at room temperature and then concentrated under vacuum to afford 200 mg (84% yield) of 3-((S)-2-aminopropoxy)-1-(1-(5-(trifluoromethyl)pyrazin-2-yl)piperidin-4-yl)pyrrolidin-2-one hydrochloride as a yellow solid. LCMS (ES, m/z): 388.20$[M+H]^+$.

Step D

A solution of 3-((S)-2-aminopropoxy)-1-(1-(5-(trifluoromethyl)pyrazin-2-yl)piperidin-4-yl)pyrrolidin-2-one hydrochloride (150 mg, 0.39 mmol, 1.0 equiv), triethylamine (78 mg, 0.77 mmol, 2.0 equiv), and 5-chloro-2-(4-methoxybenzyl)-4-(trifluoromethyl)pyridazin-3(2H)-one (136 mg, 0.43 mmol, 1.1 equiv; Intermediate I-1) in EtOH (5.00 mL) was stirred for 1 hour at 60° C. The resulting mixture was concentrated and applied onto a silica gel column eluting with ethyl acetate/petroleum ether (85:15) to afford 160 mg (62% yield) of 2-(4-methoxybenzyl)-5-(((2S)-1-((2-oxo-1-(1-(5-(trifluoromethyl)pyrazin-2-yl)piperidin-4-yl)pyrrolidin-3-yl)oxy)propan-2-yl)amino)-4-(trifluoromethyl)pyridazin-3(2H)-one as white solid. (ES, m/z): 670.20 $[M+H]^+$.

Step E

A solution of 2-(4-methoxybenzyl)-5-(((2S)-1-((2-oxo-1-(1-(5-(trifluoromethyl)pyrazin-2-yl)piperidin-4-yl)pyrrolidin-3-yl)oxy)propan-2-yl)amino)-4-(trifluoromethyl)pyridazin-3(2H)-one (150 mg, 0.22 mmol, 1.0 equiv) in TFA (3.00 mL) at −10° C. was treated with triflic acid (0.3 mL) and stirred for 1 hour at −10° C. 5 mL of ice water was added and the pH value was adjusted to 8 with saturated aqueous $Na_2CO_3$. The resulting solution was extracted with 3x10 mL of ethyl acetate and the organics were combined, dried over anhydrous sodium sulfate and concentrated under vacuum. The crude product was purified by reverse phase chromatography to afford a mixture of isomers. The mixture was further purified by chiral prep-HPLC: (CHIRALPAK IG, 2.0*25 cm, Sum; Mobile Phase A: Hex:DCM=3:1 w/10 mM $NH_3$-MeOH, Mobile Phase B: EtOH; Flow rate: 16 mL/min; 50% B for 19 min; 220/254 nm) to afford the desired isomers. The relative stereochemistry of compounds was assigned by analogy to Example 10, based on the PARP7 potency of the more active diastereomer and in analogy to the Example 10B X-ray crystal structure.

Example 13 Isomer A (13A): 5-(((S)-1-(((S)-2-oxo-1-(1-(5-(trifluoromethyl)pyrazin-2-yl)piperidin-4-yl)pyrrolidin-3-yl)oxy)propan-2-yl)amino)-4-(trifluoromethyl)pyridazin-3(2H)-one (23 mg, 27% yield) as a white solid. LCMS (ESI, m/z): 550.20 $[M+H]^+$; $^1H$ NMR (300 MHz, DMSO-$d_6$) δ 12.45 (s, 1H), 8.47 (d, J=3.1 Hz, 2H), 7.92 (s, 1H), 6.45-6.32 (m, 1H), 4.59 (d, J=13.6 Hz, 2H), 4.18-4.07 (m, 3H), 3.84 (dd, J=10.0, 4.2 Hz, 1H), 3.60 (dd, J=10.0, 6.9 Hz, 1H), 3.25-3.19 (m, 1H), 3.18-3.04 (m, 3H), 2.25-2.17 (m, 1H), 1.80-1.55 (m, 5H), 1.18 (d, J=6.0 Hz, 3H). Chiral HPLC:

(CHIRALPAK IG-3, 4.6*50 mm, 3 um; Hex:DCM=3:1 w/ 0.1% DEA:EtOH=80:20; 1.0 mL/min, tR=2.423 min.)

Example 13 Isomer B (13B): 5-(((S)-1-(((R)-2-oxo-1-(1-(5-(trifluoromethyl)pyrazin-2-yl)piperidin-4-yl)pyrrolidin-3-yl)oxy)propan-2-yl)amino)-4-(trifluoromethyl)pyridazin-3(2H)-one (45 mg, 53% yield) as a white solid. LCMS (ESI, m/z): 550.20 $[M+H]^+$; 1H NMR (300 MHz, DMSO-$d_6$) δ 12.48 (s, 1H), 8.47 (d, J=3.9 Hz, 2H), 7.95 (s, 1H), 6.46-6.32 (m, 1H), 4.59 (d, J=13.4 Hz, 2H), 4.18-4.07 (m, 3H), 3.83 (dd, J=10.0, 6.6 Hz, 1H), 3.60 (dd, J=10.0, 6.9 Hz, 1H), 3.25-3.19 (m, 1H), 3.16-2.99 (m, 3H), 2.25-2.17 (m, 1H), 1.81-1.56 (m, 5H), 1.17 (d, J=6.4 Hz, 3H). Chiral HPLC: (CHIRALPAK IG-3, 4.6*50 mm, 3 um; Hex:DCM=3:1 w/ 0.1% DEA:EtOH=80:20; 1.0 mL/min, tR=3.085 min.)

Example 14: Synthesis of 6-(4-((S)-2-oxo-3-((S)-2-((6-oxo-5-(trifluoromethyl)-1,6-dihydropyridazin-4-yl)amino)propoxy)pyrrolidin-1-yl)piperidin-1-yl)nicotinonitrile (14A) and 6-(4-((R)-2-oxo-3-((S)-2-((6-oxo-5-(trifluoromethyl)-1,6-dihydropyridazin-4-yl)amino)propoxy)pyrrolidin-1-yl)piperidin-1-yl)nicotinonitrile (14B)

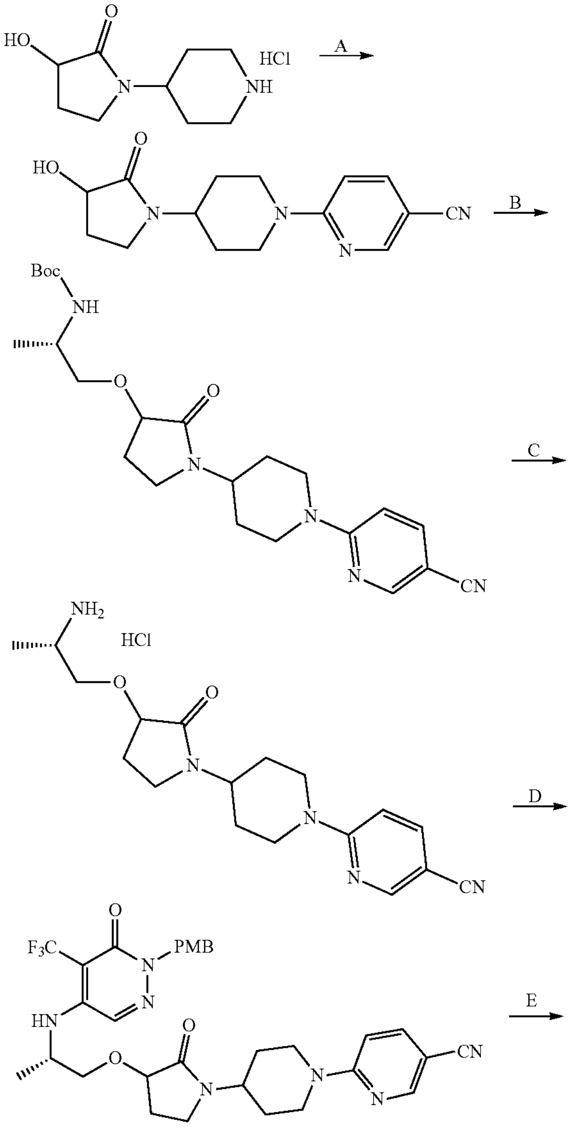

-continued

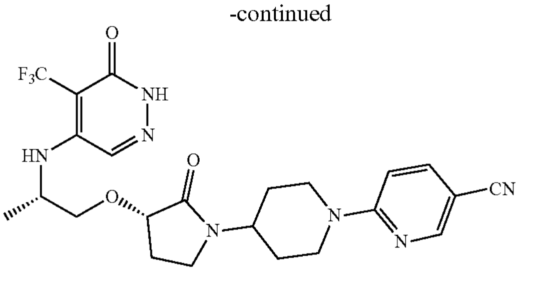

+

14A

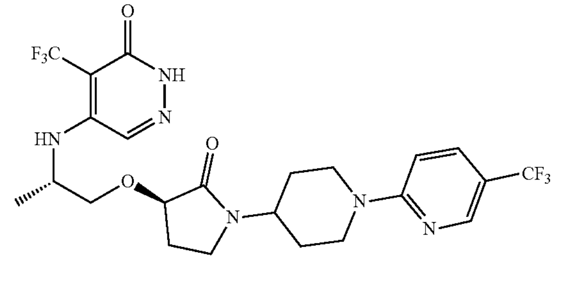

14B

Step A

A solution of 3-hydroxy-1-(piperidin-4-yl)pyrrolidin-2-one hydrochloride (700 mg, 3.17 mmol, 1.0 equiv; Intermediate I-3), 6-chloronicotinonitrile (440 mg, 3.18 mmol, 1.0 equiv), and $K_2CO_3$ (1.30 g, 9.41 mmol, 2.97 equiv) in DMF (5 mL) was stirred for 2 hours at 50° C. The resulting solution was diluted with 10 mL of water. The solids were collected by filtration to afford 530 mg (58% yield) of 6-(4-(3-hydroxy-2-oxopyrrolidin-1-yl)piperidin-1-yl)nicotinonitrile as a brown solid. LCMS (ESI, m/z): 287.20 $[M+H]^+$.

Step B

To a solution of 6-(4-(3-hydroxy-2-oxopyrrolidin-1-yl)piperidin-1-yl)nicotinonitrile (286 mg, 0.99 mmol, 1.0 equiv) in DMF (5 mL) was added NaH (60% suspension in mineral oil, 133 mg, 3.33 mmol, 3.3 equiv) at 0° C. and the solution was stirred for 15 minutes. tert-Butyl (S)-4-methyl-1,2,3-oxathiazolidine-3-carboxylate 2,2-dioxide (261 mg, 1.10 mmol, 1.10 equiv) was added and the solution was stirred for 2 hours at 0° C. Water was added and the resulting mixture was concentrated under vacuum. The crude product was purified by reverse phase chromatography eluting with $H_2O/CH_3CN$ (40/60) to afford 200 mg (45% yield) of tert-butyl ((2S)-1-((1-(1-(5-cyanopyridin-2-yl)piperidin-4-yl)-2-oxopyrrolidin-3-yl)oxy)propan-2-yl)carbamate as a yellow oil. LCMS (ESI, m/z): 444.30 $[M+H]^+$.

Step C

A solution of tert-butyl ((2S)-1-((1-(1-(5-cyanopyridin-2-yl)piperidin-4-yl)-2-oxopyrrolidin-3-yl)oxy)propan-2-yl) carbamate (180 mg, 1.0 equiv) in 4N HCl in dioxane (5 mL) was stirred for 2 hours at room temperature. The resulting mixture was concentrated under vacuum to afford 120 mg (78% yield) of 6-(4-(3-((S)-2-aminopropoxy)-2-oxopyrrolidin-1-yl)piperidin-1-yl)nicotinonitrile hydrochloride as a white solid. LCMS (ESI, m/z): 344.15 $[M+H]^+$.

Step D

A solution of 6-(4-(3-((S)-2-aminopropoxy)-2-oxopyrrolidin-1-yl)piperidin-1-yl)nicotinonitrile hydrochloride (110 mg, 0.32 mmol, 1.0 equiv), 5-chloro-2-(4-methoxybenzyl)-4-(trifluoromethyl)pyridazin-3(2H)-one (101 mg, 0.32 mmol, 1.0 equiv; Intermediate I-1), and N-methyl morpholine (97 mg, 0.96 mmol, 3.0 equiv) in MeCN (2 mL) was stirred for 12 hours at 60° C. The mixture was concentrated under vacuum and the residue was applied onto a silica gel column eluting with ethyl acetate/petroleum ether (9/1) to afford 70 mg (23% yield) of 6-(4-(3-((S)-2-((1-(4-methoxybenzyl)-6-oxo-5-(trifluoromethyl)-1,6-dihydropyridazin-4-yl)amino)propoxy)-2-oxopyrrolidin-1-yl)piperidin-1-yl) nicotinonitrile as a white solid. LCMS (ESI, m/z): 626.25 $[M+H]^+$.

Step E

A solution of 6-(4-(3-((S)-2-((1-(4-methoxybenzyl)-6-oxo-5-(trifluoromethyl)-1,6-dihydropyridazin-4-yl)amino) propoxy)-2-oxopyrrolidin-1-yl)piperidin-1-yl)nicotinonitrile (40 mg, 0.064 mmol, 1.0 equiv) in TFA (3 mL) at 0° C. was treated with trifluoromethanesulfonic acid (0.3 mL) and stirred for 1 hour at that temperature. 10 mL of ice water was added and the pH value of the solution was adjusted to 5-6 with saturated aqueous $Na_2CO_3$. The resulting solution was extracted with 3×10 mL of ethyl acetate. The organic layers were combined, dried over anhydrous sodium sulfate and concentrated. The crude product was purified by reverse phase chromatography eluting with $H_2O/CH_3CN$ (60/40) to afford a mixture of isomers. The product was further purified by chiral prep HPLC with the following conditions: (CHIRALPAK IA, 2*25 cm, 5 um; mobile phase A: Hex: EtOH=1:1 w/8 mmol/L $NH_3$-MeOH, mobile phase B: EtOH; flow rate: 16 mL/min; 50% B: for 18 min; 220/254 nm) to afford the separated isomers. The relative stereochemistry of compounds was assigned by analogy to Example 10, based on the PARP7 potency of the more active diastereomer and in analogy to the Example 10B X-ray crystal structure.

Example 14 Isomer A (14A): 6-(4-((S)-2-oxo-3-((S)-2-((6-oxo-5-(trifluoromethyl)-1,6-dihydropyridazin-4-yl) amino)propoxy)pyrrolidin-1-yl)piperidin-1-yl)nicotinonitrile (11 mg, 33% yield) as a white solid. LCMS (ESI, m/z): 506.20 $[M+H]^+$; $^1$H-NMR (Methanol-$d_4$, 400 MHz) δ 8.40 (s, 1H), 7.98 (s, 1H), 7.72 (dd, J=9.1, 2.4 Hz, 1H), 6.90 (dd, J=9.2, 0.8 Hz, 1H), 4.64 (m, J=13.5 Hz, 2H), 4.19-4.10 (m, 3H), 3.99 (dd, J=9.8, 3.8 Hz, 1H), 3.63 (dd, J=9.8, 6.8 Hz, 1H), 3.38 (dd, J=9.7, 3.6 Hz, 1H), 3.29-3.21 (m, 2H), 3.10-2.98 (m, 2H), 2.42-2.29 (m, 1H), 2.42-2.29 (m, 1H), 1.92-1.79 (m, 1H), 1.78-1.65 (m, 4H), 1.30 (d, J=6.6 Hz, 3H). Chiral HPLC: (CHIRALPAK IA-3, 4.6*50 mm, 3 um; Hex w/ 0.1% DEA:EtOH=50:50; Flow rate: 1 mL/min; tR=2.167 min).

Example 14 Isomer B (14B): 6-(4-((R)-2-oxo-3-((S)-2-((6-oxo-5-(trifluoromethyl)-1,6-dihydropyridazin-4-yl) amino)propoxy)pyrrolidin-1-yl)piperidin-1-yl)nicotinonitrile (14 mg, 43% yield) as a white solid. LCMS (ESI, m/z): 506.20 $[M+H]^+$; $^1$H NMR (400 MHz, Methanol-$d_4$) δ 8.40 (dd, J=2.4, 0.7 Hz, 1H), 8.00 (s, 1H), 7.72 (dd, J=9.1, 2.4 Hz, 1H), 6.90 (dd, J=9.2, 0.8 Hz, 1H), 4.64 (m, J=13.5 Hz, 2H), 4.19-4.10 (m, 3H), 3.99 (dd, J=9.8, 3.8 Hz, 1H), 3.63 (dd, J=9.8, 6.8 Hz, 1H), 3.38 (dd, J=9.7, 3.6 Hz, 1H), 3.29-3.21 (m, 2H), 3.10-2.98 (m, 2H), 2.42-2.29 (m, 1H), 1.92-1.79 (m, 1H), 1.78-1.65 (m, 4H), 1.30 (d, J=6.6 Hz, 3H). Chiral HPLC: (CHIRALPAK IA-3, 4.6*50 mm, 3 um; Hex w/ 0.1% DEA:EtOH=50:50; Flow rate: 1 mL/min; tR=3.159 min).

Example 15: Synthesis of 5-(((S)-1-(((S)-1-(1-(5-(difluoromethyl)pyrimidin-2-yl)piperidin-4-yl)-2-oxopyrrolidin-3-yl)oxy)propan-2-yl)amino)-4-(trifluoromethyl)pyridazin-3(2H)-one (15A) and 5-(((S)-1-(((R)-1-(1-(5-(difluoromethyl)pyrimidin-2-yl)piperidin-4-yl)-2-oxopyrrolidin-3-yl)oxy)propan-2-yl)amino)-4-(trifluoromethyl)pyridazin-3(2H)-one (15B)

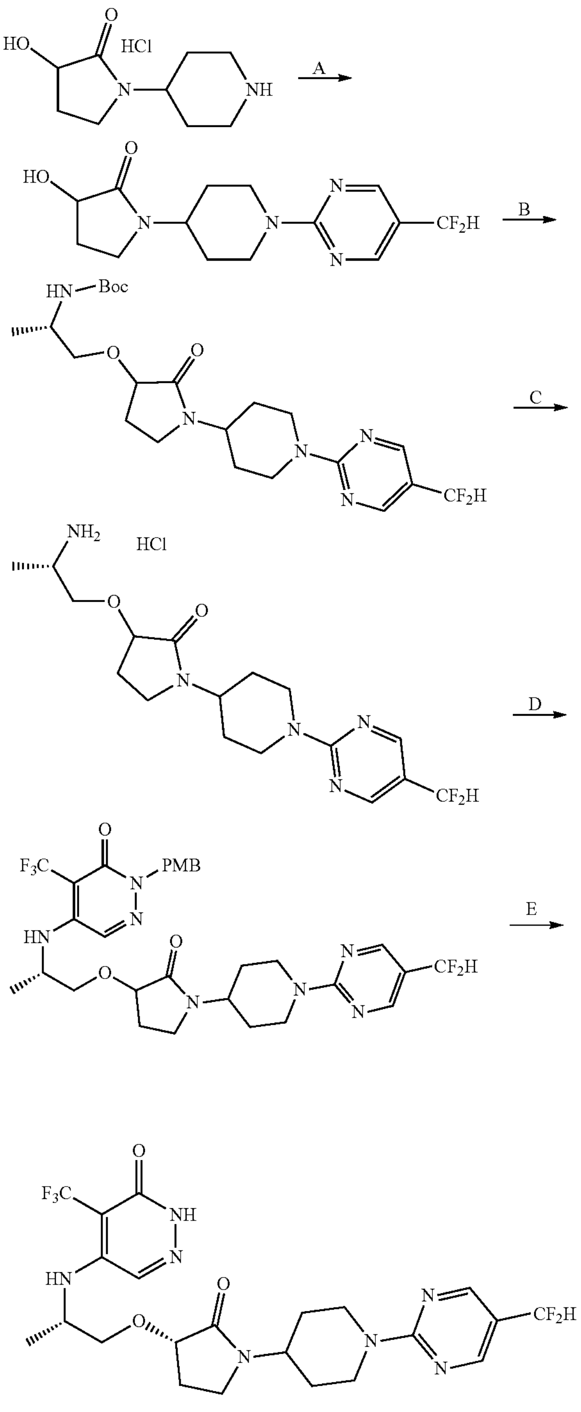

15A

-continued

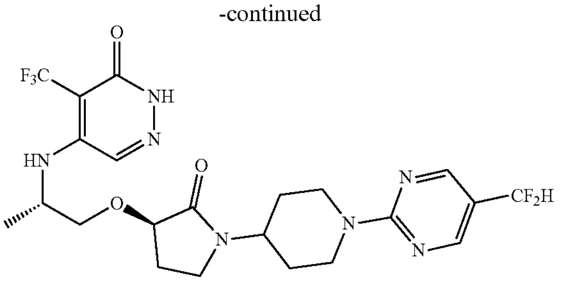

15B

Step A

A solution of 3-hydroxy-1-(piperidin-4-yl)pyrrolidin-2-one hydrochloride (1.20 g, 5.437 mmol, 1.99 equiv; Intermediate I-3), 2-chloro-5-(difluoromethyl)pyrimidine (450 mg, 2.735 mmol, 1.00 equiv) and $K_2CO_3$ (2.27 g, 16.43 mmol, 6.01 equiv) in DMF (15 mL) was stirred for hours at 80° C. After filtration, the filtrate was concentrated under vacuum and the crude product was applied onto a reverse phase column eluting with $H_2O/CH_3CN$ (1:1) to afford 450 mg (46% yield) of 1-(1-(5-(difluoromethyl)pyrimidin-2-yl) piperidin-4-yl)-3-hydroxypyrrolidin-2-one as a yellow solid. LCMS (ESI, m/z): 313.20 $[M+H]^+$.

Step B

To a solution of 1-(1-(5-(difluoromethyl)pyrimidin-2-yl) piperidin-4-yl)-3-hydroxypyrrolidin-2-one (150 mg, 0.480 mmol, 1.00 equiv) in DMF (10 mL) was added NaH (120 mg, 3.00 mmol, 6.25 equiv, 60% dispersion in mineral oil) at 0° C. and stirred for 10 min. To the solution was added tert-butyl (S)-4-methyl-1,2,3-oxathiazolidine-3-carboxylate 2,2-dioxide (177 mg, 0.746 mmol, 1.55 equiv) at 0° C. The resulting solution was stirred for 2 hours at room temperature. The reaction was then quenched by the addition of 0.2 mL of 20% aqueous sodium carbonate. The solution was concentrated and the crude product was applied onto a reverse phase column eluting with $H_2O/CH_3OH$ (40/60) to afford 224 mg (50% yield) of tert-butyl ((2S)-1-((1-(1-(5-(difluoromethyl)pyrimidin-2-yl)piperidin-4-yl)-2-oxopyrrolidin-3-yl)oxy)propan-2-yl)carbamate as an orange solid. LCMS (ESI, m/z): 470.15 $[M+H]^+$.

Step C

A solution of tert-butyl ((2S)-1-((1-(1-(5-(difluoromethyl) pyrimidin-2-yl)piperidin-4-yl)-2-oxopyrrolidin-3-yl)oxy) propan-2-yl)carbamate (250 mg, 0.532 mmol, 1.00 equiv) in 4N HCl in dioxane (5 mL) was stirred for 2 hours at room temperature. The resulting mixture was concentrated to afford 220 mg (71% yield) of 3-((S)-2-aminopropoxy)-1-(1-(5-(difluoromethyl)pyrimidin-2-yl)piperidin-4-yl)pyrrolidin-2-one hydrochloride as an orange solid. LCMS (ESI, m/z): 370.15$[M+H]^+$.

Step D

A solution of 3-[(2S)-2-aminopropoxy]-1-[1-[5-(difluoromethyl)pyrimidin-2-yl]piperidin-4-yl]pyrrolidin-2-one hydrochloride (220 mg, 0.542 mmol, 1.00 equiv), 5-chloro-2-[(4-methoxyphenyl)methyl]-4-(trifluoromethyl) pyridazin-3-one (189 mg, 0.593 mmol, 1.09 equiv) and TEA (180 mg, 1.779 mmol, 3.28 equiv) in EtOH (5 mL) was stirred for 3 hours at 60° C. The mixture was concentrated and diluted with 100 mL of ethyl acetate and washed with 2×20 mL of saturated aqueous ammonium chloride. The aqueous layers were combined and extracted with 2×50 mL of ethyl acetate. The organics were combined, dried over anhydrous sodium sulfate and concentrated. The residue was applied onto a silica gel column eluting with 100% ethyl acetate to afford 107 mg (30% yield) of 5-(((2S)-1-((1-(1-(5-(difluoromethyl)pyrimidin-2-yl)piperidin-4-yl)-2-oxopyrrolidin-3-yl)oxy)propan-2-yl)amino)-2-(4-methoxybenzyl)-4-(trifluoromethyl)pyridazin-3(2H)-one as a yellow solid. LCMS (ESI, m/z): 652.50 $[M+H]^+$.

Step E

A solution of 5-(((2S)-1-((1-(1-(5-(difluoromethyl)pyrimidin-2-yl)piperidin-4-yl)-2-oxopyrrolidin-3-yl)oxy)propan-2-yl)amino)-2-(4-methoxybenzyl)-4-(trifluoromethyl) pyridazin-3(2H)-one (100 mg, 0.153 mmol, 1.00 equiv) in trifluoromethanesulfonic acid/TFA=1:10 (1.5 mL) was stirred for 2 hours at room temperature. The resulting solution was diluted with 15 mL of $H_2O$. The pH value of the solution was adjusted to 7-8 with 20% aqueous sodium carbonate. The resulting solution was extracted with 2×20 mL of ethyl acetate. The organic layers were combined, dried over anhydrous sodium sulfate and concentrated. The crude product was purified by reverse phase chromatography eluting with $H_2O/CH_3CN$. The product was further purified by chiral prep-HPLC (CHIRAL ART Cellulose-SB, 2*25 cm, Sum; Mobile Phase A: Hex w/ 8 mmol/L $NH_3$-MeOH, Mobile Phase B: EtOH; Flow rate: 20 mL/min; Gradient: 50% B for 16 min; 220/254 nm). The relative stereochemistry of compounds was assigned by analogy to Example 10, based on the PARP7 potency of the more active diastereomer and in analogy to the Example 10B X-ray crystal structure.

Example 15 Isomer A (15A): 5-(((S)-1-(((S)-1-(1-(5-(difluoromethyl)pyrimidin-2-yl)piperidin-4-yl)-2-oxopyrrolidin-3-yl)oxy)propan-2-yl)amino)-4-(trifluoromethyl) pyridazin-3(2H)-one (16 mg, 32% yield, off-white solid). LCMS (ESI, m/z): 532.25 $[M+H]^+$; $^1H$ NMR (400 MHz, DMSO-$d_6$) δ 12.44 (s, 1H), 8.54 (s, 2H), 7.91 (s, 1H), 6.96 (t, J=55.5 Hz, 1H), 6.41-6.32 (m, 1H), 4.86-4.75 (m, 2H), 4.21-4.14 (m, 1H), 4.08-4.04 (m, 2H), 3.83 (dd, J=10.0, 4.3 Hz, 1H), 3.59 (dd, J=10.1, 7.0 Hz, 1H), 3.25-3.19 (m, 1H), 3.15-3.08 (m, 1H), 3.02-2.95 (m, 2H), 2.25-2.16 (m, 1H), 1.73-1.48 (m, 5H), 1.16 (d, J=6.5 Hz, 3H). Chiral HPLC: CHIRAL Cellulose-SB, 0.46*10 cm, 3 um; Hex w/ 0.1% DEA:EtOH=50:50; Flow rate: 1.0 mL/min; rT=2.642 min.

Example 15 Isomer B (15B): 5-(((S)-1-(((R)-1-(1-(5-(difluoromethyl)pyrimidin-2-yl)piperidin-4-yl)-2-oxopyrrolidin-3-yl)oxy)propan-2-yl)amino)-4-(trifluoromethyl) pyridazin-3(2H)-one (25 mg, 50% yield, off-white solid). LCMS (ESI, m/z): 532.20 $[M+H]^+$; $^1H$ NMR (400 MHz, DMSO-$d_6$) δ 12.46 (s, 1H), 8.54 (s, 2H), 7.94 (s, 1H), 6.96 (t, J=55.5 Hz, 1H), 6.41-6.32 (m, 1H), 4.86-4.75 (m, 2H), 4.21-4.14 (m, 1H), 4.08-4.03 (m, 2H), 3.83 (dd, J=10.0, 4.3 Hz, 1H), 3.59 (dd, J=10.1, 7.0 Hz, 1H), 3.25-3.20 (m, 1H), 3.15-3.09 (m, 1H), 3.03-2.95 (m, 2H), 2.25-2.17 (m, 1H), 1.73-1.66 (m, 1H), 1.61-1.48 (m, 4H), 1.17 (d, J=6.5 Hz, 3H). Chiral HPLC: CHIRAL Cellulose-SB, 0.46*10 cm, 3 um; Hex w/ 0.1% DEA:EtOH=50:50; Flow rate: 1.0 mL/min; rT=4.415 min.

Example 16: Synthesis of 5-(((S)-1-(((R)-1-(1-(5-chloropyrimidin-2-yl)piperidin-4-yl)-2-oxopyrrolidin-3-yl)oxy)propan-2-yl)amino)-4-(trifluoromethyl) pyridazin-3(2H)-one

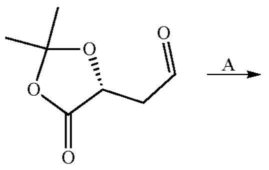

-continued

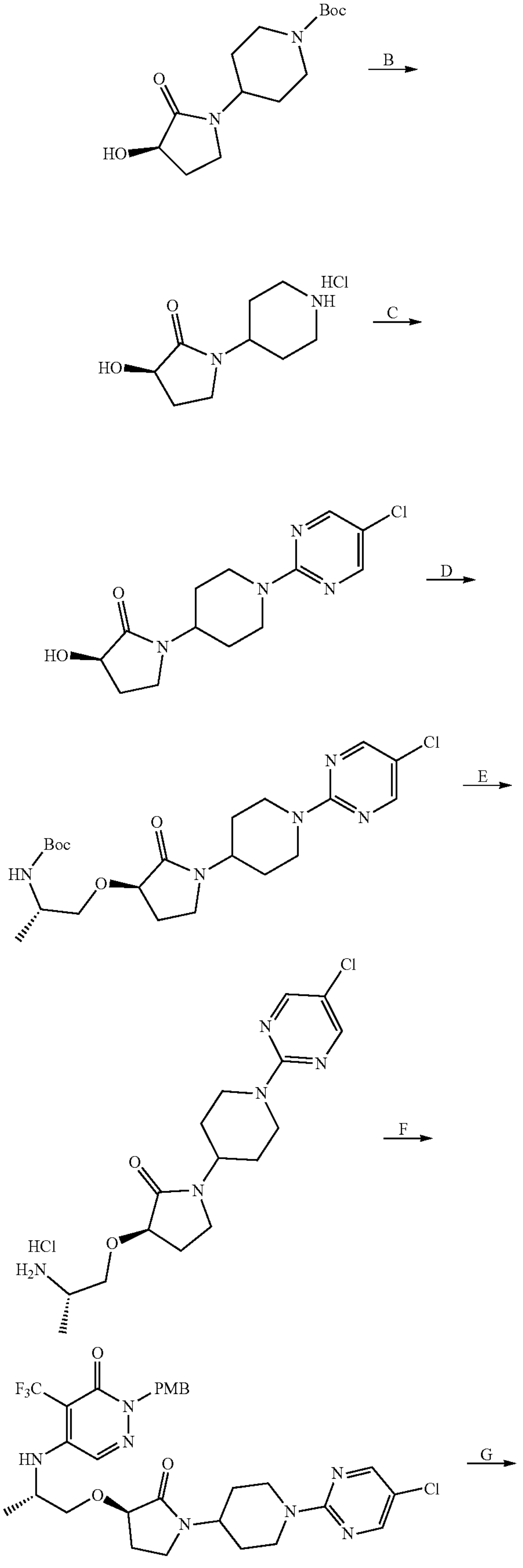

-continued

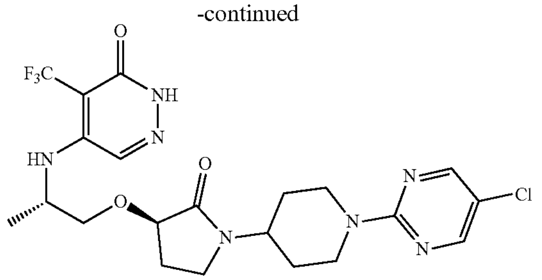

Step A

A solution of (R)-2-(2,2-dimethyl-5-oxo-1,3-dioxolan-4-yl)acetaldehyde (3.47 g, 21.941 mmol, 1.00 equiv), tert-butyl 4-aminopiperidine-1-carboxylate (6.40 g, 31.955 mmol, 1.46 equiv), and acetic acid (2.64 g, 43.962 mmol, 2.00 equiv) in DCM (200 mL) was stirred for 15 minutes. $NaBH(AcO)_3$ (14.00 g, 66.042 mmol, 3.01 equiv) was added and the solution was stirred for another 2 hours at room temperature. 300 mL of saturated aqueous $NaHCO_3$ was added. The layers were separated and the aqueous layer was extracted with 3×200 mL of dichloromethane. The organic layers were combined, dried over anhydrous sodium sulfate and concentrated under vacuum. The crude product was applied onto a silica gel column eluting with ethyl acetate/petroleum ether (75/25) to afford 2.9 g (46% yield) of tert-butyl (R)-4-(3-hydroxy-2-oxopyrrolidin-1-yl)piperidine-1-carboxylate as a yellow solid. LCMS (ESI, m/z): 285.15 $[M+H]^+$.

Step B

A solution of tert-butyl (R)-4-(3-hydroxy-2-oxopyrrolidin-1-yl)piperidine-1-carboxylate (2.90 g, 10.2 mmol, 1.00 equiv) in 1,4-dioxane (10 mL) and 4N HCl in dioxane (30 mL) was stirred for 15 hours at room temperature. The solution was concentrated to afford 2.2 g (98% yield) of (R)-3-hydroxy-1-(piperidin-4-yl)pyrrolidin-2-one hydrochloride as a yellow solid. LCMS (ESI, m/z): 185.15 $[M+H]^+$.

Step C

A solution of (R)-3-hydroxy-1-(piperidin-4-yl)pyrrolidin-2-one hydrochloride (700 mg, 3.172 mmol, 1.00 equiv), $K_2CO_3$ (1310 mg, 9.479 mmol, 2.99 equiv) and 2,5-dichloropyrimidine (492 mg, 3.303 mmol, 1.04 equiv) in DMF (5 mL) was stirred for 4 hours at 80° C. 25 mL of water was added and the resulting solution was extracted with 3×20 mL dichloromethane. The organic layers were combined, dried over anhydrous sodium sulfate, filtered and concentrated under vacuum. The crude product was applied onto a silica gel column eluting with dichloromethane/MeOH (10:1) to afford 750 mg (80% yield) of (R)-1-(1-(5-chloropyrimidin-2-yl)piperidin-4-yl)-3-hydroxypyrrolidin-2-one as a light yellow solid. LCMS (ESI, m/z): 297.05 $[M+H]^+$.

Step D

To a solution of (R)-1-(1-(5-chloropyrimidin-2-yl)piperidin-4-yl)-3-hydroxypyrrolidin-2-one (350 mg, 1.179 mmol, 1.00 equiv) in DMF (6 mL) at 0° C. was added NaH (60% dispersion in mineral oil, 236 mg, 5.901 mmol, 5 equiv) portionwise. To the solution was added tert-butyl (S)-4-methyl-1,2,3-oxathiazolidine-3-carboxylate 2,2-dioxide (420 mg, 1.770 mmol, 1.50 equiv). The resulting solution was allowed to warm to room temperature. 0.5 mL of water was added and the solvent was removed in vacuo. The crude product was purified by reverse phase chromatography eluting with $H_2O/CH_3OH$ (7/3) to afford 490 mg (82% yield) of tert-butyl ((S)-1-(((R)-1-(1-(5-chloropyrimidin-2- yl)piperidin-4-yl)-2-oxopyrrolidin-3-yl)oxy)propan-2-yl) carbamate as a light yellow solid. LCMS (ESI, m/z): 454.15 $[M+H]^+$.

Step E

A solution of tert-butyl ((S)-1-(((R)-1-(1-(5-chloropyrimidin-2-yl)piperidin-4-yl)-2-oxopyrrolidin-3-yl)oxy)propan-2-yl)carbamate (490 mg, 1.079 mmol, 1.00 equiv) in 1,4-dioxane (10.00 mL) and 4N HCl in dioxane (5.00 mL) was stirred for 2 hours at room temperature. The resulting mixture was concentrated to afford 420 mg (90% yield) of (R)-3-((S)-2-aminopropoxy)-1-(1-(5-chloropyrimidin-2-yl)piperidin-4-yl)pyrrolidin-2-one hydrochloride as a light yellow solid. LCMS (ESI, m/z): 354.15$[M+H]^+$.

Step F

A solution of (R)-3-((S)-2-aminopropoxy)-1-(1-(5-chloropyrimidin-2-yl)piperidin-4-yl)pyrrolidin-2-one hydrochloride (210 mg, 0.538 mmol, 1.00 equiv), TEA (190 mg, 1.878 mmol, 3.49 equiv) and 5-chloro-2-[(4-methoxyphenyl)methyl]-4-(trifluoromethyl)pyridazin-3-one (205 mg, 0.643 mmol, 1.20 equiv) in EtOH (5 mL) was stirred for 4 hours at 50° C. The mixture was concentrated, diluted with 60 mL of ethyl acetate, and washed with 2×20 mL of saturated aqueous $NH_4Cl$. The layers were separated and the aqueous layer was extracted with 2×50 mL of ethyl acetate. The organic layers were combined, dried over anhydrous sodium sulfate and concentrated. The residue was applied onto a silica gel column eluting with ethyl acetate/petroleum ether (3/1) to afford 240 mg (70% yield) of 5-(((S)-1-(((R)-1-(1-(5-chloropyrimidin-2-yl)piperidin-4-yl)-2-oxopyrrolidin-3-yl)oxy)propan-2-yl)amino)-2-(4-methoxybenzyl)-4-(trifluoromethyl)pyridazin-3(2H)-one as a white solid. LCMS (ESI, m/z): 652.50 $[M+H]^+$.

Step G

A solution of 5-(((S)-1-(((R)-1-(1-(5-chloropyrimidin-2-yl)piperidin-4-yl)-2-oxopyrrolidin-3-yl)oxy)propan-2-yl)amino)-2-(4-methoxybenzyl)-4-(trifluoromethyl)pyridazin-3(2H)-one (230 mg, 0.362 mmol, 1.00 equiv) in trifluoromethanesulfonic acid/TFA=1:10 (2.50 mL) was stirred for 2 hour at room temperature. 15 mL of water was added and the pH value of the solution was adjusted to 7-8 with 20% aqueous sodium bicarbonate. The solution was extracted with 3×20 mL of ethyl acetate. The organic layers were combined, dried over anhydrous sodium sulfate and concentrated. The crude product was purified by reverse phase chromatography eluting with $H_2O/CH_3CN$ to afford 99 mg of 5-(((S)-1-(((R)-1-(1-(5-chloropyrimidin-2-yl)piperidin-4-yl)-2-oxopyrrolidin-3-yl)oxy)propan-2-yl)amino)-4-(trifluoromethyl)pyridazin-3(2H)-one. LCMS (ESI, m/z): 516.15 $[M+H]^+$; $^1H$ NMR (400 MHz, DMSO-$d_6$) δ 12.47 (s, 1H), 8.42 (s, 2H), 7.95 (s, 1H), 6.36-6.33 (m, 1H), 4.70-4.67 (m, 2H), 4.18-4.02 (m, 3H), 3.83 (dd, J=10.0, 6.6 Hz, 1H), 3.61 (dd, J=10.0, 4.7 Hz, 1H), 3.34-3.21 (m, 1H), 3.14-3.11 (m, 1H), 2.98-2.92 (m, 2H), 2.25-2.23 (m, 1H), 1.74-1.69 (m, 1H), 1.60-1.51 (m, 4H), 1.17 (d, J=6.5 Hz, 3H).

Example 17: Synthesis of 6-(4-((S)-3-((S)-3-methoxy-2-((6-oxo-5-(trifluoromethyl)-1,6-dihydropyridazin-4-yl)amino)propoxy)-2-oxopyrrolidin-1-yl)piperidin-1-yl)nicotinonitrile (17A) and 6-(4-((R)-3-((S)-3-methoxy-2-((6-oxo-5-(trifluoromethyl)-1,6-dihydropyridazin-4-yl)amino)propoxy)-2-oxopyrrolidin-1-yl)piperidin-1-yl)nicotinonitrile (17B)

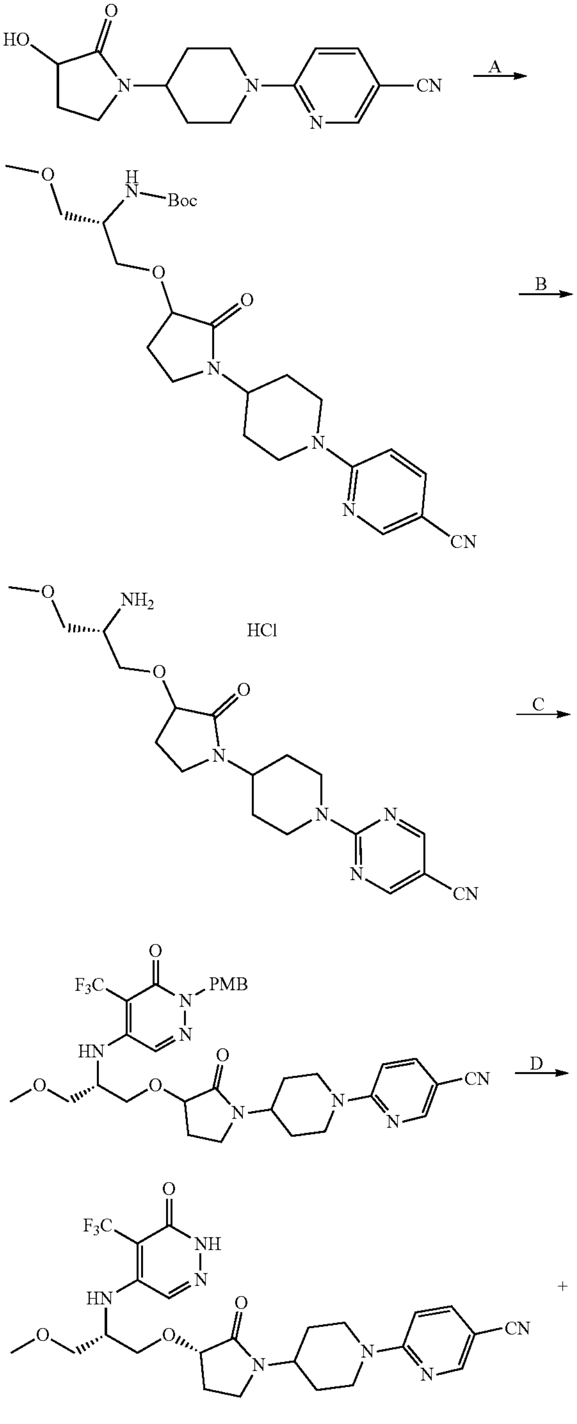

17A

-continued

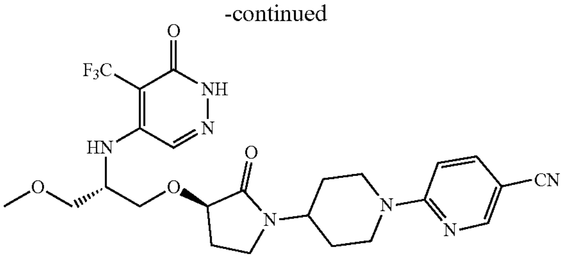

17B

Step A

To a solution of 6-(4-(3-hydroxy-2-oxopyrrolidin-1-yl)piperidin-1-yl)nicotinonitrile (300 mg, 1.048 mmol, 1.00 equiv; Example 14, Step A) in DMF (5 mL) was added NaH (126 mg, 5.239 mmol, 5 equiv) at 0° C. The solution was stirred for 10 min at 0° C. and then tert-butyl (S)-4-(methoxymethyl)-1,2,3-oxathiazolidine-3-carboxylate 2,2-dioxide (336 mg, 1.26 mmol, 1.2 equiv) was added. The solution was stirred for another 1 hour at 0° C. 20 mL of methanol was added and the solution was concentrated. The crude product was purified by C18 reverse phase chromatography eluting with water/ACN (30/70) to afford 121 mg (24% yield) of tert-butyl ((2S)-1-((1-(1-(5-cyanopyridin-2-yl)piperidin-4-yl)-2-oxopyrrolidin-3-yl)oxy)-3-methoxypropan-2-yl)carbamate as a yellow solid. LCMS (ESI, m/z): 474.25 [M+H]$^+$.

Step B

A solution of tert-butyl ((2S)-1-((1-(1-(5-cyanopyridin-2-yl)piperidin-4-yl)-2-oxopyrrolidin-3-yl)oxy)-3-methoxypropan-2-yl)carbamate (121 mg, 0.256 mmol, 1.00 equiv) in 4N HCl in dioxane (8 mL) was stirred for 1.5 hours at room temperature. The mixture was concentrated under vacuum to afford 89 mg (93% yield) of 6-(4-(3-((S)-2-amino-3-methoxypropoxy)-2-oxopyrrolidin-1-yl)piperidin-1-yl)nicotinonitrile hydrochloride as a yellow oil. LCMS (ESI, m/z): 374.10 [M+H]$^+$.

Step C

A solution of 5-chloro-2-(4-methoxybenzyl)-4-(trifluoromethyl)pyridazin-3(2H)-one (61 mg, 0.191 mmol, 1.00 equiv; Intermediate I-1), 6-(4-(3-((S)-2-amino-3-methoxypropoxy)-2-oxopyrrolidin-1-yl)piperidin-1-yl)nicotinonitrile hydrochloride (71 mg, 0.191 mmol, 1.0 equiv) and TEA (58 mg, 0.574 mmol, 3.0 equiv) in ethanol (4.00 mL) was stirred for 4 hours at 70° C. in an oil bath. The mixture was concentrated under vacuum and the crude product was applied onto a silica gel column eluting with ethyl acetate/petroleum ether (10:1) to afford 60 mg (48% yield) of 6-(4-(3-((S)-3-methoxy-2-((1-(4-methoxybenzyl)-6-oxo-5-(trifluoromethyl)-1,6-dihydropyridazin-4-yl)amino)propoxy)-2-oxopyrrolidin-1-yl)piperidin-1-yl)nicotinonitrile as a yellow oil. LCMS (ESI, m/z): 656.20 [M+H]$^+$.

Step D

A solution of 6-(4-(3-((S)-3-methoxy-2-((1-(4-methoxybenzyl)-6-oxo-5-(trifluoromethyl)-1,6-dihydropyridazin-4-yl)amino)propoxy)-2-oxopyrrolidin-1-yl)piperidin-1-yl)nicotinonitrile (54 mg, 0.082 mmol, 1.00 equiv) in TFA (2 mL) at 0° C. was treated with triflic acid (0.2 mL) and stirred for 30 min at the same temperature. 10 mL of ice water was added and the pH value of the solution was adjusted to 8 with 40% aqueous sodium hydroxide. The resulting solution was extracted with 3×20 mL of ethyl acetate. The organic layers were combined, dried over magnesium sulfate, filtered, and concentrated under vacuum. The crude product was purified by reverse phase chromatography eluting with water/ACN (60/40) to afford a mixture of isomers. The diastereomers were separated by chiral prep-HPLC with the following conditions: CHIRALPAK IF, 2*25 cm, 5 um; Mobile Phase A: Hex w/ 8 mM $NH_3$-MeOH, Mobile Phase B: EtOH; Flow rate: 20 mL/min; Gradient: 50% B for 22 min; 220/254 nm.) The relative stereochemistry of compounds was assigned by analogy to Example 10, based on the PARP7 potency of the more active diastereomer and in analogy to the Example 10B X-ray crystal structure.

Example 17 Isomer A (17A): 6-(4-((S)-3-((S)-3-methoxy-2-((6-oxo-5-(trifluoromethyl)-1,6-dihydropyridazin-4-yl)amino)propoxy)-2-oxopyrrolidin-1-yl)piperidin-1-yl)nicotinonitrile (5.3 mg, 12% yield, white solid). LCMS (ESI, m/z): 536.20[M+H]$^+$; $^1$H NMR (400 MHz, DMSO-$d_6$) δ 12.48 (s, 1H), 8.47 (s, 1H), 7.93 (s, 1H), 7.83 (d, J=9.1 Hz, 1H), 6.96 (d, J=9.2 Hz, 1H), 6.33-6.28 (m, 1H), 4.58-4.50 (m, 2H), 4.33-4.26 (m, 1H), 4.09-4.01 (m, 2H), 3.92-3.87 (m, 1H), 3.69-3.63 (m, 1H), 3.48 (d, J=5.7 Hz, 2H), 3.28-3.27 (m, 3H), 3.23-3.19 (m, 1H), 3.15-3.08 (m, 1H), 3.03-2.95 (m, 2H), 2.27-2.19 (m, 1H), 1.73-1.48 (m, 5H). Chiral HPLC: CHIRALPAK IF-3, 4.6*50 mm, 3 μm; Hex w/ 0.1% DEA:EtOH=50:50; Flow rate: 1 mL/min; rT=2.405 min.

Example 17 Isomer B (17B): 6-(4-((R)-3-((S)-3-methoxy-2-((6-oxo-5-(trifluoromethyl)-1,6-dihydropyridazin-4-yl)amino)propoxy)-2-oxopyrrolidin-1-yl)piperidin-1-yl)nicotinonitrile (9 mg, 20% yield, white solid). LCMS (ESI, m/z): 536.20 [M+H]$^+$; $^1$H NMR (400 MHz, DMSO-$d_6$) δ 12.50 (s, 1H), 8.47 (s, 1H), 7.96 (s, 1H), 7.83 (d, J=9.1 Hz, 1H), 6.96 (d, J=9.0 Hz, 1H), 6.33-6.28 (m, 1H), 4.58-4.50 (m, 2H), 4.33-4.26 (m, 1H), 4.11-4.01 (m, 2H), 3.92-3.87 (m, 1H), 3.69-3.63 (m, 1H), 3.49 (d, J=5.3 Hz, 2H), 3.29-3.26 (m, 3H), 3.23-3.19 (m, 1H), 3.15-3.08 (m, 1H), 3.03-2.94 (m, 2H), 2.27-2.18 (m, 1H), 1.73-1.48 (m, 5H). Chiral HPLC: CHIRALPAK IF-3, 4.6*50 mm, 3 μm; Hex w/ 0.1% DEA:EtOH=50:50; Flow rate: 1 mL/min; rT=3.678 min.

Example 18 was synthesized according to the procedures described for the synthesis of 6-(4-((S)-3-((S)-3-methoxy-2-((6-oxo-5-(trifluoromethyl)-1,6-dihydropyridazin-4-yl)amino)propoxy)-2-oxopyrrolidin-1-yl)piperidin-1-yl)nicotinonitrile and 6-(4-((R)-3-((S)-3-methoxy-2-((6-oxo-5-(trifluoromethyl)-1,6-dihydropyridazin-4-yl)amino)propoxy)-2-oxopyrrolidin-1-yl)piperidin-1-yl)nicotinonitrile (see Example 17) using appropriate building blocks and modified reaction conditions (such as reagent ratio, temperature, coupling conditions, and reaction time) as needed. The relative stereochemistry of compounds was assigned by analogy to Example 10, based on the PARP7 potency of the more active diastereomer and in analogy to the Example 10B X-ray crystal structure.

| Example No. | Structure | Analytical Data |
|---|---|---|
| 18A | 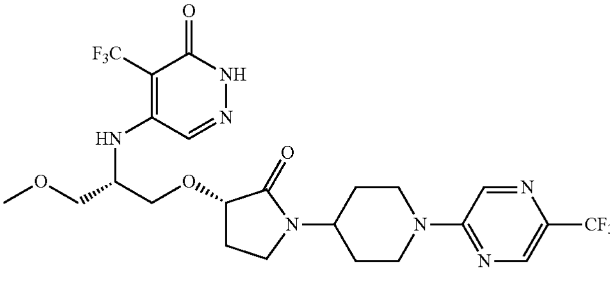 5-(((S)-1-methoxy-3-(((S)-2-oxo-1-(1-(5-(trifluoromethyl)pyrazin-2-yl)piperidin-4-yl)pyrrolidin-3-yl)oxy)propan-2-yl)amino)-4-(trifluoromethyl)pyridazin-3(2H)-one | LCMS (ESI, m/z): 580.20 [M + H]+; $^1$H NMR (400 MHz, DMSO-$d_6$) δ 12.48 (s, 1H), 8.46 (d, J = 4.2 Hz, 2H), 7.93 (s, 1H), 6.41-6.29 (m, 1H), 4.62-4.55 (m, 2H), 4.34-4.27 (m, 1H), 4.11-4.03 (m, 2H), 3.90 (dd, J = 10.2, 4.7 Hz, 1H), 3.66 (dd, J = 10.2, 6.5 Hz, 1H), 3.48 (d, J = 5.5 Hz, 2H), 3.31-3.30 (m, 3H), 3.28-3.21 (m, 2H), 3.09-3.04 (m, 2H), 2.29-2.17 (m, 1H), 1.75-1.54 (m, 5H); Chiral HPLC: CHIRALPAK IF-3, 4.6 * 50 mm, 3 μm; Hex w/ 0.1% DEA:EtOH = 50:50; Flow rate: 1 mL/min; rT = 1.858 min. |
| 18B | 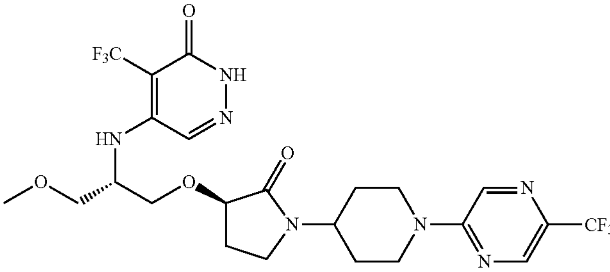 5-(((S)-1-methoxy-3-(((R)-2-oxo-1-(1-(5-(trifluoromethyl)pyrazin-2-yl)piperidin-4-yl)pyrrolidin-3-yl)oxy)propan-2-yl)amino)-4-(trifluoromethyl)pyridazin-3(2H)-one | LCMS (ESI, m/z): 580.20 [M + H]+; $^1$H NMR (400 MHz, DMSO-$d_6$) δ 12.50 (s, 1H), 8.49-8.43 (d, J = 4.0 Hz, 2H), 7.96 (s, 1H), 6.31-6.23 (m, 1H), 4.61-4.54 (m, 2H), 4.33-4.28 (m, 1H), 4.14-4.03 (m, 2H), 3.90 (dd, J = 10.2, 4.7 Hz, 1H), 3.66 (dd, J = 10.2, 6.5 Hz, 1H), 3.49 (d, J = 5.3 Hz, 2H), 3.28-3.27 (m, 3H), 3.26-3.21 (m, 2H), 3.15-3.02 (m, 2H), 2.25-2.18 (m, 1H), 1.78-1.56 (m, 5H); Chiral HPLC: CHIRALPAK IF-3, 4.6 * 50 mm, 3 μm; Hex w/ 0.1% DEA:EtOH = 50:50; Flow rate: 1 mL/min; rT = 2.577 min. |

Example 19: Synthesis of 5-(((S)-1-methoxy-3-(((S)-2-oxo-1-(1-(5-trifluoromethyl)pyrimidin-2-yl)piperidin-4-yl)pyrrolidin-3-yl)oxy)propan-2-yl)amino)-4-(trifluoromethyl)pyridazin-3(2H)-one (19A) and 5-(((S)-1-methoxy-3-(((R)-2-oxo-1-(1-(5-(trifluoromethyl)pyrimidin-2-yl)piperidin-4-yl)pyrrolidin-3-yl)oxy)propan-2-yl)amino)-4-(trifluoromethyl)pyridazin-3(2H)-one (19B)

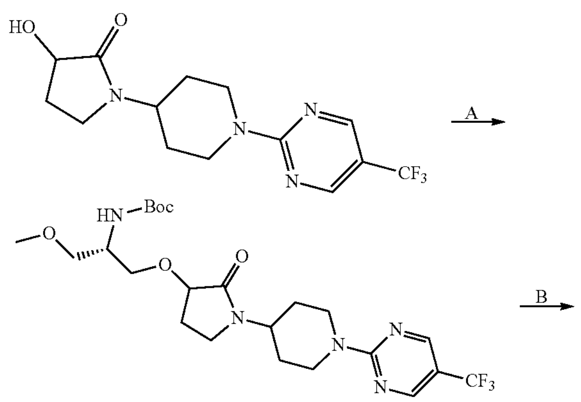

-continued

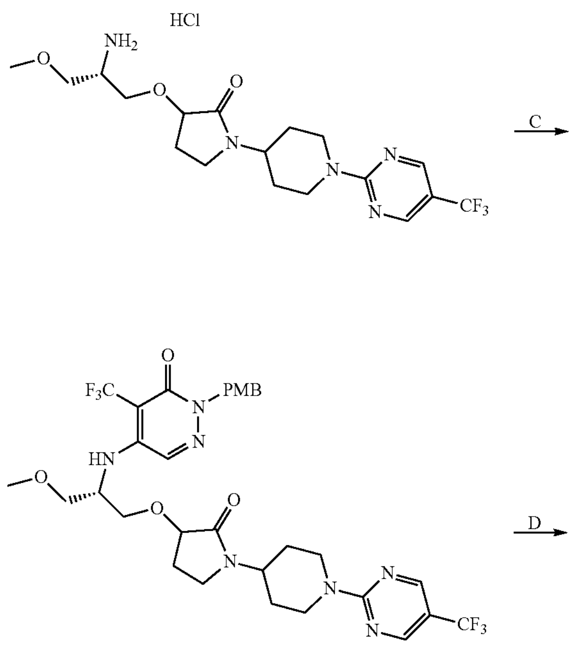

-continued

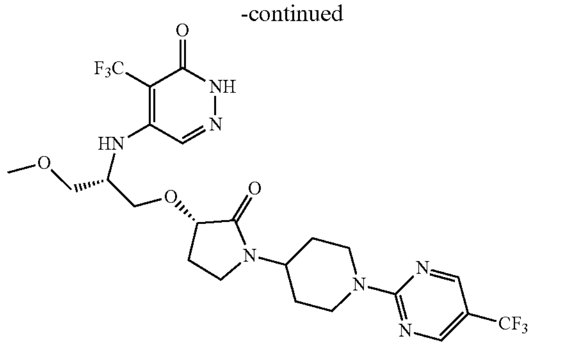

19A

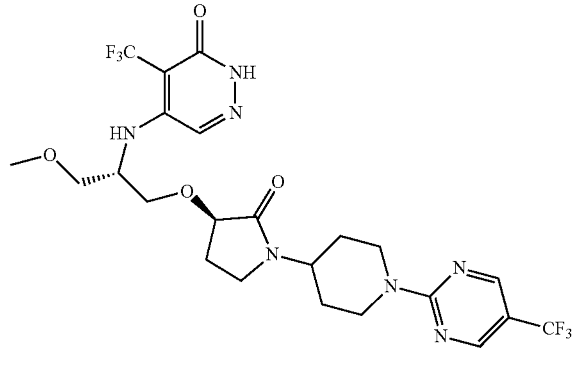

19B

Step A

To a solution of 3-hydroxy-1-(1-(5-(trifluoromethyl)pyrimidin-2-yl)piperidin-4-yl)pyrrolidin-2-one (500 mg, 1.51 mmol, 1.00 equiv) in DMF (5 mL) at 0° C. was added NaH (60% dispersion in mineral oil, 121 mg, 3.02 mmol, 2.0 equiv). After stirring at that temperature for 15 minutes, a solution of tert-butyl (S)-4-(methoxymethyl)-1,2,3-oxathiazolidine-3-carboxylate 2,2-dioxide (605 mg 2.26 mmol, 1.50 equiv) in DMF (3 mL) at 0° C. was added dropwise. The resulting solution was stirred for 2 h at 0° C. 50 mL of water was added and the solution was extracted with 3×50 mL of EtOAc. The organic layers were combined, washed with 50 mL of brine, dried over anhydrous sodium sulfate and concentrated under vacuum. The crude product was applied onto a silica gel column eluting with EtOAc/petroleum ether (11:9) to afford 500 mg (64% yield) of tert-butyl ((2S)-1-methoxy-3-((2-oxo-1-(1-(5-(trifluoromethyl)pyrimidin-2-yl)piperidin-4-yl)pyrrolidin-3-yl)oxy)propan-2-yl)carbamate as a brown oil. LCMS (ESI, m/z): 518.20 $[M+H]^+$ Step B A solution of tert-butyl ((2S)-1-methoxy-3-((2-oxo-1-(1-(5-(trifluoromethyl)pyrimidin-2-yl)piperidin-4-yl)pyrrolidin-3-yl)oxy)propan-2-yl)carbamate (500 mg, 0.97 mmol, 1.00 equiv) in 4N HCl in 1,4-dioxane (4 mL) was stirred for 1 h at room temperature. After concentration, the crude product was purified by C18 reverse phase chromatography eluting with $H_2O/CH_3CN$ (1:1) to afford 260 mg (65% yield) of 3-((S)-2-amino-3-methoxypropoxy)-1-(1-(5-(trifluoromethyl)pyrimidin-2-yl)piperidin-4-yl)pyrrolidin-2-one as a yellow solid. LCMS (ESI, m/z): 418.20 $[M+H]^+$.

Step C

A solution of 3-((S)-2-amino-3-methoxypropoxy)-1-(1-(5-(trifluoromethyl)pyrimidin-2-yl)piperidin-4-yl)pyrrolidin-2-one (250 mg, 0.60 mmol, 1.00 equiv), 5-chloro-2-(4- methoxybenzyl)-4-(trifluoromethyl)pyridazin-3(2H)-one (286 mg, 0.90 mmol, 1.50 equiv; Intermediate I-1), and N-methyl morpholine (91 mg, 0.90 mmol, 1.50 equiv) in $CH_3CN$ (4 mL) was stirred for 1 h at 60° C. The solution was diluted with 50 ml of water and extracted with 3×50 mL of EtOAc. The organic layers were combined, washed with 50 mL of brine, dried over anhydrous sodium sulfate and concentrated under vacuum. The residue was applied onto a silica gel column eluting with EtOAc/petroleum ether (7:13) to afford 100 mg (24% yield) of 5-(((2S)-1-methoxy-3-((2-oxo-1-(1-(5-(trifluoromethyl)pyrimidin-2-yl)piperidin-4-yl)pyrrolidin-3-yl)oxy)propan-2-yl)amino)-2-(4-methoxybenzyl)-4-(trifluoromethyl)pyridazin-3(2H)-one as a yellow solid. LCMS (ESI, m/z): 700.20$[M+H]^+$ Step D A solution of 5-(((2S)-1-methoxy-3-((2-oxo-1-(1-(5-(trifluoromethyl)pyrimidin-2-yl)piperidin-4-yl)pyrrolidin-3-yl)oxy)propan-2-yl)amino)-2-(4-methoxybenzyl)-4-(trifluoromethyl)pyridazin-3(2H)-one (90 mg, 0.13 mmol, 1.00 equiv) in TFA (1.00 mL) and triflic acid (0.20 mL) was stirred for 1 h at room temperature. The residue was diluted with 20 ml of water and the pH was adjusted to 7-8 with saturated aqueous $Na_2CO_3$ solution. The resulting solution was extracted with 3×20 mL of EtOAc. The organic layers were combined, washed with 20 mL of brine, dried over anhydrous sodium sulfate and concentrated under vacuum. The crude product was purified by C18 reverse phase column eluting with $H_2O/CH_3CN$ (16:29). The product was further purified by chiral prep-HPLC (CHIRALPAK IA, 2*25 cm, 5um; Mobile Phase A: Hex (8 mmol/L $NH_3$-MeOH), Mobile Phase B: EtOH; Flow rate: 18 mL/min; 50% B for 20 min; 220/254 nm). The relative stereochemistry of compounds was assigned by analogy to Example 10, based on the PARP7 potency of the more active diastereomer and in analogy to the Example 10B X-ray crystal structure.

Example 19 Isomer A (19A): 5-(((S)-1-methoxy-3-(((S)-2-oxo-1-(1-(5-(trifluoromethyl)pyrimidin-2-yl)piperidin-4-yl)pyrrolidin-3-yl)oxy)propan-2-yl)amino)-4-(trifluoromethyl)pyridazin-3(2H)-one (20.8 mg, 28% yield, white solid). LCMS (ESI, m/z): 580.20 $[M+H]^+$; $^1H$ NMR (400 MHz, DMSO-$d_6$) δ 12.48 (s, 1H), 8.69 (s, 2H), 7.93 (s, 1H), 6.37-6.30 (m, 1H), 4.88-4.74 (m, 2H), 4.35-4.24 (m, 1H), 4.14-4.03 (m, 2H), 3.90 (dd, J=10.0 Hz, 3.6 Hz, 1H), 3.70-3.61 (m, 1H), 3.51-3.44 (m, 2H), 3.29-3.25 (m, 3H), 3.23-3.17 (m, 1H), 3.17-2.97 (m, 3H), 2.26-2.18 (m, 1H), 1.78-1.49 (m, 5H); Chiral HPLC: CHIRALPAK IA-3, 4.6*50 mm, 3 μm; Hex:EtOH=50:50; Flow rate=1.3 mL/min; rT=1.33 min.

Example 19 Isomer B (19B): 5-(((S)-1-methoxy-3-(((R)-2-oxo-1-(1-(5-(trifluoromethyl)pyrimidin-2-yl)piperidin-4-yl)pyrrolidin-3-yl)oxy)propan-2-yl)amino)-4-(trifluoromethyl)pyridazin-3(2H)-one (25.0 mg, 34% yield, white solid). LCMS (ESI, m/z): 580.20 $[M+H]^+$. $^1H$ NMR (400 MHz, DMSO-$d_6$) δ 12.49 (s, 1H), 8.69 (s, 2H), 7.96 (s, 1H), 6.32-6.24 (m, 1H), 4.86-4.77 (m, 2H), 4.35-4.24 (m, 1H), 4.15-4.00 (m, 2H), 3.90 (dd, J=10.0 Hz, 3.6 Hz, 1H), 3.71-3.63 (m, 1H), 3.52-3.45 (m, 2H), 3.28-3.27 (m, 3H) 3.24-3.21 (m, 1H), 3.18-2.97 (m, 3H), 2.31-2.19 (m, 1H), 1.77-1.49 (m, 5H). Chiral HPLC: CHIRALPAK IA-3, 4.6*50 mm, 3 m; Hex:EtOH=50:50; Flow rate=1.3 mL/min; rT=2.91 min Example 20: Synthesis of 5-(((S)-1-(((S)-2-oxo-1-(1-(5-(trifluoromethyl)pyrimidin-2-yl)piperidin-4-yl)pyrrolidin-3-yl)oxy)propan-2-yl)oxy)-4-(trifluoromethyl)pyridazin-3(2H)-one (20A) and 5-(((S)-1-(((R)-2-oxo-1-(1-(5-(trifluoromethyl)pyrimidin-2-yl)piperidin-4-yl)pyrrolidin-3-yl)oxy)propan-2-yl)oxy)-4-(trifluoromethyl)pyridazin-3(2H)-one (20B)

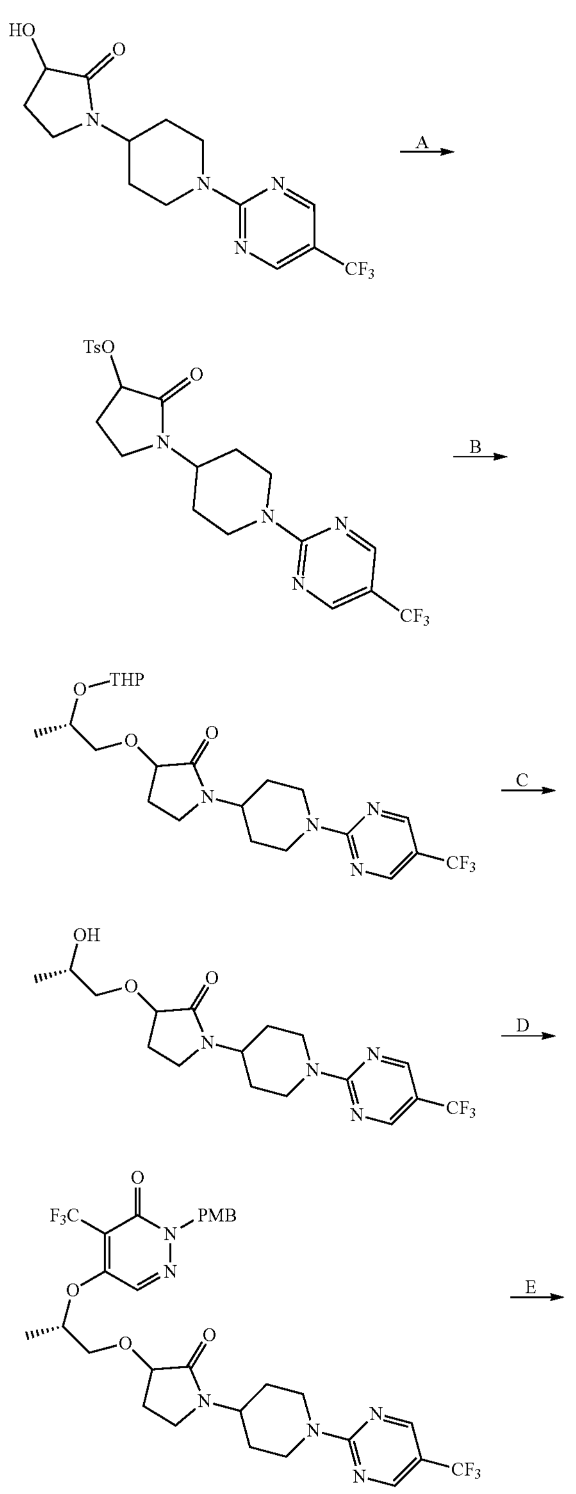

-continued

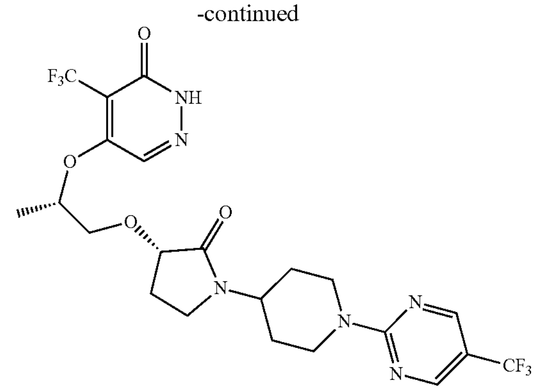

20A

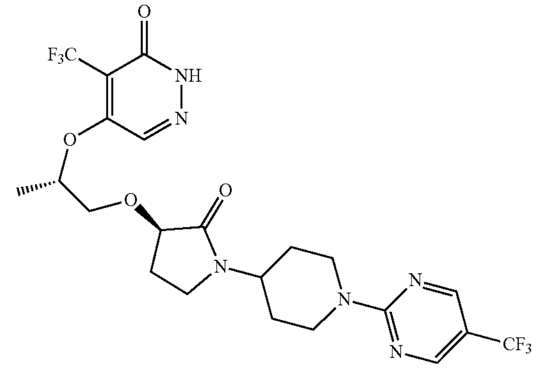

20B

Step A

A solution of 3-hydroxy-1-(1-(5-(trifluoromethyl)pyrimidin-2-yl)piperidin-4-yl)pyrrolidin-2-one (500 mg, 1.51 mmol, 1.00 equiv), 4-methylbenzenesulfonyl chloride (864 mg, 4.53 mmol, 2.99 equiv), and TEA (612 mg, 6.06 mmol, 4.00 equiv) in DCM (15 mL) was stirred for 4 hours at 25° C. The resulting solution was diluted with 50 mL of water. The layers were separated and the aqueous layer was extracted with 3×50 mL of dichloromethane. The organic layers were combined, dried over anhydrous sodium sulfate, filtered and concentrated under vacuum to afford 500 mg (68% yield) of 2-oxo-1-(1-(5-(trifluoromethyl)pyrimidin-2-yl)piperidin-4-yl)pyrrolidin-3-yl 4-methylbenzenesulfonate as a brown solid. LCMS (ESI, m/z): 485.20 $[M+H]^+$.

Step B

A solution of (2S)-2-((tetrahydro-2H-pyran-2-yl)oxy)propan-1-ol (264 mg, 1.65 mmol, 2.00 equiv) in DMF (4 mL) at 0° C. was treated with NaH (60% dispersion in mineral oil, 67 mg, 1.65 mmol, 2.00 equiv) in DMF (4 mL) and stirred at that temperature for 15 minutes. 2-oxo-1-(1-(5-(trifluoromethyl)pyrimidin-2-yl)piperidin-4-yl)pyrrolidin-3-yl 4-methylbenzenesulfonate (400 mg, 0.83 mmol, 1.00 equiv) was added and the solution was stirred for 2 hours at room temperature. 20 mL of saturated aqueous $NH_4Cl$ and ethyl acetate were added. The layers were separated and the aqueous layer was extracted with EtOAc (3×50 mL). The organic layers were combined, washed with 5 mL brine, dried over anhydrous sodium sulfate and concentrated under vacuum to afford 450 mg of 3-((2S)-2-((tetrahydro-2H-pyran-2-yl)oxy)propoxy)-1-(1-(5-(trifluoromethyl)pyrimidin-2-yl)piperidin-4-yl)pyrrolidin-2-one as a brown oil that was carried on without further purification. LCMS (ESI, m/z): 473.0 $[M+H]^+$.

Step C

A solution of 3-((2S)-2-((tetrahydro-2H-pyran-2-yl)oxy)propoxy)-1-(1-(5-(trifluoromethyl)pyrimidin-2-yl)piperidin-4-yl)pyrrolidin-2-one (900 mg, 1.91 mmol, 1.00 equiv) in 4N HCl in dioxane (6 mL) was stirred for 1 hour at room temperature. The resulting mixture was concentrated and the residue was applied onto a reverse phase column eluting with $H_2O/CH_3CN$ (1:2) to afford 250 mg (34% yield) of 3-((S)-2-hydroxypropoxy)-1-(1-(5-(trifluoromethyl)pyrimidin-2-yl)piperidin-4-yl)pyrrolidin-2-one as a yellow solid. LCMS (ESI, m/z): 389.10 $[M+H]^+$.

Step D

A solution of 3-((S)-2-hydroxypropoxy)-1-(1-(5-(trifluoromethyl)pyrimidin-2-yl)piperidin-4-yl)pyrrolidin-2-one (75 mg, 0.16 mmol, 1.00 equiv), 5-chloro-2-(4-methoxybenzyl)-4-(trifluoromethyl)pyridazin-3(2H)-one (184 mg, 0.58 mmol, 3.64 equiv; Intermediate I-1) and potassium tert-butoxide (65 mg, 0.58 mmol, 3.65 equiv) in DCM (3.00 mL) was stirred for 15 hours at room temperature. The resulting solution was diluted with 50 mL of DCM and washed with 50 ml $H_2O$ and 50 mL of brine. The mixture was dried over anhydrous sodium sulfate and concentrated. The crude product was applied onto a silica gel column eluting with EtOAc/Petroleum ether (7/3) to afford 70 mg (66% yield) of 2-(4-methoxybenzyl)-5-(((2S)-1-((2-oxo-1-(1-(5-(trifluoromethyl)pyrimidin-2-yl)piperidin-4-yl)pyrrolidin-3-yl)oxy)propan-2-yl)oxy)-4-(trifluoromethyl)pyridazin-3(2H)-one as a colorless oil. LCMS (ESI, m/z): 671.20 $[M+H]^+$.

Step E

A solution of 2-(4-methoxybenzyl)-5-(((2S)-1-((2-oxo-1-(1-(5-(trifluoromethyl)pyrimidin-2-yl)piperidin-4-yl)pyrrolidin-3-yl)oxy)propan-2-yl)oxy)-4-(trifluoromethyl)pyridazin-3(2H)-one (65 mg, 0.10 mmol, 1.00 equiv) in TFA (1 mL) and triflic acid (0.20 mL) was stirred for 1 hour at room temperature. The solution was diluted with water and adjusted to pH 7~8 with saturated aqueous $Na_2CO_3$. After concentration, the crude product was purified by C18 reverse phase chromatography eluting with $H_2O/CH_3CN$ (52:48). The product was further purified by Chiral-Prep-HPLC with following conditions: (CHIRALPAK IA, 2*25 cm, 5 μm; mobile phase A: Hex w/ 8 mM $NH_3$-MeOH, mobile phase B: EtOH; Flow rate: 20 mL/min; 50% B for 15 min; 220/254 nm.) The relative stereochemistry of compounds was assigned by analogy to Example 10, based on the PARP7 potency of the more active diastereomer and in analogy to the Example 10A X-ray crystal structure.

Example 20 Isomer A (20A): 5-(((S)-1-(((S)-2-oxo-1-(1-(5-(trifluoromethyl)pyrimidin-2-yl)piperidin-4-yl)pyrrolidin-3-yl)oxy)propan-2-yl)oxy)-4-(trifluoromethyl)pyridazin-3(2H)-one (13 mg, 24% yield, white solid). LCMS (ESI, m/z): 551.20 $[M+H]^+$; $^1H$ NMR (400 MHz, DMSO-$d_6$) δ 13.22 (s, 1H), 8.69 (s, 2H), 8.28 (s, 1H), 5.22-5.12 (m, 1H), 4.86-4.76 (m, 2H), 4.11-3.94 (m, 3H), 3.65-3.58 (m, 1H), 3.24-3.16 (m, 1H), 3.15-3.09 (m, 1H), 3.08-2.97 (m, 2H), 2.24-2.13 (m, 1H), 1.68-1.47 (m, 5H), 1.27 (d, J=6.2 Hz, 3H). Chiral HPLC: CHIRALPAK IA-3, 4.6*50 mm, 3 μm; Hex w/ 0.1% DEA:EtOH=50:50; Flow rate=1.0 mL/min; rT=1.981 min.

Example 20 Isomer B (20B): 5-(((S)-1-(((R)-2-oxo-1-(1-(5-(trifluoromethyl)pyrimidin-2-yl)piperidin-4-yl)pyrrolidin-3-yl)oxy)propan-2-yl)oxy)-4-(trifluoromethyl)pyridazin-3(2H)-one (17.5 mg, 33% yield, white solid). LCMS (ESI, m/z): 551.20 $[M+H]^+$. 1H NMR (400 MHz, DMSO-$d_6$) δ: 13.22 (s, 1H), 8.69 (s, 2H), 8.30 (s, 1H), 5.22-5.12 (m, 1H), 4.86-4.77 (m, 2H), 4.11-3.99 (m, 2H), 3.89-3.82 (m, 1H), 3.77-3.70 (m, 1H), 3.25-3.17 (m, 1H), 3.16-3.08 (m, 1H), 3.07-2.98 (m, 2H), 2.28-2.17 (m, 1H), 1.75-1.47 (m, 5H), 1.27 (d, J=6.2 Hz, 3H). Chiral HPLC: CHIRALPAK IA-3, 4.6*50 mm, 3 μm; Hex w/ 0.1% DEA: EtOH=50:50; Flow rate=1.0 mL/min; rT=2.695 min.

The compounds of Examples 21-33B were synthesized analogously to the compounds described in Example 1-20.

| Ex. No. | Name | Structure | Analytical Data |
|---|---|---|---|
| 21 | 4-(trifluoromethyl)-5-(((2S)-1-((1-(1-(5-(trifluoromethyl)pyrimidin-2-yl)piperidin-4-yl)pyrrolidin-3-yl)oxy)propan-2-yl)amino)pyridazin-3(2H)-one | 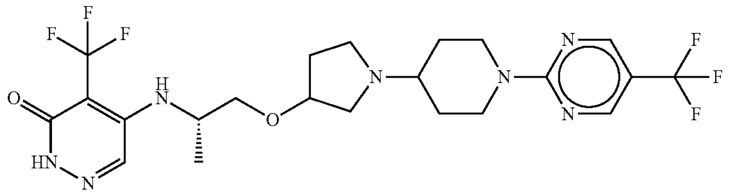 | LCMS (ESI, m/z): 536.20 $[M + H]^+$ |
| 22A* | 5-(((S)-1-(((S)-1-(1-(5-(difluoromethyl)pyrazin-2-yl)piperidin-4-yl)-2-oxopyrrolidin-3-yl)oxy)propan-2-yl)amino)-4-(trifluoromethyl)pyridazin-3(2H)-one | 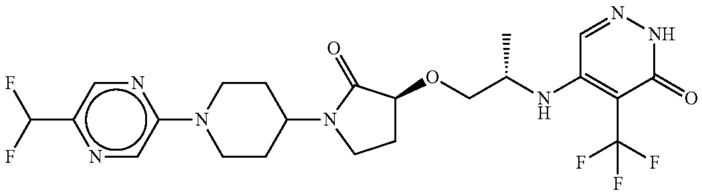 | LCMS (ESI, m/z): 532.2 $[M + H]^+$ |
| 22B* | 5-(((S)-1-(((R)-1-(1-(5-(difluoromethyl)pyrazin-2-yl)piperidin-4-yl)-2-oxopyrrolidin-3-yl)oxy)propan-2-yl)amino)-4-(trifluoromethyl)pyridazin-3(2H)-one | 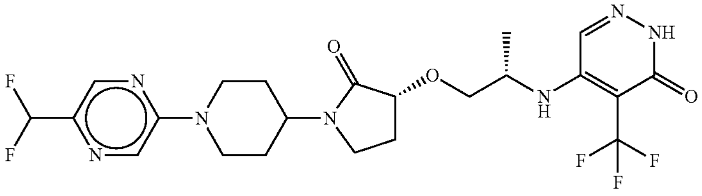 | LCMS (ESI, m/z): 532.2 $[M + H]^+$ |

-continued

| Ex. No. | Name | Structure | Analytical Data |
|---|---|---|---|
| 23 | 4-bromo-5-(((S)-1-(((S)-2-oxo-1-(1-(5-(trifluoromethyl)pyrimidin-2-yl)piperidin-4-yl)pyrrolidin-3-yl)oxy)propan-2-yl)oxy)pyridazin-3(2H)-one | 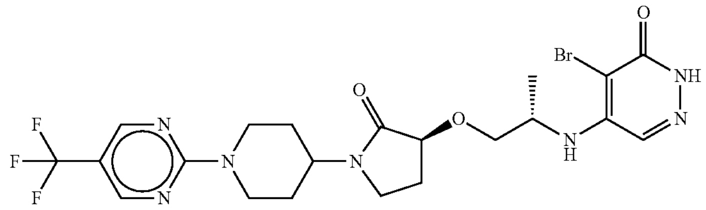 | LCMS (ESI, m/z): 561.1 [M + H]+ |
| 24 | 5-(((S)-1-(((R)-1-(1-(5-bromopyrimidin-2-yl)piperidin-4-yl)-2-oxopyrrolidin-3-yl)oxy)propan-2-yl)amino)-4-(trifluoromethyl)pyridazin-3(2H)-one | 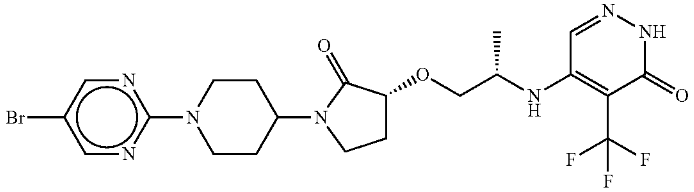 | LCMS (ESI, m/z): 561.1 [M + H]+ |
| 25 | (S)-N-methyl-2-(2-((6-oxo-5-(trifluoromethyl)-1,6-dihydropyridazin-4-yl)oxy)propoxy)-N-(1-(5-(trifluoromethyl)pyrimidin-2-yl)piperidin-4-yl)acetamide | 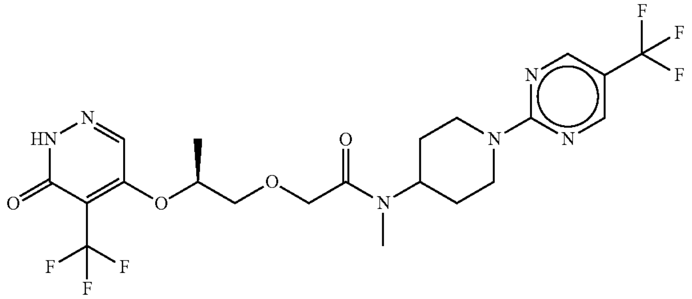 | LCMS (ESI, m/z): 539.2 [M + H]+ |
| 26A± | 5-(((S)-1-(((S)-2-oxo-1-(1-(5-(trifluoromethyl)pyrimidin-2-yl)piperidin-4-yl)pyrrolidin-3-yl)amino)propan-2-yl)amino)-4-(trifluoromethyl)pyridazin-3(2H)-one | 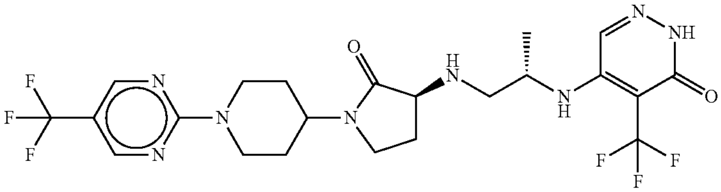 | LCMS (ESI, m/z): 549.2 [M + H]+ |
| 26B* | 5-(((S)-1-(((R)-2-oxo-1-(1-(5-(trifluoromethyl)pyrimidin-2-yl)piperidin-4-yl)pyrrolidin-3-yl)amino)propan-2-yl)amino)-4-(trifluoromethyl)pyridazin-3(2H)-one | 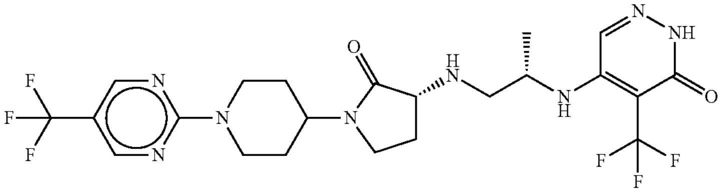 | LCMS (ESI, m/z): 549.2 [M + H]+ |
| 26C± | 5-(((R)-1-(((S)-2-oxo-1-(1-(5-(trifluoromethyl)pyrimidin-2-yl)piperidin-4-yl)pyrrolidin-3-yl)amino)propan-2-yl)amino)-4-(trifluoromethyl)pyridazin-3(2H)-one | 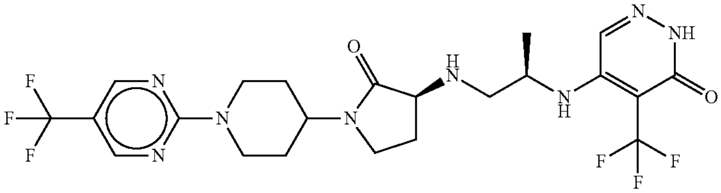 | LCMS (ESI, m/z): 549.2 [M + H]+ |
| 26D± | 5-(((R)-1-(((R)-2-oxo-1-(1-(5-(trifluoromethyl)pyrimidin-2-yl)piperidin-4-yl)pyrrolidin-3-yl)amino)propan-2-yl)amino)-4-(trifluoromethyl)pyridazin-3(2H)-one | 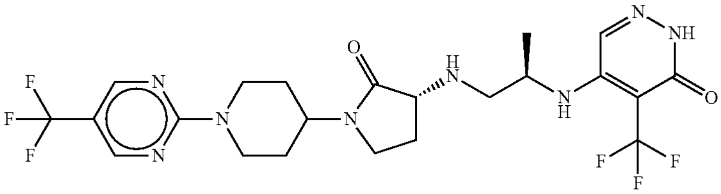 | LCMS (ESI, m/z): 549.2 [M + H]+ |

-continued

| Ex. No. | Name | Structure | Analytical Data |
|---|---|---|---|
| 27 | 5-(((2S)-1-((1-(1-(5-(difluoromethyl)pyrimidin-2-yl)piperidin-4-yl)-2-oxopyrrolidin-3-yl)oxy)propan-2-yl)oxy)-4-(trifluoromethyl)pyridazin-3(2H)-one | 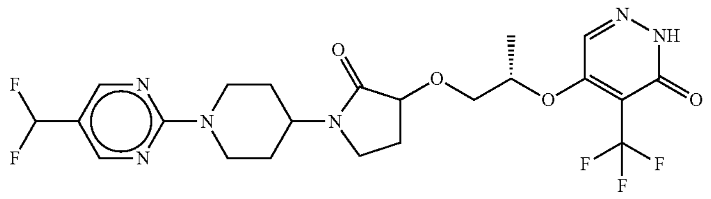 | LCMS (ESI, m/z): 533.2 [M + H]+ |
| 28 | (S)-2-(2-((5-bromo-6-oxo-1,6-dihydropyridazin-4-yl)oxy)propoxy)-N-methyl-N-(1-(5-(trifluoromethyl)pyrimidin-2-yl)piperidin-4-yl)azetamide | 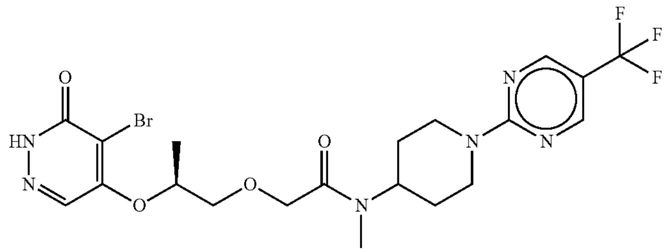 | LCMS (ESI, m/z): 549.1 [M + H]+ |
| 29 | 5-(((S)-1-(methyl(2-oxo-1-(1-(5-(trifluoromethyl)pyrimidin-2-yl)piperidin-4-yl)pyrrolidin-3-yl)amino)propan-2-yl)amino)-4-(trifluoromethyl)pyridazin-3(2H)-one | 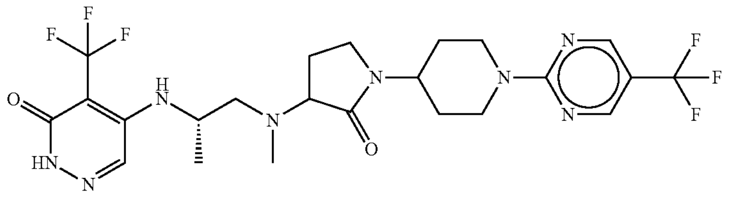 | LCMS (ESI, m/z): 563.2 [M + H]+ |
| 30 | 6-(4-(2-oxo-3-((S)-2-((6-oxo-5-(trifluoromethyl)-1,6-dihydropyridazin-4-yl)oxy)propoxy)pyrrolidin-1-yl)piperidin-1-yl)nicotinonitrile | 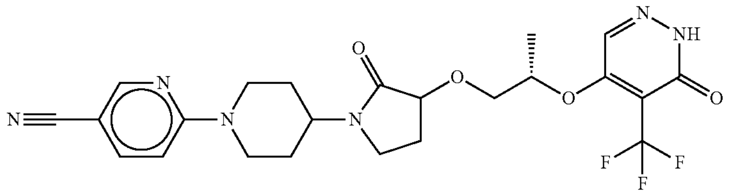 | LCMS (ESI, m/z): 507.2 [M + H]+ |
| 31A* | 5-(((S)-1-(((S)-2-oxo-1-(1-(5-(trifluoromethyl)pyrazin-2-yl)piperidin-4-yl)pyrrolidin-3-yl)oxy)propan-2-yl)oxy)-4-(trifluoromethyl)pyridazin-3(2H)-one | 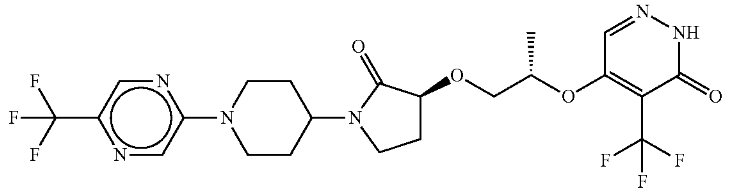 | LCMS (ESI, m/z): 551.2 [M + H]+ |
| 31B* | 5-(((S)-1-(((R)-2-oxo-1-(1-(5-(trifluoromethyl)pyrazin-2-yl)piperidin-4-yl)pyrrolidin-3-yl)oxy)propan-2-yl)oxy)-4-(trifluoromethyl)pyridazin-3(2H)-one | 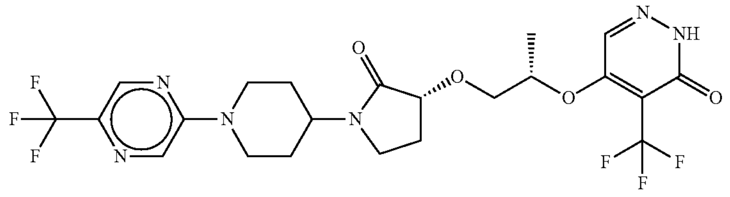 | LCMS (ESI, m/z): 551.2 [M + H]+ |
| 32 | 4-bromo-5-(((S)-1-(((R)-2-oxo-1-(1-(5-(trifluoromethyl)pyrimidin-2-yl)piperidin-4-yl)pyrrolidin-3-yl)oxy)propan-2-yl)amino)pyridazin-3(2H)-one | 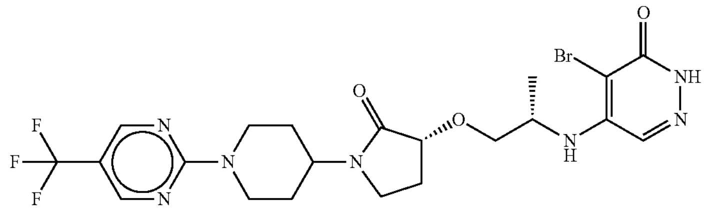 | LCMS (ESI, m/z): 562.2 [M + H]+ |

-continued

| Ex. No. | Name | Structure | Analytical Data |
|---|---|---|---|
| 33A‡ | N-((3R,4R)-3-hydroxy-1-(5-(trifluoromethyl)pyrimidin-2-yl)piperidin-4-yl)-2-((S)-2-((6-oxo-5-(trifluoromethyl)-1,6-dihydropyridazin-4-yl)amino)propoxy)acetamide | 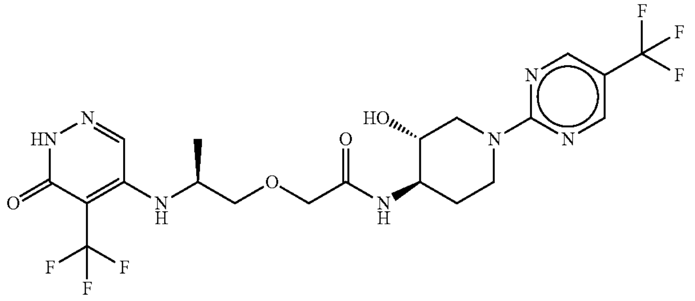 | LCMS (ESI, m/z): 540.2 $[M+H]^+$ |
| 33B‡ | N-((3S,4S)-3-hydroxy-1-(5-(trifluoromethyl)pyrimidin-2-yl)piperidin-4-yl)-2-((S)-2-((6-oxo-5-(trifluoromethyl)-1,6-dihydropyridazin-4-yl)amino)propoxy)acetamide | 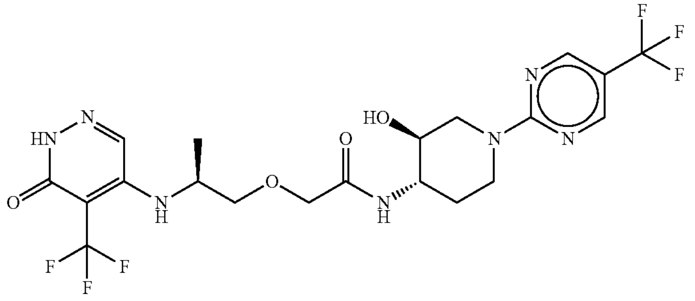 | LCMS (ESI, m/z): 540.2 $[M+H]^+$ |

*The stereochemistry of compound was assigned by analogy to Example 10, based on the PARP7 potency of the more active diastereomer and in analogy to the Example 10B X-ray crystal structure.

‡The stereochemistry of compounds was arbitrarily assigned.

Intermediate I-7: Synthesis of 3-hydroxy-[1,4'-bipiperidin]-2-one hydrochloride

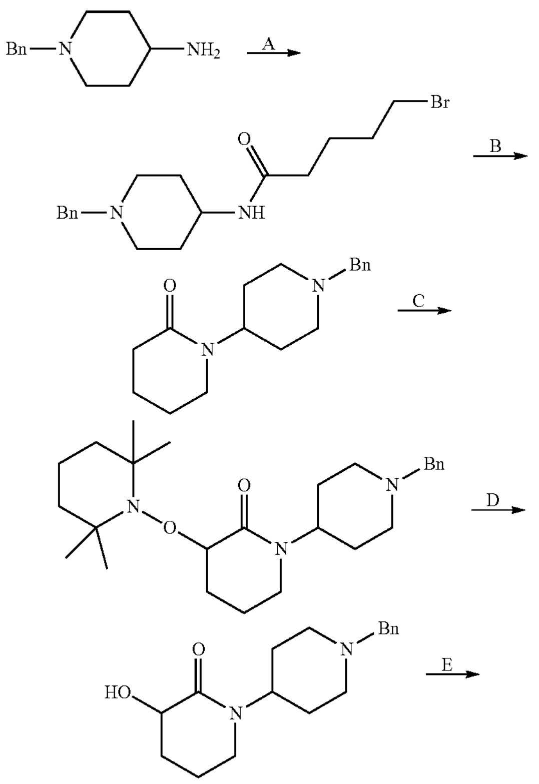

-continued

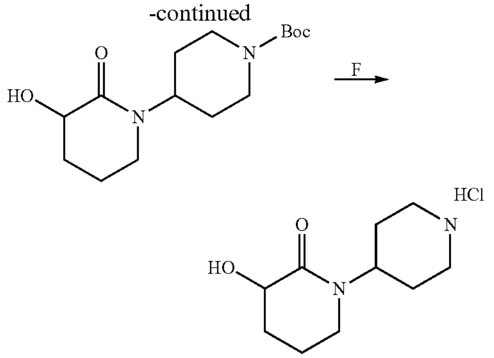

Step A

To a solution of 1-benzylpiperidin-4-amine (1.91 g, 10.0 mmol, 1.0 equiv) in water (5 mL) and ethyl acetate (10 mL) was added $K_2CO_3$ (2.08 g, 15.0 mmol, 1.5 equiv) and 5-bromopentanoyl chloride (2.00 g, 10.0 mmol, 1.0 equiv). The reaction mixture stirred for 1 hour and was diluted with water (20 mL) and extracted with 3×20 mL of ethyl acetate. The combined organic extracts were washed with water (10 mL), dried over anhydrous sodium sulfate, and concentrated in vacuo to afford 3.5 g (99% yield) of N-(1-benzylpiperidin-4-yl)-5-bromopentanamide as a white solid. LCMS (ESI, m/z): 355.00 $[M+H]^+$.

Step B

To a solution of N-(1-benzylpiperidin-4-yl)-5-bromopentanamide (3.40 g, 9.60 mmol, 1.0 equiv) in THF (20 mL) was added t-BuOK (1.62 g, 14.4 mmol, 1.5 equiv). The reaction mixture stirred for 1 hour and then was quenched by the addition of water (20 mL). The resulting solution was extracted with 3×50 mL of ethyl acetate, and the combined organic layers were dried over anhydrous sodium sulfate and concentrated in vacuo to afford 2.5 g (95% yield) of 1'-benzyl-[1,4'-bipiperidin]-2-one as a white solid. LCMS (ESI, m/z): 273.10 $[M+H]^+$.

Step C

To a solution of 1'-benzyl-[1,4'-bipiperidin]-2-one (2.00 g, 7.30 mmol, 1.0 equiv) in DCM (20 mL) was added TEMPO (2.50 g, 16.0 mmol, 2.2 equiv), 3A molecular sieves (2 g), and $Tf_2O$ (2.28 g, 8.08 mmol, 1.1 equiv) at 0° C. The resulting solution was stirred for 2 hours and was then diluted with water (20 mL). The solution was extracted with 3×50 mL of DCM, and the combined organic layers were dried over anhydrous sodium sulfate and concentrated in vacuo. The crude product was applied onto a silica gel column eluting with ethyl acetate/petroleum ether (4/1) to afford 1.5 g (48% yield) of 1'-benzyl-3-((2,2,6,6-tetramethylpiperidin-1-yl)oxy)-[1,4'-bipiperidin]-2-one as a yellow oil. LCMS (ESI, m/z): 428.20 $[M+H]^+$.

Step D

To a solution of 1'-benzyl-3-((2,2,6,6-tetramethylpiperidin-1-yl)oxy)-[1,4'-bipiperidin]-2-one (800 mg, 1.87 mmol, 1.0 equiv) in a mixture of AcOH, THE and water (20 mL, 3:1:1) was added zinc powder (2.00 g, 30.6 mmol, 16 equiv). The resulting solution was stirred for 1 hour at 70° C. The solution was diluted with water (20 mL). The pH of the solution was adjusted to 12 with saturated aqueous NaOH. After filtration, the filtrate was extracted with 3×50 mL of ethyl acetate, and the organic layers were combined, dried over anhydrous sodium sulfate, and concentrated in vacuo. The crude product was applied onto a silica gel column eluting with DCM/MeOH to afford 300 mg (56% yield) of 1'-benzyl-3-hydroxy-[1,4'-bipiperidin]-2-one as a yellow oil. LCMS (ESI, m/z): 289.05 $[M+H]^+$.

Step E

To a solution of 1'-benzyl-3-hydroxy-[1,4'-bipiperidin]-2-one (400 mg, 1.4 mmol, 1.0 equiv) in EtOH (10 mL) was added Pd/C (20 mg, 0.19 mmol, 0.1 equiv) and di-tert-butyl dicarbonate (605 mg, 2.77 mmol, 2.0 equiv). The resulting solution was stirred for 1 hour under an atmosphere of hydrogen. The solids were filtered, and the filtrate was concentrated in vacuo to afford 380 mg (92% yield) of tert-butyl 3-hydroxy-2-oxo-[1,4'-bipiperidine]-1'-carboxylate as a colorless oil. LCMS (ESI, m/z): 299.15 $[M+H]^+$.

Step F

A solution of tert-butyl 3-hydroxy-2-oxo-[1,4'-bipiperidine]-1'-carboxylate (370 mg, 1.24 mmol, 1.0 equiv) in 4M HCl in dioxane (10 mL) was stirred for 1 hour at room temperature. The resulting mixture was concentrated in vacuo to afford 280 mg (96% yield) of 3-hydroxy-[1,4'-bipiperidin]-2-one hydrochloride as a colorless oil. LCMS (ESI, m/z): 199.00 $[M+H]^+$.

Intermediate I-8: Synthesis of 3-hydroxy-4,4-dimethyl-1-(piperidin-4-yl)pyrrolidin-2-one hydrochloride

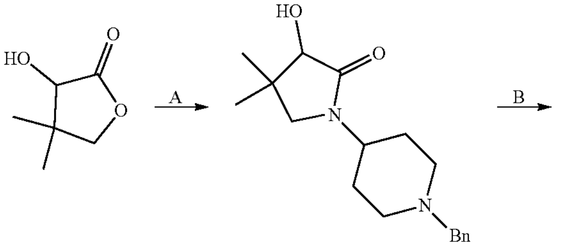

-continued

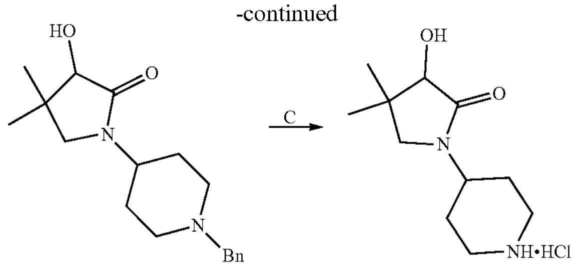

Step A

To a solution of 1-benzylpiperidin-4-amine (1.90 g, 9.99 mmol, 1.0 equiv), in 1-methoxy-2-(2-methoxyethoxy)ethane (1 mL) was added TsOH (0.28 g, 1.6 mmol, 0.2 equiv) and 3-hydroxy-4,4-dimethyldihydrofuran-2(3H)-one (1.56 g, 12.0 mmol, 1.2 equiv). The reaction mixture was irradiated with microwave radiation for 1 hour at 150° C. The resulting solution was stirred for an additional 2 hours at 200° C. and then diluted with ethyl acetate (2 mL). The crude product was applied onto a silica gel column eluting with dichloromethane/methanol (9/1) to afford 840 mg (28% yield) of 1-(1-benzylpiperidin-4-yl)-3-hydroxy-4,4-dimethylpyrrolidin-2-one as a brown solid. LC-MS (ES, m/z): 303.00 $[M+H]^+$.

Step B

To a solution of 1-(1-benzylpiperidin-4-yl)-3-hydroxy-4,4-dimethylpyrrolidin-2-one (837 mg, 2.77 mmol, 1.0 equiv) in EtOH (20 mL) was added Pd/C (80 mg, 0.75 mmol, 0.3 equiv), and di-tert-butyl dicarbonate (1.2 g, 5.5 mmol, 1.2 equiv). The resulting solution was stirred for 2 hours under an atmosphere of hydrogen. After filtration, the filtrate was concentrated in vacuo, and the crude product was applied onto a silica gel column eluting with ethyl acetate/petroleum ether (9/1) to afford 660 mg (76% yield) of tert-butyl 4-(3-hydroxy-4,4-dimethyl-2-oxopyrrolidin-1-yl)piperidine-1-carboxylate as a white solid. LC-MS (ES, m/z): 313.10 $[M+H]^+$ Step C To a solution of tert-butyl 4-(3-hydroxy-4,4-dimethyl-2-oxopyrrolidin-1-yl)piperidine-1-carboxylate (660 mg, 2.11 mmol, 1.0 equiv) in dioxane (5 mL) was added 4M HCl in 1,4-dioxane (5 mL). The resulting solution stirred for 2 hours and then was concentrated in vacuo to afford 680 mg (91% yield) of 3-hydroxy-4,4-dimethyl-1-(piperidin-4-yl) pyrrolidin-2-one hydrochloride as a yellow solid. LCMS (ESI, m/z): 213.15 $[M+H]^+$.

Intermediate I-9: Synthesis of (S)-3-hydroxy-1-(piperidin-4-yl)pyrrolidin-2-one hydrochloride

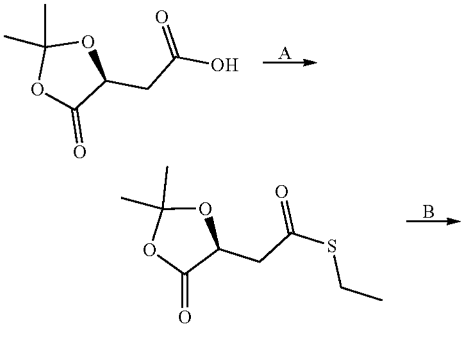

-continued

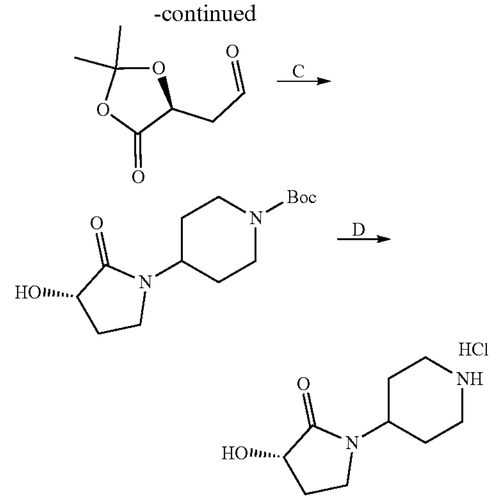

Step A

To a solution of (S)-2-(2,2-dimethyl-5-oxo-1,3-dioxolan-4-yl)acetic acid (10.0 g, 57.4 mmol, 1.0 equiv) in DCM (150 mL) was added DCC (17.8 g, 86.3 mmol, 1.5 equiv), DMAP (701 mg, 5.74 mmol, 0.1 equiv) and ethanethiol (7.14 g, 115 mmol, 2 equiv) at 0° C. The resulting solution was stirred for 10 min at 0° C. and then for 10 hours at room temperature. The solids were filtered, and the filtrate was concentrated in vacuo. The crude product was applied on a silica gel column and was eluted with ethyl acetate/petroleum ether (6/94) to afford 5.8 g (47% yield) of S-ethyl (S)-2-(2,2-dimethyl-5-oxo-1,3-dioxolan-4-yl)ethanethioate as a colorless oil.

Step B

To a solution of S-ethyl (S)-2-(2,2-dimethyl-5-oxo-1,3-dioxolan-4-yl)ethanethioate (5.80 g, 26.6 mmol, 1.0 equiv) in DCM (100 mL) was added triethylsilane (4.60 g, 39.5 mmol, 1.5 equiv) and Pd/C (2.00 g, 18.8 mmol, 0.7 equiv). The resulting solution was stirred for 3 hours at 25° C. The solids were filtered, and the filtrate was concentrated in vacuo. The crude product was cooled, and the isolated solid was collected to afford 5 g of crude (S)-2-(2,2-dimethyl-5-oxo-1,3-dioxolan-4-yl)acetaldehyde as a colorless solid.

Step C

To a solution of (S)-2-(2,2-dimethyl-5-oxo-1,3-dioxolan-4-yl)acetaldehyde (4.90 g, 30.9 mmol, 1.0 equiv) in DCM (100 mL) was added tert-butyl 4-aminopiperidine-1-carboxylate (9.31 g, 46.5 mmol, 1.5 equiv) and AcOH (3.72 g, 0.1 mmol, 2.0 equiv). The resulting solution was stirred for 1 hour, and then STAB (19.7 g, 93.0 mmol, 3.0 equiv) was added, and the reaction mixture stirred for an additional 3 hours. Saturated aqueous $NaHCO_3$ was added, and the aqueous layers were extracted with 2×50 mL of DCM. The combined organics were dried over anhydrous sodium sulfate and concentrated in vacuo. The residue was applied onto a silica gel column eluting with ethyl acetate/petroleum ether (30/70) to afford 6 g (68% yield) of tert-butyl (S)-4-(3-hydroxy-2-oxopyrrolidin-1-yl)piperidine-1-carboxylate as a yellow solid. LCMS (ESI, m/z): 285.20 $[M+H]^+$.

Step D

A solution of tert-butyl (S)-4-(3-hydroxy-2-oxopyrrolidin-1-yl)piperidine-1-carboxylate (6.00 g, 0.02 mmol, 1.0 equiv) in 4M HCl in dioxane (15 mL) was stirred for 1 hour and then was concentrated to afford 4.5 g (96% yield) of (S)-3-hydroxy-1-(piperidin-4-yl)pyrrolidin-2-one hydrochloride as a yellow solid. LCMS (ESI, m/z): 185.10 $[M+H]^+$.

Intermediate I-11: Synthesis of (R)-1-((1R,5S,6s)-3-azabicyclo[3.1.0]hexan-6-yl)-3-hydroxypyrrolidin-2-one hydrogen chloride

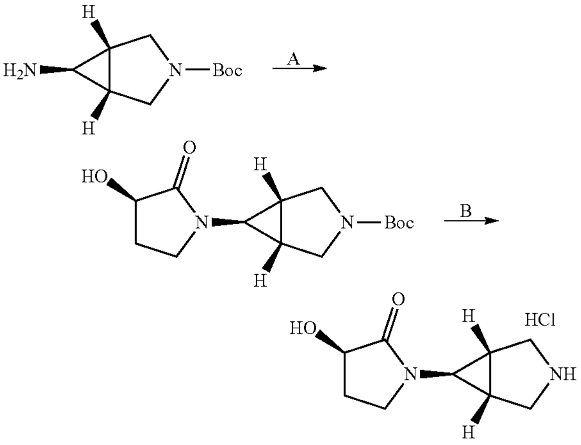

Step A

To a solution of tert-butyl (1R,5S,6s)-6-amino-3-azabicyclo[3.1.0]hexane-3-carboxylate (2.00 g, 10.1 mmol, 1.0 equiv) in DCM (40 mL) was added 2-[(4R)-2,2-dimethyl-5-oxo-1,3-dioxolan-4-yl]acetaldehyde (5.00 g, 31.6 mmol, 3.1 equiv) and AcOH (0.20 g, 3.33 mmol, 0.3 equiv). The reaction mixture stirred for 1 hour, and then STAB (4.10 g, 19.4 mmol, 1.9 equiv) was added, and the reaction was stirred for an additional 1.5 hours. The solution was washed with 2×50 mL of aqueous $NaHCO_3$, and the organic layers were combined, dried over anhydrous sodium sulfate and concentrated. The crude product was applied onto a silica gel column eluting with ethyl acetate/MeOH (4/1) to afforded 600 mg (21% yield) of tert-butyl (1R,5S,6s)-6-((R)-3-hydroxy-2-oxopyrrolidin-1-yl)-3-azabicyclo[3.1.0]hexane-3-carboxylate as a yellow solid. LCMS (ESI, m/z): 283.15 $[M+H]^+$.

Step B

A solution of tert-butyl (1R,5S,6s)-6-((R)-3-hydroxy-2-oxopyrrolidin-1-yl)-3-azabicyclo[3.1.0]hexane-3-carboxylate (600 mg, 2.13 mmol, 1.0 equiv) in 4M HCl in dioxane (5 mL) was stirred for 1 hour. The mixture was concentrated to afford 400 mg (crude) of (R)-1-((1R,5S,6s)-3-azabicyclo[3.1.0]hexan-6-yl)-3-hydroxypyrrolidin-2-one hydrogen chloride as a yellow solid. LCMS (ES, m/z): 183.20 $[M+H]^+$.

Intermediate I-12: Synthesis of (3R,4S)-3-hydroxy-4-methyl-1-(piperidin-4-yl)pyrrolidin-2-one hydrochloride and (3S,4R)-3-hydroxy-4-methyl-1-(piperidin-4-yl)pyrrolidin-2-one hydrochloride

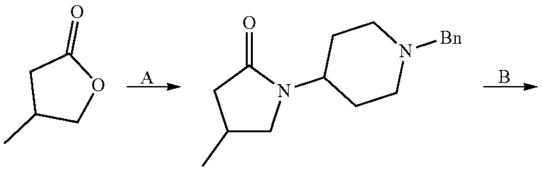

-continued

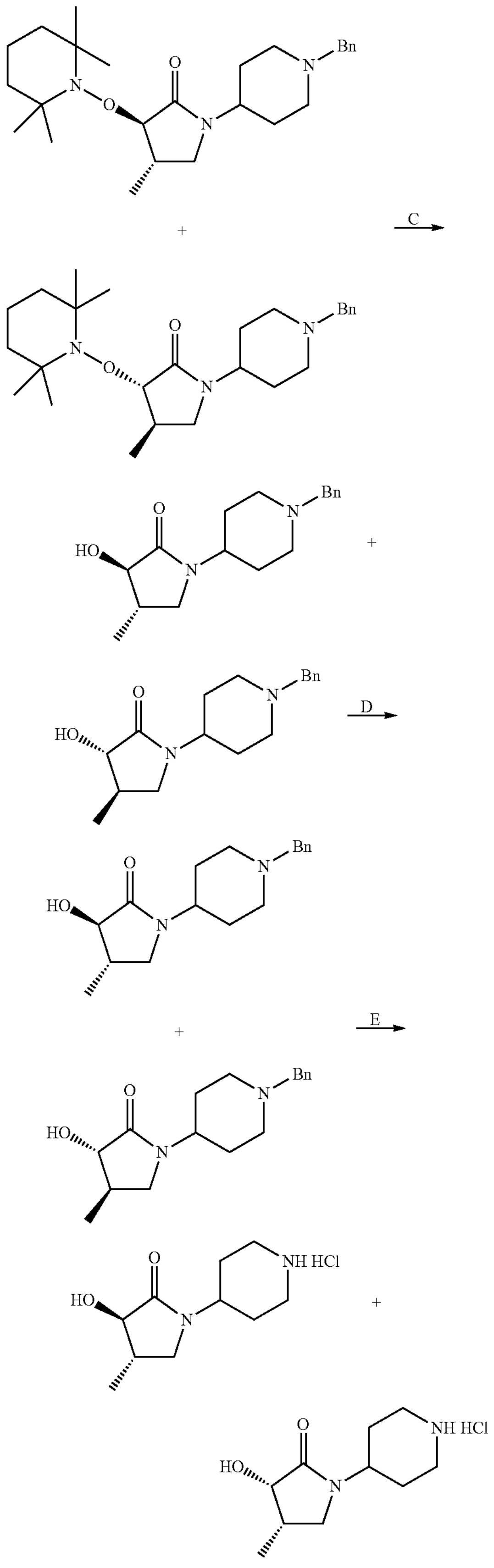

Step A

To a solution of 4-methyldihydrofuran-2(3H)-one (5.30 g, 52.9 mmol, 1.0 equiv) in diethylene glycol dimethyl ether (4 mL) was added 1-benzylpiperidin-4-amine (15.1 g, 79.4 mmol, 1.5 equiv) and 4-methylbenzenesulfonic acid (1.37 g, 7.94 mmol, 0.2 equiv). The resulting solution was stirred for 16 hours at 180° C. and then was diluted with 6 mL of ethyl acetate and applied onto a silica gel column eluting with dichloromethane/methanol (87/13) to afford 2.49 g (17% yield) of 1-(1-benzylpiperidin-4-yl)-4-methylpyrrolidin-2-one as a yellow oil. LCMS (ESI, m/z): 273.05 $[M+H]^+$.

Step B

To a solution of 1-(1-benzylpiperidin-4-yl)-4-methylpyrrolidin-2-one (3.10 g, 11.4 mmol, 1.0 equiv) in DCM (20 mL) under a nitrogen atmosphere was added 3A molecular sieves (2 g), TEMPO (3.91 g, 25.0 mmol, 2.2 equiv) and $Tf_2O$ (6.42 g, 22.8 mmol, 2.0 equiv) at 0° C. The resulting solution was stirred for 30 min and then for another 2 hours at room temperature. The solids were filtered, and the filtrate was then concentrated and applied onto a silica gel column eluting with dichloromethane/methanol (97/3) to afford 1.3 g (20% yield) of (3R,4S)-1-(1-benzylpiperidin-4-yl)-4-methyl-3-((2,2,6,6-tetramethylpiperidin-1-yl)oxy)pyrrolidin-2-one and (3S,4R)-1-(1-benzylpiperidin-4-yl)-4-methyl-3-((2,2,6,6-tetramethylpiperidin-1-yl)oxy)pyrrolidin-2-one as a yellow solid. LCMS (ESI, m/z): 428.30 $[M+H]^+$.

Step C

To a mixture of (3R,4S)-1-(1-benzylpiperidin-4-yl)-4-methyl-3-((2,2,6,6-tetramethylpiperidin-1-yl)oxy)pyrrolidin-2-one and (3S,4R)-1-(1-benzylpiperidin-4-yl)-4-methyl-3-((2,2,6,6-tetramethylpiperidin-1-yl)oxy)pyrrolidin-2-one (1.30 g, 3.04 mmol, 1.0 equiv) in AcOH/THF/water (15 mL, 3:1:1) was added Zn (3.98 g, 60.8 mmol, 20 equiv). The resulting solution was stirred for 2 hours at 70° C. and then was diluted with water (15 mL). The pH was adjusted to 12 with aqueous NaOH and extracted with 3×30 mL of ethyl acetate. The combined organic layers were dried over anhydrous sodium sulfate and concentrated in vacuo. The crude product was applied onto a silica gel column eluting with dichloromethane/methanol (93/7) to afford 180 mg (21% yield) of (3R,4S)-1-(1-benzylpiperidin-4-yl)-3-hydroxy-4-methylpyrrolidin-2-one and (3S,4R)-1-(1-benzylpiperidin-4-yl)-3-hydroxy-4-methylpyrrolidin-2-one as yellow oil. LCMS (ESI, m/z): 289.20 $[M+H]^+$.

Step D

To a solution of (3R,4S)-1-(1-benzylpiperidin-4-yl)-3-hydroxy-4-methylpyrrolidin-2-one and (3S,4R)-1-(1-benzylpiperidin-4-yl)-3-hydroxy-4-methylpyrrolidin-2-one in MeOH (4 mL) was added di-tert-butyl dicarbonate (272 mg, 1.25 mmol, 2.0 equiv) and Pd/C (7 mg, 0.06 mmol, 0.1 equiv). The resulting solution was stirred for 1 hour under an atmosphere of hydrogen. The solids were filtered, and the filtrate was concentrated to afford 226 mg of crude tert-butyl (3R,4S)-4-(3-hydroxy-4-methyl-2-oxopyrrolidin-1-yl)piperidine-1-carboxylate and tert-butyl (3S,4R)-4-(3-hydroxy-4-methyl-2-oxopyrrolidin-1-yl)piperidine-1-carboxylate as a yellow oil. LCMS (ESI, m/z): 299.05 $[M+H]^+$.

Step E

A solution of crude tert-butyl (3R,4S)-4-(3-hydroxy-4-methyl-2-oxopyrrolidin-1-yl)piperidine-1-carboxylate and tert-butyl (3S,4R)-4-(3-hydroxy-4-methyl-2-oxopyrrolidin-1-yl)piperidine-1-carboxylate (226 mg, 0.76 mmol, 1.0 equiv) in HCl/dioxane (10 mL, 4 M) was stirred for 1 hour and then was concentrated to afford 168 mg of crude (3R,4S)-3-hydroxy-4-methyl-1-(piperidin-4-yl)pyrrolidin-2-one hydrochloride and (3S,4R)-3-hydroxy-4-methyl-1-

(piperidin-4-yl)pyrrolidin-2-one hydrochloride as a white solid. LCMS (ESI, m/z): 199.05 $[M+H]^+$.

Intermediate I-13: Synthesis of (R)-1-((3R,4R)-3-fluoropiperidin-4-yl)-3-hydroxypyrrolidin-2-one-TFA salt and (R)-1-((3S,4S)-3-fluoropiperidin-4-yl)-3-hydroxypyrrolidin-2-one-TFA salt

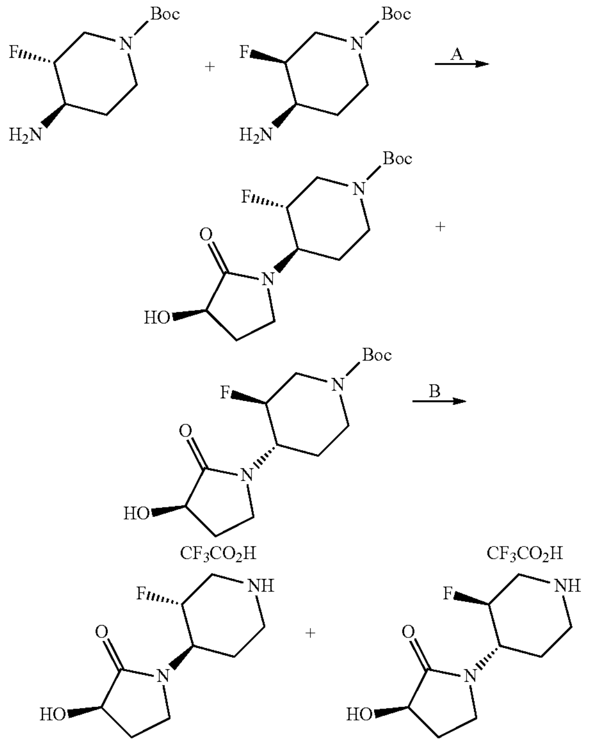

Step A

To a solution of tert-butyl (3R,4R)-4-amino-3-fluoropiperidine-1-carboxylate and tert-butyl (3S,4S)-4-amino-3-fluoropiperidine-1-carboxylate (1.00 g, 4.51 mmol, 1.0 equiv) in DCM (20 mL) was added (R)-2-(2,2-dimethyl-5-oxo-1,3-dioxolan-4-yl)acetaldehyde (1.10 g, 6.96 mmol, 1.5 equiv) and AcOH (1.70 g, 0.03 mmol, 0.01 equiv). The resulting solution was stirred for 1 hour, and then STAB (2.90 g, 0.01 mmol, 3.0 equiv) was added, and the reaction mixture stirred for an additional 3 hours. The reaction was quenched by the addition of saturated aqueous $NaHCO_3$. The aqueous layer was extracted with 2×50 mL of DCM. The combined organic layers were dried over anhydrous sodium sulfate and concentrated in vacuo. The residue was applied onto a silica gel column eluting with MeOH/DCM (5/95) to afford 700 mg (51% yield) of tert-butyl (3R,4R)-3-fluoro-4-((R)-3-hydroxy-2-oxopyrrolidin-1-yl)piperidine-1-carboxylate and tert-butyl (3S,4S)-3-fluoro-4-((R)-3-hydroxy-2-oxopyrrolidin-1-yl)piperidine-1-carboxylate as an off-white oil.

Step B

To a solution of tert-butyl (3R,4R)-3-fluoro-4-((R)-3-hydroxy-2-oxopyrrolidin-1-yl)piperidine-1-carboxylate and tert-butyl (3S,4S)-3-fluoro-4-((R)-3-hydroxy-2-oxopyrrolidin-1-yl)piperidine-1-carboxylate (700 mg, 2.32 mmol, 1.0 equiv) in DCM (5 mL) was added TFA (0.5 mL). The resulting solution was stirred for 1 hour and then concentrated to afford 600 mg of crude (R)-1-((3R,4R)-3-fluoropiperidin-4-yl)-3-hydroxypyrrolidin-2-one-TFA salt and (R)-1-((3S,4S)-3-fluoropiperidin-4-yl)-3-hydroxypyrrolidin-2-one-TFA salt as a brown oil.

Intermediate I-14: Synthesis of (R)-1-((3R,4S)-3-fluoropiperidin-4-yl)-3-hydroxypyrrolidin-2-one hydrochloride and (R)-1-((3S,4R)-3-fluoropiperidin-4-yl)-3-hydroxypyrrolidin-2-one hydrochloride

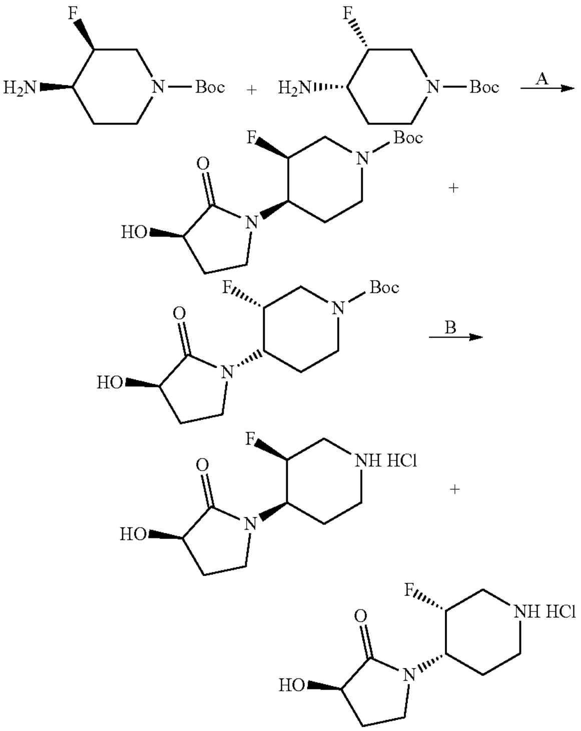

Step A

To a solution of (R)-2-(2,2-dimethyl-5-oxo-1,3-dioxolan-4-yl)acetaldehyde (2.90 g, 18.34 mmol, 4.0 equiv) in DCM (20 mL) was added AcOH (550 mg, 9.16 mmol, 2.0 equiv) and a mixture of tert-butyl (3 S,4R)-4-amino-3-fluoropiperidine-1-carboxylate and tert-butyl (3R,4S)-4-amino-3-fluoropiperidine-1-carboxylate (1.00 g, 4.51 mmol, 1.0 equiv). The resulting solution was stirred for 0.5 hours, and then STAB (2.91 g, 13.74 mmol, 3.0 equiv) was added, and the reaction was stirred for an additional 3 hours. The reaction was then quenched by the addition of 20 mL of aqueous $NaHCO_3$. The resulting solution was extracted with 3×50 mL of DCM. The organic layers were combined, dried over anhydrous sodium sulfate and concentrated in vacuo. The crude product was applied onto a silica gel column eluting with dichloromethane/methanol (2/3) to afford 0.66 g (48% yield) of tert-butyl (3S,4R)-3-fluoro-4-((R)-3-hydroxy-2-oxopyrrolidin-1-yl)piperidine-1-carboxylate and tert-butyl (3R,4S)-3-fluoro-4-((R)-3-hydroxy-2-oxopyrrolidin-1-yl)piperidine-1-carboxylate as yellow oil. LCMS (ESI, m/z): 303.15 $[M+H]^+$.

Step B

A solution of tert-butyl (3S,4R)-3-fluoro-4-((R)-3-hydroxy-2-oxopyrrolidin-1-yl)piperidine-1-carboxylate and tert-butyl (3R,4S)-3-fluoro-4-((R)-3-hydroxy-2-oxopyrrolidin-1-yl)piperidine-1-carboxylate (660 mg, 2.18 mmol, 1.0 equiv) in HCl/dioxane (15 mL, 4 M) was stirred for 15 hours. The resulting mixture was concentrated to afford 510 mg (98% yield) of (R)-1-((3R,4S)-3-fluoropiperidin-4-yl)-3-hydroxypyrrolidin-2-one hydrochloride and (R)-1-((3S,4R)-3-fluoropiperidin-4-yl)-3-hydroxypyrrolidin-2-one hydrochloride as a yellow oil. LCMS (ESI, m/z): 203.15 $[M+H]^+$.

Intermediate I-15: Synthesis of (R)-1-((R)-3,3-difluoropiperidin-4-yl)-3-hydroxypyrrolidin-2-one hydrochloride and (R)-1-((S)-3,3-difluoropiperidin-4-yl)-3-hydroxypyrrolidin-2-one hydrochloride

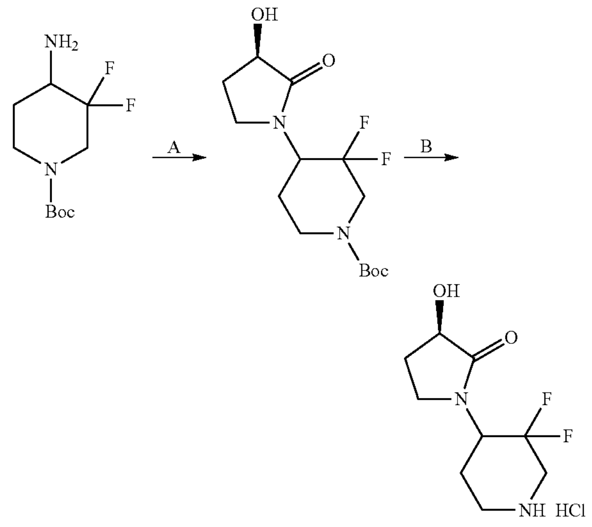

Step A

To a solution of tert-butyl 4-amino-3,3-difluoropiperidine-1-carboxylate (1.00 g, 4.23 mmol, 1.0 equiv) in DCM (50 mL) was added (R)-2-(2,2-dimethyl-5-oxo-1,3-dioxolan-4-yl)acetaldehyde (1004 mg, 6.35 mmol, 1.5 equiv), STAB (3.59 g, 16.9 mmol, 4.0 equiv) and AcOH (250 mg, 4.2 mmol, 1.0 equiv). The resulting solution stirred for 12 hours and was concentrated in vacuo. The crude product was applied onto a silica gel column with eluting DCM/methanol (9/1) to afford 1.5 g (crude) of tert-butyl 3,3-difluoro-4-((R)-3-hydroxy-2-oxopyrrolidin-1-yl)piperidine-1-carboxylate as a yellow solid. LCMS (ESI, m/z): 321.30 $[M+H]^+$.

Step B

A solution of tert-butyl 3,3-difluoro-4-((R)-3-hydroxy-2-oxopyrrolidin-1-yl)piperidine-1-carboxylate (1.50 g, 4.68 mmol, 1.0 equiv) in 4M HCl in dioxane (10 mL) was stirred for 6 hours and was then concentrated in vacuo to afford 1.5 g (crude) of (R)-1-((R)-3,3-difluoropiperidin-4-yl)-3-hydroxypyrrolidin-2-one hydrochloride and (R)-1-((S)-3,3-difluoropiperidin-4-yl)-3-hydroxypyrrolidin-2-one hydrochloride as a yellow oil. LCMS (ESI, m/z): 221.10 $[M+H]^+$.

Intermediate I-16: Synthesis of (1-(4-methoxybenzyl)-6-oxo-5-(trifluoromethyl)-1,6-dihydropyridazin-4-yl)-L-alanine

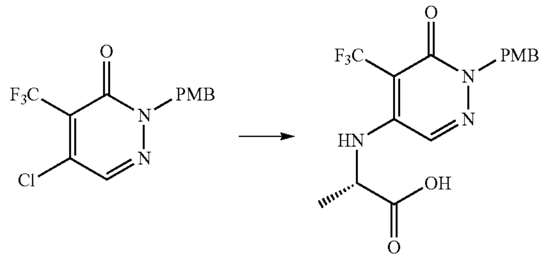

To a solution of 5-chloro-2-(4-methoxybenzyl)-4-(trifluoromethyl)pyridazin-3(2H)-one (2.00 g, 6.28 mmol, 1.0 equiv) in DMF (15 mL) was added L-alanine (725 mg, 8.14 mmol, 1.3 equiv) and $K_2CO_3$ (2.60 g, 18.8 mmol, 3.0 equiv). The resulting solution was stirred for 2 hours at 60° C. and then was quenched by the addition of 100 mL of water. The pH was adjusted to 2-3 with aqueous 1N HCl. The solution was extracted with 3×150 mL of DCM. The organic layers were combined, dried over anhydrous sodium sulfate and concentrated in vacuo. The crude product was applied onto a reverse phase column eluting with water/$CH_3CN$ (1/1) to afford 1.4 g (60% yield) of (1-(4-methoxybenzyl)-6-oxo-5-(trifluoromethyl)-1,6-dihydropyridazin-4-yl)-L-alanine as a light yellow solid. LCMS (ES, m/z): 372.11 $[M+H]^+$.

Examples 34-37

Examples 34-37 were synthesized according to the procedures described for the synthesis of 5-((S)-1-((S)-1-(1-(5-(trifluoromethyl)pyrimidin-2-yl)piperidin-4-yl)-2-oxopyrrolidin-3-yloxy)propan-2-ylamino)-4-(trifluoromethyl)pyridazin-3(2H)-one and 5-((S)-1-((R)-1-(1-(5-(trifluoromethyl)pyrimidin-2-yl)piperidin-4-yl)-2-oxopyrrolidin-3-yloxy)propan-2-ylamino)-4-(trifluoromethyl)pyridazin-3(2H)-one (see Example 10) using appropriate building blocks and modified reaction conditions (such as reagent ratio, temperature, coupling conditions, and reaction time) as needed. The relative stereochemistry of compounds was assigned by analogy to Example 10, based on the PARP7 potency of the more active diastereomer and in analogy to the Example 10B X-ray crystal structure.

| Example No. | Structure | Analytical Data |
|---|---|---|
| 34A | 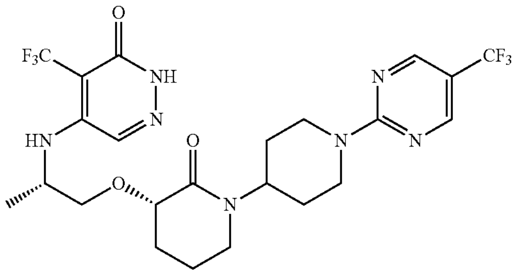 (S)-3-((S)-2-((6-oxo-5-(trifluoromethyl)-1,6-dihydropyridazin-4-yl)amino)propoxy)-1′-(5-(trifluoromethyl)pyrimidin-2-yl)-[1,4′-bipiperidin]-2-one | LCMS (ESI, m/z): 564.20 $[M + H]^+$; $^1H$ NMR (300 MHz, DMSO-d6) δ: 12.42 (s, 1H), 8.69 (d, J = 0.9 Hz, 2H), 7.92 (s, 1H), 6.48 (br, 1H), 4.83 (d, J = 12.9 Hz, 1H), 4.57-4.45 (m, 1H), 4.20-4.00 (m, 1H), 3.86-3.78 (m, 2H), 3.62-3.53 (m, 1H), 3.20-2.90 (m, 4H), 1.95-1.51 (m, 8H), 1.16 (d, J = 6.3 Hz, 3H). |
| 34B | 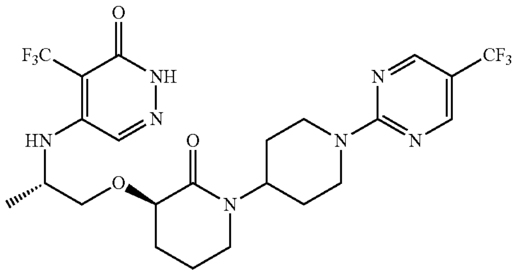 (R)-3-((S)-2-((6-oxo-5-(trifluoromethyl)-1,6-dihydropyridazin-4-yl)amino)propoxy)-1′-(5-(trifluoromethyl)pyrimidin-2-yl)-[1,4′-bipiperidin]-2-one | LCMS (ESI, m/z): 564.20 $[M + H]^+$; $^1H$ NMR (300 MHz, DMSO-d6) δ: 12.45 (s, 1H), 8.69 (d, J = 0.9 Hz, 2H), 7.94 (s, 1H), 6.47 (br, 1H), 4.84 (d, J = 12.9 Hz, 1H), 4.65-4.35 (m, 1H), 4.22-4.01 (m, 1H), 3.89-3.72 (m, 2H), 3.68-3.58 (m, 1H), 3.15-2.90 (m, 4H), 2.00-1.47 (m, 8H), 1.15 (d, J = 6.3 Hz, 3H). |
| 35A | 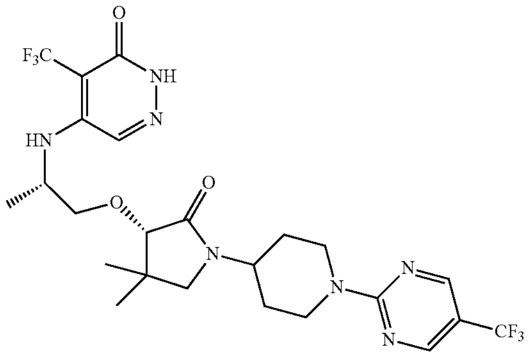 5-(((S)-(((S)-4,4-dimethyl-2-oxo-1-(1-(5-(trifluoromethyl)pyrimidin-2-yl)piperidin-4-yl)pyrrolidin-3-yl)oxy-propan-2-yl)amino-4-(trifluoromethyl)pyridazin-3(2H)-one | LCMS (ESI, m/z): 578.30 $[M + H]^+$; $^1H$ NMR (400 MHz, DMSO-$d_6$) δ 12.38 (s, 1H), 8.69 (s, 2H), 7.93 (s, 1H), 6.39 (br, 1H), 4.80 (d, J = 13.2 Hz, 2H), 4.27-4.21 (m, 1H), 4.09-4.03 (m, 2H), 3.65 (s, 1H), 3.59-3.55 (m, 1H), 3.09-3.00 (m, 2H), 2.91 (s, 2H), 1.67-1.46 (m, 4H), 1.17 (d, J = 6.5 Hz, 3H), 1.00 (s, 3H), 0.77 (s, 3H). |

-continued

| Example No. | Structure | Analytical Data |
|---|---|---|
| 35B | 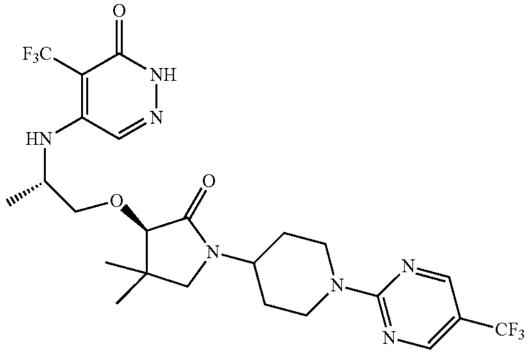 5-(((S)-(((R)-4,4-dimethyl-2-oxo-1-(1-(5-(trifluoromethyl)pyrimidin-2-yl)piperidin-4-yl)pyrrolidin-3-yl)oxy-propan-2-yl)amino-4-(trifluoromethyl)pyridazin-3(2H)-one | LCMS (ESI, m/z): 578.30 $[M+H]^+$; $^1H$ NMR (400 MHz, DMSO-$d_6$) δ 12.45 (s, 1H), 8.69 (s, 2H), 7.95 (s, 1H), 6.30 (br, 1H), 4.80 (d, J = 13.2 Hz, 2H), 4.26-4.18 (m, 1H), 4.10-4.04 (m, 1H), 4.00-3.96 (m, 1H), 3.68-3.63 (m, 2H), 3.07-3.00 (m, 2H), 2.92 (s, 2H), 1.66-1.48 (m, 4H), 1.19 (d, J = 6.4 Hz, 3H), 1.04 (s, 3H), 0.85 (s, 3H). |
| 36A | 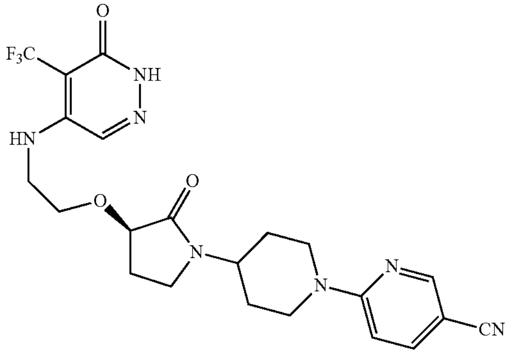 (R)-6-(4-(2-oxo-3-(2-((6-oxo-5-(trifluoromethyl)-1,6-dihydropyridazin-4-yl)amino)ethoxy)pyrrolidin-1-yl)piperidin-1-yl)nicotinonitrile | LCMS (ESI, m/z): 492.25 $[M+H]^+$ |
| 36B | 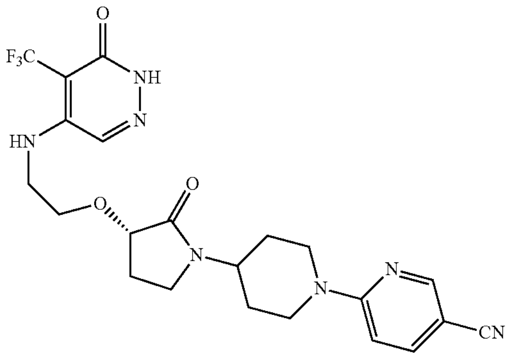 (S)-6-(4-(2-oxo-3-(2-((6-oxo-5-(trifluoromethyl)-1,6-dihydropyridazin-4-yl)amino)ethoxy)pyrrolidin-1-yl)piperidin-1-yl)nicotinonitrile | LCMS (ESI, m/z): 492.25 $[M+H]^+$ |

-continued

| Example No. | Structure | Analytical Data |
|---|---|---|
| 37A | 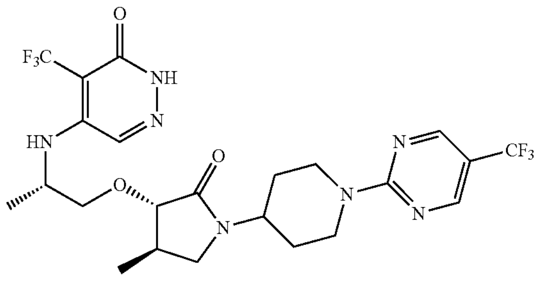<br>5-(((S)-1-(((3S,4R)-4-methyl-2-oxo-1-(1-(5-(trifluoromethyl)pyrimidin-2-yl)piperidin-4-yl)pyrrolidin-3-yl)oxy)propan-2-yl)amino)-4-(trifluoromethyl)pyridazin-3(2H)-one | LCMS (ESI, m/z): 564.20 $[M + H]^+$ |
| 37B | 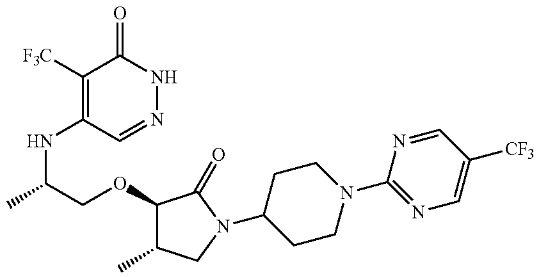<br>5-(((S)-1-(((3R,4S)-4-methyl-2-oxo-1-(1-(5-(trifluoromethyl)pyrimidin-2-yl)piperidin-4-yl)pyrrolidin-3-yl)oxy)propan-2-yl)amino)-4-(trifluoromethyl)pyridazin-3(2H)-one | LCMS (ESI, m/z): 564.20 $[M + H]^+$ |

Examples 38-40

Examples 38-40 were synthesized according to the procedures described for the synthesis of 5-((S)-1-((S)-1-(1-(5-(trifluoromethyl)pyrimidin-2-yl)piperidin-4-yl)-2-oxopyrrolidin-3-yloxy)propan-2-ylamino)-4-(trifluoromethyl)pyridazin-3(2H)-one and 5-((S)-1-((R)-1-(1-(5-(trifluoromethyl)pyrimidin-2-yl)piperidin-4-yl)-2-oxopyrrolidin-3-yloxy)propan-2-ylamino)-4-(trifluoromethyl)pyridazin-3(2H)-one (see Example 10) using appropriate building blocks and modified reaction conditions (such as reagent ratio, temperature, coupling conditions, and reaction time) as needed. The absolute stereochemistry of the substituted piperidine moieties was arbitrarily assigned.

| Example No. | Structure | Analytical Data |
|---|---|---|
| 38A | 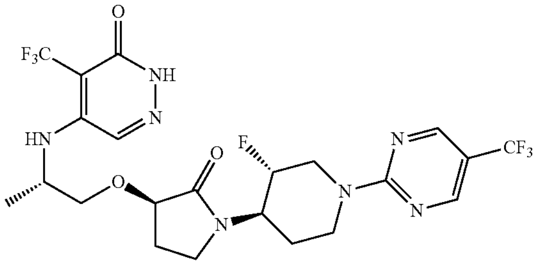<br>5-(((S)-1-(((R)-1-((3R,4R)-3-fluoro-1-(5-(trifluoromethyl)pyrimidin-2-yl)piperidin-4-yl)-2-oxopyrrolidin-3-yl)oxy)propan-2-yl)amino)-4-(trifluoromethyl)pyridazin-3(2H)-one | LCMS (ESI, m/z): 568.20 $[M + H]^+$ |

-continued

| Example No. | Structure | Analytical Data |
|---|---|---|
| 38B | 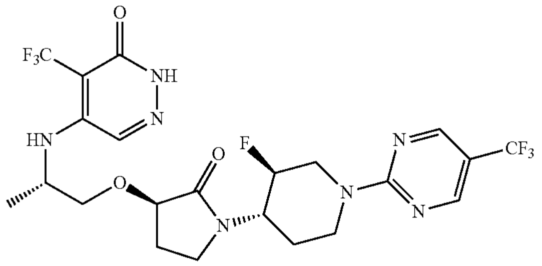<br>5-(((S)-1-(((R)-1-((3S,4S)-3-fluoro-1-(5-(trifluoromethyl)pyrimidin-2-yl)piperidin-4-yl)-2-oxopyrrolidin-3-yl)oxy)propan-2-yl)amino)-4-(trifluoromethyl)pyridazin-3(2H)-one | LCMS (ESI, m/z): 568.20 $[M + H]^+$ |
| 39A | 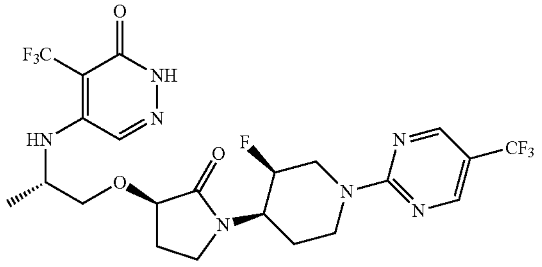<br>5-(((S)-1-(((R)-1-((3S,4R)-3-fluoro-1-(5-(trifluoromethyl)pyrimidin-2-yl)piperidin-4-yl)-2-oxopyrrolidin-3-yl)oxy)propan-2-yl)amino)-4-(trifluoromethyl)pyridazin-3(2H)-one | LCMS (ESI, m/z): 568.15 $[M + H]^+$; $^1H$ NMR (400 MHz, DMSO-$d_6$) δ 12.46 (s, 1H), 8.71 (s, 2H), 7.95 (s, 1H), 6.33-6.31 (m, 1H), 5.08 (t, J = 11.6 Hz, 1H), 4.97-4.86 (m, 2H), 4.29-4.13 (m, 3H), 3.83 (dd, J = 10.0, 6.3 Hz, 1H), 3.62 (dd, J = 10.0, 4.8 Hz, 1H), 3.43-3.33 (m, 2H), 3.30-3.24 (m, 1H), 3.19 (t, J = 12.6 Hz, 1H), 2.33-2.23 (m, 1H), 2.02-1.89 (m, 1H), 1.84-1.74 (m, 1H), 1.68-1.62 (m, 1H), 1.18 (d, J = 6.4 Hz, 3H). |
| 39B | 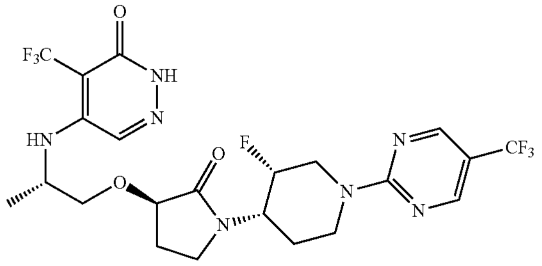<br>5-(((S)-1-(((R)-1-((3R,4S)-3-fluoro-1-(5-(trifluoromethyl)pyrimidin-2-yl)piperidin-4-yl)-2-oxopyrrolidin-3-yl)oxy)propan-2-yl)amino)-4-(trifluoromethyl)pyridazin-3(2H)-one | LCMS (ESI, m/z): 568.10 $[M + H]^+$; $^1H$ NMR (400 MHz, DMSO-$d_6$) δ 12.46 (s, 1H), 8.71 (s, 2H), 7.95 (s, 1H), 6.32-6.30 (m, 1H),5.09 (t, J = 11.6 Hz, 1H), 4.98-4.83 (m, 2H), 4.37-4.14 (m, 3H), 3.83 (dd, J = 10.0, 6.5 Hz, 1H), 3.62 (dd, J = 10.0, 4.7 Hz, 1H), 3.45-3.35 (m, 1H), 3.33-3.30 (m, 1H), 3.28-3.12 (m, 2H), 2.33-2.23 (m, 1H), 2.02-1.89 (m, 1H), 1.84-1.74 (m, 1H), 1.68-1.62 (m, 1H), 1.18 (d, J = 6.4 Hz, 3H). |
| 40A | 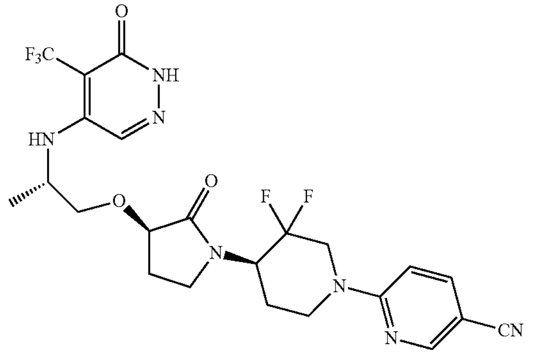<br>6-((R)-3,3-difluoro-4-((R)-2-oxo-3-((S)-2-((6-oxo-5-(trifluoromethyl)-1,6-dihydropyridazin-4-yl)amino)propoxy)pyrrolidin-1-yl)piperidin-1-yl)nicotinonitrile | LCMS (ESI, m/z): 542.15 $[M + H]^+$; $^1H$ NMR (300 MHz, DMSO-d6) δ 12.45 (s, 1H), 8.50 (d, J = 2.1 Hz, 1H), 7.94 (s, 1H),7.92-7.89 (m, 1H), 7.11 (d, J = 9.2 Hz, 1H), 6.31- 6.26 (m, 1H), 4.90-4.88 (m, 1H), 4.70-4.50 (m, 2H), 4.25-4.12 (m, 2H), 3.90-3.80 (m, 1H), 3.70-3.65 (m, 1H), 3.55-3.45(m, 1H), 3.43-3.38 (m, 2H), 3.29-3.22 (m, 1H), 2.28-2.20 (m, 1H), 1.85-1.72 (m, 3H), 1.16 (d, J = 6.5 Hz, 3H). |

-continued

| Example No. | Structure | Analytical Data |
|---|---|---|
| 40B | 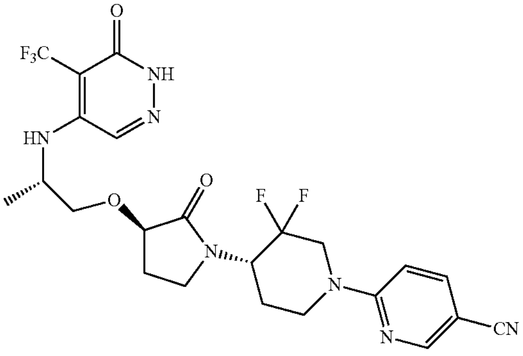 6-((S)-3,3-difluoro-4-((R)-2-oxo-3-((S)-2-((6-oxo-5-(trifluoromethyl)-1,6-dihydropyridazin-4-yl)amino)propoxy)pyrrolidin-1-yl)piperidin-1-yl)nicotinonitrile | LCMS (ESI, m/z): 542.15 [M + H]$^+$; $^1$H NMR (300 MHz, DMSO-$d_6$) δ 12.44 (s, 1H), 8.50 (d, J = 2.3 Hz, 1H), 7.96(s, 1H)7.94-7.85 (m, 1H), 7.11 (d, J = 9.1 Hz, 1H), 6.31-6.25(m, 1H), 4.87-4.80(m, 1H), 4.72-4.65 (m, 2H), 4.35-4.22(m, 2H), 3.85-3.80 (m, 1H), 3.70-3.63 (m, 1H), 3.55-3.35 (m, 2H), 3.31-3.17 (m, 2H), 2.32-2.28 (m, 1H), 2.02-1.90 (m, 1H), 1.73-1.67 (m, 2H), 1.16 (d, J = 6.4 Hz, 3H). |

Examples 41-45

Examples 41-45 were synthesized according to the procedures described for the synthesis of 5-(((S)-1-(((R)-1-(1-(5-chloropyrimidin-2-yl)piperidin-4-yl)-2-oxopyrrolidin-3-yl)oxy)propan-2-yl)amino)-4-(trifluoromethyl)pyridazin-3(2H)-one (see Example 16) using appropriate building blocks and modified reaction conditions (such as reagent ratio, temperature, coupling conditions, and reaction time) as needed.

| Example No. | Structure | Analytical Data |
|---|---|---|
| 41 | 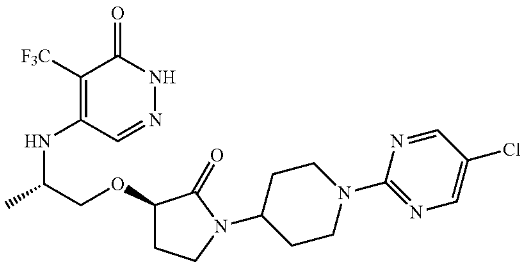 5-(((S)-1-(((R)-1-(1-(5-chloropyrazin-2-yl)piperidin-4-yl)-2-oxopyrrolidin-3-yl)oxy)propan-2-yl)amino)-4-(trifluoromethyl)pyridazin-3(2H)-one | LCMS (ESI, m/z): 516.10 [M + H]$^+$ |
| 42 | 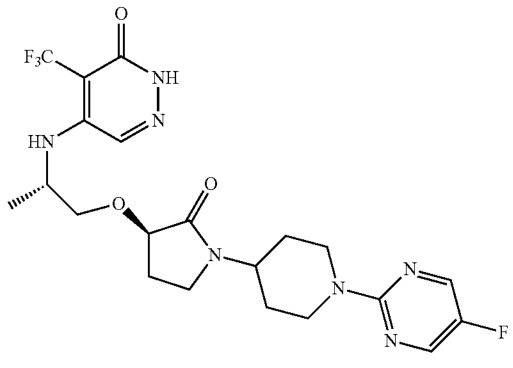 5-(((S)-1-(((R)-1-(1-(5-fluoropyrimidin-2-yl)piperidin-4-yl)-2-oxopyrrolidin-3-yl)oxy)propan-2-yl)amino)-4-(trifluoromethyl)pyridazin-3(2H)-one | LCMS (ESI, m/z): 500.20 [M + H]$^+$ |

-continued

| Example No. | Structure | Analytical Data |
|---|---|---|
| 43 | 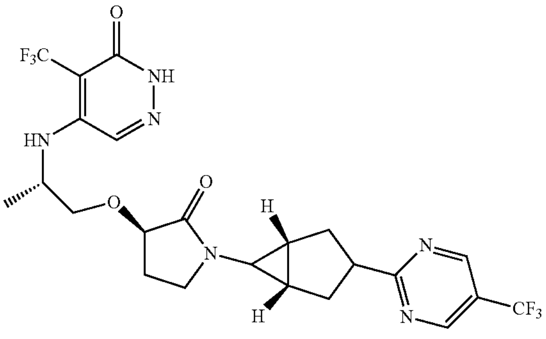 5-(((S)-1-(((R)-2-oxo-1-((1R,5S,6s)-3-(5-(trifluoromethyl)pyrimidin-2-yl)-3-azabicyclo[3.1.0]hexan-6-yl)pyrrolidin-3-yl)oxy)propan-2-yl)amino)-4-(trifluoromethyl)pyridazin-3(2H)-one | LCMS (ESI, m/z): 548.20 $[M + H]^+$ |
| 44 | 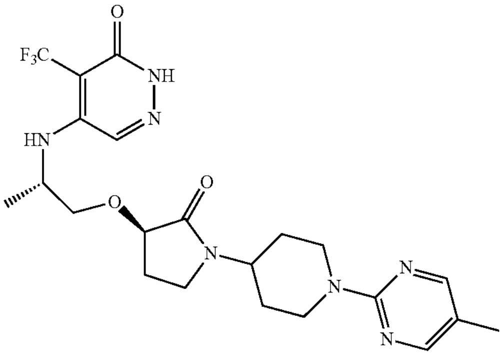 5-(((S)-1-(((R)-1-(1-(5-methylpyrimidin-2-yl)piperidin-4-yl)-2-oxopyrrolidin-3-yl)oxy)propan-2-yl)amino)-4-(trifluoromethyl)pyridazin-3(2H)-one | LCMS (ESI, m/z): 496.52 $[M + H]^+$; $^1$H NMR (400 MHz, $CDCl_3$) δ ppm 1.25 (s, 2 H) 1.33 (br d, J = 6.36 Hz, 4 H) 1.44 (br s, 1 H) 1.50-1.60 (m, 5 H) 1.63-1.75 (m, 3 H) 1.92 (br dd, J = 14.18, 7.34 Hz, 1 H) 2.03 (s, 1 H) 2.12 (s, 3 H) 2.28-2.38 (m, 1 H) 2.87-2.97 (m, 2 H) 3.15-3.23 (m, 1 H) 3.28-3.36 (m, 1H) 3.71 (br dd, J = 9.78, 4.40 Hz, 1 H) 3.91-4.00 (m, 1 H) 4.05 (t, J = 7.58 Hz, 1 H) 4.13-4.26(m, 2H) 4.84 (br dd, J = 9.54, 2.69 Hz, 2 H) 5.96 (br s, 1 H) 7.70 (s, 1 H) 8.15 (s, 2 H). |
| 45 | 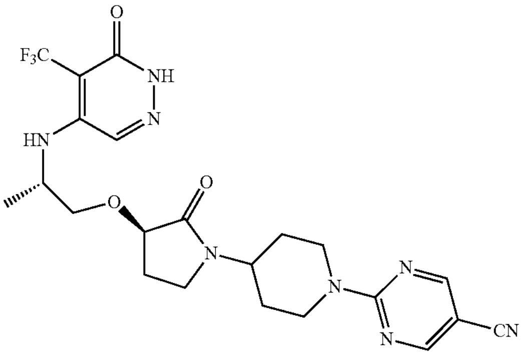 5-(4-((R)-2-oxo-3-((S)-2-((6-oxo-5-(trifluoromethyl)-1,6-dihydropyridazin-4-yl)amino)propoxy)pyrrolidin-1-yl)piperidin-1-yl)pyrazine-2-carbonitrile | LCMS (ESI, m/z): 507.43 $[M + H]^+$; $^1$H NMR ($CDCl_3$, 400 MHz) δ 10.46 (br s, 1H), 8.32 (s, 1H), 8.15 (s, 1H), 7.71 (s, 1H), 5.8-6.0 (m, 1H), 4.60 (br t, 2H, J = 14.7 Hz), 4.26 (tt, 1H, J = 4.3, 12.1 Hz), 4.1-4.2 (m, 1H), 4.05 (dd, 1H, J = 6.6, 7.6 Hz), 3.9-4.0 3.9, 9.8 Hz), 3.30 (dt, 1H, J = 4.4, 9.0 Hz), 3.2-3.2 (m, 1H), 3.0-3.1 (m, 2H), 2.3-2.4 (m, 1H), 1.9-2.0 (m, 1H), 1.83 (br d, 2H, J = 11.7 Hz), 1.6-1.7 (m, 2H), 1.5-1.6 (m, 1H), 1.32 (d, 3H, J = 6.8 Hz), 1.25 (s, 2H). |

Examples 46-49

Examples 46-49 were synthesized according to the procedures described for the synthesis of 5-(((S)-1-(((S)-2-oxo-1-(1-(5-(trifluoromethyl)pyrimidin-2-yl)piperidin-4-yl)pyrrolidin-3-yl)oxy)propan-2-yl)oxy)-4-(trifluoromethyl) pyridazin-3(2H)-one and 5-(((S)-1-(((R)-2-oxo-1-(1-(5-(trifluoromethyl)pyrimidin-2-yl)piperidin-4-yl)pyrrolidin-3-yl)oxy)propan-2-yl)oxy)-4-(trifluoromethyl)pyridazin-3 (2N)-one (see Examples 20A and 20B) using appropriate building blocks and modified reaction conditions (such as reagent ratio, temperature, coupling conditions, and reaction time) as needed. The relative stereochemistry of compounds was assigned by analogy to Example 10, based on the PARP7 potency of the more active diastereomer and in analogy to the Example 10B X-ray crystal structure.

| Example No. | Structure | Analytical Data |
| --- | --- | --- |
| 46A | 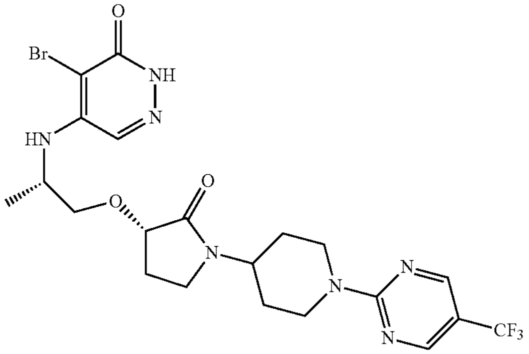<br>4-bromo-5-(((S)-1-(((S)-2-oxo-1-(1-(5-(trifluoromethyl)pyrazin-2-yl)piperidin-4-yl)pyrrolidin-3-yl)oxy)propan-2-yl)oxy)pyridazin-3(2H)-one | LCMS (ESI, m/z): 563.10 $[M + H]^+$; 1H NMR (300 MHz, DMSO-d6) δ 12.42 (s, 1H), 8.69 (d, J = 0.9 Hz, 2H), 7.92 (s, 1H), 6.48 (br s, 1H), 4.83 (d, J = 12.9 Hz, 1H), 4.57-4.45 (m, 1H), 4.20-4.00 (m, 1H), 3.86-3.78 (m, 2H), 3.62-3.53 (m, 1H), 3.20-2.90 (m, 4H), 1.95-1.51 (m, 8H), 1.16 (d, J = 6.3 Hz, 3H). |
| 46B | 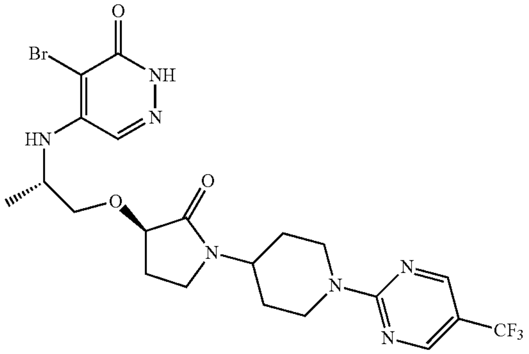<br>4-bromo-5-(((S)-1-(((R)-2-oxo-1-(1-(5-(trifluoromethyl)pyrazin-2-yl)piperidin-4-yl)pyrrolidin-3-yl)oxy)propan-2-yl)oxy)pyridazin-3(2H)-one | LCMS (ESI, m/z): 563.10 $[M + H]^+$; 1H NMR (300 MHz, DMSO-d6) δ 12.45 (s, 1H), 8.69 (d, J = 0.9 Hz, 2H), 7.94 (s, 1H), 6.47 (br s, 1H), 4.84 (d, J = 12.9 Hz, 1H), 4.65-4.35 (m, 1H), 4.22-4.01 (m, 1H), 3.89-3.72 (m, 2H), 3.68-3.58 (m, 1H), 3.15-2.90 (m, 4H), 2.00-1.47 (m, 8H), 1.15 (d, J = 6.3 Hz, 3H). |
| 47A | 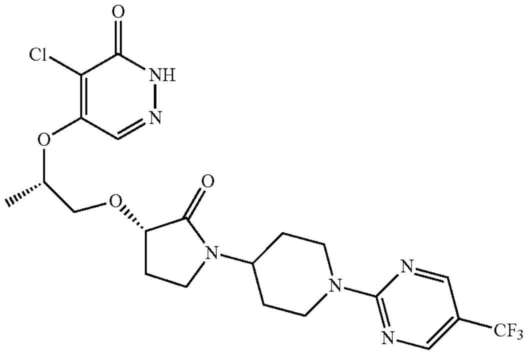<br>4-chloro-5-(((S)-1-(((S)-2-oxo-1-(1-(5-(trifluoromethyl)pyrimidin-2-yl)piperidin-4-yl)pyrrolidin-3-yl)oxy)propan-2-yl)oxy)pyridazin-3(2H)-one | LCMS (ESI, m/z): 517.10 $[M + H]^+$; $^1H$ NMR(300 MHz, DMSO-$d_6$) δ 13.22 (s, 1H), 8.70 (s, 2H), 8.21 (s, 1H), 5.30-5.10 (m, 1H), 4.83 (d, J = 13.5 Hz, 2H), 4.21-3.90 (m, 3H), 3.72-3.61 (m, 1H), 3.25-2.98 (m, 4H), 2.27-2.06 (m, 1H), 1.72-1.48 (m, 5H), 1.29 (d, J = 6.3 Hz, 3H). |

-continued

| Example No. | Structure | Analytical Data |
|---|---|---|
| 47B | 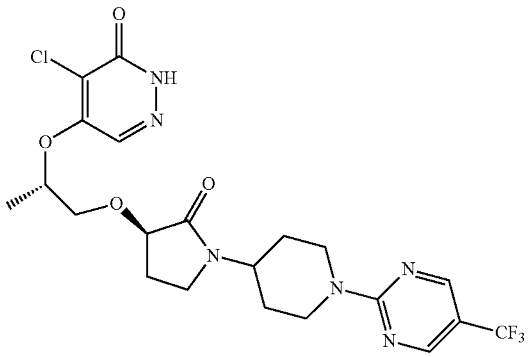 4-chloro-5-(((S)-1-(((R)-2-oxo-1-(1-(5-(trifluoromethyl)pyrimidin-2-yl)piperidin-4-yl)pyrrolidin-3-yl)oxy)propan-2-yl)oxy)pyridazin-3(2H)-one | LCMS (ESI, m/z): 517.10 $[M+H]^+$; $^1H$ NMR (300 MHz, DMSO-$d_6$) δ 13.22 (s, 1H), 8.70 (s, 2H), 8.23 (s, 1H), 5.11-4.99 (m, 1H), 4.82 (d, J = 13.4 Hz, 2H), 4.17-3.99 (m, 2H), 3.98-3.85 (m, 1H), 3.82-3.74 (m, 1H), 3.27-2.96 (m, 4H), 2.33-2.18 (m, 1H), 1.81-1.49 (m, 5H), 1.29 (d, J = 6.3 Hz, 3H). |
| 48A | 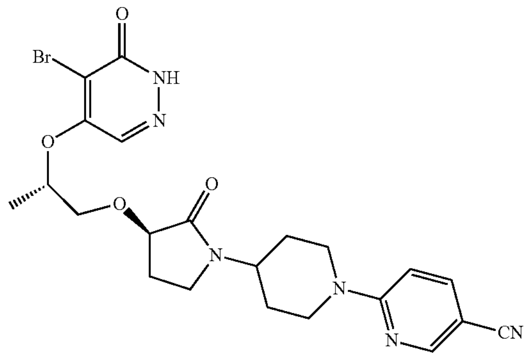 6-(4-((R)-3-((S)-2-((5-bromo-6-oxo-1,6-dihydropyridazin-4-yl)oxy)propoxy)-2-oxopyrrolidin-1-yl)piperidin-1-yl)nicotinonitrile | LCMS (ESI, m/z): 519.10 $[M+H]^+$ |
| 48B | 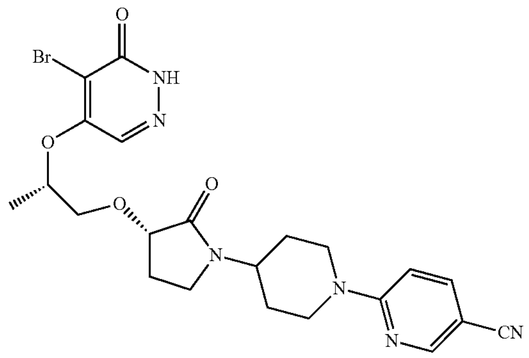 6-(4-((S)-3-((S)-2-((5-bromo-6-oxo-1,6-dihydropyridazin-4-yl)oxy)propoxy)-2-oxopyrrolidin-1-yl)piperidin-1-yl)nicotinonitrile | LCMS (ESI, m/z): 519.10 $[M+H]^+$ |

-continued
| Example No. | Structure | Analytical Data |
|---|---|---|
| 49A | 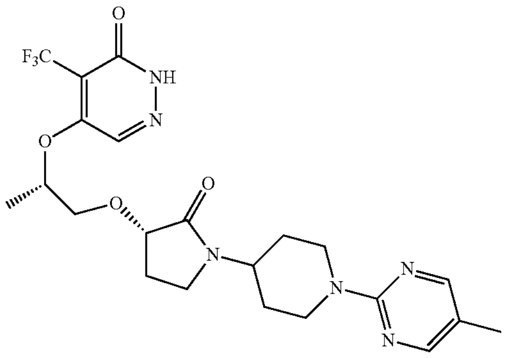 5-(((S)-1-(((S)-1-(1-(5-methylpyrdimidin-2-yl)piperidin-4-yl)-2-oxypyrrolidin-3-yl)oxy)propan-2-yl)oxy)-4-(trifluoromethyl)pyridazin-3(2H)-one | LCMS (ESI, m/z): 497.30 $[M + H]^+$ |
| 49B | 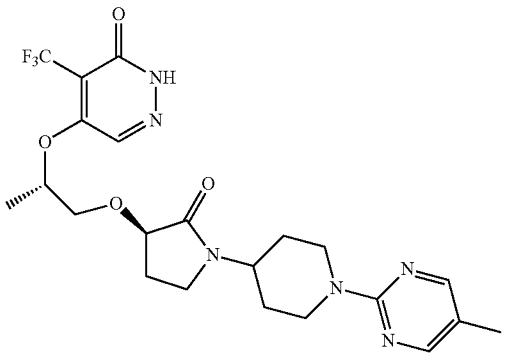 5-(((S)-1-(((R)-1-(1-(5-methylpyrdimidin-2-yl)piperidin-4-yl)-2-oxypyrrolidin-3-yl)oxy)propan-2-yl)oxy)-4-(trifluoromethyl)pyridazin-3(2H)-one | LCMS (ESI, m/z): 497.30 $[M + H]^+$ |

Example 50: Synthesis of 6-(4-((R)-3-((S)-3-methoxy-2-((6-oxo-5-(trifluoromethyl)-1,6-dihydropyridazin-4-yl)oxy)propoxy)-2-oxopyrrolidin-1-yl)piperidin-1-yl)nicotinonitrile and 6-(4-((S)-3-((S)-3-methoxy-2-((6-oxo-5-(trifluoromethyl)-1,6-dihydropyridazin-4-yl)oxy)propoxy)-2-oxopyrrolidin-1-yl)piperidin-1-yl)nicotinonitrile

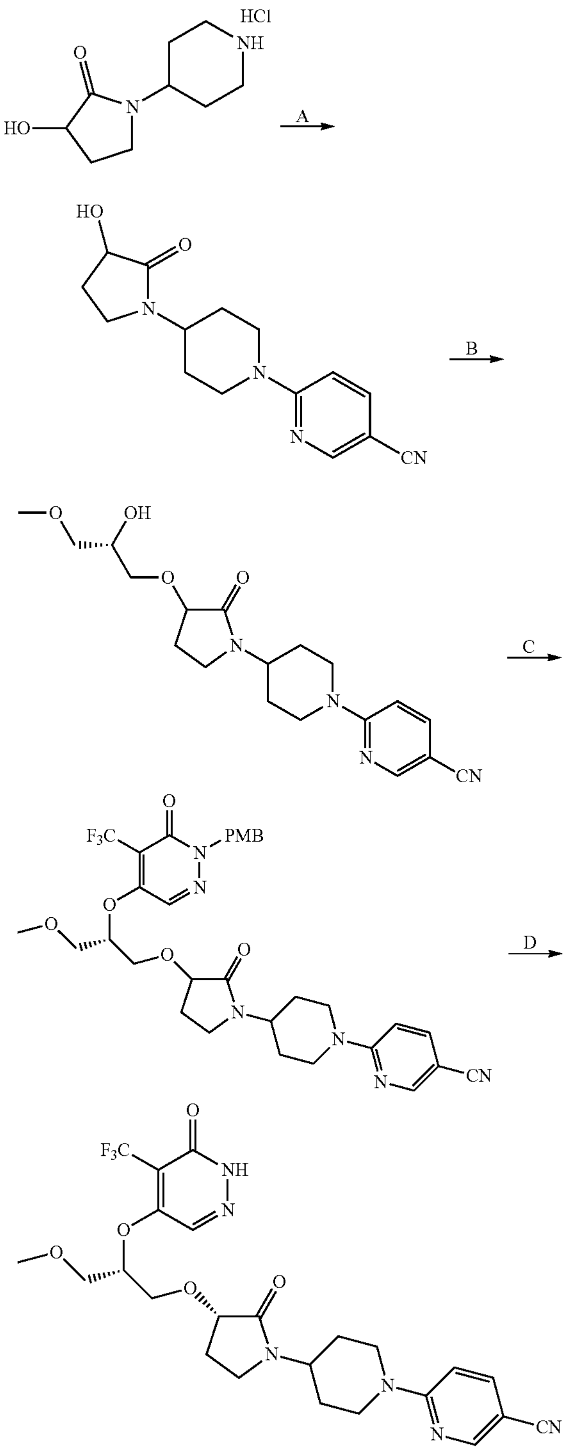

50A

-continued

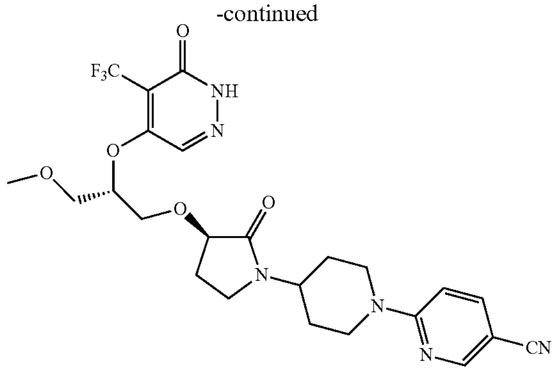

50B

Step A

To a solution of 3-hydroxy-1-(piperidin-4-yl)pyrrolidin-2-one hydrochloride (2.00 g, 9.06 mmol, 1.0 equiv) in DMF (8 mL) was added 6-chloronicotinonitrile (1.26 g, 9.09 mmol, 1.0 equiv) and $K_2CO_3$ (2.50 g, 18.1 mmol, 2.0 equiv). The resulting solution was stirred for 2 hours at 80° C. and then was quenched by the addition of water (20 mL). The solution was extracted with 2×50 mL of ethyl acetate. The organic layers were combined, dried over anhydrous sodium sulfate, and concentrated in vacuo. The crude product was applied onto a silica gel column eluting with ethyl acetate/petroleum ether (60/40) to afford 1.8 g (69% yield) of 6-(4-(3-hydroxy-2-oxopyrrolidin-11-yl)piperidin-1-yl)nicotinonitrile as a white solid. (ES, m/z). 287.15 $[M+H]^+$.

Step B

To a solution of 6-(4-(3-hydroxy-2-oxopyrrolidin-11-yl)piperidin-11-yl)nicotinonitrile (600 mg, 2.10 mmol, 1.0 equiv) in DMF (5 mL) was added NaH (334 mg, 8.35 mmol, 4.0 equiv, 60% dispersion in mineral oil) at 0° C. The solution was stirred for 10 min at 0° C., and then (S)-oxiran-2-ylmethyl 3-nitrobenzenesulfonate (650 mg, 2.51 mmol, 1.2 equiv) was added. The solution was stirred for 25 hours at 50° C. MeOH (5 mL) was added, and the reaction was stirred for an additional 2 hours at 50° C. After concentration the crude product was purified by reverse phase chromatography eluting with water/$CH_3CN$ (45/55) to afford 300 mg (39% yield) of 6-(4-(3-((S)-2-hydroxy-3-methoxypropoxy)-2-oxopyrrolidin-1-yl)piperidin-1-yl)nicotinonitrile as a white solid. (ES, m/z): 375.25 $[M+H]^+$.

Step C

To a solution of 6-(4-(3-((S)-2-hydroxy-3-methoxypropoxy)-2-oxopyrrolidin-1-yl)piperidin-1-yl)nicotinonitrile (120 mg, 0.32 mmol, 1.0 equiv) in DCM (4 mL) was added 5-chloro-2-(4-methoxybenzyl)-4-(trifluoromethyl)pyridazin-3(2H)-one (120 mg, 0.38 mmol, 1.2 equiv) and t-BuOK (72 mg, 0.64 mmol, 2.0 equiv). The resulting solution was stirred for 2 hours and then concentrated in vacuo. The crude product was applied onto a silica gel column eluting with MeOH/DCM (8/92) to afford 160 mg (68% yield) of 6-(4-(3-((S)-3-methoxy-2-((1-(4-methoxybenzyl)-6-oxo-5-(trifluoromethyl)-1,6-dihydropyridazin-4-yl)oxy)propoxy)-2-oxopyrrolidin-1-yl)piperidin-1-yl)nicotinonitrile as a white solid. LCMS (ESI, m/z): 657.25 $[M+H]^+$.

Step D

A solution of 6-(4-(3-((S)-3-methoxy-2-((1-(4-methoxybenzyl)-6-oxo-5-(trifluoromethyl)-1,6-dihydropyridazin-4-yl)oxy)propoxy)-2-oxopyrrolidin-1-yl)piperidin-1-yl)nicotinonitrile (160 mg, 0.244 mmol, 1.00 equiv) in 1.2 ml of TFA and triflic acid (5/1) was stirred for 10 minutes at 0° C. The reaction was then quenched by addition of water/ice (10 mL). The pH of the solution was adjusted to ~7-8 with saturated aqueous $Na_2CO_3$. The resulting solution was extracted with 3×50 mL of DCM. The organic layers were combined and concentrated in vacuo. The crude product was purified by reverse phase chromatography, and the isomeric mixture was separated by chiral prep HPLC: CHIRALPAK IA, 2*25 cm, 5 μm; Mobile Phase A: MTBE (10 mM $NH_3$-MEOH), Mobile Phase B: EtOH; Flow rate: 16 mL/min; Gradient: 30% B for 15 min; 220/254 nm to afford the separated compounds. The relative stereochemistry of compounds was assigned by analogy to Example 10, based on the PARP7 potency of the more active diastereomer and in analogy to the Example 10B X-ray crystal structure.

Example 50 Isomer A (50A): 6-(4-((S)-3-((S)-3-methoxy-2-((6-oxo-5-(trifluoromethyl)-1,6-dihydropyridazin-4-yl)oxy)propoxy)-2-oxopyrrolidin-1-yl)piperidin-1-yl)nicotinonitrile (46 mg, 35% yield, white solid). LCMS (ESI, m/z): 537.15$[M+H]^+$; $^1$HNMR (300 MHz, DMSO-$d_6$) δ 13.21 (s, 1H), 8.45 (d, J=2.3 Hz, 1H), 8.27 (s, 1H), 7.80 (dd, J=9.1, 2.4 Hz, 1H), 6.94 (d, J=9.1 Hz, 1H), 5.21 (br, 1H), 4.52 (d, J=13.4 Hz, 2H), 4.09-3.96 (m, 3H), 3.77-3.64 (m, 1H), 3.62-3.47 (m, 2H), 3.26 (s, 3H), 3.23-3.04 (m, 2H), 3.02-2.89 (m, 2H), 2.25-2.11 (m, 1H), 1.69-1.46 (m, 5H). CHIRALPAK IA-3, 4.6*100 mm 3 μm; Mobile Phase A: MtBE (0.1% Diethyl amine): EtOH=75:25; Flow rate: 1 mL/min; Retention time: 1.589 min (faster peak).

Example 50 Isomer A (50B): 6-(4-((R)-3-((S)-3-methoxy-2-((6-oxo-5-(trifluoromethyl)-1,6-dihydropyridazin-4-yl)oxy)propoxy)-2-oxopyrrolidin-1-yl)piperidin-1-yl)nicotinonitrile (54 mg, 41% yield, white solid). LCMS (ESI, m/z): 537.15$[M+H]^+$, $^1$H NMR (300 MHz, DMSO-$d_6$) δ 13.21 (s, 1H), 8.45 (d, J=2.4 Hz, 1H), 8.29 (s, 1H), 7.80 (dd, J=9.1, 2.4 Hz, 1H), 6.94 (d, J=9.1 Hz, 1H), 5.21 (br, 1H), 4.52 (d, J=13.3 Hz, 2H), 4.11-3.87 (m, 3H), 3.85-3.75 (m, 1H), 3.64-3.47 (m, 2H), 3.25 (s, 3H), 3.24-2.87 (m, 4H), 2.27-2.13 (m, 1H), 1.76-1.47 (m, 5H). CHIRALPAK IA-3, 4.6*100 mm 3 μm; Mobile Phase A: MtBE (0.1% Diethyl amine):EtOH=75:25; Flow rate: 1 mL/min; Retention time: 1.992 min (slower peak).

Examples 51-52

Examples 51-52 were synthesized according to the procedures described for the synthesis of 6-(4-((R)-3-((S)-3-methoxy-2-((6-oxo-5-(trifluoromethyl)-1,6-dihydropyri dazin-4-yl)oxy)propoxy)-2-oxopyrrolidin-1-yl)piperidin-1-yl)nicotinonitrile and 6-(4-((S)-3-((S)-3-methoxy-2-((6-oxo-5-(trifluoromethyl)-1,6-dihydropyridazin-4-yl)oxy)propoxy)-2-oxopyrrolidin-1-yl)piperidin-1-yl)nicotin onitrile (see Example 50) using appropriate building blocks and modified reaction conditions (such as reagent ratio, temperature, coupling conditions, and reaction time) as needed. The relative stereochemistry of compounds was assigned by analogy to Example 10, based on the PARP7 potency of the more active diastereomer and in analogy to the Example 10B X-ray crystal structure.

| Example No. | Structure | Analytical Data |
|---|---|---|
| 51A | 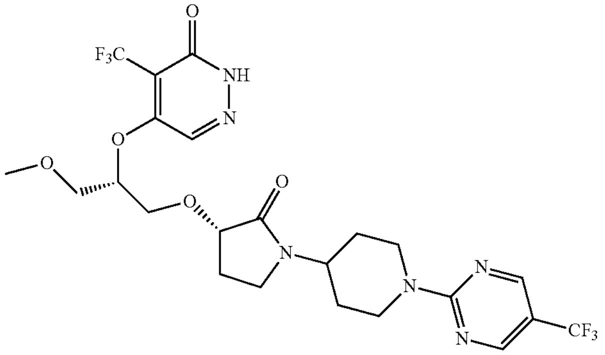<br>5-(((S)-1-methoxy-3-(((S)-2-oxo-1-(1-(5-(trifluoromethyl)pyrimidin-2-yl)piperidin-4-yl)pyrrolidin-3-yl)oxy)propan-2-yl)oxy)-4-(trifluoromethyl)pyridazin-3(2H)-one | LCMS (ESI, m/z): 581.20 $[M + H]^+$ |

-continued

| Example No. | Structure | Analytical Data |
|---|---|---|
| 51B | 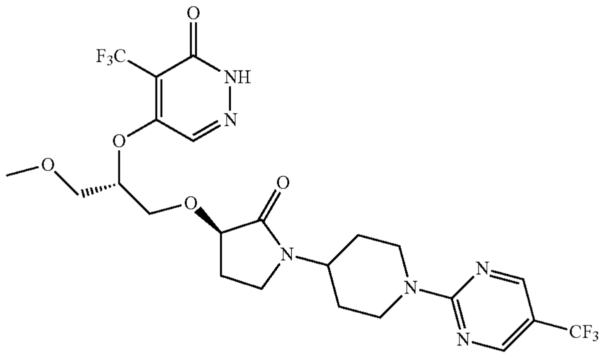<br>5-(((S)-1-methoxy-3-(((R)-2-oxo-1-(1-(5-(trifluoromethyl)pyrimidin-2-yl)piperidin-4-yl)pyrrolidin-3-yl)oxy)propan-2-yl)oxy)-4-(trifluoromethyl)pyridazin-3(2H)-one | LCMS (ESI, m/z): 581.20 $[M + H]^+$ |
| 52A | 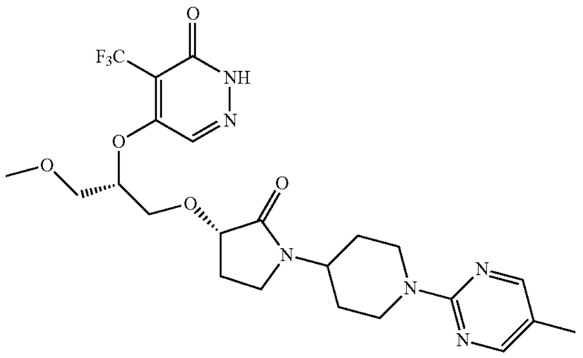<br>5-(((S)-1-methoxy-3-(((S)-1-(1-(5-methylpyrimidin-2-yl)piperidin-4-yl)-2-oxopyrrolidin-3-yl)oxy)propan-2-yl)oxy)-4-trifluoromethyl)pyridazin-3(2H)-one | LCMS (ESI, m/z): 527.20 $[M + H]^+$ |
| 52B | 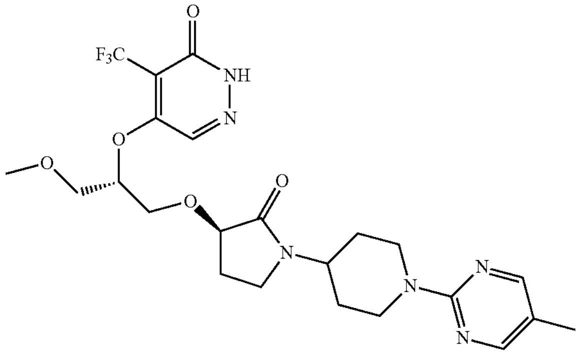<br>5-(((S)-1-methoxy-3-(((R)-1-(1-(5-methylpyrimidin-2-yl)piperidin-4-yl)-2-oxopyrrolidin-3-yl)oxy)propan-2-yl)oxy)-4-trifluoromethyl)pyridazin-3(2H)-one | LCMS (ESI, m/z): 527.15 $[M + H]^+$ |

Examples 53 and 54

Examples 53 and 54 were synthesized according to the procedures described for the synthesis of 6-(4-((S)-3-((S)-3-methoxy-2-((6-oxo-5-(trifluoromethyl)-1,6-dihydropy ridazin-4-yl)amino)propoxy)-2-oxopyrrolidin-1-yl)piperi-din-1-yl)nicotinonitrile and 6-(4-((R)-3-((S)-3-methoxy-2-((6-oxo-5-(trifluoromethyl)-1,6-dihydropyridazin-4-yl)am ino)propoxy)-2-oxopyrrolidin-1-yl)piperidin-1-yl)nicotino-nitrile (see Examples 17A and 17B) using appropriate build-ing blocks and modified reaction conditions (such as reagent ratio, temperature, coupling conditions, and reaction time) as needed.

| Example No. | Structure | Analytical Data |
| --- | --- | --- |
| 53 | 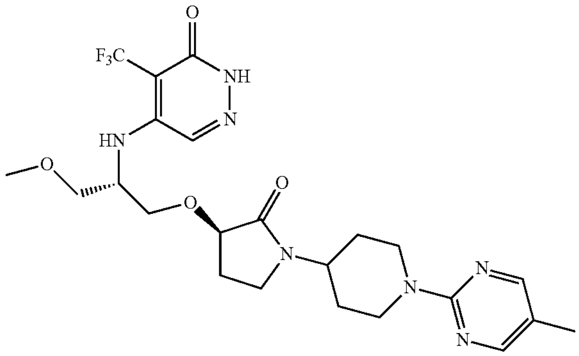<br>5-(((S)-1-methoxy-3-(((R)-1-(1-(5-methylpyrimidin-2-yl)piperidin-4-yl)-2-oxopyrrolidin-3-yl)oxy)propan-2-yl)amino)-4-trifluoromethyl)pyridazin-3(2H)-one | LCMS (ESI, m/z): 526.30 $[M + H]^+$ |
| 54 | 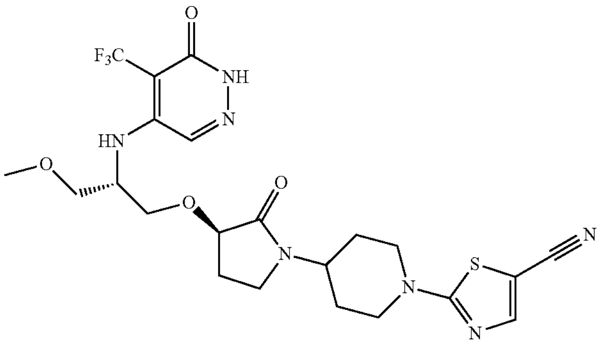<br>2-(4-((R)-3-((S)-3-methoxy-2-((6-oxo-5-trifluoromethyl)-1,6-dihydropyridazin-4-yl)amino)propoxy)-2-oxopyrrolidin-1-yl)piperidin-1-yl)thiazole-5-carbonitrile | LCMS (ESI, m/z): 542.20 $[M + H]^+$; $^1H$ NMR (300 MHz, DMSO-$d_6$) δ 12.49 (s, 1H), 7.97 (d, J = 14.5 Hz, 2H), 6.28 (br, 1H), 4.30 (br, 1H), 4.11-3.95 (m, 4H), 3.70-3.58 (m, 3H), 3.48 (d, J = 5.2 Hz, 3H), 3.27-3.22 (m, 3H), 3.18-3.06 (m, 2H), 2.25 (br, 1H), 1.78-1.62 (m, 5H). |

Example 55: Synthesis of 6-(4-((R)-3-((S)-2-((5-bromo-6-oxo-1,6-dihydropyridazin-4-yl)oxy)-3-methoxypropoxy)-2-oxopyrrolidin-1-yl)piperidin-1-yl)nicotinonitrile and 6-(4-((S)-3-((S)-2-((5-bromo-6-oxo-1,6-dihydropyridazin-4-yl)oxy)-3-methoxypropoxy)-2-oxopyrrolidin-1-yl)piperidin-1-yl)nicotinonitrile

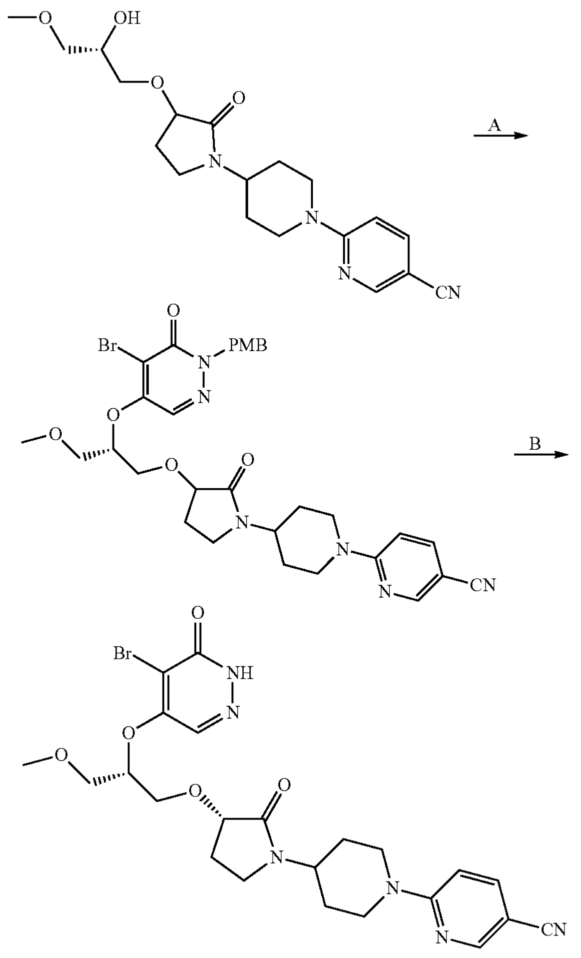

55A

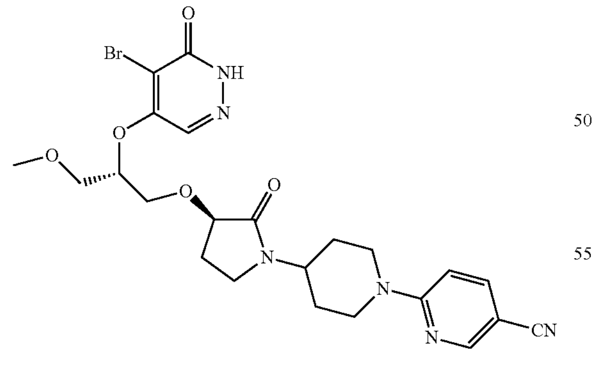

55B

Step A

To a solution of 6-(4-(3-((S)-2-hydroxy-3-methoxypropoxy)-2-oxopyrrolidin-1-yl)piperidin-1-yl)nicotinonitrile (280 mg, 0.75 mmol, 1.0 equiv) at 0° C. in DMF (3 mL) was added NaH (60 mg, 1.50 mmol, 2.01 equiv, 60% dispersion in mineral oil). The mixture was stirred for 10 min at 0° C. and then 4,5-dibromo-2-(4-methoxybenzyl)pyridazin-3(2H)-one (330 mg, 0.88 mmol, 1.2 equiv) was added, and the resulting solution stirred for 1 hour at room temperature. The reaction was then quenched with saturated aqueous $NH_4Cl$ (0.5 mL), and the resulting mixture was concentrated. The crude product was purified by reverse phase column eluting with water/$CH_3CN$ (65/45) to afford 150 mg (30% yield) of 6-(4-(3-((S)-2-((5-bromo-1-(4-methoxybenzyl)-6-oxo-1,6-dihydropyridazin-4-yl)oxy)-3-methoxypropoxy)-2-oxopyrrolidin-1-yl)piperidin-1-yl) nicotinonitrile as a yellow solid. (ES, m/z): 669.30 $[M+H]^+$.

Step B

A solution of 6-(4-(3-((S)-2-((5-bromo-1-(4-methoxybenzyl)-6-oxo-1,6-dihydropyridazin-4-yl)oxy)-3-methoxypropoxy)-2-oxopyrrolidin-1-yl)piperidin-1-yl)nicotinonitrile (150 mg, 0.23 mmol, 1.0 equiv) in 1:5 TfOH/TFA (1.5 mL) was stirred for 15 min at room temperature. The resulting solution was diluted with water (15 mL), and the pH was adjusted to 7-8 with sodium bicarbonate solution. The solution was extracted with 3×50 mL of DCM. The organic layers were combined, dried over anhydrous sodium sulfate and concentrated. The crude product was purified by reverse phase chromatography eluting with water/$CH_3CN$, and the isomeric mixture was separated by chiral prep HPLC: CHIRAL ART Cellulose-SB, 2*25 cm, 5 μm; Mobile Phase A: MTBE (10 mM $NH_3$-MEOH), Mobile Phase B: EtOH; Flow rate: 20 mL/min; Gradient: 20% B for 15 min; 220/254 nm. The relative stereochemistry of compounds was assigned by analogy to Example 10, based on the PARP7 potency of the more active diastereomer and in analogy to the Example 10B X-ray crystal structure.

Example 55 Isomer A (55A): 6-(4-((S)-3-((S)-2-((5-bromo-6-oxo-1,6-dihydropyridazin-4-yl)oxy)-3-methoxypropoxy)-2-oxopyrrolidin-1-yl)piperidin-1-yl)nicotinonitrile (31 mg, 25% yield, white solid). LCMS (ESI, m/z): 549.10 $[M+H]^+$; 1H NMR (400 MHz, DMSO-$d_6$) δ 13.13 (s, 1H), 8.47 (s, 1H), 8.11 (s, 1H), 7.83 (d, J=9.1 Hz, 1H), 6.96 (d, J=9.1 Hz, 1H), 5.08 (br, 1H), 4.59-4.48 (m, 2H), 4.12-3.95 (m, 3H), 3.79-3.70 (m, 1H), 3.65-3.54 (m, 2H), 3.29 (s, 3H), 3.25-3.06 (m, 2H), 3.04-2.91 (m, 2H), 2.27-2.15 (m, 1H), 1.72-1.46 (m, 5H). Chiral HPLC: Column: CHIRAL ART Cellulose-SB, 4.6*100 mm, 3 um; Mobile Phase: MtBE (0.1% diethyl amine):EtOH=80:20; Flow rate: 1 mL/min. Retention time: 3.928 min (faster peak).

Example 55 Isomer A (55B): 6-(4-((R)-3-((S)-2-((5-bromo-6-oxo-1,6-dihydropyridazin-4-yl)oxy)-3-methoxypropoxy)-2-oxopyrrolidin-1-yl)piperidin-1-yl)nicotinonitrile (42 mg, 35% yield, white solid). LCMS (ESI, m/z): 549.15 $[M+H]^+$; 1H NMR (400 MHz, DMSO-$d_6$) δ 13.14 (s, 1H), 8.47 (s, 1H), 8.13 (s, 1H), 7.85 (d, J=9.2 Hz, 1H), 6.96 (d, J=9.2 Hz, 1H), 5.08 (br, 1H), 4.57-4.49 (m, 2H), 4.14-3.91 (m, 3H), 3.86-3.79 (m, 1H), 3.65-3.53 (m, 2H), 3.29 (s, 3H), 3.25-3.07 (m, 2H), 3.05-2.92 (m, 2H), 2.34-2.19 (m, 1H), 1.78-1.46 (m, 5H). Chiral HPLC: Column: CHIRAL ART Cellulose-SB, 4.6*100 mm, 3 μm; Mobile Phase: MtBE (0.1% diethyl amine):EtOH=80:20; Flow rate: 1 mL/min. Retention time: 4.384 min (slower peak).

Example 56

Example 56 was synthesized according to the procedures described for the synthesis of 6-(4-((R)-3-((S)-2-((5-bromo-6-oxo-1,6-dihydropyridazin-4-yl)oxy)-3-methoxypropoxy)-2-oxopyrrolidin-1-yl)piperidin-1-yl)nicotinonitrile and 6-(4-((S)-3-((S)-2-((5-bromo-6-oxo-1,6-dihydropyridazin-4-yl) oxy)-3-methoxypropoxy)-2-oxopyrrolidin-1-yl)piperidin-1-yl)nicotinonitrile (see Example 55) using appropriate building blocks and modified reaction conditions (such as reagent ratio, temperature, coupling conditions, and reaction time) as needed. The relative stereochemistry of compounds was assigned by analogy to Example 10, based on the PARP7 potency of the more active diastereomer and in analogy to the Example 10B X-ray crystal structure.

| Example No. | Structure | Analytical Data |
|---|---|---|
| 56A | 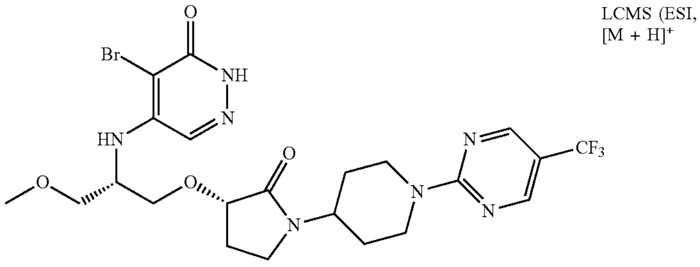<br>4-Bromo-5-(((S)-1-methoxy-3-(((S)-2-oxo-1-(1-(5-(trifluoromethyl)pyrimidin-2-yl)piperidin-4-yl)pyrrolidin-3-yl)oxy)propan-2-yl)oxy)pyridazin-3(2H)-one | LCMS (ESI, m/z): 593.10 $[M + H]^+$ |
| 56B | 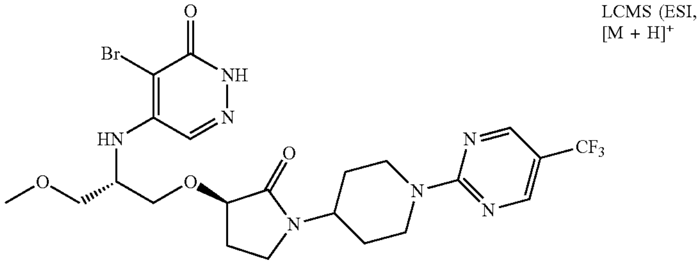<br>4-Bromo-5-(((S)-1-methoxy-3-(((R)-2-oxo-1-(1-(5-(trifluoromethyl)pyrimidin-2-yl)piperidin-4-yl)pyrrolidin-3-yl)oxy)propan-2-yl)oxy)pyridazin-3(2H)-one | LCMS (ESI, m/z): 593.10 $[M + H]^+$ |

Example 57: Synthesis of 5-(((S)-1-(((R)-1-((3R,4R)-3-hydroxy-1-(5-(trifluoromethyl)pyrimidin-2-yl)piperidin-4-yl)-2-oxopyrrolidin-3-yl)oxy)propan-2-yl)amino)-4-(trifluoromethyl)pyridazin-3(2H)-one

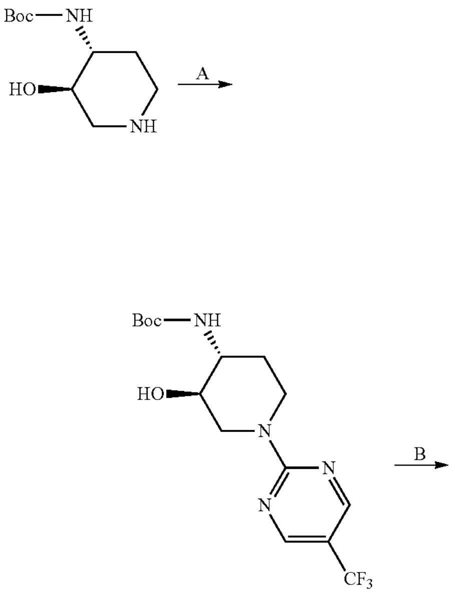

-continued

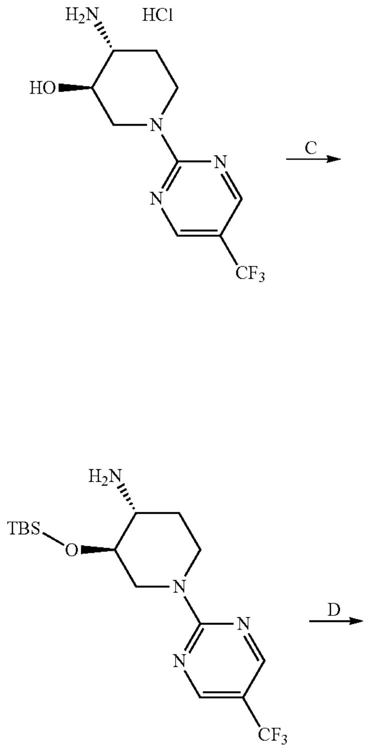

-continued

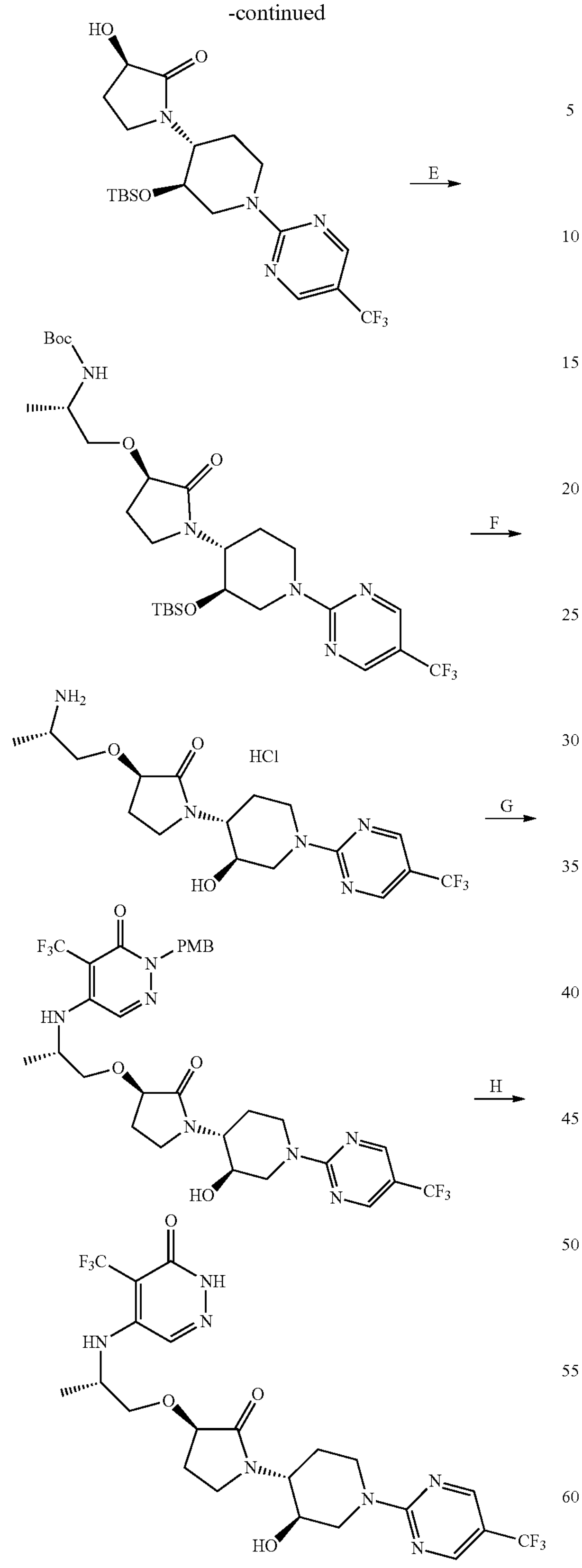

Step A

To a solution of tert-butyl ((3R,4R)-3-hydroxypiperidin-4-yl)carbamate (980 mg, 4.53 mmol, 1.0 equiv) in DMF (5 mL) was added 2-chloro-5-(trifluoromethyl)pyrimidine (825 mg, 4.52 mmol, 1.0 equiv) and $K_2CO_3$ (940 mg, 6.80 mmol, 1.5 equiv). The resulting solution stirred for 1 hour at 50° C. and then was quenched by the addition of water (15 mL). The solids were collected by filtration to afford 1.6 g (97% yield) of tert-butyl ((3R,4R)-3-hydroxy-1-(5-(trifluoromethyl)pyrimidin-2-yl)piperidin-4-yl)carbamate as a white solid. (ESI, m/z): 363.10 $[M+H]^+$.

Step B

A solution of tert-butyl ((3R,4R)-3-hydroxy-1-(5-(trifluoromethyl)pyrimidin-2-yl)piperidin-4-yl)carbamate (1.60 g, 4.42 mmol, 1.0 equiv) in 4M HCl in 1,4-dioxane (30 mL) was stirred for 1 hour at 40° C. The resulting mixture was concentrated in vacuo to afford 1.1 g (95% yield) of (3R,4R)-4-amino-1-(5-(trifluoromethyl)pyrimidin-2-yl)piperidin-3-ol hydrochloride as a white solid. (ESI, m/z): 263.05 $[M+H]^+$.

Step C

To a solution of (3R,4R)-4-amino-1-(5-(trifluoromethyl)pyrimidin-2-yl)piperidin-3-ol hydrochloride (980 mg, 3.74 mmol, 1.0 equiv) in $CH_3CN$ (30 mL) was added imidazole (1.27 g, 18.7 mmol, 5.0 equiv) and tert-butylchlorodimethylsilane (1.69 g, 11.2 mmol, 3.0 equiv). The resulting solution was stirred for 30 hours at 60° C. After filtration, the filtrate was concentrated in vacuo, and the crude product was applied onto a silica gel column eluting with MeOH/DCM (3:97) to afford 1.3 g (92% yield) of (3R,4R)-3-((tert-butyldimethylsilyl)oxy)-1-(5-(trifluoromethyl)pyrimidin-2-yl)piperidin-4-amine as a yellow oil. (ESI, m/z): 377.4 $[M+H]^+$.

Step D

To a solution of (3R,4R)-3-((tert-butyldimethylsilyl)oxy)-1-(5-(trifluoromethyl)pyrimidin-2-yl)piperidin-4-amine (1.28 g, 3.40 mmol, 1.0 equiv) in DCM (20 mL) was added (R)-2-(2,2-dimethyl-5-oxo-1,3-dioxolan-4-yl)acetaldehyde (1.88 g, 11.9 mmol, 3.5 equiv) and AcOH (408 mg, 6.79 mmol, 2.0 equiv). The resulting solution was stirred for 1 hour. STAB (2.16 g, 10.2 mmol, 3.0 equiv) was added, and the solution was stirred for an additional 4 hours. The reaction was quenched by the addition of saturated aqueous $NaHCO_3$. The aqueous layers were extracted with 2×50 mL of DCM. The organic layers were combined, dried over anhydrous sodium sulfate and concentrated in vacuo. The crude product was applied onto a silica gel column eluting with ethyl acetate/petroleum ether (35/65) to afford 680 mg (43% yield) of (R)-1-((3R,4R)-3-((tert-butyldimethylsilyl)oxy)-1-(5-(trifluoromethyl)pyrimidin-2-yl)piperidin-4-yl)-3-hydroxypyrrolidin-2-one as a white solid. (ESI, m/z): 461.20 $[M+H]^+$.

Step E

To a solution of (R)-1-((3R,4R)-3-((tert-butyldimethylsilyl)oxy)-1-(5-(trifluoromethyl)pyrimidin-2-yl)piperidin-4-yl)-3-hydroxypyrrolidin-2-one (670 mg, 1.46 mmol, 1.00 equiv) in DMF (7 mL) at 0° C. was added NaH (117 mg, 2.93 mmol, 2.01 equiv, 60% dispersion in mineral oil). The resulting solution was stirred for 10 min, and then tert-butyl (S)-4-methyl-1,2,3-oxathiazolidine-3-carboxylate 2,2-dioxide (518 mg, 2.18 mmol, 1.5 equiv) was added, and the solution was maintained at the same temperature for 4 hours. The reaction was then quenched by the addition of saturated aqueous $NH_4Cl$. The solution was extracted with 2×50 mL of ethyl acetate. The organic layers were combined, dried over anhydrous sodium sulfate and concentrated. The crude product was applied onto a silica gel column eluting with ethyl acetate/petroleum ether (3/2) to afford 300 mg (33% yield) of tert-butyl ((S)-1-(((R)-1-((3R,4R)-3-((tert-butyldimethylsilyl)oxy)-1-(5-(trifluoromethyl)pyrimidin-2-yl)piperidin-4-yl)-2-oxopyrrolidin-3-yl)oxy)propan-2-yl)carbamate as a yellow solid. (ESI, m/z): 618.30 $[M+H]^+$.

Step F

A solution of tert-butyl ((S)-1-(((R)-1-((3R,4R)-3-((tert-butyldimethylsilyl)oxy)-1-(5-(trifluoromethyl)pyrimidin-2-yl)piperidin-4-yl)-2-oxopyrrolidin-3-yl)oxy)propan-2-yl) carbamate (290 mg, 0.47 mmol, 1.0 equiv) in 4N HCl in 1,4-dioxane (20 mL) was stirred for 15 hours. The resulting mixture was concentrated to afford 240 mg of (R)-3-((S)-2-aminopropoxy)-1-((3R,4R)-3-hydroxy-1-(5-(trifluoromethyl)pyrimidin-2-yl)piperidin-4-yl)pyrrolidin-2-one hydrochloride as a white solid that was carried forward without further purification. (ESI, m/z): 404.15 $[M+H]^+$.

Step G

To a solution of (R)-3-((S)-2-aminopropoxy)-1-((3R,4R)-3-hydroxy-1-(5-(trifluoromethyl)pyrimidin-2-yl)piperidin-4-yl)pyrrolidin-2-one hydrochloride (230 mg, 0.57 mmol, 1.0 equiv) in EtOH (4 mL) was added 5-chloro-2-(4-methoxybenzyl)-4-(trifluoromethyl)pyridazin-3(2H)-one (181 mg, 0.57 mmol, 1.0 equiv) and triethylamine (173 mg, 1.71 mmol, 3.0 equiv). The resulting solution was stirred for 1 hour at 60° C. After completion, the crude product was applied onto a reverse phase column eluting with water/$CH_3CN$ (45/55) to afford 185 mg (47% yield) of 5-(((S)-1-(((R)-1-((3R,4R)-3-hydroxy-1-(5-(trifluoromethyl)pyrimidin-2-yl)piperidin-4-yl)-2-oxopyrrolidin-3-yl)oxy)propan-2-yl)amino)-2-(4-methoxybenzyl)-4-(trifluoromethyl) pyridazin-3(2H)-one as a white solid. (ESI, m z): 686.25 $[M+H]^+$.

Step H

A solution of 5-(((S)-1-(((R)-1-((3R,4R)-3-hydroxy-1-(5-(trifluoromethyl)pyrimidin-2-yl)piperidin-4-yl)-2-oxopyrrolidin-3-yl)oxy)propan-2-yl)amino)-2-(4-methoxybenzyl)-4-(trifluoromethyl)pyridazin-3(2H)-one (185 mg, 0.270 mmol, 1.0 equiv) in TFA (1.5 mL) and TfOH (0.3 mL) was stirred for 1 hour. The reaction was quenched by the addition of ice water (2 mL). The pH was adjusted to ~7-8 with saturated aqueous $Na_2CO_3$. The resulting solution was extracted with 2×50 mL of DCM. The organic layers were combined and concentrated. The crude product was purified by reverse phase chromatography eluting with water/$CH_3CN$ (45/55) to afford 89 mg (59% yield) of 5-(((S)-1-(((R)-1-((3R,4R)-3-hydroxy-1-(5-(trifluoromethyl)pyrimidin-2-yl)piperidin-4-yl)-2-oxopyrrolidin-3-yl)oxy)propan-2-yl)amino)-4-(trifluoromethyl)pyridazin-3(2H)-one as a white solid. (ESI, m/z): 566.15 $[M+H]^+$; 1H NMR (300 MHz, DMSO-$d_6$) δ 12.46 (s, 1H), 8.69 (d, J=0.9 Hz, 2H), 7.94 (s, 1H), 6.39-6.29 (m, 1H), 5.28 (d, J=5.3 Hz, 1H), 4.91-4.80 (m, 1H), 4.72 (d, J=13.4 Hz, 1H), 4.21-4.07 (m, 2H), 3.84-3.73 (m, 2H), 3.63-3.49 (m, 2H), 3.29-3.22 (m, 1H), 3.17-3.07 (m, 1H), 3.02-2.89 (m, 1H), 2.84-2.70 (m, 1H), 2.31-2.16 (m, 1H), 1.83-1.68 (m, 1H), 1.65-1.48 (m, 2H), 1.16 (d, J=6.4 Hz, 3H).

Example 58: Synthesis of 5-(((S)-1-(((R)-1-((3S,4S)-3-hydroxy-1-(5-(trifluoromethyl)pyrimidin-2-yl)piperidin-4-yl)-2-oxopyrrolidin-3-yl)oxy)propan-2-yl)amino)-4-(trifluoromethyl)pyridazin-3(2H)-one

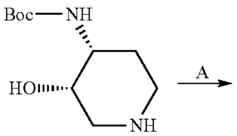

-continued

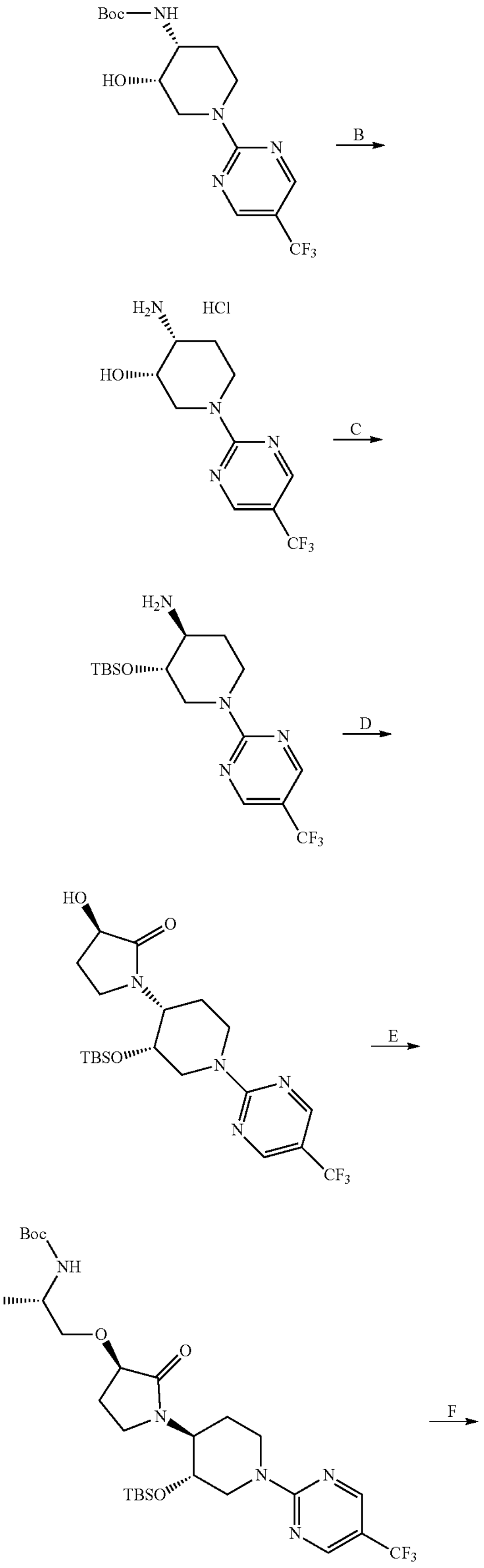

-continued

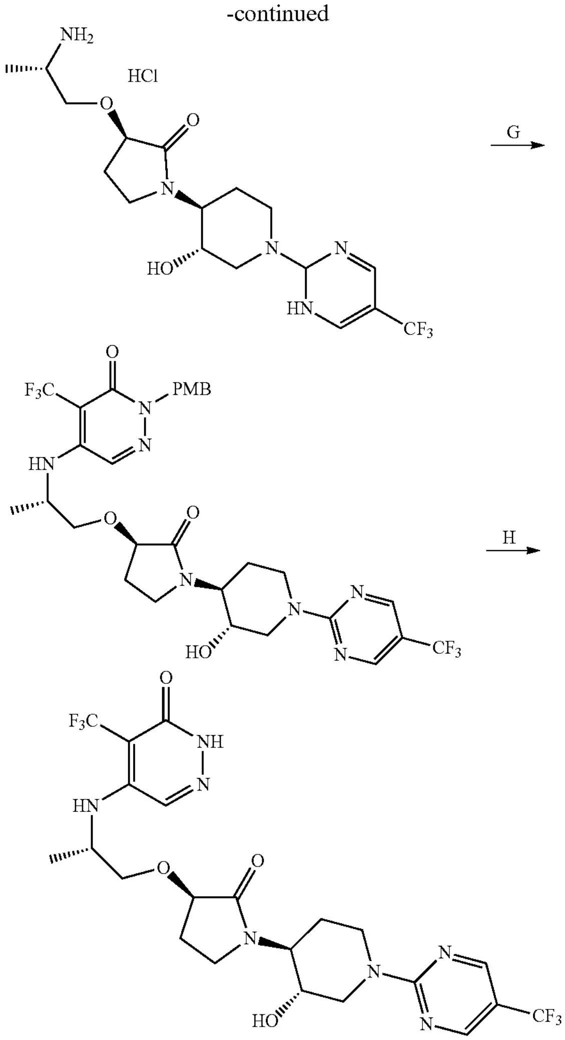

Step A

To a solution of tert-butyl ((3S,4S)-3-hydroxypiperidin-4-yl)carbamate (1.00 g, 4.62 mmol, 1.0 equiv) in DMF (5 mL) was added $K_2CO_3$ (0.96 g, 6.95 mmol, 1.5 equiv) and 2-chloro-5-(trifluoromethyl)pyrimidine (0.85 g, 4.66 mmol, 1.0 equiv). The resulting solution was stirred for 1 hour at 50° C. The reaction mixture was quenched by the addition of 10 mL of water, and the solids were collected by filtration to afford 1.45 g (87% yield) of tert-butyl ((3S,4S)-3-hydroxy-1-(5-(trifluoromethyl)pyrimidin-2-yl)piperidin-4-yl) carbamate as a white solid. LCMS (ESI, m/z): 363.10 $[M+H]^+$.

Step B

A solution of tert-butyl ((3S,4S)-3-hydroxy-1-(5-(trifluoromethyl)pyrimidin-2-yl)piperidin-4-yl)carbamate (1.45 g, 4.00 mmol, 1.0 equiv) in 4N HCl in 1,4-dioxane (30 mL) was stirred for 2 hours at 40° C. The resulting mixture was concentrated to afford 1.0 g (95% yield) of (3S,4S)-4-amino-1-(5-(trifluoromethyl)pyrimidin-2-yl)piperidin-3-ol hydrochloride as a yellow solid. LCMS (ESI, m/z): 263.05 $[M+H]^+$.

Step C

To a solution of (3S,4S)-4-amino-1-(5-(trifluoromethyl) pyrimidin-2-yl)piperidin-3-ol hydrochloride (1.19 g, 3.98 mmol, 1.0 equiv) in $CH_3CN$ (40 mL) was added tert-butyldimethylsilyl chloride (2.36 g, 15.7 mmol, 3.93 equiv) and imidazole (1.77 g, 26.0 mmol, 6.5 equiv). The resulting solution was stirred overnight at 60° C. After filtration, the filtrate was concentrated in vacuo, and the crude product was applied onto a silica gel column eluting with chloroform/methanol (10/1) to afford 1.20 g (80% yield) of (3S,4S)-3-((tert-butyldimethylsilyl)oxy)-1-(5-methylpyrimidin-2-yl) piperidin-4-amine as a white solid. LCMS (ESI, m/z): 377.10 $[M+H]^+$ Step D To a solution of (3S,4S)-3-((tert-butyldimethylsilyl)oxy)-1-(5-methylpyrimidin-2-yl)piperidin-4-amine (1.40 g, 3.72 mmol, 1.0 equiv) in DCM (20 mL) was added (R)-2-(2,2-dimethyl-5-oxo-1,3-dioxolan-4-yl)acetaldehyde (1.88 g, 11.9 mmol, 3.2 equiv) and AcOH (446 mg, 7.44 mmol, 2.0 equiv). After stirring for 15 min, STAB (2.36 g, 11.2 mmol, 3.0 equiv) was added, and the solution was stirred for an additional 5 hours. The reaction was quenched by the addition of 20 mL of saturated aqueous $NaHCO_3$ and extracted with 3×50 mL of DCM. The organic layers were combined, dried over anhydrous sodium sulfate and concentrated in vacuo. The crude product was applied onto a silica gel column eluting with ethyl acetate/petroleum ether (3/2) to afford 470 mg (27% yield) of (R)-1-((3S,4S)-3-((tert-butyldimethylsilyl)oxy)-1-(5-(trifluoromethyl)pyrimidin-2-yl)piperidin-4-yl)-3-hydroxypyrrolidin-2-one as a yellow solid. LCMS (ESI, m/z): 461.20 $[M+H]^+$.

Step E

To a solution of (R)-1-((3S,4S)-3-((tert-butyldimethylsilyl)oxy)-1-(5-(trifluoromethyl)pyrimidin-2-yl)piperidin-4-yl)-3-hydroxypyrrolidin-2-one (465 mg, 1.01 mmol, 1.0 equiv) in DMF (5 mL) was added NaH (121 mg, 3.03 mmol, 3.0 equiv, 60%) at 0° C. The reaction mixture was stirred for 10 min, and then a solution of tert-butyl (S)-4-methyl-1,2,3-oxathiazolidine-3-carboxylate 2,2-dioxide (287 mg, 1.21 mmol, 1.2 equiv) in DMF (2 mL) was added. The resulting solution was stirred for 2 hours at 0° C. The reaction was quenched by the addition of water (10 mL). The resulting solution was extracted with 2×20 mL of ethyl acetate. The organic layers were combined, dried over anhydrous sodium sulfate and concentrated in vacuo. The crude product was applied onto a silica gel column eluting with ethyl acetate/petroleum ether (3/2) to afford 480 mg (77% yield) of tert-butyl ((S)-1-(((R)-1-((3S,4S)-3-((tert-butyldimethylsilyl)oxy)-1-(5-(trifluoromethyl)pyrimidin-2-yl)piperidin-4-yl)-2-oxopyrrolidin-3-yl)oxy)propan-2-yl)carbamate as a yellow solid. LCMS (ESI, m/z): 618.35 $[M+H]^+$.

Step F

A solution of tert-butyl ((S)-1-(((R)-1-((3S,4S)-3-((tert-butyldimethylsilyl)oxy)-1-(5-(trifluoromethyl)pyrimidin-2-yl)piperidin-4-yl)-2-oxopyrrolidin-3-yl)oxy)propan-2-yl) carbamate (480 mg, 0.78 mmol, 1.0 equiv) in 4M HCl in 1,4-dioxane (10 mL, 4 M) was stirred for 1 hour at room temperature. The resulting mixture was concentrated in vacuo to afford 278 mg (81% yield) of (R)-3-((S)-2-aminopropoxy)-1-((3S,4S)-3-hydroxy-1-(5-(trifluoromethyl)pyrimidin-2-yl)piperidin-4-yl)pyrrolidin-2-one hydrochloride as a white solid. (ESI, m/z): 461.25 $[M+H]^+$.

Step G

To a solution of (R)-3-((S)-2-aminopropoxy)-1-((3S,4S)-3-hydroxy-1-(5-(trifluoromethyl)pyrimidin-2-yl)piperidin-4-yl)pyrrolidin-2-one hydrochloride (270 mg, 0.61 mmol, 1.0 equiv) in EtOH (8 mL) was added 5-chloro-2-(4-methoxybenzyl)-4-(trifluoromethyl)pyridazin-3(2H)-one (293 mg, 0.92 mmol, 1.5 equiv) and triethylamine (621 mg, 6.14 mmol, 10.0 equiv). The resulting solution was stirred for 3 hours at 60° C. and then was concentrated in vacuo. The crude product was applied onto a silica gel column eluting with ethyl acetate/petroleum ether (7/3) to afford 280 mg (67% yield) of 5-(((S)-1-(((R)-1-((3S,4S)-3-hydroxy-1-(5-(trifluoromethyl)pyridin-2-yl)piperidin-4-yl)-2-oxopyrrolidin-3-yl)oxy)propan-2-yl)amino)-2-(4-methoxybenzyl)-4-(trifluoromethyl)pyridazin-3(2H)-one as a yellow solid. LCMS (ESI, m/z): 686.20 $[M+H]^+$.

Step H

A solution of 5-(((S)-1-(((R)-1-((3S,4S)-3-hydroxy-1-(5-(trifluoromethyl)pyridin-2-yl)piperidin-4-yl)-2-oxopyrrolidin-3-yl)oxy)propan-2-yl)amino)-2-(4-methoxybenzyl)-4-(trifluoromethyl)pyridazin-3(2H)-one (270 mg, 0.39 mmol, 1.0 equiv) in TfOH/TFA=1:10 (3 mL) was stirred for 2 hours at 0° C. The reaction was quenched by the addition of water (5 mL), and the pH was adjusted to 7-8 with aqueous sodium bicarbonate. The resulting solution was extracted with 3×20 mL of ethyl acetate. The organic layers were combined, dried over anhydrous sodium sulfate and concentrated. The crude product was purified by reverse phase chromatography eluting with water/$CH_3CN$ (1/1) to afford 120 mg (54% yield) of 5-(((S)-1-(((R)-1-((3S,4S)-3-hydroxy-1-(5-(trifluoromethyl)pyrimidin-2-yl)piperidin-4-yl)-2-oxopyrrolidin-3-yl)oxy)propan-2-yl)amino)-4-(trifluoromethyl)pyridazin-3(2H)-one as an off-white solid. LCMS (ESI, m/z): 566.20 $[M+H]^+$. $^1H$ NMR (400 MHz, DMSO-$d_6$) δ 12.46 (s, 1H), 8.70 (s, 2H), 7.95 (s, 1H), 6.35-6.34 (m, 1H), 5.26 (d, J=5.0 Hz, 1H), 4.91-4.83 (m, 1H), 4.80-4.75 (m, 1H), 4.28-4.10 (m, 2H), 3.80-3.91 (m, 2H), 3.63-3.58 (m, 1H), 3.55-3.40 (m, 1H), 3.31-3.25 (m, 1H), 3.22-3.12 (m, 1H), 3.06-2.95 (m, 1H), 2.81-2.76 (m, 1H), 2.33-2.20 (m, 1H), 1.78-1.66 (m, 1H), 1.64-1.51 (m, 2H), 1.17 (d, J=6.4 Hz, 3H).

Example 59: Synthesis of 5-(((S)-1-(((R)-1-((3S,4R)-3-hydroxy-1-(5-(trifluoromethyl)pyrimidin-2-yl)piperidin-4-yl)-2-oxopyrrolidin-3-yl)oxy)propan-2-yl)amino)-4-(trifluoromethyl)pyridazin-3(2H)-one

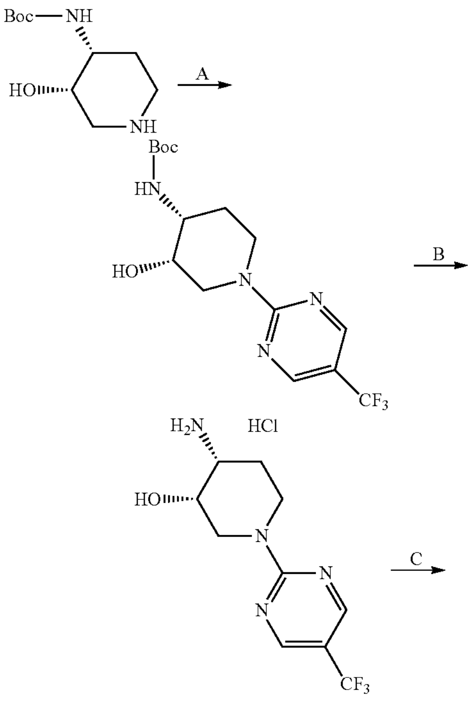

-continued

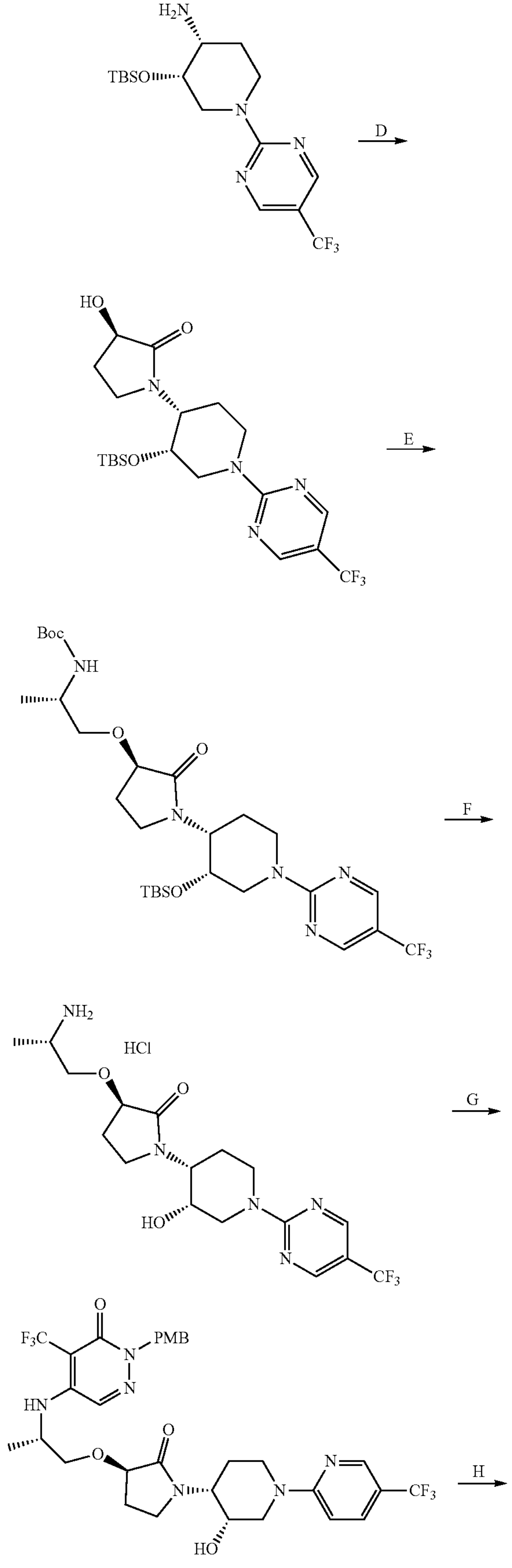

-continued

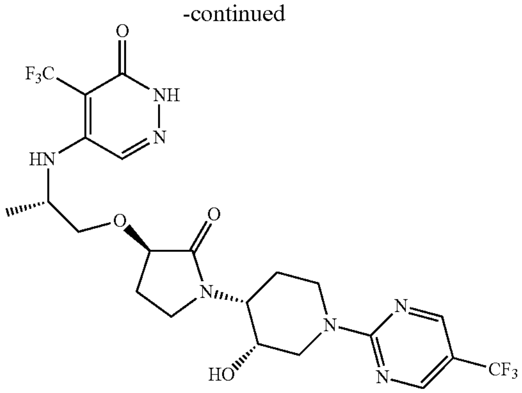

Step A

To a solution of tert-butyl ((3S,4R)-3-hydroxypiperidin-4-yl)carbamate (2.00 g, 9.2 mmol, 1.0 equiv) in DMF (10 mL) was added 2-chloro-5-(trifluoromethyl)pyrimidine (1.68 g, 9.2 mmol, 1.00 equiv) and $K_2CO_3$ (2.56 g, 18.5 mmol, 2.0 equiv). The resulting solution was stirred for 1 hour at 50° C. then diluted with water (10 mL). The solids were collected by filtration to afford 1.37 g (39% yield) of tert-butyl ((3S,4R)-3-hydroxy-1-(5-(trifluoromethyl)pyrimidin-2-yl)piperidin-4-yl)carbamate as a white solid. LCMS (ESI, m/z): 363.10 $[M+H]^+$.

Step B

A solution of tert-butyl ((3S,4R)-3-hydroxy-1-(5-(trifluoromethyl)pyrimidin-2-yl)piperidin-4-yl)carbamate (1.28 g, 3.53 mmol, 1.0 equiv) in 4M HCl in dioxane (6 mL) was stirred for 2 hours. The resulting mixture was concentrated in vacuo to afford 1.0 g (95% yield) of (3S,4R)-4-amino-1-(5-(trifluoromethyl)pyrimidin-2-yl)piperidin-3-ol hydrochloride as a yellow solid. LCMS (ESI, m/z): 263.05 $[M+H]^+$.

Step C

To a solution of (3S,4R)-4-amino-1-(5-(trifluoromethyl)pyrimidin-2-yl)piperidin-3-ol hydrochloride (2.60 g, 9.92 mmol, 1.0 equiv) in $CH_3CN$ (20 mL) was added tert-butyldimethylsilyl chloride (11.95 g, 79.35 mmol, 8.0 equiv) and imidazole (5.40 g, 79.4 mmol, 8.0 equiv). The resulting solution was stirred for 4 hours at 60° C. and then was concentrated in vacuo. The crude product was applied onto a silica gel column eluting with chloroform/methanol (9/1) to give 3.40 g (88% yield) of (3S,4R)-3-((tert-butyldimethylsilyl)oxy)-1-(5-(trifluoromethyl)pyrimidin-2-yl)piperidin-4-amine as a yellow solid. LCMS (ESI, m/z): 377.10 $[M+H]^+$.

Step D

To a solution of (3S,4R)-3-((tert-butyldimethylsilyl)oxy)-1-(5-(trifluoromethyl)pyrimidin-2-yl)piperidin-4-amine (3.20 g, 8.50 mmol, 1.0 equiv) in DCM (30 mL) was added (R)-2-(2,2-dimethyl-5-oxo-1,3-dioxolan-4-yl)acetaldehyde (1.24 g, 7.82 mmol, 0.9 equiv) and AcOH (1.53 g, 25.5 mmol, 3.0 equiv). The resulting solution was stirred for 15 min, and then STAB (14.0 g, 66.0 mmol, 3.0 equiv) was added. After 2 hours at, the reaction was quenched by the addition of 20 mL of saturated aqueous $NaHCO_3$. The solution was extracted with 3×100 mL of DCM. The organic layers were combined, dried over anhydrous sodium sulfate and concentrated in vacuo. The crude product was applied onto a silica gel column eluting with ethyl acetate/petroleum ether (3/1) to afford 0.93 g (24% yield) of (R)-1-((3S,4R)-3-((tert-butyldimethylsilyl)oxy)-1-(5-(trifluoromethyl)pyrimidin-2-yl)piperidin-4-yl)-3-hydroxypyrrolidin-2-one as a yellow solid. LCMS (ESI, m/z): 461.20 $[M+H]^+$.

Step E

To a solution of (R)-1-((3S,4R)-3-((tert-butyldimethylsilyl)oxy)-1-(5-(trifluoromethyl)pyrimidin-2-yl)piperidin-4-yl)-3-hydroxypyrrolidin-2-one (920 mg, 2.0 mmol, 1.0 equiv) in DMF (8 mL) was slowly added NaH (239 mg, 5.99 mmol, 3.0 equiv, 60% dispersion in mineral oil) at 0° C. over the course of 10 min. tert-Butyl (S)-4-methyl-1,2,3-oxathiazolidine-3-carboxylate 2,2-dioxide (568 mg, 2.40 mmol, 1.2 equiv) was then added, and the resulting solution stirred for 2 hours at 0° C. The reaction was quenched by the addition of water (10 mL) and was extracted with 2×30 mL of ethyl acetate. The organic layers were combined, dried over anhydrous sodium sulfate and concentrated in vacuo. The crude product was applied onto a silica gel column eluting with ethyl acetate/petroleum ether (3/2) to afford 767 mg (62% yield) of tert-butyl ((S)-1-(((R)-1-((3S,4R)-3-((tert-butyldimethylsilyl)oxy)-1-(5-(trifluoromethyl)pyrimidin-2-yl)piperidin-4-yl)-2-oxopyrrolidin-3-yl)oxy)propan-2-yl)carbamate as a yellow solid. LCMS (ESI, m/z): 618.35 $[M+H]^+$.

Step F

A solution of tert-butyl ((S)-1-(((R)-1-((3S,4R)-3-((tert-butyldimethylsilyl)oxy)-1-(5-(trifluoromethyl)pyrimidin-2-yl)piperidin-4-yl)-2-oxopyrrolidin-3-yl)oxy)propan-2-yl) carbamate (790 mg, 1.28 mmol, 1.0 equiv) in 4M HCl in dioxane (10 mL) was stirred for 1 hour at room temperature. The mixture was concentrated in vacuo to afford 600 mg (96% yield) of (R)-3-((S)-2-aminopropoxy)-1-((3S,4R)-3-hydroxy-1-(5-(trifluoromethyl)pyrimidin-2-yl)piperidin-4-yl)pyrrolidin-2-one hydrochloride as a white solid. (ESI, m/z): 461.25 $[M+H]^+$.

Step G

To a solution of (R)-3-((S)-2-aminopropoxy)-1-((3S,4R)-3-hydroxy-1-(5-(trifluoromethyl)pyrimidin-2-yl)piperidin-4-yl)pyrrolidin-2-one hydrochloride (650 mg, 1.6 mmol, 1.0 equiv) in ethanol (8 mL) was added 5-chloro-2-(4-methoxybenzyl)-4-(trifluoromethyl)pyridazin-3(2H)-one (616 mg, 1.93 mmol, 1.2 equiv) and triethylamine (1.04 g mg, 8.06 mmol, 5.0 equiv). The resulting solution was stirred for 4 hours at 60° C. and then was concentrated in vacuo. The crude product was applied onto a silica gel column eluting with ethyl acetate/petroleum ether (10/1) to afford 550 mg (50% yield) of 5-(((S)-1-(((R)-1-((3S,4R)-3-hydroxy-1-(5-(trifluoromethyl)pyridin-2-yl)piperidin-4-yl)-2-oxopyrrolidin-3-yl)oxy)propan-2-yl)amino)-2-(4-methoxybenzyl)-4-(trifluoromethyl)pyridazin-3(2H)-one as a yellow solid. LCMS (ESI, m/z): 686.20 $[M+H]^+$.

Step H

A solution of 5-(((S)-1-(((R)-1-((3S,4R)-3-hydroxy-1-(5-(trifluoromethyl)pyridin-2-yl)piperidin-4-yl)-2-oxopyrrolidin-3-yl)oxy)propan-2-yl)amino)-2-(4-methoxybenzyl)-4-(trifluoromethyl)pyridazin-3(2H)-one (550 mg, 0.80 mmol, 1.0 equiv) in TfOH/TFA (3 mL, 1:10) was stirred for 2 hours at room temperature and then quenched by the addition of water (5 mL). The pH was adjusted to 7-8 with sodium bicarbonate. The resulting solution was extracted with 3×20 mL of ethyl acetate. The organic layers were combined, dried over anhydrous sodium sulfate and concentrated. The crude product was purified by reverse phase chromatography eluting with water/$CH_3CN$ (3/2) to afford 189 mg (42% yield) of 5-(((S)-1-(((R)-1-((3S,4R)-3-hydroxy-1-(5-(trifluoromethyl)pyrimidin-2-yl)piperidin-4-yl)-2-oxopyrrolidin-3-yl)oxy)propan-2-yl)amino)-4-(trifluoromethyl) pyridazin-3(2H)-one as an off-white solid. LCMS (ESI, m/z): 566.25 $[M+H]^+$; $^1H$ NMR (400 MHz, DMSO-$d_6$) δ

12.47 (s, 1H), 8.65 (s, 2H), 7.96 (s, 1H), 6.38 (br, 1H), 5.06 (d, J=5.1 Hz, 1H), 4.93-4.78 (m, 2H), 4.21-4.09 (m, 2H), 4.02-3.94 (m, 1H), 3.92-3.81 (m, 2H), 3.62-3.56 (m, 2H), 3.26-3.10 (m, 2H), 3.04 (t, J=12.6 Hz, 1H), 2.29-2.18 (m, 1H), 2.12-1.99 (m, 1H), 1.83-1.69 (m, 1H), 1.53 (d, J=12.3 Hz, 1H), 1.18 (d, J=6.4 Hz, 3H).

Example 60: Synthesis of 5-(((S)-1-(((R)-1-((3R,4S)-3-hydroxy-1-(5-(trifluoromethyl)pyrimidin-2-yl)piperidin-4-yl)-2-oxopyrrolidin-3-yl)oxy)propan-2-yl)amino)-4-(trifluoromethyl)pyridazin-3(2H)-one

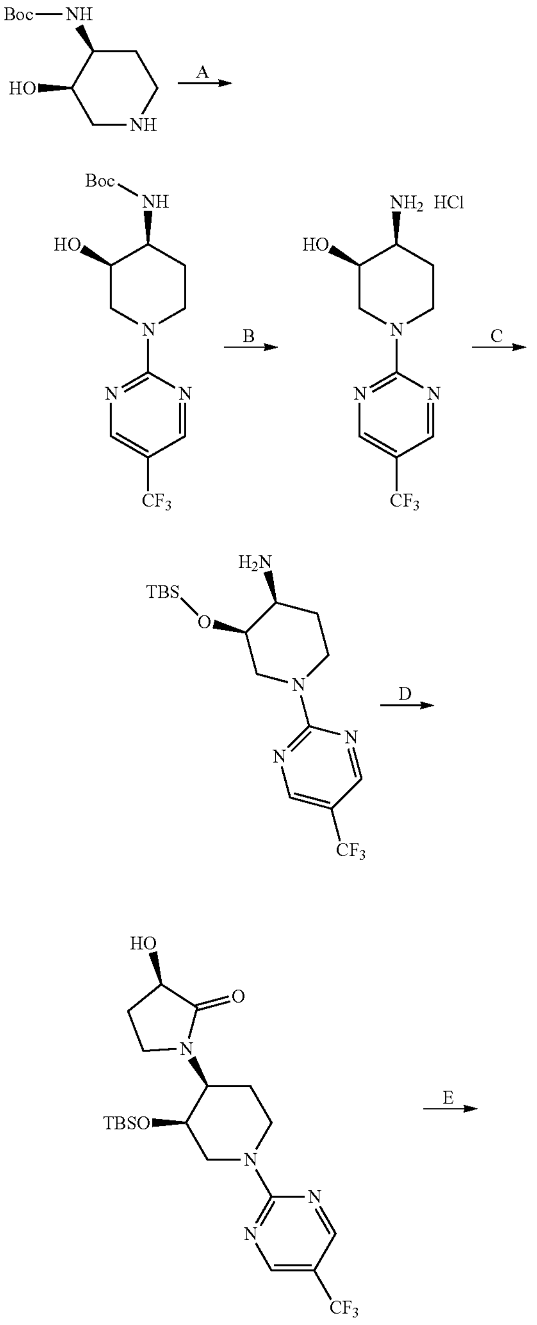

-continued

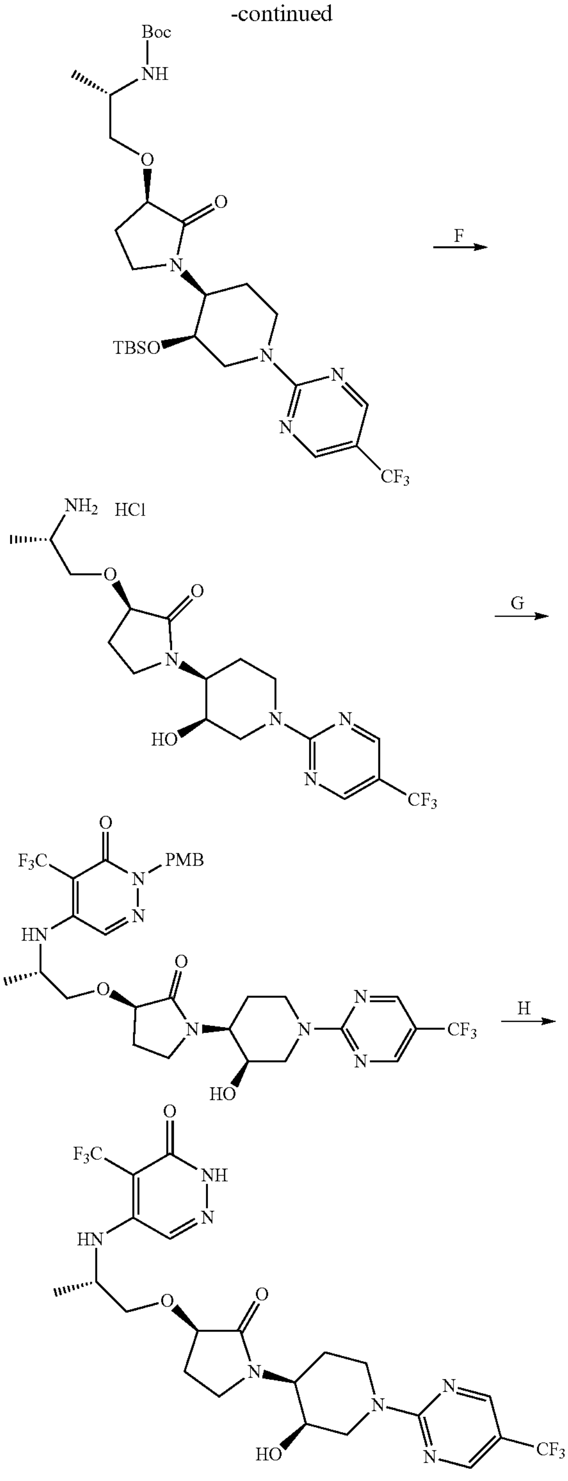

Step A

To a solution of tert-butyl ((3R,4S)-3-hydroxypiperidin-4-yl)carbamate (1.02 g, 4.71 mmol, 1.0 equiv) in DMF (6 mL) was added $K_2CO_3$ (980 mg, 7.2 mmol, 1.5 equiv) and 2-chloro-5-(trifluoromethyl)pyrimidine (863 mg, 4.73 mmol, 1.0 equiv). The resulting solution was stirred for 2 hours at 60° C. and was then quenched by the addition of water (20 mL). The solids were collected by filtration to afford 1.59 g (93% yield) of tert-butyl ((3R,4S)-3-hydroxy- 1-(5-(trifluoromethyl)pyrimidin-2-yl)piperidin-4-yl)carbamate as an off-white solid. LCMS (ESI, m/z): 363.10 $[M+H]^+$.

Step B

To a solution of tert-butyl ((3R,4S)-3-hydroxy-1-(5-(trifluoromethyl)pyrimidin-2-yl)piperidin-4-yl)carbamate (1.59 g, 4.39 mmol, 1.0 equiv) in dioxane (50 mL) was added 4N HCl in dioxane (30 mL). The resulting solution was stirred for 5 hours and was then concentrated to afford 1.43 g (97% yield) of (3R,4S)-4-amino-1-(5-(trifluoromethyl)pyrimidin-2-yl)piperidin-3-ol hydrochloride as a yellow solid that was taken on without further purification. LCMS (ESI, m/z): 263.10 $[M+H]^+$.

Step C

To a solution of (3R,4S)-4-amino-1-(5-(trifluoromethyl)pyrimidin-2-yl)piperidin-3-ol hydrochloride (1.43 g, 4.26 mmol, 1.0 equiv) in $CH_3CN$ (30 mL) was added imidazole (2.20 g, 32.3 mmol, 7.6 equiv) and tert-butylchlorodimethylsilane (4.05 g, 26.9 mmol, 6.3 equiv). The resulting solution was stirred for 15 hours at 60° C. and then was concentrated in vacuo. The crude product was applied onto a silica gel column eluting with dichloromethane/methanol (19/1) to afford 1.74 g (98% yield) of (3R,4S)-3-((tert-butyldimethylsilyl)oxy)-1-(5-(trifluoromethyl)pyrimidin-2-yl)piperidin-4-amine as an orange oil. LCMS (ESI, m/z): 377.20 $[M+H]^+$.

Step D

To a solution of (3R,4S)-3-((tert-butyldimethylsilyl)oxy)-1-(5-(trifluoromethyl)pyrimidin-2-yl)piperidin-4-amine (1.74 g, 4.16 mmol, 1.0 equiv) in DCM (50 mL) was added (R)-2-(2,2-dimethyl-5-oxo-1,3-dioxolan-4-yl)acetaldehyde (3.71 g, 23.5 mmol, 5.6 equiv) and AcOH (0.57 g, 9.6 mmol, 2.3 equiv). The resulting solution was stirred for 1 hour, and then STAB (3.04 g, 14.3 mmol, 3.5 equiv) was added, and the mixture was stirred an additional 3 hours. The reaction was quenched by the addition of 50 mL of saturated aqueous sodium bicarbonate. The resulting solution was extracted with 3×60 mL of DCM. The organic layers were combined, dried over anhydrous sodium sulfate, filtered and concentrated in vacuo. The crude product was applied onto a silica gel column eluting with ethyl acetate/petroleum ether (2/1) to afford 1.16 g (56% yield) of (R)-1-((3R,4S)-3-((tert-butyldimethylsilyl)oxy)-1-(5-(trifluoromethyl)pyrimidin-2-yl)piperidin-4-yl)-3-hydroxypyrrolidin-2-one as an off-white solid. LCMS (ESI, m/z): 461.20 $[M+H]^+$.

Step E

To a solution of (R)-1-((3R,4S)-3-((tert-butyldimethylsilyl)oxy)-1-(5-(trifluoromethyl)pyrimidin-2-yl)piperidin-4-yl)-3-hydroxypyrrolidin-2-one (1.12 g, 2.43 mmol, 1.0 equiv) in DMF (10 mL) was added NaH (437 mg, 11.0 mmol, 4.5 equiv, 60% dispersion in mineral oil) at 0° C. The resulting solution was stirred for 30 min, and then a solution of tert-butyl (S)-4-methyl-1,2,3-oxathiazolidine-3-carboxylate 2,2-dioxide (700 mg, 3 mmol, 1.2 equiv) in DMF (2 mL) was added. The reaction mixture stirred for 13 hours and then was quenched by the addition of ice water (10 mL). The pH was adjusted to ~6-7 with 2N HCl. The resulting solution was extracted with 3×60 mL of ethyl acetate. The organic layers were combined, dried over anhydrous sodium sulfate and concentrated in vacuo. The crude product was applied onto a silica gel column eluting with ethyl acetate/petroleum ether (1/2) to afford 790 mg (52% yield) of tert-butyl ((S)-1-(((R)-1-((3R,4S)-3-((tert-butyldimethylsilyl)oxy)-1-(5-(trifluoromethyl)pyrimidin-2-yl)piperidin-4-yl)-2-oxopyrrolidin-3-yl)oxy)propan-2-yl)carbamate as a light yellow solid. LCMS (ESI, m/z): 618.35 $[M+H]^+$.

Step F

A solution of tert-butyl ((S)-1-(((R)-1-((3R,4S)-3-((tert-butyldimethylsilyl)oxy)-1-(5-(trifluoromethyl)pyrimidin-2-yl)piperidin-4-yl)-2-oxopyrrolidin-3-yl)oxy)propan-2-yl)carbamate (790 mg, 1.28 mmol, 1.0 equiv) in 4N HCl in dioxane (20 mL) was stirred for 1.5 days at room temperature. The resulting mixture was concentrated in vacuo to afford 600 mg of (R)-3-((S)-2-aminopropoxy)-1-((3R,4S)-3-hydroxy-1-(5-(trifluoromethyl)pyrimidin-2-yl)piperidin-4-yl)pyrrolidin-2-one hydrochloride as a yellow solid that was carried on without further purification. LCMS (ESI, m/z): 404.20 $[M+H]^+$.

Step G

To a solution of (R)-3-((S)-2-aminopropoxy)-1-((3R,4S)-3-hydroxy-1-(5-(trifluoromethyl)pyrimidin-2-yl)piperidin-4-yl)pyrrolidin-2-one hydrochloride (593 mg, 1.35 mmol, 1.0 equiv) in $CH_3CN$ (15 mL) was added diisopropylethylamine (750 mg, 5.8 mmol, 4.3 equiv) and 5-chloro-2-(4-methoxybenzyl)-4-(trifluoromethyl)pyridazin-3(2H)-one (452 mg, 1.42 mmol, 1.1 equiv). The resulting solution was stirred for 7 hours at 60° C. and then was quenched by the addition of water (20 mL). The resulting solution was extracted with 2×30 mL of ethyl acetate. The organic layers were combined, dried over anhydrous sodium sulfate and concentrated in vacuo. The crude product was applied onto a reverse phase column eluting with water/$CH_3CN$ (1/3) to afford 706 mg (64% yield) of 5-(((S)-1-(((R)-1-((3R,4S)-3-hydroxy-1-(5-(trifluoromethyl)pyrimidin-2-yl)piperidin-4-yl)-2-oxopyrrolidin-3-yl)oxy)propan-2-yl)amino)-2-(4-methoxybenzyl)-4-(trifluoromethyl)pyridazin-3(2H)-one as an off-white solid. LCMS (ESI, m/z): 686.10 $[M+H]^+$.

Step H

A solution of 5-(((S)-1-(((R)-1-((3R,4S)-3-hydroxy-1-(5-(trifluoromethyl)pyrimidin-2-yl)piperidin-4-yl)-2-oxopyrrolidin-3-yl)oxy)propan-2-yl)amino)-2-(4-methoxybenzyl)-4-(trifluoromethyl)pyridazin-3(2H)-one (706 mg, 1.03 mmol, 1.0 equiv) in TFA/TfOH (4.5 mL, 10:1) was stirred for 1 hour at 0° C. and then was quenched by the addition of ice water (10 mL). The pH was adjusted to 7 with saturated aqueous $NaHCO_3$. The resulting solution was extracted with 3×30 mL of DCM. The organic layers were combined, dried over anhydrous sodium sulfate and concentrated in vacuo. The residue was purified by reverse phase chromatography eluting with water/$CH_3CN$ (2/1) to afford 254 mg (43% yield) of 5-(((S)-1-(((R)-1-((3R,4S)-3-hydroxy-1-(5-(trifluoromethyl)pyrimidin-2-yl)piperidin-4-yl)-2-oxopyrrolidin-3-yl)oxy)propan-2-yl)amino)-4-(trifluoromethyl)pyridazin-3(2H)-one as a light green solid. LCMS (ESI, m/z): 566.15 $[M+H]^+$; $^1H$ NMR (400 MHz, DMSO-$d_6$) δ 12.45 (s, 1H), 8.65 (s, 2H), 7.95 (s, 1H), 6.39-6.27 (m, 1H), 5.02 (d, J=5.1 Hz, 1H), 4.89-4.75 (m, 2H), 4.22-4.15 (m, 1H), 4.11 (t, J=7.6 Hz, 1H), 4.08-3.96 (m, 1H), 3.91 (br, 1H), 3.83 (dd, J=10.0, 6.5 Hz, 1H), 3.61 (dd, J=10.0, 4.7 Hz, 1H), 3.44-3.36 (m, 1H), 3.35-3.26 (m, 1H), 3.13 (d, J=13.5 Hz, 1H), 3.09-2.99 (m, 1H), 2.30-2.18 (m, 1H), 2.12-1.99 (m, 1H), 1.77-1.65 (m, 1H), 1.52-1.42 (m, 1H), 1.18 (d, J=6.5 Hz, 3H).

Example 61: Synthesis (S)—N—((R)-2-oxo-1-(1-(5-(trifluoromethyl)pyrimidin-2-yl)piperidin-4-yl)pyrrolidin-3-yl)-2-((6-oxo-5-(trifluoromethyl)-1,6-dihydropyridazin-4-yl)amino)propanamide

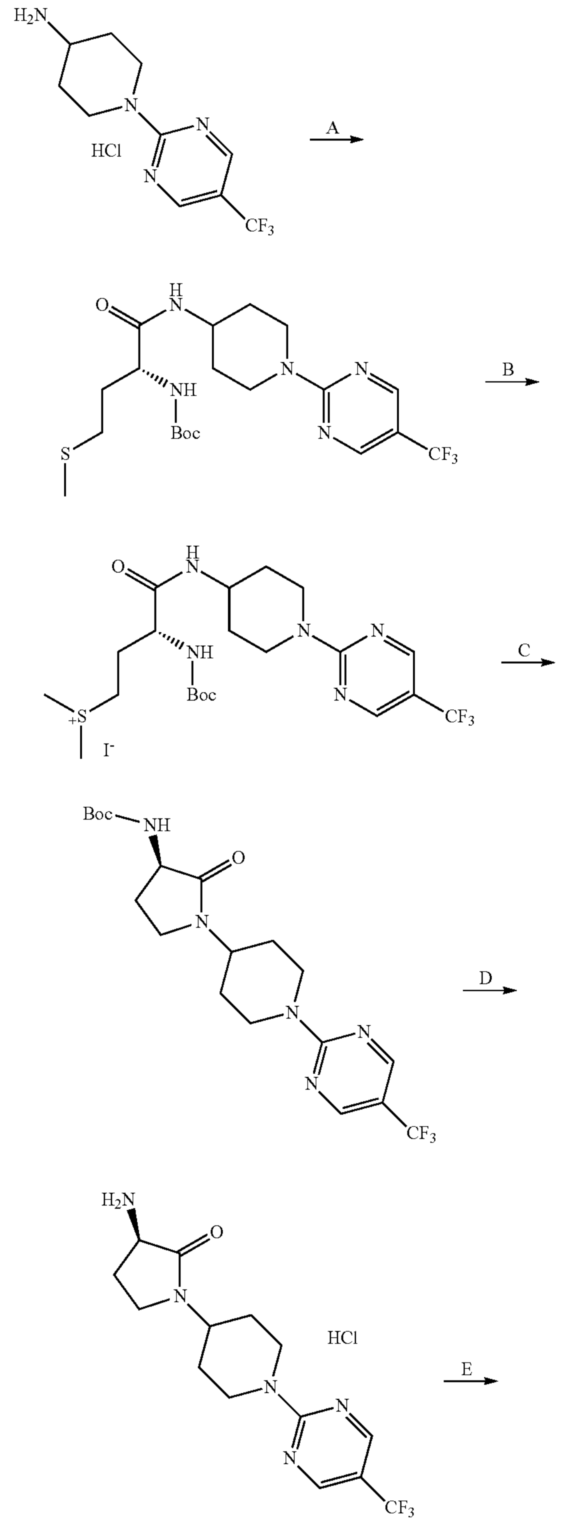

-continued

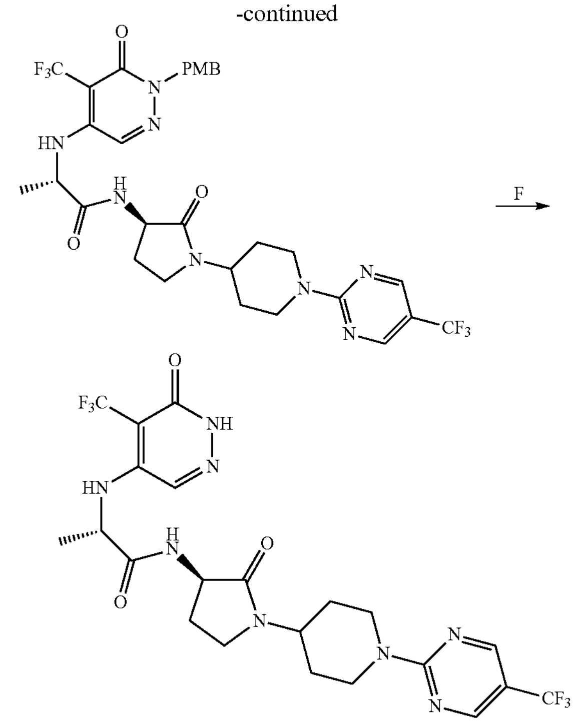

Step A

To a solution of (2R)-2-[(tert-butoxycarbonyl)amino]-4-(methylsulfanyl)butanoic acid (2.65 g, 10.6 mmol, 1.0 equiv) in DMF (20 mL) was added 1-[5-(trifluoromethyl)pyrimidin-2-yl]piperidin-4-amine hydrochloride (3.00 g, 10.6 mmol, 1.00 equiv), HATU (4.44 g, 11.7 mmol, 1.1 equiv) and diisopropylethylamine (4.11 g, 31.8 mmol, 3.0 equiv). The resulting solution was stirred for 1 hour and then was quenched by the addition of water (20 mL) and was extracted with 3x20 mL of ethyl acetate. The organic layers combined, dried over anhydrous sodium sulfate and concentrated in vacuo. The residue was applied onto a silica gel column with ethyl acetate/petroleum ether (1/1) to afford 3.9 g (77% yield) of tert-butyl (R)-(4-(methylthio)-1-oxo-1-((1-(5-(trifluoromethyl)pyrimidin-2-yl)piperidin-4-yl)amino)butan-2-yl)carbamate as a yellow oil. LCMS (ESI, m/z): 478.20 $[M+H]^+$.

Step B

To a solution of tert-butyl (R)-(4-(methylthio)-1-oxo-1-((1-(5-(trifluoromethyl)pyrimidin-2-yl)piperidin-4-yl)amino)butan-2-yl)carbamate (3.87 g, 8.10 mmol, 1.0 equiv) in DMF (50 mL) was added methyl iodide (1.73 g, 12.2 mmol, 1.5 equiv). The resulting solution was stirred overnight at 30° C. and then was concentrated in vacuo to afford 4.7 g (94% yield) of (R)-(3-((tert-butoxycarbonyl)amino)-4-oxo-4-((1-(5-(trifluoromethyl)pyrimidin-2-yl)piperidin-4-yl)amino)butyl)dimethylsulfonium iodide as a yellow oil. LCMS (ESI, m/z): 492.23 $[M]^+$.

Step C

To a solution of (R)-(3-((tert-butoxycarbonyl)amino)-4-oxo-4-((1-(5-(trifluoromethyl)pyrimidin-2-yl)piperidin-4-yl)amino)butyl)dimethylsulfonium iodide (4.7 g, 7.6 mmol, 1.0 equiv) in DMF (100 mL) was added sodium hydride (970 mg, 40.4 mmol, 5.3 equiv, 60% dispersion in mineral oil). The resulting solution was stirred overnight at 30° C. and then was quenched by the addition of 100 mL of water and was extracted with 3x100 mL of DCM. The organic layers were combined, washed with water, dried and concentrated in vacuo. The crude product was recrystallized from PE:EtOAc (10:1) to afford 2 g (61% yield) of tert-butyl (R)-(2-oxo-1-(1-(5-(trifluoromethyl)pyrimidin-2-yl)piperidin-4-yl)pyrrolidin-3-yl)carbamate as a white solid. LCMS (ESI, m/z): 430.20 $[M+H]^+$.

Step D

A solution of tert-butyl (R)-(2-oxo-1-(1-(5-(trifluoromethyl)pyrimidin-2-yl)piperidin-4-yl)pyrrolidin-3-yl)carbamate (2.00 g, 4.66 mmol, 1.00 equiv) in 4N HCl in dioxane (10 mL) was stirred for 2 hours and then was concentrated in vacuo to afford 1.5 g (98% yield) of (R)-3-amino-1-(1-(5-(trifluoromethyl)pyrimidin-2-yl)piperidin-4-yl)pyrrolidin-2-one hydrochloride as a light yellow solid. LCMS (ESI, m/z): 330.15 $[M+H]^+$.

Step E

To a solution of (1-(4-methoxybenzyl)-6-oxo-5-(trifluoromethyl)-1,6-dihydropyridazin-4-yl)-L-alanine (1.4 g, 8 equiv) in DMF (20 mL) was added (R)-3-amino-1-(1-(5-(trifluoromethyl)pyrimidin-2-yl)piperidin-4-yl)pyrrolidin-2-one hydrochloride (155 mg, 1.0 equiv), HATU (179 mg, 1 equiv) and diisopropylethylamine (243 mg). After 2 hours, the reaction was quenched by the addition of 100 mL of water and was extracted with 3×100 mL of ethyl acetate. The organic layers were combined, dried over anhydrous sodium sulfate and concentrated in vacuo. The crude product was purified by reverse phase chromatography eluting with water/$CH_3CN$ (2/3) to afford 220 mg (66% yield) of (S)-2-((1-(4-methoxybenzyl)-6-oxo-5-(trifluoromethyl)-1,6-dihydropyridazin-4-yl)amino)-N—((R)-2-oxo-1-(1-(5-(trifluoromethyl)pyrimidin-2-yl)piperidin-4-yl)pyrrolidin-3-yl)propanamide as a white solid. LC-MS (ESI, m/z): 683.25 $[M+H]^+$.

Step F

To a solution of (S)-2-((1-(4-methoxybenzyl)-6-oxo-5-(trifluoromethyl)-1,6-dihydropyridazin-4-yl)amino)-N—((R)-2-oxo-1-(1-(5-(trifluoromethyl)pyrimidin-2-yl)piperidin-4-yl)pyrrolidin-3-yl)propanamide (210 mg, 0.31 mmol, 1.0 equiv) in TFA (2.7 mL) was added TfOH (0.3 mL). The mixture was stirred for 2 hours, and then 50 mL of water was added. The pH was adjusted to 7 with saturated aqueous $Na_2CO_3$. The resulting solution was extracted with 3×100 mL of ethyl acetate. The organic layers were combined, dried over anhydrous sodium sulfate and concentrated in vacuo. The crude product was purified by reverse phase chromatography eluting with water/$CH_3CN$ (1/1) to afford 81 mg (46% yield) of (S)—N—((R)-2-oxo-1-(1-(5-(trifluoromethyl)pyrimidin-2-yl)piperidin-4-yl)pyrrolidin-3-yl)-2-((6-oxo-5-(trifluoromethyl)-1,6-dihydropyridazin-4-yl)amino)propanamide as a white solid. LCMS (ESI, m/z): 563.10 $[M+H]^+$. 1H NMR (300 MHz, DMSO-$d_6$) δ 12.61 (s, 1H), 8.70 (s, 2H), 8.59 (d, J=8.0 Hz, 1H), 7.65 (s, 1H), 6.71 (br, 1H), 4.93-4.69 (m, 2H), 4.53-4.31 (m, 2H), 4.09 (br, 1H), 3.30-3.24 (m, 1H), 3.24-3.11 (m, 1H), 3.11-2.94 (m, 2H), 2.36-2.18 (m, 1H), 1.82-1.47 (m, 5H), 1.37 (d, J=6.7 Hz, 3H).

Example 62: Synthesis of 5-(((S)-1-(((R)-2-oxo-1-(1-(5-(trifluoromethyl)pyrimidin-2-yl)piperidin-4-yl)pyrrolidin-3-yl)oxy)-3-((2,2,2-trifluoroethyl)amino)propan-2-yl)amino)-4-(trifluoromethyl)pyridazin-3(2H)-one

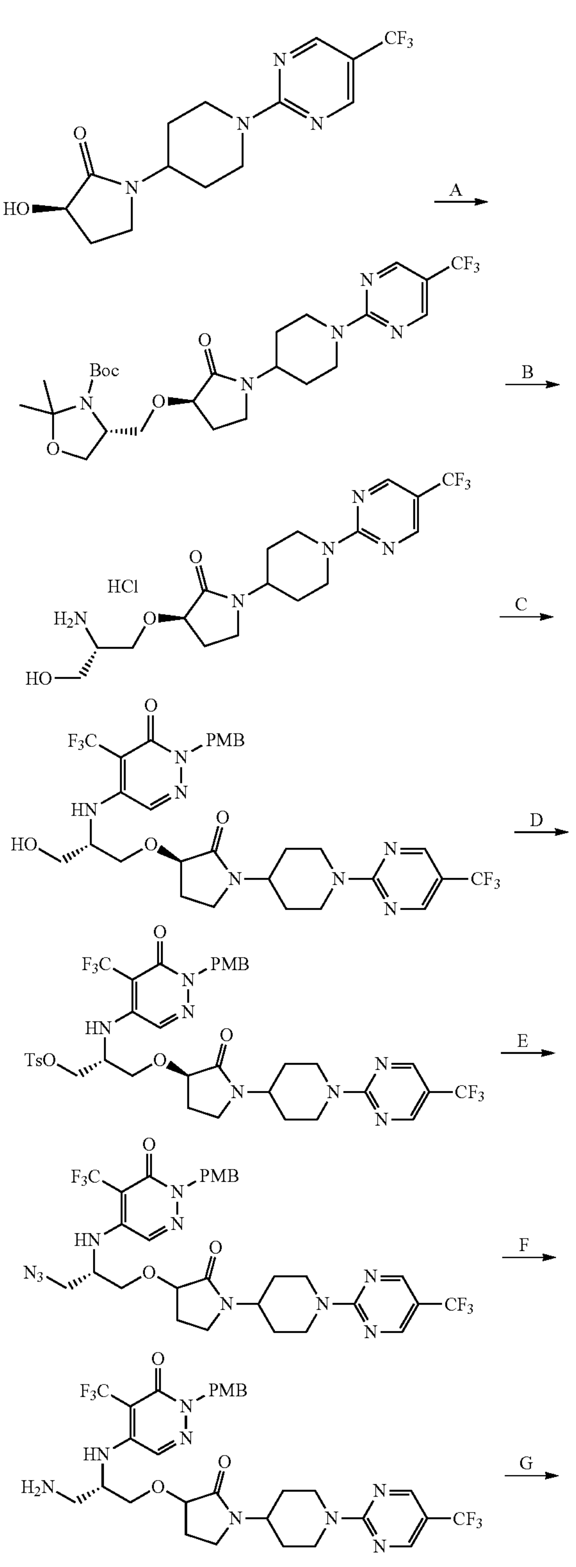

-continued

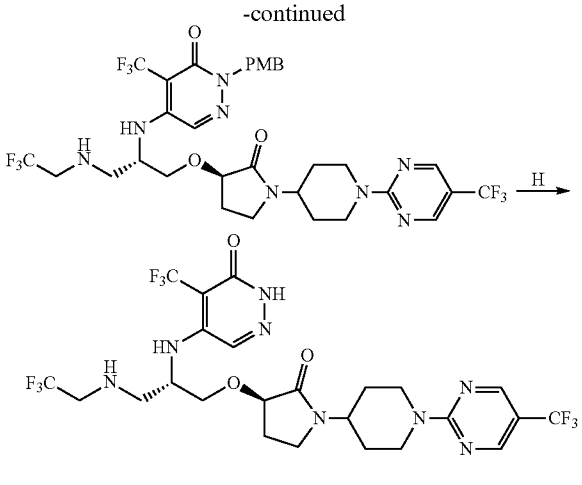

Step A

To a solution of (R)-3-hydroxy-1-(1-(5-(trifluoromethyl)pyrimidin-2-yl)piperidin-4-yl)pyrrolidin-2-one (1.30 g, 3.94 mmol, 1.0 equiv) in DMF (40 mL) was added NaH (0.47 g, 11.8 mmol, 3 equiv, 60% dispersion in mineral oil) and tert-butyl (S)-2,2-dimethyl-4-((tosyloxy)methyl)oxazolidine-3-carboxylate (6.07 g, 15.7 mmol, 4 equiv). The mixture was stirred for 7 hours at 40° C. The reaction was quenched by addition of 40 mL of water. After extraction with ethyl acetate, drying organics over sodium sulfate, and filtering, the resulting mixture was concentrated and applied onto a silica gel column eluting with ethyl acetate/petroleum ether (34/66) to afford tert-butyl (R)-2,2-dimethyl-4-((((R)-2-oxo-1-(1-(5-(trifluoromethyl)pyrimidin-2-yl)piperidin-4-yl)pyrrolidin-3-yl)oxy)methyl)oxazolidine-3-carboxylate (1.12 g, 47% yield) as a white solid. LCMS (ESI, m/z): 544.30 $[M+H]^+$.

Step B

A solution of tert-butyl (R)-2,2-dimethyl-4-((((R)-2-oxo-1-(1-(5-(trifluoromethyl)pyrimidin-2-yl)piperidin-4-yl)pyrrolidin-3-yl)oxy)methyl)oxazolidine-3-carboxylate (1.12 g, 2.06 mmol, 1.0 equiv) in 1,4-dioxane (10 mL) was treated with 4N HCl in dioxane (5 mL). The resulting solution stirred for 3 hours and was concentrated to afford (R)-3-((S)-2-amino-3-hydroxypropoxy)-1-(1-(5-(trifluoromethyl)pyrimidin-2-yl)piperidin-4-yl)pyrrolidin-2-one hydrochloride (600 mg, 65% yield) as a yellow oil. LCMS (ESI, m/z): 404.20 $[M+H]^+$.

Step C

To a solution of (R)-3-((S)-2-amino-3-hydroxypropoxy)-1-(1-(5-(trifluoromethyl)pyrimidin-2-yl)piperidin-4-yl)pyrrolidin-2-one hydrochloride (420 mg, 0.96 mmol, 1.0 equiv) in i-PrOH (45 mL) was added 5-chloro-2-(4-methoxybenzyl)-4-(trifluoromethyl)pyridazin-3(2H)-one (304 mg, 0.96 mmol, 1 equiv) and diisopropyl ethylamine (987 mg, 7.64 mmol, 8 equiv). The resulting solution was stirred for 3 hours at 80° C. and then was diluted with 150 mL of ethyl acetate. The mixture was washed with 3×50 mL of water and then was dried over anhydrous sodium sulfate and concentrated in vacuo. The residue was applied onto a silica gel column eluting with ethyl acetate to afford 5-(((S)-1-hydroxy-3-(((R)-2-oxo-1-(1-(5-(trifluoromethyl)pyrimidin-2-yl)piperidin-4-yl)pyrrolidin-3-yl)oxy)propan-2-yl)amino)-2-(4-methoxybenzyl)-4-(trifluoromethyl)pyridazin-3(2H)-one (440 mg, 60% yield) as a yellow oil. LCMS (ESI, m/z): 686.25 $[M+H]^+$.

Step D

To a solution of 5-(((S)-1-hydroxy-3-(((R)-2-oxo-1-(1-(5-(trifluoromethyl)pyrimidin-2-yl)piperidin-4-yl)pyrrolidin-3-yl)oxy)propan-2-yl)amino)-2-(4-methoxybenzyl)-4-(trifluoromethyl)pyridazin-3(2H)-one (775 mg, 1.13 mmol, 1.0 equiv) in DCM (30 mL) was added DMAP (27 mg, 0.23 mmol, 0.2 equiv), triethylamine (343 mg, 3.39 mmol, 3.0 equiv) and 4-methylbenzenesulfonyl chloride (430 mg, 2.3 mmol, 2 equiv). The resulting solution was stirred overnight and then was concentrated and applied onto a silica gel column eluting with ethyl acetate/petroleum ether (71/29) to afford (R)-2-((1-(4-methoxybenzyl)-6-oxo-5-(trifluoromethyl)-1,6-dihydropyridazin-4-yl)amino)-3-(((R)-2-oxo-1-(1-(5-(trifluoromethyl)pyrimidin-2-yl)piperidin-4-yl)pyrrolidin-3-yl)oxy)propyl 4-methylbenzenesulfonate (330 mg, 30% yield) as a yellow oil. LCMS (ESI, m/z): 840.25 $[M+H]^+$.

Step E

To a solution of (R)-2-((1-(4-methoxybenzyl)-6-oxo-5-(trifluoromethyl)-1,6-dihydropyridazin-4-yl)amino)-3-(((R)-2-oxo-1-(1-(5-(trifluoromethyl)pyrimidin-2-yl)piperidin-4-yl)pyrrolidin-3-yl)oxy)propyl 4-methylbenzenesulfonate (330 mg, 0.39 mmol, 1.0 equiv) in DMF (5 mL) was added sodium azide (38 mg, 0.59 mmol, 1.5 equiv). The solution was stirred for 1 hour at 80° C. and then was quenched by the addition of 25 mL of water. The mixture was extracted with 3×50 mL of ethyl acetate. The combined organics were dried over anhydrous sodium sulfate and concentrated to afford 5-(((2S)-1-azido-3-((2-oxo-1-(1-(5-(trifluoromethyl)pyrimidin-2-yl)piperidin-4-yl)pyrrolidin-3-yl)oxy)propan-2-yl)amino)-2-(4-methoxybenzyl)-4-(trifluoromethyl)pyridazin-3(2H)-one (330 mg, 71% yield) as a yellow oil. LCMS (ESI, m/z): 711.20 $[M+H]^+$.

Step F

To a solution of 5-(((2S)-1-azido-3-((2-oxo-1-(1-(5-(trifluoromethyl)pyrimidin-2-yl)piperidin-4-yl)pyrrolidin-3-yl)oxy)propan-2-yl)amino)-2-(4-methoxybenzyl)-4-(trifluoromethyl)pyridazin-3(2H)-one (330 mg, 0.46 mmol, 1.0 equiv, 60%) in THE (5 mL) was added triphenylphosphine (182 mg, 0.70 mmol, 1.5 equiv) and water (0.5 mL). The solution was stirred 1.5 hours at 60° C., concentrated, and applied onto a silica gel column eluting with DCM/methanol (87/13) to afford 5-(((2S)-1-amino-3-((2-oxo-1-(1-(5-(trifluoromethyl)pyrimidin-2-yl)piperidin-4-yl)pyrrolidin-3-yl)oxy)propan-2-yl)amino)-2-(4-methoxybenzyl)-4-(trifluoromethyl)pyridazin-3(2H)-one (186 mg, 92% yield) as a white solid. LCMS (ESI, m/z): 685.30 $[M+H]^+$.

Step G

To a solution of 5-(((2S)-1-amino-3-((2-oxo-1-(1-(5-(trifluoromethyl)pyrimidin-2-yl)piperidin-4-yl)pyrrolidin-3-yl)oxy)propan-2-yl)amino)-2-(4-methoxybenzyl)-4-(trifluoromethyl)pyridazin-3(2H)-one (100 mg, 0.15 mmol, 1.00 equiv) in dichloroethane (8 mL) was added 2,2,2-trifluoroacetaldehyde (57 mg, 0.44 mmol, 3 equiv), $Ti(Oi-Pr)_4$ (41 mg, 0.15 mmol, 1.0 equiv), AcOH (8 mg, 0.15 mmol, 1 equiv), and $NaBH_3CN$ (18 mg, 0.29 mmol, 2 equiv). The resulting solution was stirred for 1.5 hours at 70° C. and then was diluted with 50 mL of ethyl acetate and was washed with 3×20 ml of water. The organic layers were combined, dried over anhydrous sodium sulfate and concentrated. The residue was applied onto a silica gel column eluting with ethyl acetate/petroleum ether (91/9) to afford 2-(4-methoxybenzyl)-5-(((S)-1-(((R)-2-oxo-1-(1-(5-(trifluoromethyl)pyrimidin-2-yl)piperidin-4-yl)pyrrolidin-3-yl)oxy)-3-((2,2,2-trifluoroethyl)amino)propan-2-yl)amino)-4-(trifluoromethyl)pyridazin-3(2H)-one (67 mg, 56% yield) as a white solid. LCMS (ESI, m/z): 767.25 $[M+H]^+$.

Step H

To a solution of 2-(4-methoxybenzyl)-5-(((S)-1-(((R)-2-oxo-1-(1-(5-(trifluoromethyl)pyrimidin-2-yl)piperidin-4-yl)pyrrolidin-3-yl)oxy)-3-((2,2,2-trifluoroethyl)amino)propan-2-yl)amino)-4-(trifluoromethyl)pyridazin-3(2H)-one (60 mg, 0.08 mmol, 1.0 equiv) in TFA (1 mL) was added TfOH (0.1 mL), and the mixture was stirred for 1 hour. 8 mL of water was added, and the pH was adjusted to 9 with solid $Na_2CO_3$. The resulting solution was extracted with 2×30 mL of ethyl acetate. The organic layers were combined, dried over anhydrous sodium sulfate and concentrated in vacuo. The residue was applied onto a reverse phase column eluting with water/$CH_3CN$ (37/63) to afford 5-(((S)-1-(((R)-2-oxo-1-(1-(5-(trifluoromethyl)pyrimidin-2-yl)piperidin-4-yl)pyrrolidin-3-yl)oxy)-3-((2,2,2-trifluoroethyl)amino)propan-2-yl)amino)-4-(trifluoromethyl)pyridazin-3(2H)-one (20 mg, 39% yield) as a white solid. LCMS (ESI, m/z): 647.20 $[M+H]^+$; $^1H$ NMR (300 MHz, DMSO-$d_6$) δ 12.45 (s, 1H), 8.69 (s, 2H), 7.96 (s, 1H), 6.60-6.60 (m, 1H), 4.82 (d, J=13.2 Hz, 2H), 4.20-4.01 (m, 4H), 3.95-3.82 (m, 1H), 3.72-3.58 (m, 1H), 3.18-2.96 (m, 4H), 2.92-2.89 (m, 1H), 2.85-2.78 (m, 1H), 2.30-2.15 (m, 1H), 1.81-1.50 (m, 6H).

Example 63: Synthesis of 5-(((S)-1-hydroxy-3-(((R)-2-oxo-1-(1-(5-(trifluoromethyl)pyrimidin-2-yl)piperidin-4-yl)pyrrolidin-3-yl)oxy)propan-2-yl)amino)-4-(trifluoromethyl)pyridazin-3(2H)-one

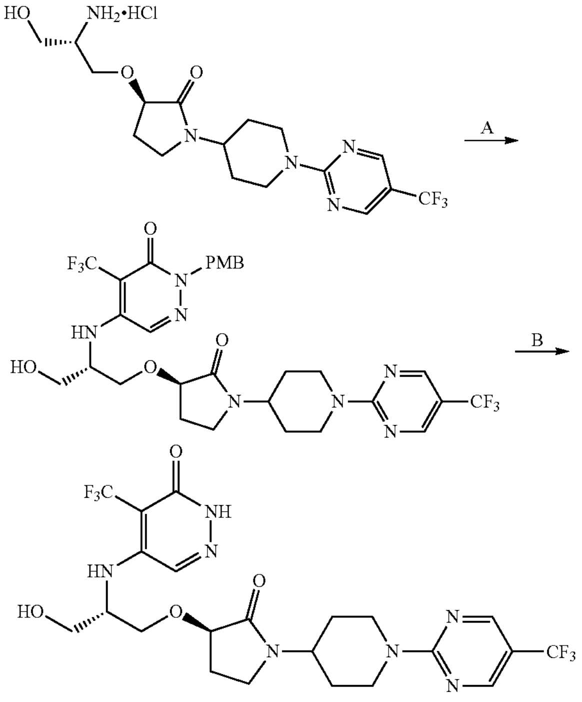

Step A

To a solution of (R)-3-((S)-2-amino-3-hydroxypropoxy)-1-(1-(5-(trifluoromethyl)pyrimidin-2-yl)piperidin-4-yl)pyrrolidin-2-one hydrochloride (130 mg, 0.29 mmol, 1.0 equiv) in $CH_3CN$ (5 mL) was added 5-chloro-2-(4-methoxybenzyl)-4-(trifluoromethyl)pyridazin-3(2H)-one (106 mg, 0.33 mmol, 1.1 equiv) and triethylamine (101 mg, 1.00 mmol, 3.4 equiv). The resulting solution was stirred for 1.5 days at 60° C. and then was concentrated in vacuo. The crude product was applied onto a reverse phase column eluting with water/$CH_3CN$ (1/1) to afford 150 mg (62% yield) of 5-(((S)-1-hydroxy-3-(((R)-2-oxo-1-(1-(5-(trifluoromethyl)pyrimidin-2-yl)piperidin-4-yl)pyrrolidin-3-yl)oxy)propan-2-yl)amino)-2-(4-methoxybenzyl)-4-(trifluoromethyl)pyridazin-3(2H)-one as a yellow solid. LCMS (ES, m/z): 686.20 $[M+H]^+$.

Step B

A solution of 5-(((S)-1-hydroxy-3-(((R)-2-oxo-1-(1-(5-(trifluoromethyl)pyrimidin-2-yl)piperidin-4-yl)pyrrolidin-3-yl)oxy)propan-2-yl)amino)-2-(4-methoxybenzyl)-4-(trifluoromethyl)pyridazin-3(2H)-one (150 mg, 0.22 mmol, 1.0 equiv) in TFA/TfOH (1.5 mL, 10:1) was stirred for 1 hour at room temperature, and then was quenched by the addition of ice water (10 mL). The pH was neutralized with saturated aqueous $NaHCO_3$, and the resulting solution was extracted with 3×30 mL of DCM. The organic layers were combined, dried over anhydrous sodium sulfate and concentrated in vacuo. The residue was purified by reverse phase chromatography eluting with water/$CH_3CN$ (3/2) to afford 15 mg (12% yield) of 5-(((S)-1-hydroxy-3-(((R)-2-oxo-1-(1-(5-(trifluoromethyl)pyrimidin-2-yl)piperidin-4-yl)pyrrolidin-3-yl)oxy)propan-2-yl)amino)-4-(trifluoromethyl)pyridazin-3(2H)-one as an off-white solid. LCMS (ESI, m/z): 566.25 $[M+H]^+$; $^1H$ NMR (400 MHz, DMSO-$d_6$) δ 12.45 (br, 1H), 8.69 (s, 1H), 7.95 (s, 1H), 6.29-6.31 (m, 1H), 5.10 (t, J=5.2 Hz, 1H), 4.82 (d, J=12.8 Hz, 1H), 4.13-4.07 (m, 3H), 3.88 (dd, J=10.1, 6.4 Hz, 1H), 3.68 (dd, J=10.2, 5.4 Hz, 1H), 3.54 (t, J=5.4 Hz, 2H), 3.28-3.22 (m, 1H), 3.16-3.10 (m, 1H), 3.04 (t, J=11.6 Hz, 2H), 2.29-2.21 (m, 1H), 1.77-1.50 (m, 5H).

Example 64: Synthesis of Syn-5-(((2S)-1-(((3S)-1-(3-hydroxy-1-(5-(trifluoromethyl)pyrimidin-2-yl)piperidin-4-yl)-2-oxopyrrolidin-3-yl)oxy)propan-2-yl)oxy)-4-(trifluoromethyl)pyridazin-3(2H)-one and Syn-5-(((2S)-1-(((3R)-1-(3-hydroxy-1-(5-(trifluoromethyl)pyrimidin-2-yl)piperidin-4-yl)-2-oxopyrrolidin-3-yl)oxy)propan-2-yl)oxy)-4-(trifluoromethyl)pyridazin-3(2H)-one

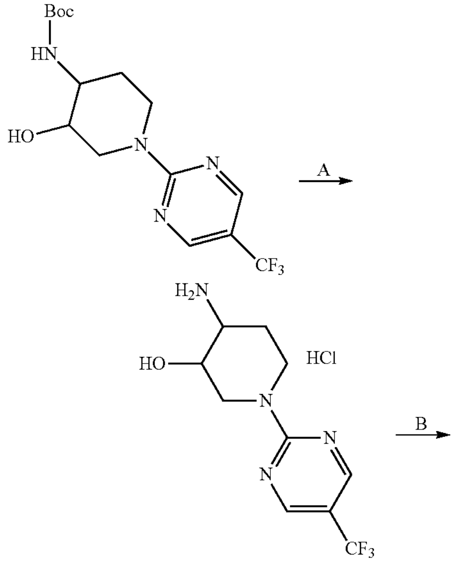

-continued

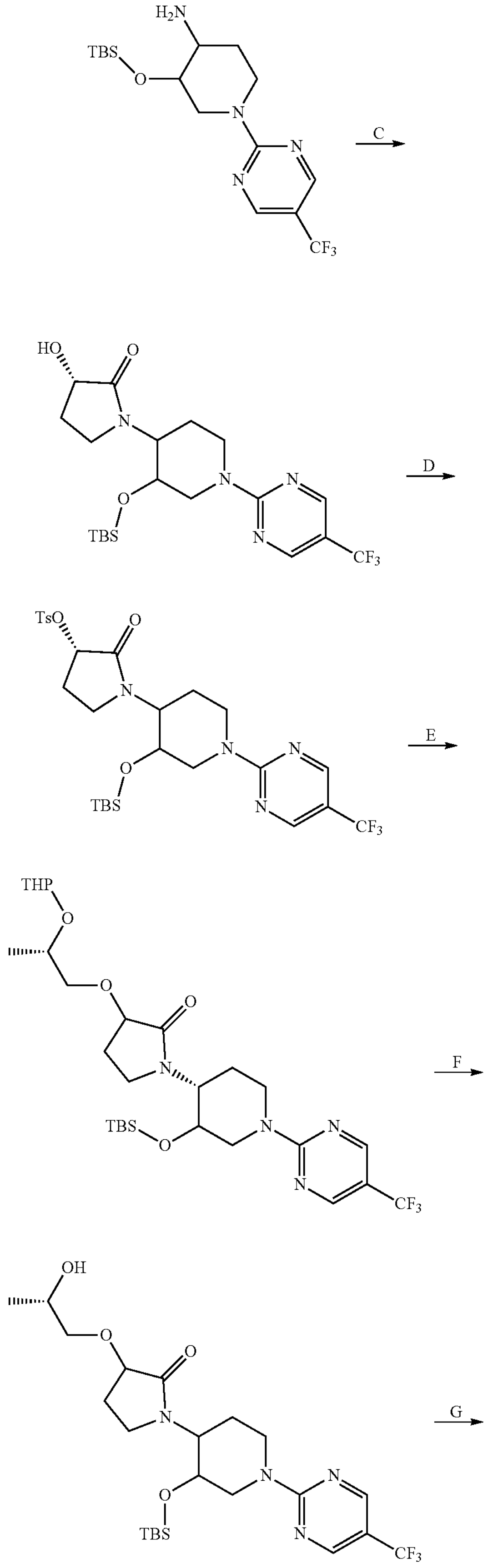

-continued

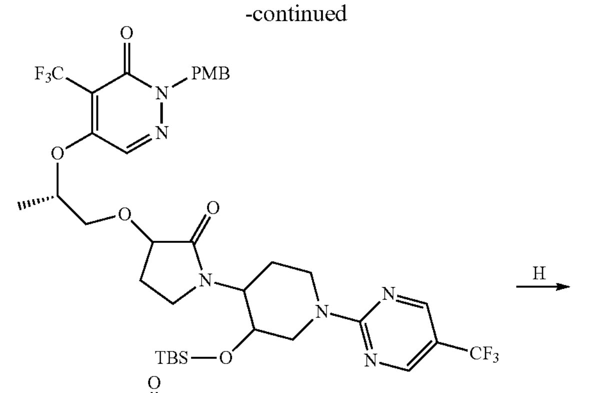

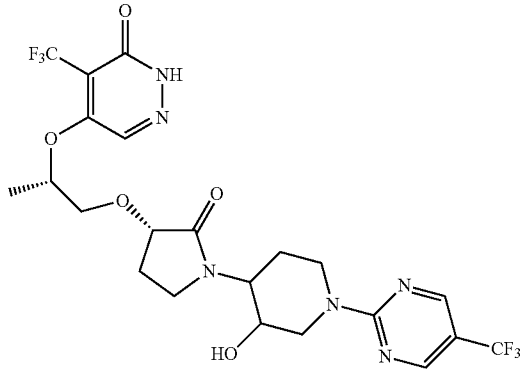

64A

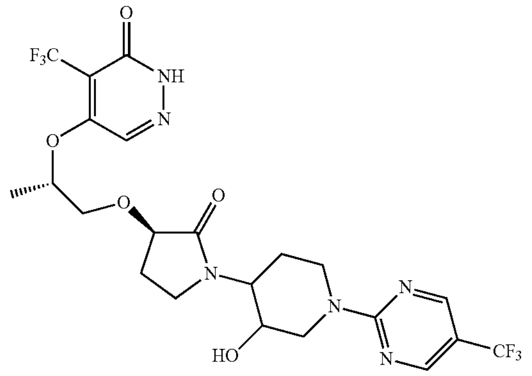 [SMILES: C[C@H](Nc1cn[nH]c(=O)c1C(F)(F)F)C(=O)N[C@@H]1CCN(C2CCN(c3ncc(C(F)(F)F)cn3)CC2)C1=O]

64B

Step A

To a solution of racemic syn-tert-butyl (3-hydroxy-1-(5-(trifluoromethyl)pyrimidin-2-yl)piperidin-4-yl)carbamate (2.22 g, 6.13 mmol, 1.0 equiv) in dioxane (10 mL) was added 4N HCl in dioxane (10 mL, 4M). The solution was stirred for 1.5 hours at 50° C. and then was concentrated in vacuo to afford 2.28 g (99% yield) of syn-4-amino-1-(5-(trifluoromethyl)pyrimidin-2-yl)piperidin-3-ol hydrochloride as an off-white solid. LCMS (ESI, m/z): 263.05 $[M+H]^+$.

Step B

To a solution of syn-4-amino-1-(5-(trifluoromethyl)pyrimidin-2-yl)piperidin-3-ol hydrochloride (2.28 g, 7.63 mmol, 1.0 equiv) in $CH_3CN$ (20 mL) was added imidazole (3.15 g, 46.3 mmol, 6.1 equiv) and tert-butylchlorodimethylsilane (5.80 g, 38.5 mmol, 5.0 equiv). The solution was stirred for 15 hours at 60° C. and then was concentrated in vacuo. The crude product was applied onto a silica gel column eluting with DCM/methanol (24/1) to afford 2.27 g (78% yield) of syn-3-((tert-butyldimethylsilyl)oxy)-1-(5-(trifluoromethyl)pyrimidin-2-yl)piperidin-4-amine as a light yellow solid. LCMS (ESI, m/z): 377.10 $[M+H]^+$.

Step C

To a solution of syn-3-((tert-butyldimethylsilyl)oxy)-1-(5-(trifluoromethyl)pyrimidin-2-yl)piperidin-4-amine (2.27 g, 6.03 mmol, 1.0 equiv) in DCM (50 mL) was added (R)-2-(2,2-dimethyl-5-oxo-1,3-dioxolan-4-yl)acetaldehyde (5.70 g, 36.0 mmol, 5.98 equiv) and AcOH (1.08 g, 17.9 mmol, 3.0 equiv). The resulting solution was stirred for 1 hour, and then STAB (3.84 g, 18.1 mmol, 3.0 equiv) was added, and the mixture was stirred for an additional 3 hours. After completion, the reaction was quenched by the addition of 50 mL of saturated aqueous sodium bicarbonate and extracted with 3×60 mL of DCM. The organic layers were combined, dried over anhydrous sodium sulfate and concentrated in vacuo. The crude product was applied onto a silica gel column eluting with DCM/methanol (24/1) to afford 2.55 g (81% yield) of syn-(3S)-1-(3-((tert-butyldimethylsilyl)oxy)-1-(5-(trifluoromethyl)pyrimidin-2-yl)piperidin-4-yl)-3-hydroxypyrrolidin-2-one as an off-white solid. LCMS (ESI, m/z): 461.15 $[M+H]^+$.

Step D

To a solution of syn-(3S)-1-(3-((tert-butyldimethylsilyl)oxy)-1-(5-(trifluoromethyl)pyrimidin-2-yl)piperidin-4-yl)-3-hydroxypyrrolidin-2-one (2.40 g, 5.21 mmol, 1.0 equiv) in DCM (30 mL) was added triethylamine (2.19 g, 21.6 mmol, 4.2 equiv), 4-methylbenzenesulfonyl chloride (2.04 g, 10.7 mmol, 2.1 equiv) and DMAP (0.13 g, 1.07 mmol, 0.2 equiv). The resulting solution was stirred overnight at room temperature, and then was quenched by the addition of 50 mL of ice water. The solution was extracted with 2×100 mL of DCM, dried over anhydrous sodium sulfate and concentrated in vacuo. The crude product was applied onto a silica gel column eluting with ethyl acetate/petroleum ether (1:2 to 10:1) to afford 3.4 g (99% yield) of syn-(3S)-1-(3-((tert-butyldimethylsilyl)oxy)-1-(5-(trifluoromethyl)pyrimidin-2-yl)piperidin-4-yl)-2-oxopyrrolidin-3-yl 4-methylbenzenesulfonate as a light yellow solid. LCMS (ESI, m/z): 615.20 $[M+H]^+$.

Step E

To a solution of (2S)-2-((tetrahydro-2H-pyran-2-yl)oxy)propan-1-ol (1.09 g, 6.80 mmol, 2.0 equiv) in DMF (20 mL) was added NaH (0.27 g, 6.85 mmol, 2.0 equiv, 60% dispersion in mineral oil) at 0° C. The reaction mixture was stirred for 15 min, and then syn-(3S)-1-(3-((tert-butyldimethylsilyl)oxy)-1-(5-(trifluoromethyl)pyrimidin-2-yl)piperidin-4-yl)-2-oxopyrrolidin-3-yl 4-methylbenzenesulfonate (2.10 g, 3.42 mmol, 1.0 equiv) was added, and the solution was stirred for 1 hour at room temperature. The reaction was treated with MeOH (5 mL), concentrated in vacuo and applied onto a silica gel column eluting with ethyl acetate/petroleum ether (1/2) to afford 775 mg (38% yield) of syn-1-(3-((tert-butyldimethylsilyl)oxy)-1-(5-(trifluoromethyl)pyrimidin-2-yl)piperidin-4-yl)-3-((2S)-2-((tetrahydro-2H-pyran-2-yl)oxy)propoxy)pyrrolidin-2-one as an off-white solid. LCMS (ESI, m/z): 603.20 $[M+H]^+$.

Step F

To a solution of syn-1-(3-((tert-butyldimethylsilyl)oxy)-1-(5-(trifluoromethyl)pyrimidin-2-yl)piperidin-4-yl)-3-((2S)-2-((tetrahydro-2H-pyran-2-yl)oxy)propoxy)pyrrolidin-2-one (500 mg, 0.8 mmol, 1 equiv) in MeOH (30 mL) was added pyridinium p-toluenesulfonate (210 mg, 0.83 mmol, 1.0 equiv). The resulting solution was stirred for 15 hours at room temperature and then was quenched by the addition of solid $Na_2CO_3$ (200 mg). The resulting mixture was concentrated and applied onto a silica gel column eluting with ethyl acetate to afford 350 mg (79% yield) of 1-syn-3-((tert-butyldimethylsilyl)oxy)-1-(5-(trifluoromethyl)pyrimidin-2-yl)piperidin-4-yl)-3-((S)-2-hydroxypropoxy)pyrrolidin-2-one as a light yellow solid. LCMS (ESI, m/z): 519.20 $[M+H]^+$.

Step G

To a solution of syn-1-3-((tert-butyldimethylsilyl)oxy)-1-(5-(trifluoromethyl)pyrimidin-2-yl)piperidin-4-yl)-3-((S)-2-hydroxypropoxy)pyrrolidin-2-one (360 mg, 0.70 mmol, 1.0 equiv) in DCM (5 mL) was added 5-chloro-2-[(4-methoxyphenyl)methyl]-4-(trifluoromethyl)pyridazin-3-one (301 mg, 0.95 mmol, 1.4 equiv) and t-BuOK (290 mg, 2.6 mmol, 3.8 equiv) at 0° C. The resulting solution stirred for 1.5 hours and then was concentrated and applied onto a silica gel column eluting with ethyl acetate/petroleum ether (1/1) to afford 471 mg (85% yield) of syn-5-(((2S)-1-((1-3-((tert-butyldimethylsilyl)oxy)-1-(5-(trifluoromethyl)pyrimidin-2-yl)piperidin-4-yl)-2-oxopyrrolidin-3-yl)oxy)propan-2-yl)oxy)-2-(4-methoxybenzyl)-4-(trifluoromethyl)pyridazin-3(2H)-one as a white solid. LCMS (ESI, m/z): 801.3$[M+H]^+$.

Step H

A solution of syn-5-(((2S)-1-((1-3-((tert-butyldimethylsilyl)oxy)-1-(5-(trifluoromethyl)pyrimidin-2-yl)piperidin-4-yl)-2-oxopyrrolidin-3-yl)oxy)propan-2-yl)oxy)-2-(4-methoxybenzyl)-4-(trifluoromethyl)pyridazin-3(2H)-one (471 mg, 0.59 mmol, 1.0 equiv) in TFA/TfOH (3 mL, 10:1) was stirred for 2 hours at room temperature. The reaction was quenched by the addition of ice water (20 mL), and the pH was adjusted to 7 with saturated aqueous $Na_2CO_3$. The solution was extracted with 3×60 mL of ethyl acetate, and the organic layers were combined, dried over anhydrous sodium sulfate and concentrated in vacuo. The residue was applied onto reverse phase chromatography eluting with water/$CH_3CN$ (1/1) and was further purified by chiral prep HPLC with the following conditions: CHIRAL ART Cellulose-SB, 2*25 cm, 5 μm; Mobile Phase A: Hex:DCM=3:1 (10 mM $NH_3$-MeOH); Mobile Phase B: IPA; Flow rate: 20 mL/min; Gradient: 30% B for 7 min; 220/254 nm. The absolute stereochemistry of the pyrrolidone stereocenter was assigned by analogy to Example 10, based on the PARP7 potency of the more active diastereomer and in analogy to the Example 10B X-ray crystal structure. The absolute stereochemistry of the piperidine stereocenters was undetermined.

Example 64 Isomer A (64A): Syn-5-(((2S)-1-(((3S)-1-(3-hydroxy-1-(5-(trifluoromethyl)pyrimidin-2-yl)piperidin-4-yl)-2-oxopyrrolidin-3-yl)oxy)propan-2-yl)oxy)-4-(trifluoromethyl)pyridazin-3(2H)-one (61 mg, 25% yield, off-white solid). LCMS (ESI, m/z): 567.20$[M+H]^+$; $^1$H NMR (400 MHz, DMSO-$d_6$) δ 13.22 (s, 1H), 8.65 (s, 2H), 8.28 (s, 1H), 5.22-5.15 (m, 1H), 5.00 (br, 1H), 4.90-4.72 (m, 2H), 4.06-3.95 (m, 3H), 3.90 (s, 1H), 3.63 (dd, J=11.1, 8.0 Hz, 1H), 3.30-3.24 (m, 2H), 3.14-2.98 (m, 2H), 2.20-2.16 (m, 1H), 2.07-2.02 (m, 1H), 1.61-1.58 (m, 1H), 1.49-1.41 (m, 1H), 1.28 (d, J=6.2 Hz, 3H). Chiral HPLC: CHIRAL Cellulose-SB, 0.46*10 cm; 3 μm; (Hex:DCM=3:1 w/ 0.1% diethyl amine:IPA=90:10; Flow rate: 1 mL/min); Retention time: 3.726 min. (faster peak).

Example 64 Isomer B (64B): Syn-5-(((2S)-1-(((3R)-1-(3-hydroxy-1-(5-(trifluoromethyl)pyrimidin-2-yl)piperidin-4-yl)-2-oxopyrrolidin-3-yl)oxy)propan-2-yl)oxy)-4-(trifluoromethyl)pyridazin-3(2H)-one (144 mg, 59% yield, off-white solid). LCMS (ESI, m/z): 567.10$[M+H]^+$ $^1$H NMR (400 MHz, DMSO-$d_6$) δ 13.21 (s, 1H), 8.65 (s, 2H), 8.31 (s, 1H), 5.19-5.15 (m, 1H), 5.00 (br, 1H), 4.88-4.76 (m, 2H), 4.07 (t, J=7.4 Hz, 1H), 4.04-3.98 (m, 1H), 3.93-3.83 (m, 2H), 3.74 (dd, J=11.1, 3.3 Hz, 1H), 3.30-3.24 (m, 2H), 3.17-2.98 (m, 2H), 2.28-2.17 (m, 1H), 2.11-1.97 (m, 1H), 1.71-1.62 (m, 1H), 1.47 (d, J=12.2 Hz, 1H), 1.28 (d, J=6.2

Hz, 3H). Chiral HPLC: CHIRAL Cellulose-SB, 0.46*10 cm; 3 μm; (Hex:DCM=3:1 w/0.1% diethyl amine:IPA=90:10; Flow rate: 1 mL/min); Retention time: 5.703 min. (slower peak).

Example 65: Synthesis of 5-(((2S)-1-((1-((3R,4R)-3-hydroxy-1-(5-(trifluoromethyl)pyrimidin-2-yl) piperidin-4-yl)-2-oxopyrrolidin-3-yl)oxy)propan-2-yl)oxy)-4-(trifluoromethyl)pyridazin-3(2H)-one

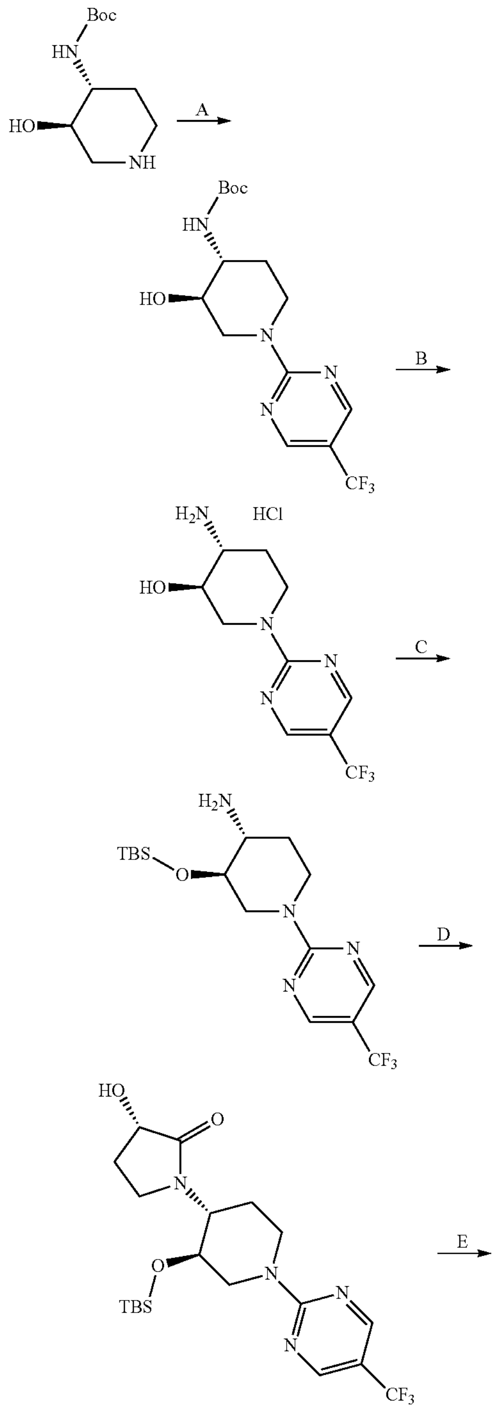

-continued

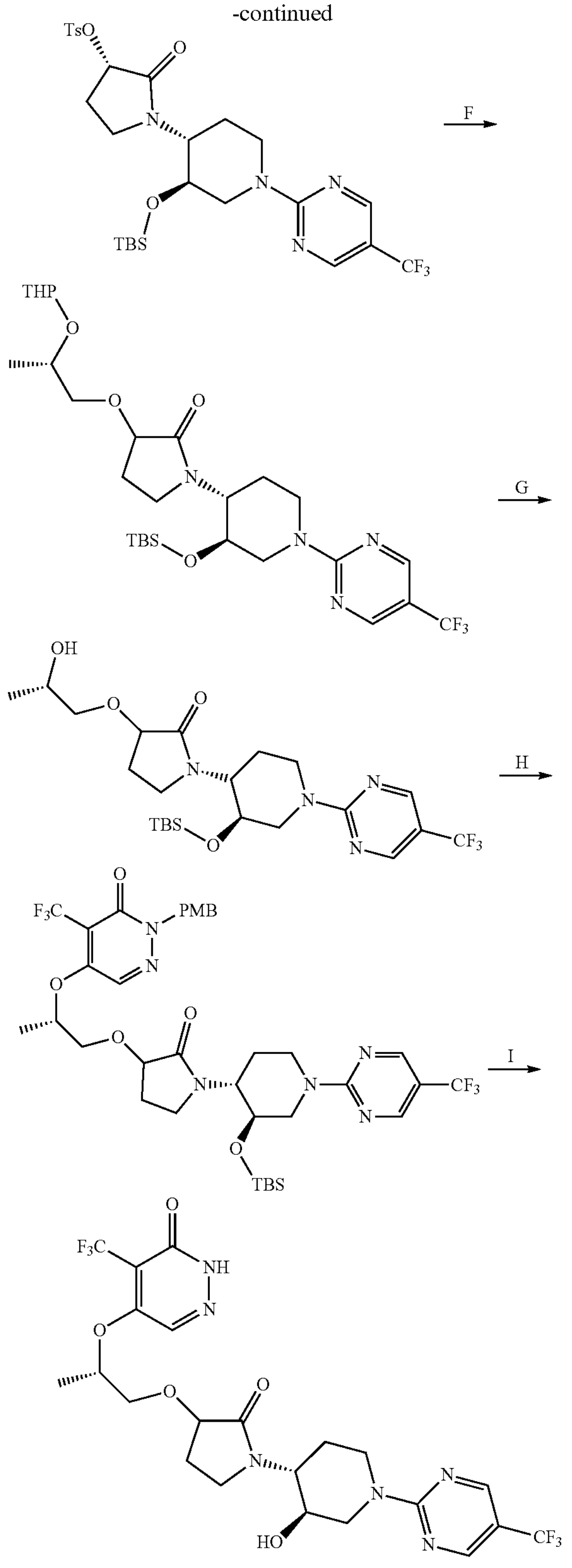

Step A

To a solution of tert-butyl ((3R,4R)-3-hydroxypiperidin-4-yl)carbamate (2.00 g, 9.25 mmol, 1.00 equiv), 2-chloro-5-(trifluoromethyl)pyrimidine (1.69 g, 9.25 mmol, 1.00 equiv) in DMF (20 mL) was added $K_2CO_3$ (2.56 g, 18.5 mmol, 2.00 equiv). The resulting solution stirred for 2 hours at 50° C. and was quenched by the addition of 50 mL of ice water. Then the solids were collected by filtration to afford 2.8 g (84% yield) of tert-butyl ((3R,4R)-3-hydroxy-1-(5-(trifluoromethyl)pyrimidin-2-yl)piperidin-4-yl)carbamate as a white solid. LCMS (ESI, m/z): 363.10 $[M+H]^+$.

Step B

A solution of tert-butyl ((3R,4R)-3-hydroxy-1-(5-(trifluoromethyl)pyrimidin-2-yl)piperidin-4-yl)carbamate (2.80 g, 7.73 mmol, 1.00 equiv) in 4N HCl in dioxane (20 mL) stirred for 1 hour. The mixture was concentrated to afford 2.6 g of crude (3R,4R)-4-amino-1-(5-(trifluoromethyl)pyrimidin-2-yl)piperidin-3-ol as a clear oil that was carried on without further purification. LCMS (ESI, m/z): 263.05$[M+H]^+$.

Step C

To a solution of (3R,4R)-4-amino-1-(5-(trifluoromethyl)pyrimidin-2-yl)piperidin-3-ol (2.60 g, 9.92 mmol, 1.00 equiv) in $CH_3CN$ (15 mL) was added tert-butyldimethylsilyl chloride (5.98 g, 39.7 mmol, 4.00 equiv) and imidazole (5.40 g, 79.3 mmol, 8.00 equiv). The resulting solution was stirred for 4 hours at 60° C. and was then concentrated in vacuo and applied onto a silica gel column eluting with DCM/methanol (99/1) to afford 2.5 g (67% yield) of (3R,4R)-3-(tert-butyldimethylsilyloxy)-1-(5-(trifluoromethyl)pyrimidin-2-yl)piperidin-4-amine as a yellow oil. LCMS (ESI, m/z): 377.15 $[M+H]^+$.

Step D

To a solution of (3R,4R)-3-(tert-butyldimethylsilyloxy)-1-(5-(trifluoromethyl)pyrimidin-2-yl)piperidin-4-amine (3.20 g, 8.50 mmol, 1.0 equiv) in DCM and DMF (1:1, 90 mL) was added (S)-2-(2,2-dimethyl-5-oxo-1,3-dioxolan-4-yl)acetaldehyde (2.69 g, 17.0 mmol, 2.0 equiv), STAB (7.21 g, 34.0 mmol, 4.0 equiv), and AcOH (0.51 g, 8.5 mmol, 1.0 equiv). The solution was stirred for 6 hours and then quenched by the addition of 90 mL of water. The solution was extracted with 3×180 mL of DCM, and the combined organics were concentrated in vacuo. The crude residue was applied onto a silica gel column with DCM/methanol (95/5) to afford 1.9 g (49% yield) of (S)-1-((3R,4R)-3-(tert-butyldimethylsilyloxy)-1-(5-(trifluoromethyl)pyrimidin-2-yl)piperidin-4-yl)-3-hydroxypyrrolidin-2-one as a white solid. LCMS (ESI, m/z): 461.20 $[M+H]^+$.

Step E

To a solution of (S)-1-((3R,4R)-3-(tert-butyldimethylsilyloxy)-1-(5-(trifluoromethyl)pyrimidin-2-yl)piperidin-4-yl)-3-hydroxypyrrolidin-2-one (1.00 g, 2.17 mmol, 1.0 equiv) and TsCl (496 mg, 2.61 mmol, 1.2 equiv) in DCM (10 mL) was added DMAP (265 mg, 2.17 mmol, 1.0 equiv) and triethylamine (439 mg, 4.34 mmol, 2.0 equiv). The solution was stirred for 2 hours and then was saturated aqueous $NaHCO_3$ was added. The layers were separated, and the aqueous layer was extracted with 3×10 mL of DCM. The combined organic layers was washed with 3×30 mL of saturated aqueous $NaHCO_3$, dried over anhydrous sodium sulfate, and concentrated in vacuo. The residue was applied onto a silica gel column eluting with ethyl acetate/petroleum ether (1/1) to afford 1.0 g (75% yield) of (S)-1-((3R,4R)-3-(tert-butyldimethylsilyloxy)-1-(5-(trifluoromethyl)pyrimidin-2-yl)piperidin-4-yl)-2-oxopyrrolidin-3-yl 4-methylbenzenesulfonate as a white solid. LCMS (ESI, m/z): 615.30 $[M+H]^+$.

Step F

To a solution of (S)-1-((3R,4R)-3-(tert-butyldimethylsilyloxy)-1-(5-(trifluoromethyl)pyrimidin-2-yl)piperidin-4-yl)-2-oxopyrrolidin-3-yl 4-methylbenzenesulfonate (540 mg, 0.88 mmol, 1.0 equiv) in DMF (5 mL) at 0° C. was added NaH (42 mg, 1.8 mmol, 2.0 equiv, 60% dispersion in mineral oil), and the mixture was stirred for 15 min at 0° C. (2S)-2-(Oxan-2-yloxy)propan-1-ol (281 mg, 1.76 mmol, 2.0 equiv) was added, and the mixture was stirred for an additional 30 min. The reaction was then quenched by the addition of 10 mL of MeOH, concentrated in vacuo, and applied onto a silica gel column eluting with ethyl acetate/petroleum ether (1/1) to afford 181 mg (34% yield) of 1-((3R,4R)-3-(tert-butyldimethylsilyloxy)-1-(5-(trifluoromethyl)pyrimidin-2-yl)piperidin-4-yl)-3-((S)-2-(tetrahydro-2H-pyran-2-yloxy)propoxy)pyrrolidin-2-one as a white solid. LCMS (ESI, m/z): 519.25 $[M+H]^+$.

Step G

To a solution of 1-((3R,4R)-3-(tert-butyldimethylsilyloxy)-1-(5-(trifluoromethyl)pyrimidin-2-yl)piperidin-4-yl)-3-((S)-2-(tetrahydro-2H-pyran-2-yloxy)propoxy)pyrrolidin-2-one (180 mg, 0.30 mmol, 1.0 equiv) in MeOH (5 mL) was added pyridinium p-toluenesulfonate (75 mg, 0.30 mmol, 1.0 equiv). The resulting solution was stirred for 1 hour at 40° C. and then was concentrated and applied onto a silica gel column eluting with ethyl acetate/petroleum ether (4/1) to afford 127 mg (82% yield) of 1-((3R,4R)-3-(tert-butyldimethylsilyloxy)-1-(5-(trifluoromethyl)pyrimidin-2-yl)piperidin-4-yl)-3-((S)-2-hydroxypropoxy)pyrrolidin-2-one as white solid. LCMS (ESI, m/z): 519.20 $[M+H]^+$.

Step H

To a solution of 1-((3R,4R)-3-(tert-butyldimethylsilyloxy)-1-(5-(trifluoromethyl)pyrimidin-2-yl)piperidin-4-yl)-3-((S)-2-hydroxypropoxy)pyrrolidin-2-one (120 mg, 0.2 mmol, 1 equiv) in DCM (5 mL) at 0° C. was added t-BuOK (50 mg, 0.5 mmol, 2 equiv). The resulting solution was stirred for 15 min, and then 5-chloro-2-(4-methoxybenzyl)-4-(trifluoromethyl)pyridazin-3(2H)-one (86 mg, 0.27 mmol, 1.2 equiv) was added, and the mixture stirred for 1.5 hours at 0° C. The mixture was concentrated, and the residue was applied onto a silica gel column eluting with ethyl acetate/petroleum ether (4/1) to afford 62 mg (34% yield) of 5-((S)-1-(1-((3R,4R)-3-(tert-butyldimethylsilyloxy)-1-(5-(trifluoromethyl)pyrimidin-2-yl)piperidin-4-yl)-2-oxopyrrolidin-3-yloxy)propan-2-yloxy)-2-(4-methoxybenzyl)-4-(trifluoromethyl)pyridazin-3(2H)-one as a white solid. LCMS (ESI, m/z): 801.35 $[M+H]^+$.

Step I

A solution of 5-[[(2S)-1-([1-[(3R,4R)-3-[(tert-butyldimethylsilyl)oxy]-1-[5-(trifluoromethyl)pyrimidin-2-yl]piperidin-4-yl]-2-oxopyrrolidin-3-yl]oxy)propan-2-yl]oxy]-2-[(4-methoxyphenyl)methyl]-4-(trifluoromethyl)pyridazin-3-one (60 mg, 0.08 mmol, 1 equiv) in TFA and TfOH (3 mL, 10:1) was stirred for 4 hours at 0° C. and then was diluted with 10 mL of ice water. The pH adjusted to 7 by adding saturated aqueous $NaHCO_3$. The resulting solution was extracted with 3×20 mL of ethyl acetate, and the combined organic layers were concentrated in vacuo. The crude product was purified by C18 reverse phase chromatography eluting with water/$CH_3CN$ (1/1) to afford 7 mg (14% yield) of 5-(((2S)-1-((1-((3R,4R)-3-hydroxy-1-(5-(trifluoromethyl)pyrimidin-2-yl)piperidin-4-yl)-2-oxopyrrolidin-3-yl)oxy)propan-2-yl)oxy)-4-(trifluoromethyl)pyridazin-3(2H)-one. LCMS (ESI, m/z): 567.40 $[M+H]^+$; $^1H$ NMR (300 MHz, DMSO-$d_6$) δ 13.21 (s, 1H), 8.69 (s, 2H), 8.31-8.27 (m, 1H), 5.31-5.20 (m, 1H), 5.19-5.12 (m, 1H), 4.89-4.81 (m, 1H), 4.73 (d, J=13.2 Hz, 1H), 4.14-3.69 (m, 4H), 3.64-3.39 (m, 2H), 3.17-3.09 (m, 2H), 3.05-2.91 (m, 1H), 2.80-2.69 (m, 1H), 2.27-2.18 (m, 1H), 1.62-1.50 (m, 3H), 1.26 (d, J=6.3 Hz, 3H).

Example 66: Synthesis of N—((S)-3-(((R)-2-oxo-1-(1-(5-(trifluoromethyl)pyrimidin-2-yl)piperidin-4-yl)pyrrolidin-3-yl)oxy)-2-((6-oxo-5-(trifluoromethyl)-1,6-dihydropyridazin-4-yl)amino)propyl)acetamide

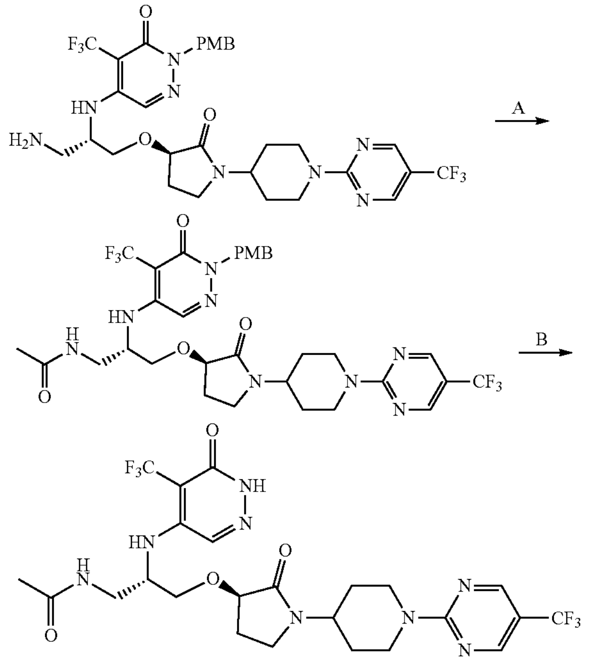

Step A

To a solution of 5-(((2S)-1-amino-3-(((R)-2-oxo-1-(1-(5-(trifluoromethyl)pyrimidin-2-yl)piperidin-4-yl)pyrrolidin-3-yl)oxy)propan-2-yl)amino)-2-(4-methoxybenzyl)-4-(trifluoromethyl)pyridazin-3(2H)-one (70 mg, 0.1 mmol, 1 equiv) in DCM (3 mL) was added DMAP (1 mg, 0.01 mmol, 0.1 equiv), acetic anhydride (15 mg, 0.15 mmol, 1.5 equiv) and triethylamine (31 mg, 0.31 mmol, 3 equiv). The resulting solution was stirred for 1 hour and then was diluted with 60 mL of ethyl acetate. The mixture was washed with 3×20 ml of water and then dried over anhydrous sodium sulfate and concentrated to afford N—((S)-2-((1-(4-methoxybenzyl)-6-oxo-5-(trifluoromethyl)-1,6-dihydropyridazin-4-yl)amino)-3-(((R)-2-oxo-1-(1-(5-(trifluoromethyl)pyrimidin-2-yl)piperidin-4-yl)pyrrolidin-3-yl)oxy)propyl)acetamide (66 mg, 71% yield) as a white solid. LCMS (ESI, m/z): 727.25 $[M+H]^+$.

Step B

To a solution of N—((S)-2-((1-(4-methoxybenzyl)-6-oxo-5-(trifluoromethyl)-1,6-dihydropyridazin-4-yl)amino)-3-(((R)-2-oxo-1-(1-(5-(trifluoromethyl)pyrimidin-2-yl)piperidin-4-yl)pyrrolidin-3-yl)oxy)propyl)acetamide (66 mg, 0.090 mmol, 1.0 equiv) in TFA (1 mL) was added TfOH (0.1 mL), and the mixture was stirred for 1 hour. The reaction was quenched by the addition of 8 mL of water, and the pH was adjusted to 9 with saturated aqueous $Na_2CO_3$. The resulting solution was extracted with 2×30 mL of ethyl acetate. The organic layers were combined, dried over anhydrous sodium sulfate and concentrated in vacuo. The residue was applied onto a C18 reverse phase column eluting with water/$CH_3CN$ (47/53) to afford of N—((S)-3-(((R)-2-oxo-1-(1-(5-(trifluoromethyl)pyrimidin-2-yl)piperidin-4-yl)pyrrolidin-3-yl)oxy)-2-((6-oxo-5-(trifluoromethyl)-1,6-dihydropyridazin-4-yl)amino)propyl)acetamide (13 mg, 22% yield) as a white solid. LCMS (ESI, m/z): 607.30 $[M+H]^+$. $^1H$ NMR (300 MHz, DMSO-$d_6$) δ 12.49 (s, 1H), 8.69 (s, 2H), 8.14 (t, J=5.9 Hz, 1H), 7.98 (s, 1H), 6.55-6.44 (m, 1H), 4.82 (d, J=13.2 Hz, 2H), 4.21-4.02 (m, 3H), 3.90-3.81 (m, 1H), 3.70-3.61 (m, 1H), 3.30-2.96 (m, 6H), 2.31-2.15 (m, 1H), 1.81 (s, 3H), 1.81-1.45 (m, 5H).

Example 67: Synthesis of 5-(((2R,3R)-3-hydroxy-1-(((R)-2-oxo-1-(1-(5-(trifluoromethyl)pyrimidin-2-yl)piperidin-4-yl)pyrrolidin-3-yl)oxy)butan-2-yl)amino)-4-(trifluoromethyl)pyridazin-3(2H)-one

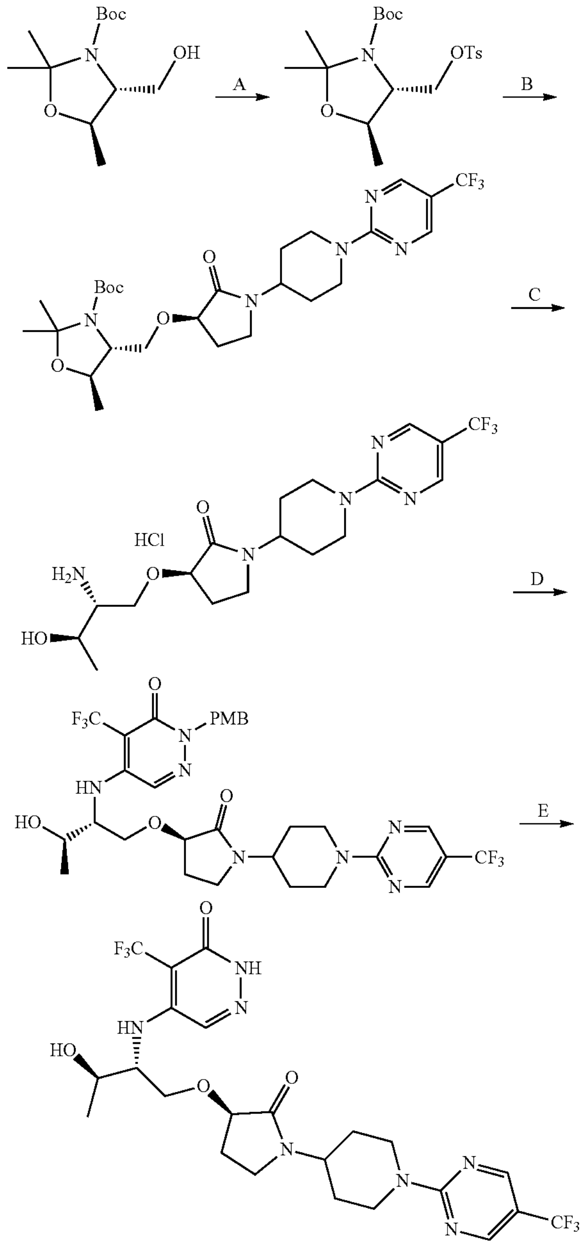

Step A

To a solution of tert-butyl (4R,5R)-4-(hydroxymethyl)-2,2,5-trimethyloxazolidine-3-carboxylate (4.0 g, 16 mmol, 1.0 equiv) in DCM (10 mL) was added 4-toluenesulfonyl chloride (3.7 g, 20 mmol, 1.2 equiv), DMAP (1.9 g, 16 mmol, 1.0 equiv) and triethylamine (3.3 g, 32.6 mmol, 2.0 equiv). The resulting solution was stirred for 4 hours and then was washed with 2×25 mL of saturated aqueous $NaHCO_3$. The organic layers were concentrated and applied onto a silica gel column eluting with ethyl acetate/petroleum ether (9/1) to afford 5.8 g (89% yield) of tert-butyl (4R,5R)-2,2,5-trimethyl-4-((tosyloxy)methyl)oxazolidine-3-carboxylate as a yellow oil. LCMS (ESI, m/z): 344.05[M+H]$^+$.

Step B

To a solution of (R)-3-hydroxy-1-(1-(5-(trifluoromethyl) pyrimidin-2-yl)piperidin-4-yl)pyrrolidin-2-one (500 mg, 1.51 mmol, 1.0 equiv) in DMF (5 mL) at 0° C. was added NaH (72 mg, 3.0 mmol, 2.0 equiv, 60% dispersion in oil). The mixture was stirred for 10 minutes and then tert-butyl (4R,5R)-2,2,5-trimethyl-4-((tosyloxy)methyl)oxazolidine-3-carboxylate (1.8 g, 4.5 mmol, 3.0 equiv) was added at 0° C. The reaction mixture stirred an additional 6 hours at 40° C. and then was concentrated and purified by silica gel chromatography eluting with ethyl acetate/petroleum ether (15/85) to afford 900 mg of tert-butyl (4R,5R)-2,2,5-trimethyl-4-((((R)-2-oxo-1-(1-(5-(trifluoromethyl)pyrimidin-2-yl)piperidin-4-yl)pyrrolidin-3-yl)oxy)methyl)oxazolidine-3-carboxylate as a yellow oil. LCMS (ESI, m/z): 558.25 [M+H]$^+$.

Step C

A solution of tert-butyl (4R,5R)-2,2,5-trimethyl-4-((((R)-2-oxo-1-(1-(5-(trifluoromethyl)pyrimidin-2-yl)piperidin-4-yl)pyrrolidin-3-yl)oxy)methyl)oxazolidine-3-carboxylate (900 mg, 1.6 mmol, 1.0 equiv) in 4M HCl in dioxane (10 mL) was stirred for 6 hours, and then was concentrated to afford 850 mg of (R)-3-((2R,3R)-2-amino-3-hydroxybutoxy)-1-(1-(5-(trifluoromethyl)pyrimidin-2-yl)piperidin-4-yl)pyrrolidin-2-one hydrogen chloride as a colorless oil that was carried on without further purification. LCMS (ESI, m/z): 418.10 [M+H]$^+$.

Step D

To a solution of (R)-3-((2R,3R)-2-amino-3-hydroxybutoxy)-1-(1-(5-(trifluoromethyl)pyrimidin-2-yl)piperidin-4-yl)pyrrolidin-2-one hydrogen chloride (400 mg, 0.96 mmol, 1.0 equiv) in isopropanol (5 mL) was added 5-chloro-2-(4-methoxybenzyl)-4-(trifluoromethyl)pyridazin-3(2H)-one (366 mg, 1.15 mmol, 1.2 equiv) and N,N-diisopropylethylamine (620 mg, 4.8 mmol, 5.0 equiv). The solution was stirred for 6 hours at 80° C. and was then concentrated and applied onto a silica gel column eluting with ethyl acetate/petroleum ether (95/5) to afford 170 mg (25% yield) of 5-(((2R,3R)-3-hydroxy-1-(((R)-2-oxo-1-(1-(5-(trifluoromethyl)pyrimidin-2-yl)piperidin-4-yl)pyrrolidin-3-yl)oxy)butan-2-yl)amino)-2-(4-methoxybenzyl)-4-(trifluoromethyl) pyridazin-3(2H)-one as a yellow solid. LCMS (ESI, m/z): 700.20 [M+H]$^+$.

Step E

A solution of 5-(((2R,3R)-3-hydroxy-1-(((R)-2-oxo-1-(1-(5-(trifluoromethyl)pyrimidin-2-yl)piperidin-4-yl)pyrrolidin-3-yl)oxy)butan-2-yl)amino)-2-(4-methoxybenzyl)-4-(trifluoromethyl)pyridazin-3(2H)-one (120 mg, 0.17 mmol, 1.0 equiv) in TFA/TfOH (3 mL, 3:1) was stirred for 40 min at −10° C. The pH was adjusted to ~6-7 with saturated aqueous $Na_2CO_3$, and the resulting solution was extracted with 3×25 mL of ethyl acetate. The organic layers were combined, dried over $Na_2SO_4$ and concentrated. The crude product was purified by C18 reverse phase chromatography eluting with $CH_3CN$/water to afford 5-(((2R,3R)-3-hydroxy-1-(((R)-2-oxo-1-(1-(5-(trifluoromethyl)pyrimidin-2-yl)piperidin-4-yl)pyrrolidin-3-yl)oxy)butan-2-yl)amino)-4-(trifluoromethyl)pyridazin-3(2H)-one 55 mg (55% yield) as a white solid. LCMS (ESI, m/z): 580.20 [M+H]$^+$; $^1$H-NMR (300 MHz, DMSO-$d_6$) δ 12.45 (s, 1H), 8.67 (s, 2H), 7.93 (s, 1H), 6.25-6.12 (m, 1H), 5.29 (d, J=4.1 Hz, 1H), 4.80 (d, J=13.2 Hz, 2H), 4.15-4.07 (m, 2H), 3.96-3.82 (m, 3H), 3.69-3.61 (m, 1H), 3.28-2.94 (m, 4H), 2.25-2.16 (m, 1H), 1.79-1.53 (m, 5H), 1.07 (d, J=6.2 Hz, 3H).

Example 68: Synthesis of 4-((R)-2-oxo-3-((S)-2-((6-oxo-5-(trifluoromethyl)-1,6-dihydropyridazin-4-yl)amino)propoxy)pyrrolidin-1-yl)-1-(5-(trifluoromethyl)pyrimidin-2-yl)piperidine-3-carboxamide

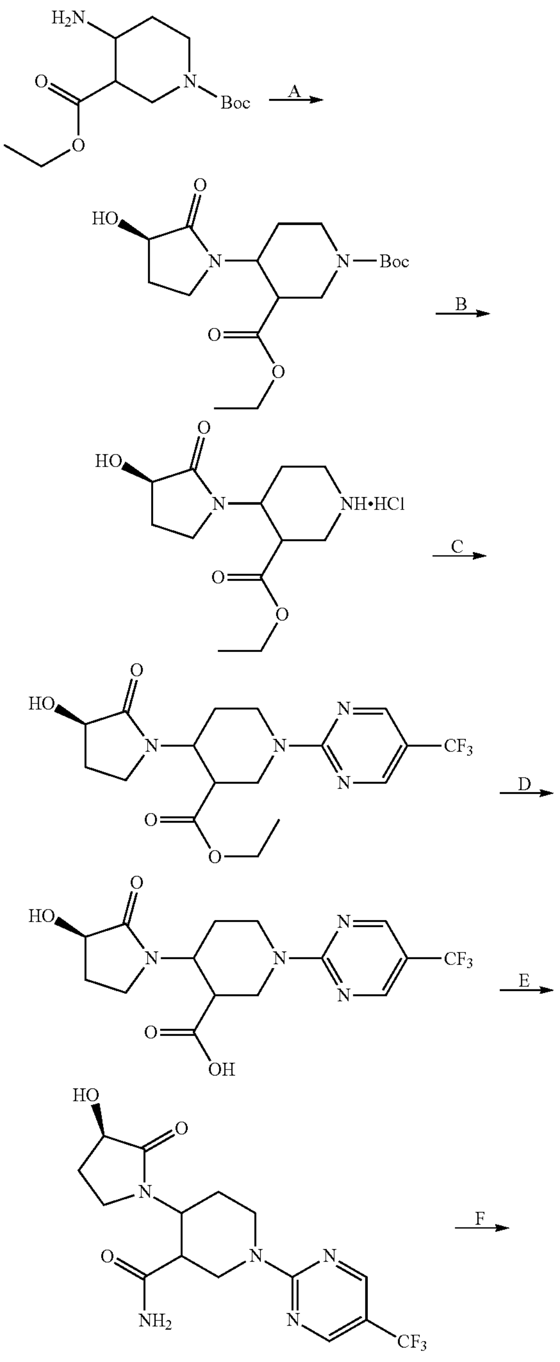

-continued

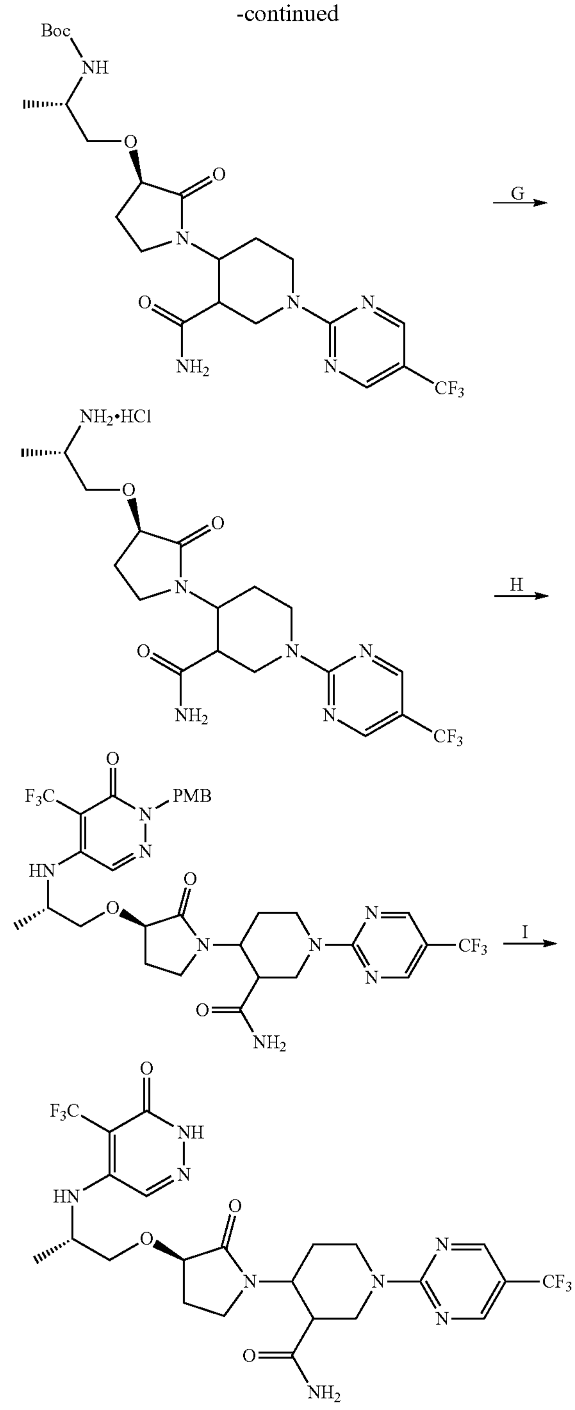

Step A

To a solution of 1-(tert-butyl) 3-ethyl 4-aminopiperidine-1,3-dicarboxylate (16.0 g, 58.7 mmol, 1.00 equiv) in DCM (200 mL) was added AcOH (5.29 g, 88.1 mmol, 1.50 equiv) and (R)-2-(2,2-dimethyl-5-oxo-1,3-dioxolan-4-yl)acetaldehyde (10.2 g, 64.6 mmol, 1.1 equiv). The resulting solution was stirred for 5 hours at room temperature, and then STAB (24.9 g, 117 mmol, 2.0 equiv) was added, and the reaction mixture was stirred for an additional 45 hours. The solution was quenched by the addition of 100 mL of ice water, and the pH was adjusted to 8 with 1% aqueous NaOH. The solution was extracted with 300 mL of DCM. The organic layers were combined, dried over anhydrous sodium sulfate, and concentrated in vacuo. The crude product was applied onto a silica gel column eluting with ethyl acetate/petroleum ether (1/9) to afford 5.7 g (27% yield) of 1-(tert-butyl) 3-ethyl 4-((R)-3-hydroxy-2-oxopyrrolidin-1-yl)piperidine-1,3-dicarboxylate as a brown oil.

Step B

A solution of 1-(tert-butyl) 3-ethyl 4-((R)-3-hydroxy-2-oxopyrrolidin-1-yl)piperidine-1,3-dicarboxylate (5.70 g, 16.0 mmol, 1.0 equiv) in 4N HCl in dioxane (40 mL) was stirred for 20 hours. The resulting mixture was concentrated in vacuo to afford 5 g of ethyl 4-((R)-3-hydroxy-2-oxopyrrolidin-1-yl)piperidine-3-carboxylate hydrochloride as a brown solid that was carried on without further purification.

Step C

To a solution of ethyl 4-((R)-3-hydroxy-2-oxopyrrolidin-1-yl)piperidine-3-carboxylate hydrochloride (5.00 g, 17.1 mmol, 1.0 equiv) in DMF (40 mL) was added 2-chloro-5-(trifluoromethyl)pyrimidine (3.12 g, 17.1 mmol, 1.0 equiv) and $K_2CO_3$ (7.08 g, 51.2 mmol, 3.0 equiv). The resulting solution was stirred for 1 hour at 60° C. and was concentrated in vacuo and purified by reverse phase chromatography eluting with water/$CH_3CN$ (9/11) to afford 1.2 g (17% yield) of ethyl 4-((R)-3-hydroxy-2-oxopyrrolidin-1-yl)-1-(5-(trifluoromethyl)pyrimidin-2-yl)piperidine-3-carboxylate as a yellow solid. LCMS (ESI, m/z): 403.2 $[M+H]^+$.

Step D

To a solution of ethyl 4-((R)-3-hydroxy-2-oxopyrrolidin-1-yl)-1-(5-(trifluoromethyl)pyrimidin-2-yl)piperidine-3-carboxylate (558 mg, 1.39 mmol, 1.0 equiv) in EtOH (5 mL) and water (1 mL) was added NaOH (111 mg, 2.78 mmol, 2.0 equiv). The resulting solution was stirred for 15 hours. The pH was adjusted to 5 with HCl (2 M) and was concentrated in vacuo. The residue was applied onto a silica gel column eluting with water/$CH_3CN$ (5:1) to afford 420 mg (81% yield) of 4-((R)-3-hydroxy-2-oxopyrrolidin-1-yl)-1-(5-(trifluoromethyl)pyrimidin-2-yl)piperidine-3-carboxylic acid as a yellow solid. LCMS (ESI, m/z): 375.10 $[M+H]^+$.

Step E

To a solution of 4-((R)-3-hydroxy-2-oxopyrrolidin-1-yl)-1-(5-(trifluoromethyl)pyrimidin-2-yl)piperidine-3-carboxylic acid (420 mg, 1.1 mmol, 1.0 equiv) in DMF (5 mL) was added N,N-diisopropylethylamine (290 mg, 2.2 mmol, 2.0 equiv), $NH_4Cl$ (90 mg, 1.7 mmol, 1.5 equiv) and HATU (640 mg, 1.7 mmol, 1.5 equiv). The resulting solution was stirred for 1.5 hours and then applied onto a reverse phase C18 column eluting with water/$CH_3CN$ (5:1) to afford 400 mg (95% yield) of 4-((R)-3-hydroxy-2-oxopyrrolidin-1-yl)-1-(5-(trifluoromethyl)pyrimidin-2-yl)piperidine-3-carboxamide as a yellow solid. LCMS (ESI, m/z): 374.10 $[M+H]^+$.

Step F

To a solution of 4-((R)-3-hydroxy-2-oxopyrrolidin-1-yl)-1-(5-(trifluoromethyl)pyrimidin-2-yl)piperidine-3-carboxamide (400 mg, 1.1 mmol, 1.0 equiv) in DMF (20 mL) at 0° C. was added NaH (86 mg, 2.2 mmol, 2.0 equiv, 60% dispersion in oil). After 15 minutes, a solution of tert-butyl (4S)-4-methyl-2,2-dioxo-1,2lambda6,3-oxathiazolidine-3-carboxylate (265 mg, 1.12 mmol, 1.0 equiv) in DMF (2 mL) was added, and the mixture stirred for 1 hour. The reaction was quenched by the addition of 2 mL of saturated aqueous sodium bicarbonate. The resulting mixture was concentrated and applied onto a reverse phase column eluting with water/$CH_3OH$ (11:9) to afford 330 mg (48% yield) of tert-butyl ((2S)-1-(((3R)-1-(3-carbamoyl-1-(5-(trifluoromethyl)pyrimidin-2-yl)piperidin-4-yl)-2-oxopyrrolidin-3-yl)oxy)propan-2-yl)carbamate as a yellow solid. LCMS (ESI, m/z): 531.30 $[M+H]^+$.

Step G

A solution of tert-butyl ((2S)-1-(((3R)-1-(3-carbamoyl-1-(5-(trifluoromethyl)pyrimidin-2-yl)piperidin-4-yl)-2-oxopyrrolidin-3-yl)oxy)propan-2-yl)carbamate (330 mg, 0.62 mmol, 1.0 equiv) in 4N HCl in dioxane (5 mL) was stirred for 1 hour, and then was concentrated in vacuo to afford 305 mg (66% yield) of 4-((R)-3-((S)-2-aminopropoxy)-2-oxopyrrolidin-1-yl)-1-(5-(trifluoromethyl)pyrimidin-2-yl)piperidine-3-carboxamide hydrochloride as a light yellow solid. LCMS (ESI, m/z): 431.20 $[M+H]^+$.

Step H

To a solution of 4-((R)-3-((S)-2-aminopropoxy)-2-oxopyrrolidin-1-yl)-1-(5-(trifluoromethyl)pyrimidin-2-yl)piperidine-3-carboxamide hydrochloride (280 mg, 0.60 mmol, 1.0 equiv) in $CH_3CN$ (5 mL) was added N,N-diisopropylethylamine (280 mg, 2.2 mmol, 3.6 equiv) and 5-chloro-2-[(4-methoxyphenyl)methyl]-4-(trifluoromethyl)pyridazin-3-one (201 mg, 0.63 mmol, 1.1 equiv). The solution was stirred for 1 hours at 80° C., and then was concentrated in vacuo. The crude product was applied onto a reverse phase C18 column eluting with water/$CH_3CN$ (1/1) to afford 290 mg (63% yield) of 4-((R)-3-((S)-2-((1-(4-methoxybenzyl)-6-oxo-5-(trifluoromethyl)-1,6-dihydropyridazin-4-yl)amino)propoxy)-2-oxopyrrolidin-1-yl)-1-(5-(trifluoromethyl)pyrimidin-2-yl)piperidine-3-carboxamide as a yellow solid. LCMS (ESI, m/z): 713.25 $[M+H]^+$.

Step I

A solution of 4-((R)-3-((S)-2-((1-(4-methoxybenzyl)-6-oxo-5-(trifluoromethyl)-1,6-dihydropyridazin-4-yl)amino)propoxy)-2-oxopyrrolidin-1-yl)-1-(5-(trifluoromethyl)pyrimidin-2-yl)piperidine-3-carboxamide (570 mg, 0.80 mmol, 1.0 equiv) in TFA/TfOH (5 mL, 10:1) was stirred for 1 hour. The reaction was quenched by the addition of 15 mL of ice water, and the pH was adjusted to ~7-8 with aqueous saturated $Na_2CO_3$. The solution was extracted with 3×60 mL of DCM. The organic layers were combined, dried over anhydrous sodium sulfate and concentrated in vacuo. The residue was purified by reverse phase chromatography eluting with water/$CH_3CN$ (3/2) to afford 314 mg (66% yield) of 4-((R)-2-oxo-3-((S)-2-((6-oxo-5-(trifluoromethyl)-1,6-dihydropyridazin-4-yl)amino)propoxy)pyrrolidin-1-yl)-1-(5-(trifluoromethyl)pyrimidin-2-yl)piperidine-3-carboxamide as a yellow solid. LCMS (ESI, m/z): 593.15 $[M+H]^+$; $^1H$ NMR (400 MHz, DMSO-$d_6$) δ 12.46 (s, 1H), 8.74 (s, 2H), 7.95 (d, J=7.9 Hz, 1H), 7.53-7.48 (m, 1H), 6.99 (s, 1H), 6.37-6.29 (m, 1H), 4.89-4.76 (m, 2H), 4.33-4.01 (m, 3H), 3.86-3.73 (m, 1H), 3.63-3.53 (m, 1H), 3.29-3.20 (m, 1H), 3.15-3.00 (m, 3H), 2.68-2.53 (m, 1H), 2.31-2.12 (m, 1H), 1.82-1.56 (m, 3H), 1.19-1.13 (m, 3H).

Example 69: Synthesis of 4-((R)-2-oxo-3-((S)-2-((6-oxo-5-(trifluoromethyl)-1,6-dihydropyridazin-4-yl)amino)propoxy)pyrrolidin-1-yl)-1-(5-(trifluoromethyl)pyrimidin-2-yl)piperidine-3-carbonitrile

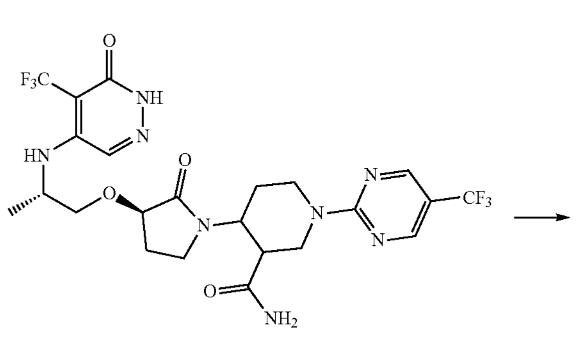

-continued

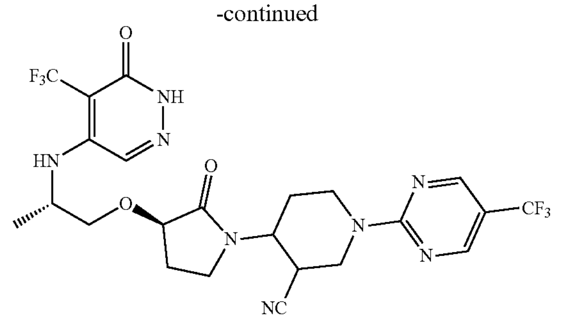

To a solution of 4-((R)-2-oxo-3-((S)-2-((6-oxo-5-(trifluoromethyl)-1,6-dihydropyridazin-4-yl)amino)propoxy)pyrrolidin-1-yl)-1-(5-(trifluoromethyl)pyrimidin-2-yl)piperidine-3-carboxamide (320 mg, 0.54 mmol, 1.0 equiv) in water (22 mL) and $CH_3CN$ (27 mL) was added palladium chloride (133 mg, 0.75 mmol, 1.4 equiv). The resulting solution was stirred overnight at 80° C. and then was extracted with 4×30 mL of ethyl acetate. The organic layers were combined, dried over anhydrous sodium sulfate, and concentrated. The residue was applied onto a C18 reverse phase column eluting with water/$CH_3CN$ (1/1) to afford 15 mg (5% yield) of 4-((R)-2-oxo-3-((S)-2-((6-oxo-5-(trifluoromethyl)-1,6-dihydropyridazin-4-yl)amino)propoxy)pyrrolidin-1-yl)-1-(5-(trifluoromethyl)pyrimidin-2-yl)piperidine-3-carbonitrile as a white solid. LCMS (ESI, m/z): 575.25 $[M+H]^+$; $^1H$ NMR (400 MHz, DMSO-$d_6$) δ 12.46 (s, 1H), 8.85 (s, 2H), 7.95 (d, J=3.6 Hz, 1H), 6.32 (br, 1H), 5.13-5.01 (m, 1H), 4.93-4.76 (m, 1H), 4.46-4.34 (m, 1H), 4.28-4.12 (m, 2H), 3.86-3.75 (m, 1H), 3.68-3.58 (m, 1H), 3.49-3.39 (m, 1H), 3.26-3.08 (m, 3H), 2.32-2.24 (m, 1H), 1.99-1.58 (m, 3H), 1.28-1.13 (m, 4H).

Example A. Enzymatic Assay for Inhibition of PARP7

Displacement of Probe A, a biotinylated probe binding to the TIPARP active site, was measured using a time-resolved fluorescence energy transfer (TR-FRET) assay. 20 nL of a dose response curve of each test compound was spotted in black 384-well polystyrene proxiplates (Perkin Elmer) using a Mosquito (TTP Labtech). Reactions were performed in a 8 μL volume by adding 6 μL of TIPARP and Probe A in assay buffer (20 mM HEPES pH=8, 100 mM NaCl, 0.1% bovine serum albumin, 2 mM DTT and 0.002% Tween20), incubating with test compound at 25° C. for 30 min, then adding 2 μL of ULight-anti 6xHis and LANCE Eu-W1024 labeled streptavidin (Perkin Elmer). The final concentrations of TIPARP and Probe A were 6 nM and 2 nM, respectively, The final concentration of ULight-anti 6xHis and LANCE Eu-W1024 labeled streptavidin were 4 nM and 0.25 nM, respectively. Reactions were incubated at 25° C. for an additional 30 min, then read on an Envision platereader equipped with a LANCE/DELFIA top mirror (Perkin Elmer) using excitation of 320 nm and emission of 615 nm and 665 nM with a 90 μs delay. The ratio of the 665/615 nm emission were calculated for each well to determine the amount of complex of TIPARP and Probe A in each well. Control wells containing a negative control of 0.25% DMSO vehicle or a positive control of 100 μM 5-(5-(piperidin-4-yloxy)isoindolin-2-yl)-4-(trifluoromethyl)pyridazin-3(2H)-one were used to calciliate the %0 inhibition as described below:

$$\% \text{ inhibition} = 100 \times \frac{TRF_{cmpd} - TRF_{min}}{TRF_{max} - TRF_{min}}$$

where $TRF_{cmpd}$ is the TR-FRET ratio from the compound treated well, $TRF_{min}$ is the TR-FRET ratio from the 5-(5-(piperidin-4-yloxy)isoindolin-2-yl)-4-(trifluoromethyl)pyridazin-3(2H)-one-treated positive control well and $TRF_{max}$ is the TR-FRET ratio from the DMSO-treated negative control well.

The % inhibition values were plotted as a function of compound concentration and the following 4-parameter fit was applied to derive the $IC_{50}$ values:

$$Y = \text{Bottom} + \frac{(\text{Top} - \text{Bottom})}{\left(1 + \left(\frac{X}{IC_{50}}\right)^{\text{Hill Coefficient}}\right)}$$

where top and bottom are normally allowed to float, but may be fixed at 100 or 0 respectively in a 3-parameter fit. The Hill Coefficient is normally allowed to float but may also be fixed at 1 in a 3-parameter fit. Y is the % inhibition and X is the compound concentration.

Synthesis of Probe A

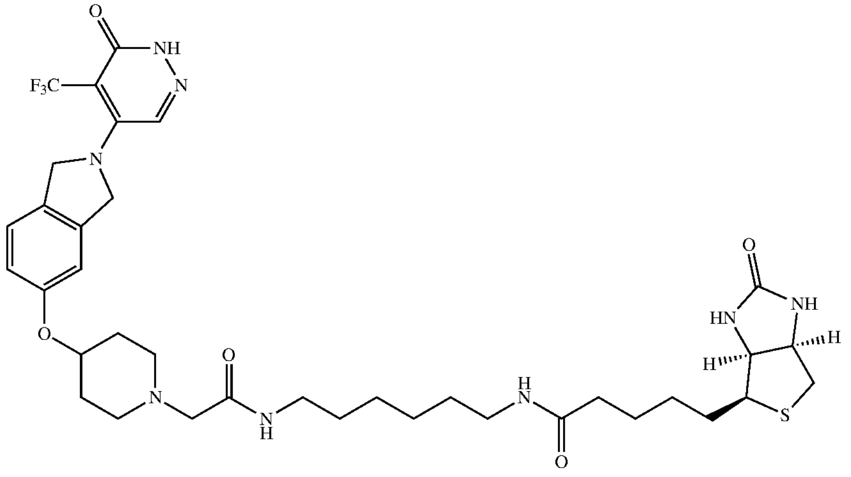 [SMILES: O=C(CCCC[C@@H]1SC[C@@H]2NC(=O)N[C@@H]21)NCCCCCCNC(=O)CN1CCC(Oc2ccc3c(c2)CN(c2cn[nH]c(=O)c2C(F)(F)F)C3)CC1]

Step A

A solution of 5-chloro-4-(trifluoromethyl)-2-[[2-(trimethylsilyl)ethoxy]methyl]-2,3-dihydropyridazin-3-one (2.8 g, 8.52 mmol, 1.00 equiv), 2,3-dihydro-1H-isoindol-5-ol hydrobromide (4.27 g, 19.76 mmol, 1.00 equiv), and TEA (10 mL) in ethanol (40 mL) was stirred for 1 h at 60° C. The resulting solution was extracted with 2×100 mL of ethyl acetate and the organic layers combined and concentrated under reduced pressure to afford 4.5 g of 5-(5-hydroxy-2,3-dihydro-1H-isoindol-2-yl)-4-(trifluoromethyl)-2-[[2-(trimethylsilyl)ethoxy]methyl]-2,3-dihydropyridazin-3-one as a yellow oil. LCMS: $[M+H]^+$ 428.23.

Step B

A solution of 5-(5-hydroxy-2,3-dihydro-1H-isoindol-2-yl)-4-(trifluoromethyl)-2-[[2-(trimethylsilyl)ethoxy]methyl]-2,3-dihydropyridazin-3-one (4.5 g, 10.53 mmol, 1.00 equiv), tert-butyl 4-iodopiperidine-1-carboxylate (20 g, 64.28 mmol, 8.00 equiv), potassium carbonate (15 g, 108.53 mmol, 10.00 equiv), and DMF (50 mL) was stirred for 2 days at 80° C. The resulting solution was extracted with 2×200 mL of ethyl acetate and the organic layers combined and concentrated under reduced pressure. The residue was applied onto a silica gel column eluting with ethyl acetate/petroleum ether to afford tert-butyl 4-([2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]oxy)piperidine-1-carboxylate (2 g, 31%) as a yellow oil. LCMS: $[M+H]^+$ 611.15.

Step C

A solution of tert-butyl 4-([2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]oxy)piperidine-1-carboxylate (2 g, 3.27 mmol, 1.00 equiv), dioxane/HCl (5 mL), and dioxane (45 mL) was stirred for 6 h at 25° C. The resulting mixture was concentrated under reduced pressure. The residue was applied onto a silica gel column and eluted with ethyl acetate/petroleum ether to afford 1 g of 5-[5-(piperidin-4-yloxy)-2,3-dihydro-1H-isoindol-2-yl]-4-(trifluoromethyl)-2-[[2-(trimethylsilyl)ethoxy]methyl]-2,3-dihydropyridazin-3-one as a yellow oil. LCMS: $[M+H]^+$ 511.28.

Step D

A solution of 5-[5-(piperidin-4-yloxy)-2,3-dihydro-1H-isoindol-2-yl]-4-(trifluoromethyl)-2-[[2-(trimethylsilyl)ethoxy]methyl]-2,3-dihydropyridazin-3-one (1 g, 1.96 mmol, 1.00 equiv), tert-butyl 2-chloroacetate (450 mg, 2.99 mmol, 3.00 equiv), DIPEA (5 mL), and dichloromethane (10 mL) was stirred overnight at 25° C. The residue was purified by C18 reverse phase chromatography eluting with $H_2O/CH_3CN$ to afford tert-butyl 2-[4-([2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]oxy)piperidin-1-yl]acetate (540 mg, 44%) as a yellow oil. LCMS: $[M+H]^+$ 625.20.

Step E

A solution of tert-butyl 2-[4-([2-[6-oxo-5-(trifluoromethyl)-1-[[2-(trimethylsilyl)ethoxy]methyl]-1,6-dihydropyridazin-4-yl]-2,3-dihydro-1H-isoindol-5-yl]oxy)piperidin-1-yl]acetate (540 mg, 0.86 mmol, 1.00 equiv) and dioxane/HCl (8 mL) was stirred overnight at 25° C. The resulting mixture was concentrated under reduced pressure. The residue was purified by C18 reverse phase chromatography eluting with $H_2O/CH_3CN$ to afford 200 mg (53%) of 2-[4-([2-[6-oxo-5-(trifluoromethyl)-1,6-dihydropyridazin-4-yl]-2,3-dihydro-1H-isoindol-5-yl]oxy)piperidin-1-yl]hydrochloride as a white solid. LCMS: $[M+H]^+$ 439.31.

Step F

A solution of 5-[(3aS,4S,6aR)-2-oxo-hexahydro-1H-thieno[3,4-d]imidazolidin-4-yl]pentanoic acid (reagent was purchased from Beijing Dragon Rui Trading Company, 976 mg, 3.99 mmol, 1.00 equiv), DIPEA (1.55 g, 11.99 mmol, 3.00 equiv), HATU (1.82 g, 4.79 mmol, 1.20 equiv), tert-butyl N-(6-aminohexyl)carbamate (864 mg, 3.99 mmol, 1.00 equiv) in DMF (15 mL) was stirred overnight at 25° C. The reaction was then quenched by the addition of 50 mL of water. The solids were collected by filtration to afford 1.5 g (85%) of tert-butyl N-(6-[5-[(3aS,4S,6aR)-2-oxo-hexahydro-1H-thieno[3,4-d]imidazolidin-4-yl]pentanamido]hexyl)carbamate as a white solid. LCMS: $[M+H]^+$ 443.26.

Step G

A solution of tert-butyl N-(6-[5-[(3aS,4S,6aR)-2-oxo-hexahydro-1H-thieno[3,4-d]imidazolidin-4-yl]pentanamido]hexyl)carbamate (800 mg, 1.81 mmol, 1.00 equiv) in hydrogen chloride/dioxane (20 mL) was stirred overnight at 25° C. The resulting mixture was concentrated under reduced pressure to afford 600 mg (88%) of 5-[(3aS,4S,6aR)-2-Oxo-hexahydro-1H-thieno[3,4-d]imidazolidin-4-yl]-N-(6-aminohexyl)pentanamide hydrochloride as a gray crude oil. LCMS: $[M+H]^+$ 343.21.

Step H

A solution of 2-[4-([2-[6-oxo-5-(trifluoromethyl)-1,6-dihydropyridazin-4-yl]-2,3-dihydro-1H-isoindol-5-yl]oxy)piperidin-1-yl]hydrochloride (175 mg, 0.40 mmol, 1.00 equiv), DIPEA (258 mg, 2.00 mmol, 5.00 equiv), HATU (228 mg, 0.60 mmol, 1.50 equiv), 5-[(3aS,4S,6aR)-2-oxo-hexahydro-1H-thieno[3,4-d]imidazolidin-4-yl]-N-(6-aminohexyl)pentanamide hydrochloride (228 mg, 0.60 mmol, 1.50 equiv) in DMF (3 mL) was stirred for 4 h at 25° C. The crude product was purified by C18 reverse phase chromatography eluting with $H_2O/CH_3CN$ to afford 5-[(3aS,4S,6aR)-2-oxo-hexahydro-1H-thieno[3,4-d]imidazolidin-4-yl]-N-(6-[2-[4-([2-[6-oxo-5-(trifluoromethyl)-1,6-dihydropyridazin-4-yl]-2,3-dihydro-1H-isoindol-5-yl]oxy)piperidin-1-yl]acetamido]hexyl)pentanamide as a white solid (118.3 mg, 39%). LCMS: $[M+H]^+$ 763.35. $^1H$ NMR (DMSO-$d_6$, 400 MHz) δ: 12.52 (s, 1H), 7.98 (s, 1H), 7.81-7.68 (m, 2H), 7.26 (d, J=8.4 Hz, 1H), 7.00 (d, J=2.2 Hz, 1H), 6.91 (dd, J=8.4, 2.3 Hz, 1H), 6.45-6.39 (m, 1H), 6.36 (s, 1H), 4.91 (d, J=6.1 Hz, 4H), 4.45 (m, 1H), 4.26 (m, 1H), 4.17-4.08 (m, 1H), 3.14-2.96 (m, 5H), 2.91 (s, 2H), 2.82 (dd, J=12.4, 5.1 Hz, 1H), 2.73-2.63 (m, 2H), 2.58 (d, J=12.4 Hz, 1H), 2.33 (ddd, J=11.8, 9.4, 3.1 Hz, 2H), 2.11-1.90 (m, 4H), 1.76-1.54 (m, 3H), 1.57-1.20 (m, 13H).

TABLE A-1

$IC_{50}$ data for the Example compounds is provided below in Table A-1 ("+" is < 0.1 μM; "++" is ≥ 0.1 μM < 1 μM; and "+++" is ≥ 1 μM).
$IC_{50}$ Data for Example Compounds

| Example No. | $IC_{50}$ |
|---|---|
| 1 | + |
| 2 | + |
| 3 | + |
| 4 | + |
| 5 | + |
| 6 | + |
| 7 | + |
| 8 | + |
| 9 | + |
| 10A | ++ |
| 10B | + |
| 11 | + |
| 12 | + |
| 13A | ++ |
| 13B | + |
| 14A | +++ |
| 14B | + |
| 15A | ++ |
| 15B | + |
| 16 | + |
| 17A | ++ |
| 17B | + |
| 18A | ++ |
| 18B | + |
| 19A | ++ |
| 19B | + |
| 20A | + |
| 20B | + |
| 21 | ++ |
| 22A | ++ |
| 22B | + |
| 23 | ++ |
| 24 | + |
| 25 | + |
| 26A | +++ |
| 26B | + |
| 26C | +++ |
| 26D | ++ |
| 27 | + |
| 28 | + |
| 29 | + |
| 30 | + |
| 31A | + |
| 31B | ++ |
| 32 | + |
| 33A | + |
| 33B | + |
| 34A | + |
| 34B | + |
| 35A | +++ |
| 35B | + |
| 36A | + |
| 36B | + |
| 37A | +++ |
| 37B | + |
| 38A | + |
| 38B | + |
| 39A | + |
| 39B | + |
| 40A | + |
| 40B | + |
| 41 | + |
| 42 | + |
| 43 | + |
| 44 | + |
| 45 | + |
| 46A | ++ |
| 46B | + |
| 47A | ++ |
| 47B | + |
| 48A | + |
| 48B | + |
| 49A | ++ |
| 49B | + |
| 50A | ++ |
| 50B | + |
| 51A | ++ |
| 51B | + |
| 52A | ++ |
| 52B | + |
| 53 | + |
| 54 | + |
| 55A | +++ |
| 55B | + |

TABLE A-1-continued $IC_{50}$ data for the Example compounds is provided below in Table A-1 ("+" is < 0.1 μM; "++" is ≥ 0.1 μM < 1 μM; and "+++" is ≥ 1 μM).
$IC_{50}$ Data for Example Compounds

| Example No. | $IC_{50}$ |
|---|---|
| 56A | +++ |
| 56B | + |
| 57 | + |
| 58 | + |
| 59 | + |
| 60 | + |
| 61 | + |
| 62 | + |
| 63 | + |
| 64A | + |
| 64B | + |
| 65 | + |
| 66 | + |
| 67 | + |
| 68 | + |
| 69 | + |

Example B. PARP7 Inhibitors' Affect on Tumor Growth in Human Lung Cancer Models NCI-H1373

FIG. 1 illustrates that PARP7 inhibitors significantly reduce tumor growth in human lung cancer models NCI-H1373. In this study, CB-17 SCID mice were inoculated subcutaneously at the right flank with NCI-H1373 cells for tumor development. Six days after tumor inoculation, 20 mice with tumor size ranging from 105-160 $mm^3$ (average tumor size 132 $mm^3$) were selected and assigned into 2 groups using stratified randomization with 10 mice in each group based upon their tumor volumes. The treatments were started from the next day post randomization (defined randomization day as day 0), and the mice were treated with vehicle (50% Labrasol), the compound of Example 57 (100 mg/kg PO. QD*28 days). The tumor sizes were measured three times per week during the treatment. The entire study was terminated on day 28.

Mean tumor volume and SEM were plotted (FIG. 1). Statistical significance, calculated using two-way ANOVA combined with Bonferroni post-test in which treatment group was compared to vehicle control, is indicated by an asterisk.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method of treating cancer in a patient in need of treatment comprising administering to said patient a therapeutically effective amount of a compound of Formula I:

I

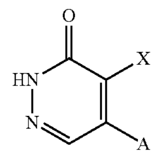

or a pharmaceutically acceptable salt thereof, wherein the cancer is associated with overexpression or increased activity of PARP7, and said cancer is selected from breast cancer, cancer of the central nervous system, endometrium cancer, kidney cancer, large intestine cancer, lung cancer, oesophagus cancer, ovarian cancer, pancreatic cancer, prostate cancer, stomach cancer, head and neck cancer (upper aerodigestive cancer), urinary tract cancer, and colon cancer; and wherein:

X is Cl, Br, F, $CH_3$, $CF_3$, $CF_2H$, CN, $OCH_3$, ethyl, cyclopropyl, $SCH_3$, or isopropyl;

A is a group having a formula that is (A-1):

(A-1)

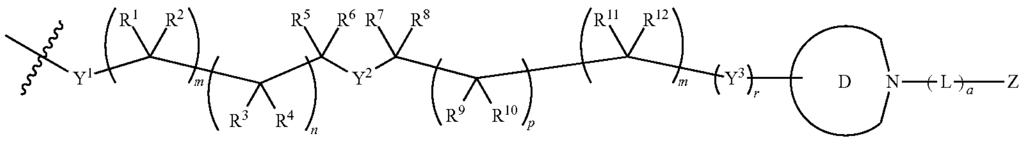

$Y^1$, $Y^2$, and $Y^3$ are each independently selected from —O—, —S—, —$N(R^Y)$—, —C(═O)—, —C(═O)O—, —C(═O)$N(R^Y)$—, —S(═O)—, —$S(═O)_2$—, —S(═O)$N(R^Y)$—, —$S(═O)_2N(R^Y)$— or —$N(R^Y)$C(═O)$N(R^Y)$—, wherein each $R^Y$ is independently H, $C_{1-4}$ alkyl, or $C_{1-4}$ haloalkyl;

L is $C_{1-3}$ alkylene, —O—, —S—, —$N(R^Y)$—, —C(═O)—, —C(═O)O—, —C(═O)$N(R^Y)$—, —S(═O)—, —S(═O)$N(R^Y)$—, or —$N(R^Y)$C(═O)$N(R^Y)$—;

Z is H, $Cy^Z$, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^c)R^b$, $C(=NR^c)NR^cR^d$, $NR^cC(=NR^c)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$, wherein said $C_{1-6}$ alkyl, $C_{2-6}$ alkenyl, $C_{2-6}$ alkynyl, and $C_{1-6}$ haloalkyl of Z are each optionally substituted with 1, 2, 3, 4, or 5 substituents independently selected from $Cy^Z$, halo, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^c)NR^cR^d$, $NR^cC(=NR^c)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$, $Cy^Z$ is selected from $C_{6-10}$ aryl, $C_{3-7}$ cycloalkyl, 5-10 membered heteroaryl, and 4-10 membered heterocycloalkyl, each optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{c1})NR^{c1}R^{d1}$, $NR^{c1}C(=NR^{c1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the alkyl, $C_{2-6}$ alkenyl, and $C_{2-6}$ alkynyl are optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{c1})NR^{c1}R^{d1}$, $NR^{c1}C(=NR^{c1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

Ring D is an azetidine ring or piperidine ring optionally substituted with 1, 2, or 3 groups independently selected from halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{c2})NR^{c2}R^{d2}$, $NR^{c2}C(=NR^{c2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$, wherein the $C_{1-6}$ alkyl, $C_{2-6}$ alkenyl, and $C_{2-6}$ alkynyl are each optionally substituted with 1, 2, or 3 groups independently selected from halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{c2})NR^{c2}R^{d2}$, $NR^{c2}C(=NR^{c2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

$R^1$, $R^2$, $R^3$, $R^4$, $R^5$, $R^6$, $R^7$, $R^8$, $R^9$, $R^{10}$, $R^{11}$, and $R^{12}$ are each independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$,$NR^{c3}S(O)R^{b3}$, $NR^{c3}S(O)_2R^{b3}$, $NR_{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$, wherein said $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of said $R^1$, $R^2$, $R^3$, $R^4$, $R^5$, $R^6$, $R^7$, $R^8$, $R^9$, $R^{10}$, $R^{11}$, and $R^{12}$ are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

or $R^1$ and an $R^Y$ group of $Y^1$, together with the atoms to which they are attached and together with the atoms forming $Y^1$ form a 4-10 membered heterocycloalkyl ring, optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

or $R^7$ and an $R^Y$ group of $Y^3$, together with the atoms to which they are attached and together with the atoms forming $Y^3$ and together with the carbon atoms substituted by $R^9$, $R^{10}$, $R^{11}$, and $R^{12}$, if present, form a 4-10 membered heterocycloalkyl ring, optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$ $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$,$NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$, or $R^1$ and $R^3$ together with the carbon atoms to which they are attached form a $C_{5-10}$ cycloalkyl ring or a 5-10 membered heterocycloalkyl ring, each optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$ $S(O)NR^{c3}R^{d3}$, $S(O)_2R^{b3}$, and $S(O)_2NR^{c3}R^{d3}$, or $R^3$ and $R^5$ together with the carbon atoms to which they are attached form a $C_{5-10}$ cycloalkyl ring or a 5-10 membered heterocycloalkyl ring, each optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$,$NR^{c3}C(O)R^{b3}$, $NR^{c3}C(O)OR^{a3}$, $NR^{c3}C(O)NR^{c3}R^{d3}$, $C(=NR^{e3})$ $R^{b3}$, $C(=NR^{e3})NR^{c3}R^{d3}$ $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

or $R^7$ and $R^9$ together with the carbon atoms to which they are attached form a $C_{5-10}$ cycloalkyl ring or a 5-10 membered heterocycloalkyl ring, each optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

or $R^9$ and $R^{11}$ together with the carbon atoms to which they are attached form a $C_{5-10}$ cycloalkyl ring or a 5-10 membered heterocycloalkyl ring, each optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

or $R^5$ and $R^7$ together with the carbon atoms to which they are attached and together with $Y^2$ form a 5-10 membered heterocycloalkyl ring optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$, or $R^1$ and $R^3$ together form a double bond between the carbon atoms to which they are attached;

or $R^3$ and $R^5$ together form a double bond between the carbon atoms to which they are attached;

or $R^7$ and $R^9$ together form a double bond between the carbon atoms to which they are attached;

or $R^9$ and $R^{11}$ together form a double bond between the carbon atoms to which they are attached;

or $R^9$, $R^{10}$, $R^{11}$, and $R^{12}$ together form a triple bond between the carbon atoms to which they are attached;

each $R^a$, $R^b$, $R^c$, $R^d$, $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of said $R^a$, $R^b$, $R^c$, $R^d$, $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, and $R^{d3}$ is optionally substituted with 1, 2, or 3 substituents independently selected from halo, $C_{1-4}$ alkyl, $C_{1-4}$ haloalkyl, $C_{2-6}$ alkenyl, $C_{2-6}$ alkynyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c3}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$, or $R^c$ and $R^d$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c3}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$, or $R^{c1}$ and $R^{d2}$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c3}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$, or $R^{c2}$ and $R^{d2}$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c3}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$, or $R^{c3}$ and $R^{d3}$ together with the N atom to which they are attached form a 4-7 membered heterocycloalkyl group optionally substituted with 1, 2, or 3 substituents independently selected from CN, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c3}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$;

$R^{a7}$, $R^{b7}$, $R^{c7}$, and $R^{d7}$ are independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl are each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

each $R^e$, $R^{e1}$, $R^{e2}$, $R^{e3}$, and $R^{e7}$ is independently selected from H, $C_{1-4}$ alkyl, and CN;

a is 0 or 1;

m is 0 or 1;

n is 0 or 1;

p is 0 or 1;

q is 0 or 1;

r is 0 or 1;

wherein any aforementioned heteroaryl or heterocycloalkyl group comprises 1, 2, 3, or 4 ring-forming heteroatoms independently selected from O, N, and S; and wherein one or more ring-forming C or N atoms of any aforementioned heterocycloalkyl group is optionally substituted by 1 or 2 oxo (=O) groups.

2. The method of claim 1 wherein said cancer is lung cancer.

3. The method of claim 1, wherein X is $CF_3$, Br, or Cl.

4. The method of claim 1, wherein $Y^1$ is —N($R^Y$)—.

5. The method of claim 1, wherein $Y^1$ is —O—.

6. The method of claim 1, wherein $Y^2$ is —O—, —N($R^Y$)—, or —C(=O)N($R^Y$)—.

7. The method of claim 1, wherein $Y^3$ is —C(=O)N($R^Y$)—.

8. The method of claim 1, wherein $R^1$, $R^2$, $R^5$, $R^6$, $R^7$, and $R^8$ are each independently selected from H, halo, $C_{1-6}$ alkyl, and $C_{1-6}$ haloalkyl, wherein said $C_{1-6}$ alkyl is optionally substituted with 1 or 2 substituents independently selected from CN, $NO_2$, $OR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $S(O)_2R^{b3}$, and $S(O)_2NR^{c3}R^{d3}$.

9. The method of claim 1, wherein $R^1$ is H or $C_{1-6}$ alkyl; wherein said $C_{1-6}$ alkyl is optionally substituted with $OR^{a3}$, $NR^{c3}R^{d3}$, and $NR^{c3}C(O)R^{b3}$.

10. The method of claim 1, wherein $R^1$ is H, methyl, methoxymethyl, $CH_2OH$, $CH(OH)CH_3$, $CH_2NHCH_2CF_3$ or $CH_2NHC(O)CH_3$.

11. The method of claim 1, wherein $R^1$ and an $R^Y$ group of $Y^1$, together with the atoms to which they are attached and together with the atoms forming $Y^1$ form a 4-10 membered heterocycloalkyl ring optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$.

12. The method of claim 1, wherein $R^1$ and an $R^Y$ group of $Y^1$, together with the atoms to which they are attached and together with the atoms forming $Y^1$ form an azetidine ring.

13. The method of claim 1, wherein $R^2$ is H.

14. The method of claim 1, wherein $R^5$ is H or $C_{1-6}$ alkyl.

15. The method of claim 1, wherein $R^6$ is H.

16. The method of claim 1, wherein $R^7$ is H or $C_{1-6}$ alkyl.

17. The method of claim 1, wherein $R^8$ is H.

18. The method of claim 1, wherein $R^Y$ of $Y^1$ is H.

19. The method of claim 1, wherein $R^Y$ of $Y^2$ is H or $C_{1-4}$ alkyl.

20. The method of claim 1, wherein $R^Y$ of $Y^3$ is H or $C_{1-4}$ alkyl.

21. The method of claim 1, wherein $R^7$ and an $R^Y$ group of $Y^3$, together with the atoms to which they are attached and together with the atoms forming $Y^3$ and together with the carbon atoms substituted by $R^9$, $R^{10}$, $R^{11}$, and $R^{12}$, if present, form an oxopyrrolidine ring.

22. The method of claim 1, wherein $R^7$ and an $R^Y$ group of $Y^3$, together with the atoms to which they are attached and together with the atoms forming $Y^3$ and together with the carbon atoms subtsituted by $R^9$, $R^{10}$, $R^{11}$, and $R^{12}$, if present, form an oxopiperidine ring.

23. The method of claim 1, wherein Ring D is an azetidine ring or piperidine ring optionally substituted with $OR^{a2}$.

24. The method of claim 1, wherein Ring D is a piperidine ring optionally substituted with 1 or 2 subsitutents independently selected from OH, F, $C(O)NH_2$, or CN.

25. The method of claim 1, wherein Z is $Cy^Z$.

26. The method of claim 1, wherein $Cy^Z$ is a 5-6 membered heteroaryl group optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$ $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the alkyl, $C_{2-6}$ alkenyl, and $C_{2-6}$ alkynyl are optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$ $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

27. The method of claim 1, wherein $Cy^Z$ is a 5 or 6-membered heteroaryl group substituted with halo, CN, methyl, or $C_{1-3}$ haloalkyl.

28. The method of claim 1, wherein $Cy^Z$ is a pyrimidinyl, pyrazinyl, pyridinyl, or thiazolyl group substituted with halo, CN or $C_{1-3}$ haloalkyl.

29. The method of claim 1, wherein $Cy^Z$ is selected from 5-(trifluoromethyl)pyrimidin-2-yl, 5-(trifluoromethyl)thiazol-2-yl, 5-(trifluoromethyl)pyrazin-2-yl, 5-(difluoromethyl)pyrimidin-2-yl, 5-(difluoromethyl)pyrazin-2-yl, 5-fluoropyrimidin-2-yl, 5-chloropyrimidin-2-yl, 5-chloropyrazin-2-yl, 5-bromopyrimidin-2-yl, 5-cyanopyridin-2-yl, 5-cyanothiazol-2-yl, 5-cyanopyrazin-2-yl, 5-methylpyrimidin-2-yl.

30. The method of claim 1, wherein $Cy^Z$ is 5-(trifluoromethyl)pyrimidin-2-yl.

31. The method of claim 1, wherein a is 0.

32. The method of claim 1, wherein X is $CF_3$, $Y^1$ is $-N(R^Y)-$, $Y^2$ is $-O-$, $Y^3$ is $-C(=O)N(R^Y)-$, $R^1$ is methyl, $R^2$ is H, $R^5$ is H, $R^6$ is H, $R^7$ is $CH_3$, $R^8$ is H, Ring D is piperidine substituted with OH, and Z is $Cy^Z$, wherein $Cy^Z$ is pyrimidinyl substituted with $CF_3$.

33. The method of claim 1, wherein the compound has Formula IIa:

IIa

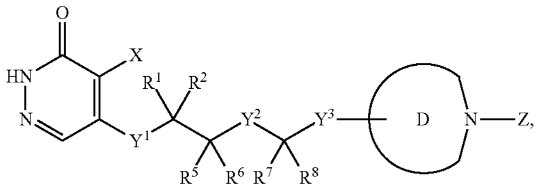

or a pharmaceutically acceptable salt thereof.

34. The method of claim 1, wherein the compound has Formula IIb:

IIb

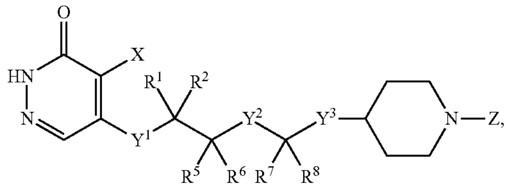

or a pharmaceutically acceptable salt thereof.

35. The method of claim 1, wherein the compound has Formula IIc:

IIc

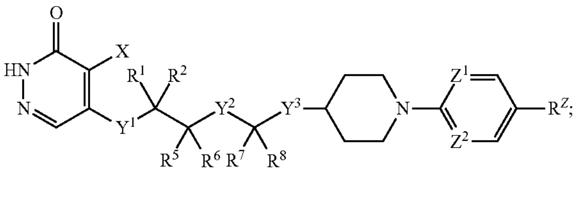

or a pharmaceutically acceptable salt thereof, wherein $Z^1$ and $Z^2$ are each independently selected from N and CH, and wherein $R^Z$ is halo, CN or $C_{1-3}$ haloalkyl.

36. The method of claim 1, wherein the compound has Formula IId:

IId

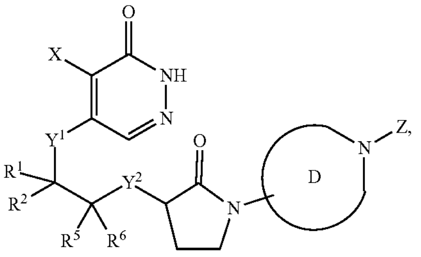

or a pharmaceutically acceptable salt thereof.

37. The method of claim 1, wherein the compound has Formula IIe:

IIe

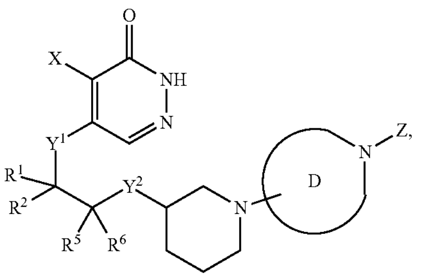

or a pharmaceutically acceptable salt thereof.

38. The method of claim 1, wherein:

X is Cl, Br, or $CF_3$;

A is a group having a formula that is (A-1a):

(A-1a)

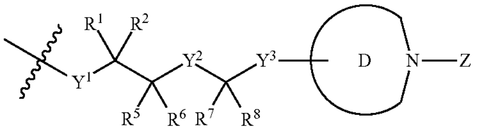

$Y^1$, $Y^2$, and $Y^3$ are each independently selected from —O—, —N($R^Y$)—, —C(=O)—, and —C(=O)N($R^Y$)—, wherein each $R^Y$ is independently H or $C_{1-4}$ alkyl;

Z is $Cy^Z$;

$Cy^Z$ is selected from 5-10 membered heteroaryl optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the alkyl, $C_{2-6}$ alkenyl, and $C_{2-6}$ alkynyl are optionally substituted with 1, 2, or 3 substituents independently selected from halo, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

Ring D is an azetidine ring or piperidine ring optionally substituted with 1, 2, or 3 groups independently selected from halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$, wherein the $C_{1-6}$ alkyl, $C_{2-6}$ alkenyl, and $C_{2-6}$ alkynyl are each optionally substituted with 1, 2, or 3 groups independently selected from halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

$R^1$, $R^2$, $R^5$, $R^6$, $R^7$, and $R^8$ are each independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of said $R^1$, $R^2$, $R^5$, $R^6$, $R^7$, and $R^8$ are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})$ $R^{b3}$, $C(=NR^{e3})NR^{c3}R^{d3}$,$NR^{c3}C(=NR^{e3})$ $NR^{c3}R^{d3}$, $NR^{c3}S(O)R^{b3}$, $NR^{c3}S(O)_2R^{b3}$, $NR^{c3}S(O)_2NR^{c3}R^{d3}$ $S(O)R^{b3}$, $S(O)NR^{c3}R^{d3}$, $S(O)_2R^{b3}$, and $S(O)_2NR^{c3}R^{d3}$, or $R^1$ and an $R^Y$ group of $Y^1$, together with the atoms to which they are attached and together with the atoms forming $Y^1$ form a 4-10 membered heterocycloalkyl ring, optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})$ $NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$, or $R^7$ and an $R^Y$ group of $Y^3$, together with the atoms to which they are attached and together with the atoms forming $Y^3$ form a 4-10 membered heterocycloalkyl ring, optionally substituted with 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

each $R^a$, $R^b$, $R^c$, $R^d$, $R^{a1}$, $R^{b1}$, $R^{e1}$, $R^{d1}$, $R^{a2}$, $R^{b2}$, $R^{e2}$, $R^{d2}$, $R^{a3}$, $R^{b3}$, $R^{e3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of said $R^a$, $R^b$, $R^c$, $R^d$, $R^{a1}$, $R^{b1}$, $R^{e1}$, $R^{d1}$, $R^{a2}$, $R^{b2}$, $R^{e2}$, $R^{d2}$, $R^{a3}$, $R^{b3}$, $R^{c3}$, and $R^{d3}$ is optionally substituted with 1, 2, or 3 substituents independently selected from halo, $C_{1-4}$ alkyl, $C_{1-4}$ haloalkyl, $C_{2-6}$ alkenyl, $C_{2-6}$ alkynyl, CN, $OR^{a7}$, $SR^{a7}$, $C(O)R^{b7}$, $C(O)NR^{c7}R^{d7}$, $C(O)OR^{a7}$, $OC(O)R^{b7}$, $OC(O)NR^{c7}R^{d7}$, $NR^{c7}R^{d7}$, $NR^{c7}C(O)R^{b7}$, $NR^{c7}C(O)NR^{c7}R^{d7}$, $NR^{c7}C(O)OR^{a7}$, $C(=NR^{e7})NR^{c7}R^{d7}$, $NR^{c7}C(=NR^{e7})NR^{c3}R^{d7}$, $S(O)R^{b7}$, $S(O)NR^{c7}R^{d7}$, $S(O)_2R^{b7}$, $NR^{c7}S(O)_2R^{b7}$, $NR^{c7}S(O)_2NR^{c7}R^{d7}$, and $S(O)_2NR^{c7}R^{d7}$, $R^{a7}$, $R^{b7}$, $R^{c7}$, and $R^{d7}$ are independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl are each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy; and each $R^e$, $R^{e1}$, $R^{e2}$, $R^{e3}$, and $R^{e7}$ is independently selected from H, $C_{1-4}$ alkyl, and CN;

wherein any aforementioned heteroaryl or heterocycloalkyl group comprises 1, 2, 3, or 4 ring-forming heteroatoms independently selected from O, N, and S; and wherein one or more ring-forming C or N atoms of any aforementioned heterocycloalkyl group is optionally substituted by 1 or 2 oxo (=O) groups.

39. The method of claim 1, wherein the compound is selected from:

(S)-2-(2-(6-oxo-5-(trifluoromethyl)-1,6-dihydropyridazin-4-ylamino)propoxy)-N-(1-(5-(trifluoromethyl)pyrimidin-2-yl)piperidin-4-yl)acetamide;

(S)—N-methyl-2-(2-(6-oxo-5-(trifluoromethyl)-1,6-dihydropyridazin-4-ylamino)propoxy)-N-(1-(5-(trifluoromethyl)pyrimidin-2-yl)piperidin-4-yl)acetamide;

(S)—N-methyl-2-(2-((6-oxo-5-(trifluoromethyl)-1,6-dihydropyridazin-4-yl)amino)propoxy)-N-(1-(5-(trifluoromethyl)thiazol-2-yl)piperidin-4-yl)acetamide;

(S)—N-methyl-2-(2-(6-oxo-5-(trifluoromethyl)-1,6-dihydropyridazin-4-ylamino)propoxy)-N-(1-(5-(trifluoromethyl)pyrazin-2-yl)piperidin-4-yl)acetamide;

((S)—N-methyl-2-(2-(6-oxo-5-(trifluoromethyl)-1,6-dihydropyridazin-4-ylamino)propoxy)-N-(1-(5-(trifluoromethyl)pyrimidin-2-yl)azetidin-3-yl)acetamide;

(S)—N-(1-(5-cyanopyridin-2-yl)piperidin-4-yl)-N-methyl-2-(2-((6-oxo-5-(trifluoromethyl)-1,6-dihydropyridazin-4-yl)amino)propoxy)acetamide;

(S)—N-ethyl-2-(2-((6-oxo-5-(trifluoromethyl)-1,6-dihydropyridazin-4-yl)amino)propoxy)-N-(1-(5-(trifluoromethyl)pyrimidin-2-yl)piperidin-4-yl)acetamide;

(S)—N-methyl-2-((1-(6-oxo-5-(trifluoromethyl)-1,6-dihydropyridazin-4-yl)azetidin-2-yl)methoxy)-N-(1-(5-(trifluoromethyl)pyrimidin-2-yl)piperidin-4-yl)acetamide;

(S)-2-(3-methoxy-2-((6-oxo-5-(trifluoromethyl)-1,6-dihydropyridazin-4-yl)amino)propoxy)-N-methyl-N-(1-(5-(trifluoromethyl)pyrimidin-2-yl)piperidin-4-yl)acetamide;

5-((S)-1-((S)-1-(1-(5-(trifluoromethyl)pyrimidin-2-yl)piperidin-4-yl)-2-oxopyrrolidin-3-yloxy)propan-2-ylamino)-4-(trifluoromethyl)pyridazin-3(2H)-one;

5-((S)-1-((R)-1-(1-(5-(trifluoromethyl)pyrimidin-2-yl)piperidin-4-yl)-2-oxopyrrolidin-3-yloxy)propan-2-ylamino)-4-(trifluoromethyl)pyridazin-3(2H)-one;

4-chloro-5-((S)-1-(2-oxo-1-(1-(5-(trifluoromethyl)pyrimidin-2-yl)piperidin-4-yl)pyrrolidin-3-yloxy)propan-2-ylamino)pyridazin-3(2H)-one;

4-bromo-5-(((2S)-1-((2-oxo-1-(1-(5-(trifluoromethyl)pyrazin-2-yl)piperidin-4-yl)pyrrolidin-3-yl)oxy)propan-2-yl)amino)pyridazin-3(2H)-one;

5-(((S)-1-(((S)-2-oxo-1-(1-(5-(trifluoromethyl)pyrazin-2-yl)piperidin-4-yl)pyrrolidin-3-yl)oxy)propan-2-yl)amino)-4-(trifluoromethyl)pyridazin-3(2H)-one;

5-(((S)-1-(((R)-2-oxo-1-(1-(5-(trifluoromethyl)pyrazin-2-yl)piperidin-4-yl)pyrrolidin-3-yl)oxy)propan-2-yl)amino)-4-(trifluoromethyl)pyridazin-3(2H)-one;

6-(4-((R)-2-oxo-3-((S)-2-((6-oxo-5-(trifluoromethyl)-1,6-dihydropyridazin-4-yl)amino)propoxy)pyrrolidin-1-yl)piperidin-1-yl)nicotinonitrile;

6-(4-((S)-2-oxo-3-((S)-2-((6-oxo-5-(trifluoromethyl)-1,6-dihydropyridazin-4-yl)amino)propoxy)pyrrolidin-1-yl)piperidin-1-yl)nicotinonitrile;

5-(((S)-1-(((S)-1-(1-(5-(difluoromethyl)pyrimidin-2-yl)piperidin-4-yl)-2-oxopyrrolidin-3-yl)oxy)propan-2-yl)amino)-4-(trifluoromethyl)pyridazin-3(2H)-one;

5-(((S)-1-(((R)-1-(1-(5-(difluoromethyl)pyrimidin-2-yl)piperidin-4-yl)-2-oxopyrrolidin-3-yl)oxy)propan-2-yl)amino)-4-(trifluoromethyl)pyridazin-3(2H)-one;

5-(((S)-1-(((R)-1-(1-(5-chloropyrimidin-2-yl)piperidin-4-yl)-2-oxopyrrolidin-3-yl)oxy)propan-2-yl)amino)-4-(trifluoromethyl)pyridazin-3(2H)-one;

6-(4-((S)-3-((S)-3-methoxy-2-((6-oxo-5-(trifluoromethyl)-1,6-dihydropyridazin-4-yl)amino)propoxy)-2-oxopyrrolidin-1-yl)piperidin-1-yl)nicotinonitrile;

6-(4-((R)-3-((S)-3-methoxy-2-((6-oxo-5-(trifluoromethyl)-1,6-dihydropyridazin-4-yl)amino)propoxy)-2-oxopyrrolidin-1-yl)piperidin-1-yl)nicotinonitrile;

5-(((S)-1-methoxy-3-(((S)-2-oxo-1-(1-(5-(trifluoromethyl)pyrazin-2-yl)piperidin-4-yl)pyrrolidin-3-yl)oxy)propan-2-yl)amino)-4-(trifluoromethyl)pyridazin-3(2H)-one;

(S)—N-methyl-2-(2-(6-oxo-5-(trifluoromethyl)-1,6-dihydropyridazin-4-ylamino)propoxy)-N-(1-(5-(trifluoromethyl)pyrazin-2-yl)piperidin-4-yl)acetamide;

5-(((S)-1-methoxy-3-(((S)-2-oxo-1-(1-(5-(trifluoromethyl)pyrimidin-2-yl)piperidin-4-yl)pyrrolidin-3-yl)oxy)propan-2-yl)amino)-4-(trifluoromethyl)pyridazin-3(2H)-one;

5-(((S)-1-methoxy-3-(((R)-2-oxo-1-(1-(5-(trifluoromethyl)pyrimidin-2-yl)piperidin-4-yl)pyrrolidin-3-yl)oxy)propan-2-yl)amino)-4-(trifluoromethyl)pyridazin-3(2H)-one;

5-(((S)-1-(((S)-2-oxo-1-(1-(5-(trifluoromethyl)pyrimidin-2-yl)piperidin-4-yl)pyrrolidin-3-yl)oxy)propan-2-yl)oxy)-4-(trifluoromethyl)pyridazin-3(2H)-one;

5-(((S)-1-(((R)-2-oxo-1-(1-(5-(trifluoromethyl)pyrimidin-2-yl)piperidin-4-yl)pyrrolidin-3-yl)oxy)propan-2-yl)oxy)-4-(trifluoromethyl)pyridazin-3(2H)-one;

4-(trifluoromethyl)-5-(((2S)-1-((1-(1-(5-(trifluoromethyl)pyrimidin-2-yl)piperidin-4-yl)pyrrolidin-3-yl)oxy)propan-2-yl)amino)pyridazin-3(2H)-one;

5-(((S)-1-(((S)-1-(1-(5-(difluoromethyl)pyrazin-2-yl)piperidin-4-yl)-2-oxopyrrolidin-3-yl)oxy)propan-2-yl)amino)-4-(trifluoromethyl)pyridazin-3(2H)-one;

5-(((S)-1-(((R)-1-(1-(5-(difluoromethyl)pyrazin-2-yl)piperidin-4-yl)-2-oxopyrrolidin-3-yl)oxy)propan-2-yl)amino)-4-(trifluoromethyl)pyridazin-3(2H)-one;

4-bromo-5-(((S)-1-(((S)-2-oxo-1-(1-(5-(trifluoromethyl)pyrimidin-2-yl)piperidin-4-yl)pyrrolidin-3-yl)oxy)propan-2-yl)oxy)pyridazin-3(2H)-one;

5-(((S)-1-(((R)-1-(1-(5-bromopyrimidin-2-yl)piperidin-4-yl)-2-oxopyrrolidin-3-yl)oxy)propan-2-yl)amino)-4-(trifluoromethyl)pyridazin-3(2H)-one;

(S)—N-methyl-2-(2-((6-oxo-5-(trifluoromethyl)-1,6-dihydropyridazin-4-yl)oxy)propoxy)-N-(1-(5-(trifluoromethyl)pyrimidin-2-yl)piperidin-4-yl)acetamide;

5-(((S)-1-(((S)-2-oxo-1-(1-(5-(trifluoromethyl)pyrimidin-2-yl)piperidin-4-yl)pyrrolidin-3-yl)amino)propan-2-yl)amino)-4-(trifluoromethyl)pyridazin-3(2H)-one;

5-(((S)-1-(((R)-2-oxo-1-(1-(5-(trifluoromethyl)pyrimidin-2-yl)piperidin-4-yl)pyrrolidin-3-yl)amino)propan-2-yl)amino)-4-(trifluoromethyl)pyridazin-3(2H)-one;

5-(((R)-1-(((S)-2-oxo-1-(1-(5-(trifluoromethyl)pyrimidin-2-yl)piperidin-4-yl)pyrrolidin-3-yl)amino)propan-2-yl)amino)-4-(trifluoromethyl)pyridazin-3(2H)-one;

5-(((R)-1-(((R)-2-oxo-1-(1-(5-(trifluoromethyl)pyrimidin-2-yl)piperidin-4-yl)pyrrolidin-3-yl)amino)propan-2-yl)amino)-4-(trifluoromethyl)pyridazin-3(2H)-one;

5-(((2S)-1-((1-(1-(5-(difluoromethyl)pyrimidin-2-yl)piperidin-4-yl)-2-oxopyrrolidin-3-yl)oxy)propan-2-yl)oxy)-4-(trifluoromethyl)pyridazin-3(2H)-one;

(S)-2-(2-((5-bromo-6-oxo-1,6-dihydropyridazin-4-yl)oxy)propoxy)-N-methyl-N-(1-(5-(trifluoromethyl)pyrimidin-2-yl)piperidin-4-yl)acetamide;

5-(((2S)-1-(methyl (2-oxo-1-(1-(5-(trifluoromethyl)pyrimidin-2-yl)piperidin-4-yl)pyrrolidin-3-yl)amino)propan-2-yl)amino)-4-(trifluoromethyl)pyridazin-3(2H)-one;

6-(4-(2-oxo-3-((S)-2-((6-oxo-5-(trifluoromethyl)-1,6-dihydropyridazin-4-yl)oxy)propoxy)pyrrolidin-1-yl)piperidin-1-yl)nicotinonitrile;

5-(((S)-1-(((S)-2-oxo-1-(1-(5-(trifluoromethyl)pyrazin-2-yl)piperidin-4-yl)pyrrolidin-3-yl)oxy)propan-2-yl)oxy)-4-(trifluoromethyl)pyridazin-3(2H)-one;

5-(((S)-1-(((R)-2-oxo-1-(1-(5-(trifluoromethyl)pyrazin-2-yl)piperidin-4-yl)pyrrolidin-3-yl)oxy)propan-2-yl)oxy)-4-(trifluoromethyl)pyridazin-3(2H)-one;

4-bromo-5-(((S)-1-(((R)-2-oxo-1-(1-(5-(trifluoromethyl)pyrimidin-2-yl)piperidin-4-yl)pyrrolidin-3-yl)oxy)propan-2-yl)amino)pyridazin-3(2H)-one;

N-((3R,4R)-3-hydroxy-1-(5-(trifluoromethyl)pyrimidin-2-yl)piperidin-4-yl)-2-((S)-2-((6-oxo-5-(trifluoromethyl)-1,6-dihydropyridazin-4-yl)amino)propoxy)acetamide; and N-((3S,4S)-3-hydroxy-1-(5-(trifluoromethyl)pyrimidin-2-yl)piperidin-4-yl)-2-((S)-2-((6-oxo-5-(trifluoromethyl)-1,6-dihydropyridazin-4-yl)amino)propoxy)acetamide;

or a pharmaceutically acceptable salt of any of the aforementioned.

40. The method of claim 1, wherein the compound is selected from:

(S)-3-((S)-2-((6-oxo-5-(trifluoromethyl)-1,6-dihydropyridazin-4-yl)amino)propoxy)-1'-(5-(trifluoromethyl)pyrimidin-2-yl)-[1,4'-bipiperidin]-2-one;

(R)-3-((S)-2-((6-oxo-5-(trifluoromethyl)-1,6-dihydropyridazin-4-yl)amino)propoxy)-1'-(5-(trifluoromethyl)pyrimidin-2-yl)-[1,4'-bipiperidin]-2-one;

5-(((S)-1-(((S)-4,4-dimethyl-2-oxo-1-(1-(5-(trifluoromethyl)pyrimidin-2-yl)piperidin-4-yl)pyrrolidin-3-yl)oxy)propan-2-yl)amino)-4-(trifluoromethyl)pyridazin-3(2H)-one;

5-(((S)-1-(((R)-4,4-dimethyl-2-oxo-1-(1-(5-(trifluoromethyl)pyrimidin-2-yl)piperidin-4-yl)pyrrolidin-3-yl)oxy)propan-2-yl)amino)-4-(trifluoromethyl)pyridazin-3(2H)-one;

(R)-6-(4-(2-oxo-3-(2-((6-oxo-5-(trifluoromethyl)-1,6-dihydropyridazin-4-yl)amino) ethoxy)pyrrolidin-1-yl)piperidin-1-yl)nicotinonitrile;

(S)-6-(4-(2-oxo-3-(2-((6-oxo-5-(trifluoromethyl)-1,6-dihydropyridazin-4-yl)amino) ethoxy)pyrrolidin-1-yl)piperidin-1-yl)nicotinonitrile;

5-(((S)-1-(((3S,4R)-4-methyl-2-oxo-1-(1-(5-(trifluoromethyl)pyrimidin-2-yl)piperidin-4-yl)pyrrolidin-3-yl)oxy)propan-2-yl)amino)-4-(trifluoromethyl)pyridazin-3(2H)-one;

5-(((S)-1-(((3R,4S)-4-methyl-2-oxo-1-(1-(5-(trifluoromethyl)pyrimidin-2-yl)piperidin-4-yl)pyrrolidin-3-yl)oxy)propan-2-yl)amino)-4-(trifluoromethyl)pyridazin-3(2H)-one;

5-(((S)-1-(((R)-1-((3R,4R)-3-fluoro-1-(5-(trifluoromethyl)pyrimidin-2-yl)piperidin-4-yl)-2-oxopyrrolidin-3-yl)oxy)propan-2-yl)amino)-4-(trifluoromethyl)pyridazin-3(2H)-one;

5-(((S)-1-(((R)-1-((3S,4S)-3-fluoro-1-(5-(trifluoromethyl)pyrimidin-2-yl)piperidin-4-yl)-2-oxopyrrolidin-3-yl)oxy)propan-2-yl)amino)-4-(trifluoromethyl)pyridazin-3(2H)-one;

5-(((S)-1-(((R)-1-((3S,4R)-3-fluoro-1-(5-(trifluoromethyl)pyrimidin-2-yl)piperidin-4-yl)-2-oxopyrrolidin-3-yl)oxy)propan-2-yl)amino)-4-(trifluoromethyl)pyridazin-3(2H)-one;

5-(((S)-1-(((R)-1-((3R,4S)-3-fluoro-1-(5-(trifluoromethyl)pyrimidin-2-yl)piperidin-4-yl)-2-oxopyrrolidin-3-yl)oxy)propan-2-yl)amino)-4-(trifluoromethyl)pyridazin-3(2H)-one;

6-((R)-3,3-difluoro-4-((R)-2-oxo-3-((S)-2-((6-oxo-5-(trifluoromethyl)-1,6-dihydropyridazin-4-yl)amino)propoxy)pyrrolidin-1-yl)piperidin-1-yl)nicotinonitrile;

6-((S)-3,3-difluoro-4-((R)-2-oxo-3-((S)-2-((6-oxo-5-(trifluoromethyl)-1,6-dihydropyridazin-4-yl)amino)propoxy)pyrrolidin-1-yl)piperidin-1-yl)nicotinonitrile;

5-(((S)-1-(((R)-1-(1-(5-chloropyrazin-2-yl)piperidin-4-yl)-2-oxopyrrolidin-3-yl)oxy)propan-2-yl)amino)-4-(trifluoromethyl)pyridazin-3(2H)-one;

5-(((S)-1-(((R)-1-(1-(5-fluoropyrimidin-2-yl)piperidin-4-yl)-2-oxopyrrolidin-3-yl)oxy)propan-2-yl)amino)-4-(trifluoromethyl)pyridazin-3(2H)-one;

5-(((S)-1-(((R)-1-(1-(5-methylpyrimidin-2-yl)piperidin-4-yl)-2-oxopyrrolidin-3-yl)oxy)propan-2-yl)amino)-4-(trifluoromethyl)pyridazin-3(2H)-one;

5-(4-((R)-2-oxo-3-((S)-2-((6-oxo-5-(trifluoromethyl)-1,6-dihydropyridazin-4-yl)amino)propoxy)pyrrolidin-1-yl)piperidin-1-yl)pyrazine-2-carbonitrile;

4-bromo-5-(((S)-1-(((S)-2-oxo-1-(1-(5-(trifluoromethyl)pyrazin-2-yl)piperidin-4-yl)pyrrolidin-3-yl)oxy)propan-2-yl)oxy)pyridazin-3(2H)-one;

4-bromo-5-(((S)-1-(((R)-2-oxo-1-(1-(5-(trifluoromethyl)pyrazin-2-yl)piperidin-4-yl)pyrrolidin-3-yl)oxy)propan-2-yl)oxy)pyridazin-3(2H)-one;

4-chloro-5-(((S)-1-(((S)-2-oxo-1-(1-(5-(trifluoromethyl)pyrimidin-2-yl)piperidin-4-yl)pyrrolidin-3-yl)oxy)propan-2-yl)oxy)pyridazin-3(2H)-one;

4-chloro-5-(((S)-1-(((R)-2-oxo-1-(1-(5-(trifluoromethyl)pyrimidin-2-yl)piperidin-4-yl)pyrrolidin-3-yl)oxy)propan-2-yl)oxy)pyridazin-3(2H)-one;

6-(4-((R)-3-((S)-2-((5-bromo-6-oxo-1,6-dihydropyridazin-4-yl)oxy)propoxy)-2-oxopyrrolidin-1-yl)piperidin-1-yl)nicotinonitrile;

6-(4-((S)-3-((S)-2-((5-bromo-6-oxo-1,6-dihydropyridazin-4-yl)oxy)propoxy)-2-oxopyrrolidin-1-yl)piperidin-1-yl)nicotinonitrile;

5-(((S)-1-(((S)-1-(1-(5-methylpyrimidin-2-yl)piperidin-4-yl)-2-oxopyrrolidin-3-yl)oxy)propan-2-yl)oxy)-4-(trifluoromethyl)pyridazin-3(2H)-one;

5-(((S)-1-(((R)-1-(1-(5-methylpyrimidin-2-yl)piperidin-4-yl)-2-oxopyrrolidin-3-yl)oxy)propan-2-yl)oxy)-4-(trifluoromethyl)pyridazin-3(2H)-one;

6-(4-((S)-3-((S)-3-methoxy-2-((6-oxo-5-(trifluoromethyl)-1,6-dihydropyridazin-4-yl)oxy)propoxy)-2-oxopyrrolidin-1-yl)piperidin-1-yl)nicotinonitrile;

6-(4-((R)-3-((S)-3-methoxy-2-((6-oxo-5-(trifluoromethyl)-1,6-dihydropyridazin-4-yl)oxy)propoxy)-2-oxopyrrolidin-1-yl)piperidin-1-yl)nicotinonitrile;

5-(((S)-1-methoxy-3-(((S)-2-oxo-1-(1-(5-(trifluoromethyl)pyrimidin-2-yl)piperidin-4-yl)pyrrolidin-3-yl)oxy)propan-2-yl)oxy)-4-(trifluoromethyl)pyridazin-3(2H)-one;

5-(((S)-1-methoxy-3-(((R)-2-oxo-1-(1-(5-(trifluoromethyl)pyrimidin-2-yl)piperidin-4-yl)pyrrolidin-3-yl)oxy)propan-2-yl)oxy)-4-(trifluoromethyl)pyridazin-3(2H)-one;

5-(((S)-1-methoxy-3-(((S)-1-(1-(5-methylpyrimidin-2-yl)piperidin-4-yl)-2-oxopyrrolidin-3-yl)oxy)propan-2-yl)oxy)-4-(trifluoromethyl)pyridazin-3(2H)-one;

5-(((S)-1-methoxy-3-(((R)-1-(1-(5-methylpyrimidin-2-yl)piperidin-4-yl)-2-oxopyrrolidin-3-yl)oxy)propan-2-yl)oxy)-4-(trifluoromethyl)pyridazin-3(2H)-one;

5-(((S)-1-methoxy-3-(((R)-1-(1-(5-methylpyrimidin-2-yl)piperidin-4-yl)-2-oxopyrrolidin-3-yl)oxy)propan-2-yl)amino)-4-(trifluoromethyl)pyridazin-3(2H)-one;

2-(4-((R)-3-((S)-3-methoxy-2-((6-oxo-5-(trifluoromethyl)-1,6-dihydropyridazin-4-yl)amino)propoxy)-2-oxopyrrolidin-1-yl)piperidin-1-yl) thiazole-5-carbonitrile;

6-(4-((S)-3-((S)-2-((5-bromo-6-oxo-1,6-dihydropyridazin-4-yl)oxy)-3-methoxypropoxy)-2-oxopyrrolidin-1-yl)piperidin-1-yl)nicotinonitrile;

6-(4-((R)-3-((S)-2-((5-bromo-6-oxo-1,6-dihydropyridazin-4-yl)oxy)-3-methoxypropoxy)-2-oxopyrrolidin-1-yl)piperidin-1-yl)nicotinonitrile;

4-Bromo-5-(((S)-1-methoxy-3-(((S)-2-oxo-1-(1-(5-(trifluoromethyl)pyrimidin-2-yl)piperidin-4-yl)pyrrolidin-3-yl)oxy)propan-2-yl)oxy)pyridazin-3(2H)-one;

4-Bromo-5-(((S)-1-methoxy-3-(((R)-2-oxo-1-(1-(5-(trifluoromethyl)pyrimidin-2-yl)piperidin-4-yl)pyrrolidin-3-yl)oxy)propan-2-yl)oxy)pyridazin-3(2H)-one;

5-(((S)-1-(((R)-1-((3R,4R)-3-hydroxy-1-(5-(trifluoromethyl)pyrimidin-2-yl)piperidin-4-yl)-2-oxopyrrolidin-3-yl)oxy)propan-2-yl)amino)-4-(trifluoromethyl)pyridazin-3(2H)-one;

5-(((S)-1-(((R)-1-((3S,4S)-3-hydroxy-1-(5-(trifluoromethyl)pyrimidin-2-yl)piperidin-4-yl)-2-oxopyrrolidin-3-yl)oxy)propan-2-yl)amino)-4-(trifluoromethyl)pyridazin-3(2H)-one;

5-(((S)-1-(((R)-1-((3S,4R)-3-hydroxy-1-(5-(trifluoromethyl)pyrimidin-2-yl)piperidin-4-yl)-2-oxopyrrolidin-3-yl)oxy)propan-2-yl)amino)-4-(trifluoromethyl)pyridazin-3(2H)-one;

5-(((S)-1-(((R)-1-((3R,4S)-3-hydroxy-1-(5-(trifluoromethyl)pyrimidin-2-yl)piperidin-4-yl)-2-oxopyrrolidin-3-yl)oxy)propan-2-yl)amino)-4-(trifluoromethyl)pyridazin-3(2H)-one;

(S)—N—((R)-2-oxo-1-(1-(5-(trifluoromethyl)pyrimidin-2-yl)piperidin-4-yl)pyrrolidin-3-yl)-2-((6-oxo-5-(trifluoromethyl)-1,6-dihydropyridazin-4-yl)amino)propanamide;

5-(((S)-1-(((R)-2-oxo-1-(1-(5-(trifluoromethyl)pyrimidin-2-yl)piperidin-4-yl)pyrrolidin-3-yl)oxy)-3-((2,2,2-trifluoroethyl)amino)propan-2-yl)amino)-4-(trifluoromethyl)pyridazin-3(2H)-one;

5-(((S)-1-hydroxy-3-(((R)-2-oxo-1-(1-(5-(trifluoromethyl)pyrimidin-2-yl)piperidin-4-yl)pyrrolidin-3-yl)oxy)propan-2-yl)amino)-4-(trifluoromethyl)pyridazin-3(2H)-one;

5-(((S)-1-(((S)-1-((3R,4S)-3-hydroxy-1-(5-(trifluoromethyl)pyrimidin-2-yl)piperidin-4-yl)-2-oxopyrrolidin-3-yl)oxy)propan-2-yl)oxy)-4-(trifluoromethyl)pyridazin-3(2H)-one;

5-(((S)-1-(((R)-1-((3S,4R)-3-hydroxy-1-(5-(trifluoromethyl)pyrimidin-2-yl)piperidin-4-yl)-2-oxopyrrolidin-3-yl)oxy)propan-2-yl)oxy)-4-(trifluoromethyl)pyridazin-3(2H)-one;

5-(((2S)-1-((1-((3R,4R)-3-hydroxy-1-(5-(trifluoromethyl)pyrimidin-2-yl)piperidin-4-yl)-2-oxopyrrolidin-3-yl)oxy)propan-2-yl)oxy)-4-(trifluoromethyl)pyridazin-3(2H)-one;

N—((S)-3-(((R)-2-oxo-1-(1-(5-(trifluoromethyl)pyrimidin-2-yl)piperidin-4-yl)pyrrolidin-3-yl)oxy)-2-((6-oxo-5-(trifluoromethyl)-1,6-dihydropyridazin-4-yl)amino)propyl)acetamide;

5-(((2R,3R)-3-hydroxy-1-(((R)-2-oxo-1-(1-(5-(trifluoromethyl)pyrimidin-2-yl)piperidin-4-yl)pyrrolidin-3-yl)oxy)butan-2-yl)amino)-4-(trifluoromethyl)pyridazin-3(2H)-one;

4-((R)-2-oxo-3-((S)-2-((6-oxo-5-(trifluoromethyl)-1,6-dihydropyridazin-4-yl)amino)propoxy)pyrrolidin-1-yl)-1-(5-(trifluoromethyl)pyrimidin-2-yl)piperidine-3-carboxamide; and 4-((R)-2-oxo-3-((S)-2-((6-oxo-5-(trifluoromethyl)-1,6-dihydropyridazin-4-yl)amino)propoxy)pyrrolidin-1-yl)-1-(5-(trifluoromethyl)pyrimidin-2-yl)piperidine-3-carbonitrile;

or a pharmaceutically acceptable salt of any of the aforementioned.

* * * * *